United States Patent
Scharenberg et al.

(10) Patent No.: US 11,987,804 B2
(45) Date of Patent: May 21, 2024

(54) RAPAMYCIN RESISTANT CELLS

(71) Applicant: Seattle Children's Hospital, Seattle, WA (US)

(72) Inventors: Andrew M. Scharenberg, Seattle, WA (US); David J. Rawlings, Seattle, WA (US); Karen Sommer, Seattle, WA (US); Samuel West, Seattle, WA (US); Yuchi Chiang Honaker, Seattle, WA (US); Ryo Takeuchi, Seattle, WA (US)

(73) Assignee: Seattle Children's Hospital, Seattle, WA (US)

( * ) Notice: Subject to any disclaimer, the term of this patent is extended or adjusted under 35 U.S.C. 154(b) by 826 days.

(21) Appl. No.: 17/049,782

(22) PCT Filed: Apr. 25, 2019

(86) PCT No.: PCT/US2019/029118
§ 371 (c)(1),
(2) Date: Oct. 22, 2020

(87) PCT Pub. No.: WO2019/210057
PCT Pub. Date: Oct. 31, 2019

(65) Prior Publication Data
US 2021/0340573 A1   Nov. 4, 2021

Related U.S. Application Data

(60) Provisional application No. 62/663,562, filed on Apr. 27, 2018.

(51) Int. Cl.
| | | |
|---|---|---|
| C12N 15/90 | (2006.01) | |
| C07K 14/715 | (2006.01) | |
| C12N 15/113 | (2010.01) | |
| C12N 15/86 | (2006.01) | |

(52) U.S. Cl.
CPC .......... C12N 15/90 (2013.01); C07K 14/7155 (2013.01); C12N 15/113 (2013.01); C12N 15/86 (2013.01); *C07K 2317/53* (2013.01); *C07K 2319/02* (2013.01); *C07K 2319/03* (2013.01); *C12N 2740/16043* (2013.01); *C12N 2750/14143* (2013.01)

(58) Field of Classification Search
None
See application file for complete search history.

(56) References Cited

U.S. PATENT DOCUMENTS

| | | |
|---|---|---|
| 3,687,808 A | 8/1972 | Merigan et al. |
| 4,469,863 A | 9/1984 | Ts'o et al. |
| 4,476,301 A | 10/1984 | Imbach et al. |
| 4,587,044 A | 5/1986 | Miller et al. |
| 4,605,735 A | 8/1986 | Miyoshi et al. |
| 4,667,025 A | 5/1987 | Miyoshi et al. |
| 4,762,779 A | 8/1988 | Snitman |
| 4,789,737 A | 12/1988 | Miyoshi et al. |
| 4,824,941 A | 4/1989 | Gordon et al. |
| 4,828,979 A | 5/1989 | Klevan et al. |
| 4,835,263 A | 5/1989 | Nguyen et al. |
| 4,845,205 A | 7/1989 | Huynh et al. |
| 4,876,335 A | 10/1989 | Yamane et al. |
| 4,904,582 A | 2/1990 | Tullis |
| 4,948,882 A | 8/1990 | Ruth |
| 4,958,013 A | 9/1990 | Letsinger |
| 5,023,243 A | 6/1991 | Tullis |
| 5,034,506 A | 7/1991 | Summerton et al. |
| 5,082,830 A | 1/1992 | Brakel et al. |
| 5,109,124 A | 4/1992 | Ramachandran et al. |
| 5,112,963 A | 5/1992 | Pieles et al. |
| 5,118,802 A | 6/1992 | Smith et al. |
| 5,130,302 A | 7/1992 | Spielvogel et al. |
| 5,134,066 A | 7/1992 | Rogers et al. |
| 5,138,045 A | 8/1992 | Cook et al. |
| 5,166,315 A | 11/1992 | Summerton et al. |
| 5,173,414 A | 12/1992 | Lebkowski et al. |
| 5,175,273 A | 12/1992 | Bischofberger et al. |
| 5,177,196 A | 1/1993 | Meyer et al. |
| 5,185,444 A | 2/1993 | Summerton et al. |
| 5,188,897 A | 2/1993 | Suhadolnik et al. |
| 5,214,134 A | 5/1993 | Weis et al. |
| 5,214,136 A | 5/1993 | Lin et al. |

(Continued)

FOREIGN PATENT DOCUMENTS

| | | |
|---|---|---|
| WO | WO 93/07883 | 4/1993 |
| WO | WO 94/018317 | 8/1994 |

(Continued)

OTHER PUBLICATIONS

Veverka et al., Structural Characterization of the interaction of mTOR with phosphatidic acid and a novel class of inhibitor: compelling evidence for a central role of the FRB domain in small molecule-mediated regulation of mTOR, Oncogene, 27(5):585-595.
Altschul et al., 1996, [27] Local alignment statistics, Methods in Enzymology, 266:460-480.
Angart et al., 2013, Design of siNRA therapeutics from the molecular scale, Pharmaceuticals, 6(4):440-468.

(Continued)

*Primary Examiner* — Emily A Cordas
(74) *Attorney, Agent, or Firm* — Knobbe, Martens, Olson & Bear LLP

(57) ABSTRACT

The present application relates to, inter alia, compositions including proteins for expression in host cells to render them resistant to rapamycin. The application further relates to methods of using the proteins, cells, and compositions disclosed therein for modulating cell signaling and for selective expansion of cells.

29 Claims, 21 Drawing Sheets

Specification includes a Sequence Listing.

(56) References Cited

U.S. PATENT DOCUMENTS

| | | |
|---|---|---|
| 5,216,141 A | 6/1993 | Benner |
| 5,218,105 A | 6/1993 | Cook et al. |
| 5,235,033 A | 8/1993 | Summerton et al. |
| 5,245,022 A | 9/1993 | Weis et al. |
| 5,254,469 A | 10/1993 | Warren et al. |
| 5,258,506 A | 11/1993 | Urdea et al. |
| 5,262,536 A | 11/1993 | Hornes et al. |
| 5,264,423 A | 11/1993 | Cohen et al. |
| 5,264,562 A | 11/1993 | Matteucci |
| 5,264,564 A | 11/1993 | Matteucci |
| 5,272,250 A | 12/1993 | Spielvogel et al. |
| 5,276,019 A | 1/1994 | Cohen et al. |
| 5,278,302 A | 1/1994 | Caruthers et al. |
| 5,286,717 A | 2/1994 | Cohen et al. |
| 5,292,873 A | 3/1994 | Rokita et al. |
| 5,317,098 A | 5/1994 | Shizuya et al. |
| 5,321,131 A | 6/1994 | Agrawal et al. |
| 5,367,066 A | 11/1994 | Urdea et al. |
| 5,371,241 A | 12/1994 | Brush |
| 5,391,723 A | 2/1995 | Priest |
| 5,399,676 A | 3/1995 | Froehler |
| 5,405,938 A | 4/1995 | Summerton et al. |
| 5,405,939 A | 4/1995 | Suhadolnik et al. |
| 5,414,077 A | 5/1995 | Lin et al. |
| 5,416,203 A | 5/1995 | Letsinger et al. |
| 5,432,272 A | 7/1995 | Benner et al. |
| 5,434,257 A | 7/1995 | Matteucci et al. |
| 5,451,463 A | 9/1995 | Nelson et al. |
| 5,453,496 A | 9/1995 | Caruthers et al. |
| 5,455,233 A | 10/1995 | Spielvogel et al. |
| 5,457,187 A | 10/1995 | Gmeiner et al. |
| 5,459,255 A | 10/1995 | Cook et al. |
| 5,466,677 A | 11/1995 | Baxter et al. |
| 5,470,967 A | 11/1995 | Huie et al. |
| 5,476,925 A | 12/1995 | Letsinger et al. |
| 5,484,908 A | 1/1996 | Froehler et al. |
| 5,486,603 A | 1/1996 | Buhr et al. |
| 5,489,677 A | 2/1996 | Sanghvi et al. |
| 5,502,177 A | 3/1996 | Matteucci et al. |
| 5,510,475 A | 4/1996 | Agrawal et al. |
| 5,512,439 A | 4/1996 | Hornes et al. |
| 5,512,667 A | 4/1996 | Reed et al. |
| 5,514,785 A | 5/1996 | Van Ness et al. |
| 5,519,126 A | 5/1996 | Hecht |
| 5,525,465 A | 6/1996 | Haralambidis et al. |
| 5,525,711 A | 6/1996 | Hawkins et al. |
| 5,536,821 A | 7/1996 | Agrawal et al. |
| 5,539,082 A | 7/1996 | Nielsen et al. |
| 5,541,306 A | 7/1996 | Agrawal et al. |
| 5,541,307 A | 7/1996 | Cook et al. |
| 5,541,313 A | 7/1996 | Ruth |
| 5,545,730 A | 8/1996 | Urdea et al. |
| 5,550,111 A | 8/1996 | Suhadolnik et al. |
| 5,552,538 A | 9/1996 | Urdea et al. |
| 5,552,540 A | 9/1996 | Haralambidis |
| 5,561,225 A | 10/1996 | Maddry et al. |
| 5,563,253 A | 10/1996 | Agrawal et al. |
| 5,565,552 A | 10/1996 | Magda et al. |
| 5,567,810 A | 10/1996 | Weis et al. |
| 5,571,799 A | 11/1996 | Tkachuk et al. |
| 5,574,142 A | 11/1996 | Meyer et al. |
| 5,578,717 A | 11/1996 | Urdea et al. |
| 5,578,718 A | 11/1996 | Cook et al. |
| 5,580,731 A | 12/1996 | Chang et al. |
| 5,585,481 A | 12/1996 | Arnold et al. |
| 5,587,361 A | 12/1996 | Cook et al. |
| 5,587,371 A | 12/1996 | Sessler et al. |
| 5,587,469 A | 12/1996 | Cook et al. |
| 5,591,584 A | 1/1997 | Chang et al. |
| 5,595,726 A | 1/1997 | Magda et al. |
| 5,596,086 A | 1/1997 | Matteucci et al. |
| 5,596,091 A | 1/1997 | Switzer |
| 5,597,696 A | 1/1997 | Linn et al. |
| 5,599,923 A | 2/1997 | Sessler et al. |
| 5,599,928 A | 2/1997 | Hemmi et al. |
| 5,602,240 A | 2/1997 | De Mesmaeker et al. |
| 5,608,046 A | 3/1997 | Cook et al. |
| 5,610,289 A | 3/1997 | Cook et al. |
| 5,614,617 A | 3/1997 | Cook et al. |
| 5,618,704 A | 4/1997 | Cook et al. |
| 5,623,070 A | 4/1997 | Cook et al. |
| 5,625,050 A | 4/1997 | Beaton et al. |
| 5,633,360 A | 5/1997 | Bischofberger et al. |
| 5,658,776 A | 8/1997 | Flotte et al. |
| 5,663,312 A | 9/1997 | Chaturvedula et al. |
| 5,677,437 A | 10/1997 | Teng et al. |
| 5,677,439 A | 10/1997 | Weis et al. |
| 5,688,941 A | 11/1997 | Cook et al. |
| 5,714,331 A | 2/1998 | Buchardt et al. |
| 5,719,262 A | 2/1998 | Buchardt et al. |
| 5,750,692 A | 5/1998 | Cook et al. |
| 5,763,588 A | 6/1998 | Matteucci et al. |
| 5,786,211 A | 7/1998 | Johnson et al. |
| 5,830,653 A | 11/1998 | Froehler et al. |
| 5,871,982 A | 2/1999 | Wilson et al. |
| 6,005,096 A | 12/1999 | Matteucci et al. |
| 6,103,521 A | 8/2000 | Capon et al. |
| 6,165,787 A | 12/2000 | Crabtree et al. |
| 6,258,595 B1 | 7/2001 | Gao et al. |
| 6,287,860 B1 | 9/2001 | Monia et al. |
| 2003/0158403 A1 | 8/2003 | Manoharan |
| 2003/0206891 A1 | 11/2003 | Clackson et al. |
| 2010/0034777 A1 | 2/2010 | Wandless et al. |
| 2014/0068797 A1 | 3/2014 | Doudna |
| 2015/0038684 A1 | 2/2015 | Jensen |
| 2015/0266973 A1 | 9/2015 | Jarjour et al. |
| 2016/0311901 A1 | 10/2016 | Jarjour |
| 2017/0166877 A1 | 6/2017 | Bayle et al. |
| 2017/0175128 A1 | 6/2017 | McPherson |
| 2017/0176128 A1 | 6/2017 | McPherson |
| 2018/0037630 A1 | 2/2018 | Tanaka et al. |
| 2018/0244797 A1 | 8/2018 | Pule et al. |

FOREIGN PATENT DOCUMENTS

| | | | |
|---|---|---|---|
| WO | WO 95/13365 | 5/1995 | |
| WO | WO 95/13392 | 5/1995 | |
| WO | WO 96/17947 | 6/1996 | |
| WO | WO 96/24671 | 8/1996 | |
| WO | WO 96/41865 | 12/1996 | |
| WO | WO 97/06243 | 2/1997 | |
| WO | WO 97/08298 | 3/1997 | |
| WO | WO 97/09441 | 3/1997 | |
| WO | WO 97/21825 | 6/1997 | |
| WO | WO 98/02558 | 1/1998 | |
| WO | WO 99/11764 | 3/1999 | |
| WO | WO 99/36553 | 7/1999 | |
| WO | WO 08/006588 | 1/2008 | |
| WO | WO 08/097875 | 8/2008 | |
| WO | WO 13/123061 | 8/2013 | |
| WO | WO 13/176772 | 11/2013 | |
| WO | WO 14/127261 | 8/2014 | |
| WO | WO 15/017214 | 2/2015 | |
| WO | WO 15/090229 | 6/2015 | |
| WO | WO 2016/098078 A2 | 6/2016 | |
| WO | WO-2016098078 A2 * | 6/2016 | ............. A61K 35/17 |
| WO | WO 16/127257 | 8/2016 | |
| WO | WO 16/135470 | 9/2016 | |
| WO | WO 2016/201047 A1 | 12/2016 | |
| WO | WO 17/029512 | 2/2017 | |
| WO | WO 17/068360 | 4/2017 | |
| WO | WO 18/111834 | 6/2018 | |
| WO | WO 18/161038 | 9/2018 | |
| WO | WO 19/210281 | 10/2019 | |
| WO | WO 20/097582 | 5/2020 | |

OTHER PUBLICATIONS

Ausubel et al., ed., 1987, Current Protocols in Molecular Biology New York, NY: Wiley (TOC).

Ayuso et al., 2010, Production, purification and characterization of adeno-associated vectors, Curr. Gene Ther., 10(6):423-436.

(56) References Cited

OTHER PUBLICATIONS

Bayle et al., 2006, Rapamycin analogs with differential binding specificity permit orthogonal control of protein activity, Chem. Biol., 13(1):99-107.
Behlke, 2008, Chemical modification of siRNAs for in vivo use, Oligonucleotides, 18(4):305-319.
Braasch et al., Apr. 9, 2002, Novel antisense and peptide nucleic acid strategies for controlling gene expression, Biochemistry, 41(14):4503-4510.
Bramsen et al., Aug. 2012, Development of therapeutic-grade small interfering RNAs by chemical engineering, Front. Genet., 3(154):1-22.
Burnett et al., Sep. 2011, Current progress of siRNA/shRNA therapeutics in clinical trials, Biotechnol. J., 6(9):1130-1146.
Chen et al., May 1995, Identification of an 11-kDa FKBP12-rapamycin-binding domain within the 289-kDa FKBP12-rapamycin-associated protein and characterization of a critical serine residue, Proc. Natl. Acad. Sci. U.S.A., 92(11):4947-4951.
Chernolovskaya, et al., 2010, Chemical modification of siRNA, Curr. Opin. Mol Ther., 12(2):158-167.
Choi et al., 1996, Structure of the FKBP12-rapamycin complex interacting with the binding domain of the human FRAP, Science, 273(5272):239-242.
Fonfara et al., 2014, Phylogeny of Cas9 determines functional exchangeability of dual-RNA and Cas9 among orthologous type II CRISPR-Cas systems, Nucl. Acids Res., 42(4):2577-2590.
Fucini et al., 2012, Adenosine modification may be preferred for reducing siRNA immune stimulation, Nucleic Acid Ther., 22(3):205-210.
Gaglione et al., 2010, Recent progress in chemically modified siRNAs, Mini Rev. Med. Chem., 10(7):578-595.
Gebeyehu et al., 1987, Novel biotinylated nucleotide—analogs for labeling and colorimetric detection of DNA, Nucl Acids Res., 15(11):4513-4534.
Grupp et al., 2013, Chimeric antigen receptor-modified T cells for acute lymphoid leukemia. N Engl J Med 368:1509-1518.
Heasman, 2002, Morpholine oligos: making sense of antisense? Dev. Biol., 243(2):209-214.
Hermonat et al., Oct. 1984, Use of adeno-associated virus as a mammalian DNA cloning vector: transduction of neomycin resistance into mammalian tissue culture cells, Proc. Natl. Acad. Sci. U.S.A., 81(2):6466-6470.
Jinek et al., Aug. 17, 2012, A programmable dual-RNA-guided DNA endonuclease in adaptive bacterial immunity, Science, 337(6096):816-821.
Judge et al., 2006, Design of noninflammatory synthetic siRNA medicating potent gene silencing in vivo, Mol. Ther., 13:494-505.
Judge et al., Feb. 2008, Hum. Gene Ther., Overcoming the innate immune response to small interfering RNA, 19(2):111-124.
Kabanov et al., Jan. 1990, A new class of antivirals; antisense oligonucleotides combined with a hydrophobic substituent effectively inhibit influenza virus reproduction and synthesis of virus-specific proteins in MDCK cells, FEBS Lett., 259(2):327-330.
Kalos et al., 2011, T cells with chimeric antigen receptors have potent antitumor effects and can establish memory in patients with advanced leukemia, Sci. Transl. Med. 3(95):95ra73.
Kanasty et al., 2012, Action and reaction: the biological response to siRNA And its delivery vehicles, Mol. Ther., 20(3):513-524.
Kariko et al., Aug. 2005, Suppression of RNA recognition by toll-like receptors; the Impact of nucleoside modification and the evolutionary origin of NRA, Immunity, 23(2):165-175.
Kim, et al., May 11, 2007, NMR Structural Studies of Interaction of a Small, Nonpeptidyl Tpo Mimic with the Thrombopoietin Receptor Extracellular Juxtamembrane and Transmembrane Domains, J Biol Chem, 282(19):14253-14261.
Kole et al., 2012, RNA therapeutics; beyond RNA interference and antisense oligonucleotides, Nat. Rev. Drug Disc., 11(2):125-140.
Kormann et al., 2011, Expression of therapeutic proteins after delivery of chemically modified mRNA in mice, Nat. Biotechnol., 29:154-157.
Lacerra et al., Aug. 15, 2000, Restoration of hemoglobin A synthesis in erythroid cells from peripheral blood of thalassemic patients, Proc. Natl. Acad. Sci. U.S.A., 97(17):9591-9596.
Lebkowski, et al., Oct. 1988, Adeno-associated virus: a vector system for efficient introduction and integration of DNA into a variety of mammalian cell types, Mol. Cell. Biol., 8(10):3988-3996.
Letsinger et al., Sep. 1989, Cholesteryl-conjugated oligonucleotides: synthesis, properties, and activity as inhibitors of replication of human immunodeficiency virus in cell culture, Proc. Natl. Acad. Sci. U.S.A., 86(17):6553-6556.
Love et al., 2010, Lipid-like materials for low-dose, in vivo gene silencing, Proc. Nat. Acad. Sci. U.S.A., 107(5):1864-1869.
Ma et al., 2014, Pol III promoters to express small RNAs: delineation of transcription initiation, Mol. Ther.—Nucleic Acids 3:e161, doi:10.1038/mtna.2014.12.
McLaughlin et al., Jun. 1988, Adeno-associated virus general transduction vectors: analysis of proviral structures, J. Virol., 62(6):1963-1973.
Mietzsch et al., 2014, OneBac: platform for scalable and high-titer production of adeno-associated virus serotype 1-12 vectors for gene therapy, Hum. Gene Ther., 25(3):212-222.
Mietzsch et al., 2015, OncBac 2.0: Sf9 cell lines for production f AAV5 vectors with enhanced infectivity and minimal encapsidation of foreign DNA, Hum. Gene Ther., 26(10):688-697.
Mietzsch et al., 2017, OneBac 2.0: Sf9 cell lines for production of AAV1, AAV2, and AAV8 vectors with minimal encapsidation of foreign DNA, Hum. Gene Ther. Method, 28(1):15-22.
Nasevicius et al., Oct. 2000, Effective targeted gene 'knockdown' in zebrafish, Nat. Genet., 26(2):216-220.
Nielsen et al., 1991, Sequence-selective recognition of DNA by strand displacement with a thymine-substitute polyamide, Science, 254(5037):1497-1500.
Oberhauser et al., 1992, Effective incorporation of 2'-O-methyl-oligoribonucleotides into liposomes and enhanced cell association through modification with thiocholesterol, Nucl. Acids Res., 20(3):533-538.
Peer et al., 2011, Special delivery: targeted therapy with small RNAs, Gene Ther., 18:1127-1133.
Restifo et al., 2012, Adoptive immunotherapy for cancer: harnessing the T cell response, Nat. Rev. Immunol. 12(4):269-281.
Sambrook et al., 2012, Molecular Cloning: A Laboratory Manual ($4^{th}$ ed.), Cold Spring Harbor, NY: Cold Spring Harbor Laboratory (TOC).
Samulski et al., 1982, Cloning of adeno-associated virus into pBR322: rescue of intact virus from the recombinant plasmid in human cells, Proc. Natl. Acad. Sci. U.S.A., 79(6):2077-2081.
Samulski et al., 1989, Helper-free stocks of recombinant adeno-associated viruses: normal integration does not require viral gene expression, J. Virol., 63(9):3822-3828.
Sander et al., Apr. 2014, CRPSPR-Cas systems for genome editing, regulation and targeting, Nat. Biotechnol., 32(4):347-355.
Sapranauskas et al., 2011, The streptococcus thermophilus CRISPR/Cas system provides immunity in *Escherichia coli*, Nucl. Acids Res., 39(21):9275-9282.
Senapathy et al., Apr. 10, 1984, Molecular cloning of adeno-associate virus variant genomes and generation of infectious virus by recombination in mammalian cells, J. Biol. Chem., 259(7):4661-4666.
Shea et al., 1990, Synthesis, hybridization properties and antiviral activity of lipid-oligodeoxynucleotide conjugates, Nucl. Acids Res., 18(13):3777-3783.
Soutschek et al., Nov. 11, 2004, Therapeutic silencing of an endogenous gene by systemic administration of modified siRNAs, Nature, 432:173-178.
Stankunas et al., Dec. 2003, Conditional protein alleles using knockin mice and a chemical inducer of dimerization, Mol. Cell., 12(6):1615-1624.
Tratschin et al., 1984, A human parvovirus, adeno-associated virus, as a eucaryotic vector: transient expression and encapsidation of the procaryotic gene for chloramphenicol acetyltransferase, Mol. Cell. Biol., 4(10):2072-2081.

(56) References Cited

OTHER PUBLICATIONS

Tratschin et al., Nov. 1985, Adeno-associated virus vector for high-frequency integration, expression, and rescue of genes in mammalian cells, Mol. Cell. Biol., 5(11):3251-3260.
Vilella-Bach et al., Feb. 12, 1999, The FKBP12-reapamycin-binding domain is required for FSBP12-rapamycin-associated protein kinase activity and $G_1$ progression, J. Biol. Chem., 274(7):4266-4272.
Volkov et al., 2009, Selective protection of nuclease-sensitive sites in siRNA prolongs silencing effect, Oligonucleotides, 19(2):191-202.
Warren et al., 2010, Highly efficient reprogramming to pluripotency and directed differentiation of human cells with synthetic modified mRNA, Cell Stem Cell, 7(5):618-630.
Winkler, 2013, Oligonucleotide conjugates for therapeutic applications, Ther. Deliv., 4(7):791-809.
Banaszynski et al., Apr. 2005, Characterization of the FKBP-rapamycin-FRB ternary complex, Journal of the American Chemical Society, 127(13):4715-4721.
Banaszynski et al., Sep. 8, 2006, A rapid, reversible, and tunable method to regulate protein function in living cells using synthetic small molecules, Cell, 126(5):995-1004.
DeRose et al., Mar. 2013, Manipulating signaling at will: chemically-inducible dimerization (CID) techniques resolve problems in cell biology, Pflugers Arch. 465(3):409-417.
Graef et al., 1997, Proximity and orientation underlie signaling by the non-receptor tyrosine kinase ZAP70, EMBO J. 16(18):5618-5628.
Kanamori et al., Nov. 2016, Induced regulatory T cells; their development, stability, and applications, Trends in Immunology, 37(11):803-811.
Li et al., 2002, A novel conditional Akt 'survival switch' reversibly protects cells from apoptosis, Gene Therapy. 9(4):233-244.
Ogawa et al., Aug. 29, 2013, Construction of unnatural heterodimeric receptor based on IL-2 and IL-t receptor subunits, Biotechnol Prog. 29(6):1512-1518, 2013.

Schlessinger et al., Sep. 20, 2002, Ligand-induced, receptor-mediated dimerization and activation of EGF receptor, Cell, 110(6):669-672.
Sogo et al., 2008, Selective expansion of genetically modified T cells using an antibody/interleukin-2 receptor chimera, J Immunol Methods. 337(1):16-23.
Vivien et al., Mar. 31, 1995, Signaling activity of homologous and heterologous transforming growth factor-β receptor kinase complexes, J Biol Chem. 270(13):7134-7141.
Wells et al., Feb. 26, 1999, Transforming growth factor-β induces formation of dithiothreitol-resistant type I/type II receptor complex in live cells, J Biol Chem. 274(9):5716-5722.
Wrana et al. Dec. 11, 1992, TGFβ signals through a heteromeric protein kinase receptor complex, Cell. 71(6):1003-1014.
Choi et al., "Structure of the FKBP12-rapamycin complex interacting with the binding domain of human FRAP" Science. 1996. 273(5272):239-242.
Kapp et al., 2009, Post-Targeting Functions of Signal Peptides. In: Madame Curie BioScience Database. Landes Bioscience, Austin, TX, 22 pp.
Liang et al., "1NSG. The Structure of the Immunophilin-Immunosuppressant FKBP12-Rapamycin Complex Interacting With Human Frap", PDB DOI: 10.2210/pdb1NSG/pdb, Mar. 18, 1998.
Liang et al., "Refined structure of the FKBP12-rapamycin-FRB ternary complex at 2.2 A resolution" Acta Crystallogr D Biol Crystallogr. 1999. 55(4):736-744.
Ruiz-Medina et al., Interleukin-2 Receptor B Thr-450 Phosphorylation Is a Positive Regulator for Receptor Complex Stability and Activation of Signaling Molecules, J Biol Chem. 2015. 290(34):20972-20983.
Watanabe et al., 2017, Genetic visualization of protein interactions harnessing liquid phase transitions, Scientific Reports, 7:46380, 32 pp.
International Search Report for PCT/US2019/029118 dated Sep. 16, 2019.

\* cited by examiner

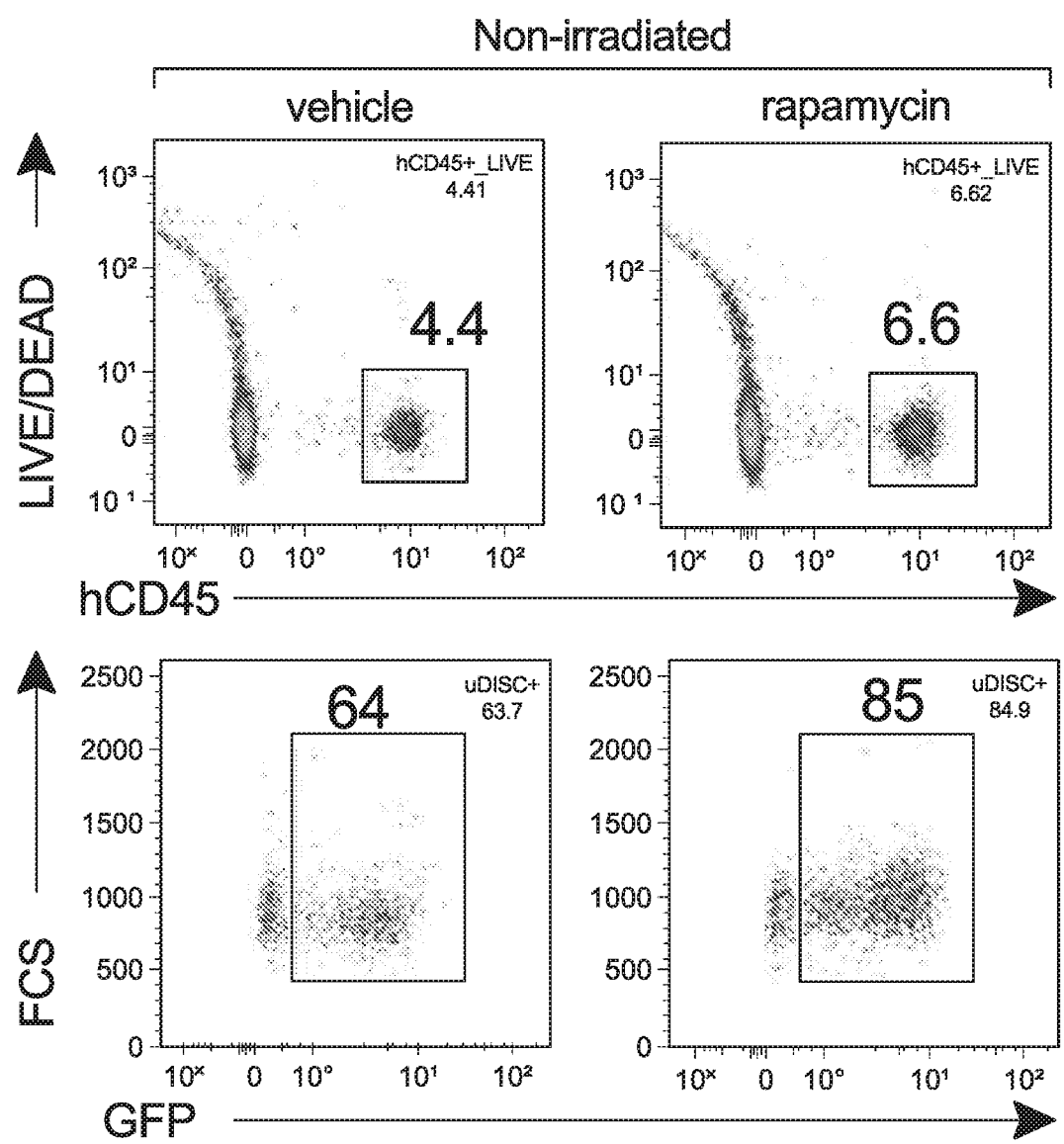
FIG. 16A (Con'd)

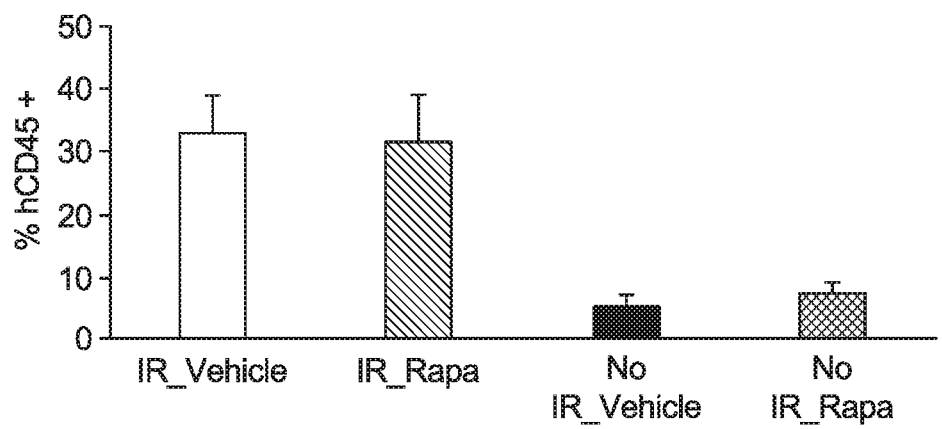
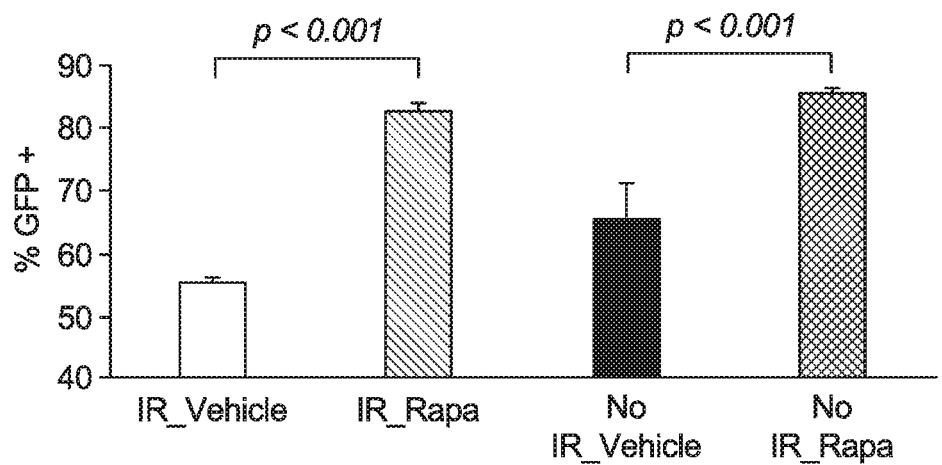
FIG. 16A (Con'd)

RAPAMYCIN RESISTANT CELLS

CROSS-REFERENCE TO RELATED APPLICATIONS

This application is a U.S. National Phase Application of PCT International Application Number PCT/US2019/029118, filed on Apr. 25, 2019, designating the United States of America and published in the English language, which is an International Application of and claims the benefit of priority to U.S. Provisional Application No. 62/663,562, filed on Apr. 27, 2018. The disclosures of the above-referenced applications are hereby expressly incorporated by reference in their entireties.

REFERENCE TO SEQUENCE LISTING

The present application is being filed along with a Sequence Listing in electronic format. The Sequence Listing is provided as a file entitled SeqList-SCRI-186NP.txt, created Aug. 5, 2020, which is approximately 121 Kb in size. The information in the electronic format of the Sequence Listing is incorporated herein by reference in its entirety.

FIELD

Provided herein are chemical-induced signaling complexes in which two components are brought together in the presence of rapamycin or related chemical compounds to generate an active signaling complex for use in conjunction with an intracellularly expressed naked FKBP-rapamycin binding protein to confer rapamycin resistance upon a host cell.

BACKGROUND

Rapamycin, also known as sirolimus, is a complex macrolide natural product isolated from the bacterium *Streptomyces hygroscopicus* which was found in a soil sample on Easter Island (a.k.a. *Rapa nui*) in 1975 (Huang, S. et al. (2003). *Cancer Biol. Ther.*, 2(3):222-232; Abraham, R. T. et al. (1996). *Ann. Rev. Immunol.*, 14:483-510; Pollock, R. et al. (2002). *Curr. Opin. Biotechnol.*, 13(5):459-467; Bayle, J. H. et al. (2006). *Chem. Biol.*, 13(1):99-107). Rapamycin mediates heterodimerization of the proteins FKBP12 (FK506 binding protein 12) and FRB (FKBP12 rapamycin binding domain) (Huang, S. et al. (2003). *Cancer Biol. Ther.*, 2(3):222-232). Due to the excellent physiological properties of rapamycin, including good pharmacokinetic parameters such as good levels of solubility and membrane permeability across the blood-brain barrier, as well as oral bioavailability (Abraham, R. T. et al. (1996). *Ann. Rev. Immunol.*, 14:483-510), it has been used as a small molecule dimerizer in a wide range of applications in mammalian cells and organisms (e.g., Pollock, R. et al. (2002). *Curr. Opin. Biotechnol.*, 13(5):459-467).

The CISC (chemically induced signaling complex) is a multicomponent synthetic protein complex configured for co-expression in a host cell as two chimeric proteins as described in International Patent Application No. PCT/US2017/065746, the disclosure of which is incorporated by reference herein in its entirety. Each chimeric protein component of the CISC has one half of a rapamycin binding complex as an extracellular domain, fused to one half of an intracellular signaling complex. Delivery of nucleic acids encoding the CISC to host cells permits intracellular signaling in the cells that can be controlled by the presence of rapamycin or a rapamycin-related chemical compound.

However, while rapamycin-driven CISC dimerization can trigger intracellular signaling, the presence of rapamycin can also inhibit the growth and the viability of host cells, thereby limiting their utility for use in therapeutic as well as research endeavors. Consequently, new compositions and methods are needed which permit the use of rapamycin-mediated CISC intracellular signaling but which remediate the negative effects that rapamycin or rapamycin-related compounds have on the growth and viability of host cells.

SUMMARY

Provided herein, inter alia, are compositions and methods for rendering cells resistant to rapamycin.

In one aspect, described herein is a system including (i) a deoxyribonucleic acid (DNA) endonuclease or nucleic acid encoding the DNA endonuclease; (ii) a guide RNA (gRNA) including a spacer sequence complementary to a target sequence within a target genomic locus in a cell, or nucleic acid encoding the gRNA; and (iii) a donor template including a donor cassette including a nucleic acid sequence encoding a naked FKBP-rapamycin binding (FRB) domain polypeptide, wherein the DNA endonuclease, gRNA, and donor template are configured such that a complex formed by association of the DNA endonuclease with the gRNA is capable of promoting targeted integration of the donor cassette into the target genomic locus in a cell to generate a genetically modified cell capable of expressing the naked FRB domain polypeptide. In some embodiments, the DNA endonuclease is a Cas9 endonuclease. In some embodiments, the nucleic acid encoding the DNA endonuclease is codon-optimized for expression in the genetically modified cell; the nucleic acid encoding the gRNA is codon-optimized for expression in the genetically modified cell; and/or one or more coding sequences in the donor cassette is codon-optimized for expression in the genetically modified cell. In some embodiments, the donor template is configured such that the donor cassette is capable of being integrated into the target genomic locus by homology directed repair (HDR). In some embodiments, the donor template is configured such that the donor cassette is capable of being integrated into the target genomic locus by non-homologous end joining (NHEJ). In some embodiments, the DNA endonuclease or nucleic acid encoding the DNA endonuclease is formulated in a liposome or lipid nanoparticle. In some embodiments, the liposome or lipid nanoparticle further includes the gRNA or nucleic acid encoding the gRNA. In some embodiments, the system further includes the DNA endonuclease associated with the gRNA in a ribonucleoprotein (RNP) complex.

In some embodiments, a naked FKBP-rapamycin binding (FRB) domain polypeptide is provided. In some embodiments, the naked FRB polypeptide includes the amino acid sequence of SEQ ID NO: 1 or SEQ ID NO: 2.

In some embodiments, the donor cassette further includes one or more nucleic acid sequences encoding polypeptide components of a dimerization activatable chemical-induced signaling complex (CISC), wherein the polypeptide components of the CISC include (i) a first CISC component including a first extracellular binding domain or functional derivative thereof, a hinge domain, a transmembrane domain, and a signaling domain or functional derivative thereof; and (ii) a second CISC component including a second extracellular binding domain or functional derivative thereof, a hinge domain, a transmembrane domain, and a signaling domain or functional derivative thereof; wherein the first CISC component and the second CISC component are configured such that when expressed in a cell, they are capable of dimerizing in the presence of rapamycin or a rapalog to generate a signaling-competent CISC.

In some embodiments, the first or second extracellular binding domain or functional derivative thereof includes an FK506 binding protein (FKBP) domain or a functional derivative thereof and/or the other extracellular binding domain or functional derivative thereof includes an FRB domain or a functional derivative thereof. In some embodiments, the transmembrane domain of the first CISC component includes an IL-2 receptor transmembrane domain and/or the transmembrane domain of the second CISC components includes an IL-2 receptor transmembrane domain. In some embodiments, the signaling domain or functional derivative thereof of the first or second CISC component includes an IL-2 receptor subunit gamma (IL2Rγ) domain or a functional derivative thereof and/or the signaling domain or functional derivative thereof of the other CISC component includes an IL-2 receptor subunit beta (IL2Rβ) domain or a functional derivative thereof. In some embodiments, the IL2Rβ domain polypeptide is truncated. In some embodiments, the nucleic acid encoding the IL2Rβ domain includes the nucleotide sequence of SEQ ID NO: 4. In some embodiments, the IL2Rβ domain includes the amino acid sequence of SEQ ID NO: 5.

In some embodiments, wherein the rapalog is selected from the group consisting of everolimus, CCI-779, C20-methallylrapamycin, C16-(S)-3-methylindolerapamycin, C16-iRap, AP21967, sodium mycophenolic acid, benidipine hydrochloride, AP1903, and AP23573, and metabolites and derivatives thereof.

In some embodiments, the nucleic acid encoding the naked FRB domain is downstream of the one or more nucleic acid sequences encoding polypeptide components of the CISC. In some embodiments, the donor cassette further includes a nucleic acid sequences encoding a self-cleaving polypeptide between (i) each of the one or more nucleic acid sequences encoding polypeptide components of the CISC; and/or (ii) the nucleic acid encoding the naked FRB domain and an adjacent nucleic acid sequence encoding a polypeptide component of the CISC.

In some embodiments, each of the self-cleaving polypeptides encoded in the donor cassette is independently selected from the group consisting of P2A, T2A, E2A, and F2A. In some embodiments, the donor cassette further includes a promoter operably linked to one or more coding sequences in the donor cassette. In some embodiments, the promoter is an inducible promoter or a constitutive promoter. In some embodiments, the promoter is an MND promoter. In some embodiments, the donor cassette further includes a nucleic acid encoding a detectable marker. In some embodiments, the detectable marker is a green fluorescent protein (GFP) polypeptide, an mCherry polypeptide, or a low affinity nerve growth factor receptor (LNGFR). In some embodiments, the nucleic acid encoding the naked FRB domain polypeptide lacks a nucleic acid encoding an endoplasmic reticulum localization signal polypeptide. In some embodiments, the donor cassette includes a nucleic acid sequence from the nucleotide sequence of SEQ ID NO: 3.

In some embodiments, the donor template is a viral vector. In some embodiments, the viral vector is a lentiviral, adenoviral, or adeno-associated viral (AAV) vector.

In one aspect, described herein is a method of editing a cell genome, including providing to the cell: (i) a deoxyribonucleic acid (DNA) endonuclease or nucleic acid encoding the DNA endonuclease; (ii) a guide RNA (gRNA) including a spacer sequence complementary to a target sequence within a target genomic locus in the cell, or nucleic acid encoding the gRNA; and (iii) a donor template including a donor cassette including a nucleic acid sequence encoding a naked FKBP-rapamycin binding (FRB) domain polypeptide, wherein the DNA endonuclease, gRNA, and donor template are configured such that a complex formed by association of the DNA endonuclease with the gRNA is capable of promoting targeted integration of the donor cassette into the target genomic locus in the cell to generate a genetically modified cell capable of expressing the naked FRB domain polypeptide.

In one aspect, provided herein is a genetically modified cell prepared according to the method of editing a cell genome as described herein, including providing to the cell: (i) a deoxyribonucleic acid (DNA) endonuclease or nucleic acid encoding the DNA endonuclease; (ii) a guide RNA (gRNA) including a spacer sequence complementary to a target sequence within a target genomic locus in the cell, or nucleic acid encoding the gRNA; and (iii) a donor template including a donor cassette including a nucleic acid sequence encoding a naked FKBP-rapamycin binding (FRB) domain polypeptide, wherein the DNA endonuclease, gRNA, and donor template are configured such that a complex formed by association of the DNA endonuclease with the gRNA is capable of promoting targeted integration of the donor cassette into the target genomic locus in the cell to generate a genetically modified cell capable of expressing the naked FRB domain polypeptide. In some embodiments, the donor cassette is configured such that naked FRB domain polypeptide is expressed intracellularly. In some embodiments, the cell is a eukaryotic cell. In some embodiments, the cell is a mammalian cell. In some embodiments, the cell is a hematopoietic stem cell. In some embodiments, the cell is a lymphocyte. In some embodiments, the cell is a precursor T cell or a T regulatory ($T_{reg}$) cell. In some embodiments, the cell is a CD34+, CD8+, or a CD4+ cell. In some embodiments, the cell is a CD8+ T cytotoxic lymphocyte cell selected from the group consisting of naïve CD8+ T cells, central memory CD8+ T cells, effector memory CD8+ T cells, and bulk CD8+ T cells. In some embodiments, the cell is a CD4+ T helper lymphocyte cell selected from the group consisting of naïve CD4+ T cells, central memory CD4+ T cells, effector memory CD4+ T cells, and bulk CD4+ T cells. In some embodiments, the cell proliferates to a greater extent in the presence of rapamycin or a rapalog as compared to a corresponding cell where the donor cassette lacks a nucleic acid encoding a naked FRB domain polypeptide. In some embodiments, the rapamycin or rapalog is present in a concentration of from or from about 0.1 nM to or to about 100 nM.

In another aspect, described herein is a method of activating the genetically modified cell as disclosed herein, the method including contacting the cell with rapamycin or a rapalog. In some embodiments, the rapalog is selected from the group consisting of everolimus, CCI-779, C20-methallylrapamycin, C16-(S)-3-methylindolerapamycin, C16-iRap, AP21967, sodium mycophenolic acid, benidipine hydrochloride, AP1903, or AP23573, or metabolites, derivatives, and/or combinations of any thereof. In some embodiments, the rapamycin or rapalog contacting the cell is at a concentration of from at or about 0.1 nM to at or about 100 nM. In some embodiments, wherein following contact with rapamycin or the rapalog, cells expressing the CISC components are selectively expanded.

In yet another aspect, described herein is a method of selectively expanding a population of genetically modified cells as described herein, contained in a mixed population of cells, the method including contacting the mixed population of cells with rapamycin or a rapalog, wherein the genetically modified cells expressing the CISC components and naked FRB domain are activated and expanded in vitro or in vivo to a greater extent than the other cells in the mixed population of cells. In some embodiments, the rapalog is selected from the group consisting of everolimus, CCI-779, C20-methallylrapamycin, C16-(S)-3-methylindolerapamycin, C16-iRap, AP21967, sodium mycophenolic acid, benidipine hydrochloride, AP1903, or AP23573, or metabolites, derivatives, and/or combinations of any thereof. In some embodiments, the rapamycin or rapalog contacting the mixed population of cells is at a concentration of from at or about 0.1 nM to at or about 100 nM.

Each of the aspects and embodiments described herein are capable of being used together, unless excluded either explicitly or clearly from the context of the embodiment or aspect.

Throughout this specification, various patents, patent applications and other types of publications (e.g., journal articles, electronic database entries, etc.) are referenced. The disclosure of all patents, patent applications, and other publications cited herein are hereby incorporated by reference in their entirety for all purposes.

BRIEF DESCRIPTION OF THE DRAWINGS

FIG. 16B shows the average±s.d. number GFP+ cells in the 75 μL peripheral blood sample. IR=irradiation; Rapa=rapamycin, 0.1 mg/kg i.p. every two days throughout experiment. P value was obtained using Student's T test.

DETAILED DESCRIPTION

Described herein, inter alia, are compositions and methods, intended for use with chemical-induced signaling complex (CISC) polypeptides, for resulting in rapamycin-mediated intracellular signaling via the CISC in engineered host cells but without the attendant cytotoxicity associated with rapamycin's effects on the host cells by, e.g., rendering the engineered host cells resistant to growth inhibition by rapamycin or a rapamycin-related chemical compound (such as a rapalog). The compositions and methods disclosed herein are, in some embodiments, intended for use with CISC polypeptides, which are multicomponent synthetic protein complexes configured for co-expression in a host cell as two chimeric proteins. The CISC signaling system described in International Patent Application No. PCT/US2017/065746 (incorporated by reference herein) can be engineered to induce intracellular signaling in response to rapamycin, which is a macrolide compound used for a variety of therapeutic and research applications. Each chimeric protein component of the CISC can have one half of a rapamycin binding complex (either an FK506 binding protein (FKPB) domain or an FKBP rapamycin binding (FRB) domain, respectively) as an extracellular domain, fused to one half of an intracellular signaling complex. Binding of rapamycin to the extracellular domains of the CISC induces the formation of CISC heterodimers and subsequent intracellular signaling via the intracellular signaling complex portion of the chimeric polypeptides.

While useful, CISC-expressing cells exposed to rapamycin have been observed to undergo less proliferation compared to the amount of proliferation achieved using the rapalog AP21967. The mammalian target of rapamycin (mTOR), also known as FK506-binding protein 12-rapamycin-associated protein 1 (FRAP1), is a kinase that in humans is encoded by the MTOR gene. mTOR is a member of the phosphatidylinositol 3-kinase-related kinase family of protein kinases. This protein is a growth regulator that stimulates cellular growth by phosphorylating substrates that govern anabolic processes such as lipid synthesis and mRNA translation, as well as retarding catabolic processes such as autophagy.

Figure 2:
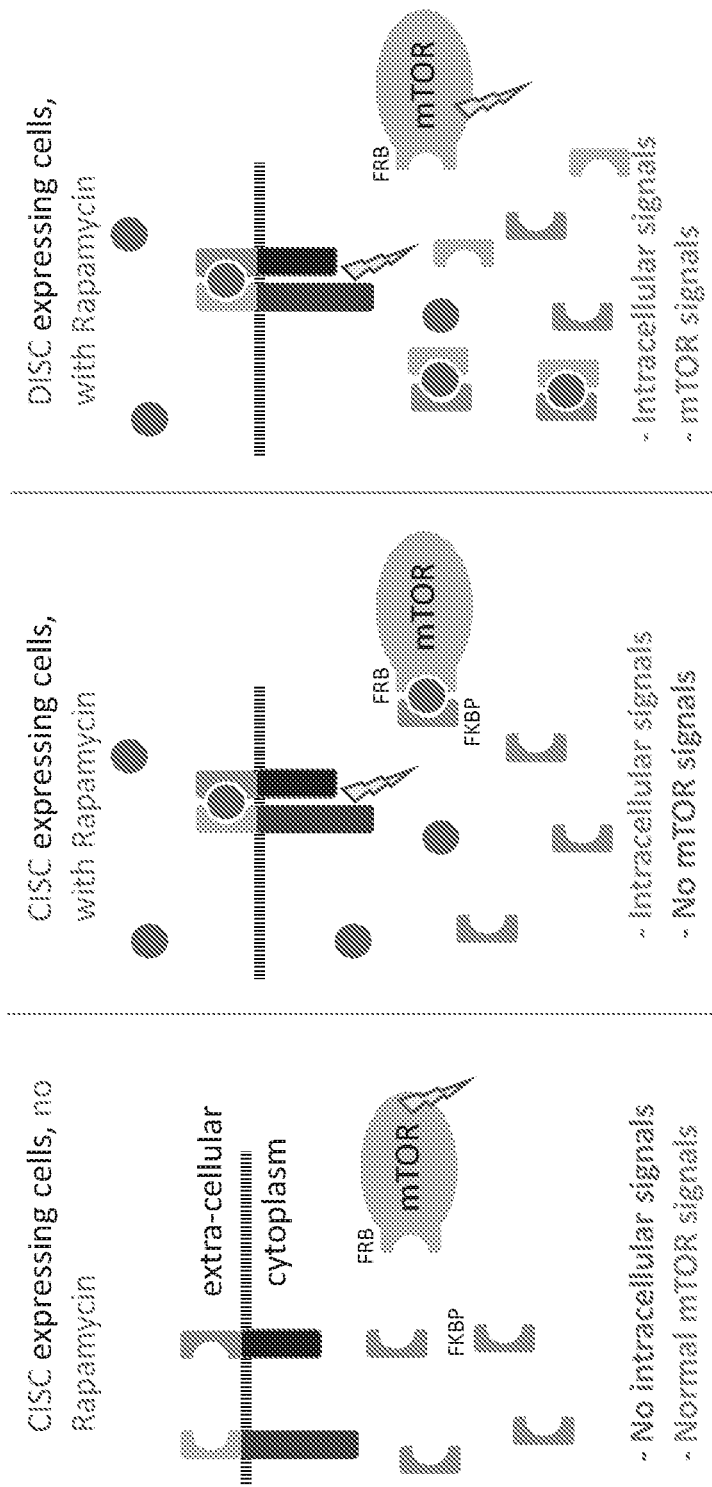
FIG. 2 is a conceptual diagram showing the hypothesized mechanism of action of naked FRB in T cells.

Applicants have devised constructs and methods to overcome the problem of inhibition of proliferation. As shown in FIG. 2, FKBP domain-containing proteins are naturally expressed in the cytoplasm of cells while mTOR contains an FRB domain. Without being bound by theory, it is believed that the binding of a rapamycin/FKBP complex to the FRB domain of mTOR blocks or decreases mTOR-mediated intracellular signaling leading to decreased mRNA translation and cellular growth. As such, again without being bound by theory, the inventors of the present application hypothesized that intracellular expression of a naked FRB protein domain (untethered from mTOR) could be used to bind intracellular rapamycin/FKBP complexes, thereby attenuating the negative effects of rapamycin on the growth of CISC-expressing cells. Previous reports indicated that intracellular expression of the naked FRB domain of mTOR is toxic to mammalian cells and thus would not be a suitable means to intracellularly buffer rapamycin-FKBP interactions with the FRB domain of mTOR in human cells (see Vilella-Bach, M. et al. (1999). *J. Biol. Chem.*, 274(7):4266-4272). Moreover, a T2098L mutation (sequence numbering relative to the mTOR amino acid sequence) in the FRB domain destabilizes it relative to the wild type protein, making it degrade faster in the cell. However, the mutant protein is stabilized by binding to rapamycin (Stankunas, K. et al. (2003). *Mol. Cell.*, 12(6):1615-1624).

By contrast to these previous reports, and as will be further described herein, the inventors of the present application have surprisingly discovered that intracellular expression of a naked "decoy" FRB (FRB*) domain in CISC-expressing host cells can effectively attenuate the growth inhibitory effects of rapamycin. Constructs that express the extra FRB* domain along with the CISC were designated as "decoy-CISC," or "DISC." The rapamycin resistance conferred by the naked intracellularly expressed FRB domain thus increases the utility of rapamycin responsive CISC-expressing cells for both therapeutic applications as well as researching intracellular signaling pathways.

Definitions

Unless defined otherwise, all technical and scientific terms used herein have the same meaning as commonly understood by one of ordinary skill in the art to which the disclosure pertains. All patents, applications, published applications and other publications referenced herein are expressly incorporated by reference in their entireties unless stated otherwise. In the event that there are a plurality of definitions for a term herein, those in this section prevail unless stated otherwise.

As used herein, the singular forms "a," "an" and "the" include plural references unless the context clearly dictates otherwise.

"About" has its plain and ordinary meaning when read in light of the specification, and may be used, for example, when referring to a measurable value and may be meant to encompass variations of ±20%, or ±10%, or ±5%, or ±1%, or ±0.1% from the specified value.

As used herein, "protein sequence" refers to a polypeptide sequence of amino acids that is the primary structure of a protein. As used herein "upstream" refers to positions 5' of a location on a polynucleotide, and positions toward the N-terminus of a location on a polypeptide. As used herein "downstream" refers to positions 3' of a location on nucleotide, and positions toward the C-terminus of a location on a polypeptide. Thus, the term "N-terminal" refers to the position of an element or location on a polynucleotide toward the N-terminus of a location on a polypeptide.

"Nucleic acid" or "nucleic acid molecule" refers to polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., enantiomeric forms of naturally-occurring nucleotides), or a combination of both. The term "nucleic acid molecule" also includes so-called "peptide nucleic acids," which include naturally-occurring or modified nucleic acid bases attached to a polyamide backbone. Nucleic acids can be either single stranded or double stranded. In some embodiments, a nucleic acid sequence encoding a fusion protein is provided. In some embodiments, the nucleic acid is RNA or DNA.

"Coding for" or "encoding" are used herein, and refers to the property of specific sequences of nucleotides in a polynucleotide, such as a gene, a cDNA, or an mRNA, to serve as templates for synthesis of other macromolecules such as a defined sequence of amino acids. Thus, a gene codes for a protein if transcription and translation of mRNA corresponding to that gene produces the protein in a cell or other biological system.

A "nucleic acid sequence coding for a polypeptide" includes all nucleotide sequences that are degenerate versions of each other and that code for the same amino acid sequence. In some embodiments, a nucleic acid is provided, wherein the nucleic acid encodes a fusion protein.

"Vector," "expression vector," or "construct" is a nucleic acid used to introduce heterologous nucleic acids into a cell that has regulatory elements to provide expression of the heterologous nucleic acids in the cell. Vectors include but are not limited to plasmid, minicircles, yeast, and viral genomes. In some embodiments, the vectors are plasmid, minicircles, yeast, or viral genomes. In some embodiments, the vector is a viral vector. In some embodiments, the viral vector is a lentivirus. In some embodiments, the vector is an adeno-associated viral (AAV) vector (such as, without limitation, AAV1, AAV2, AAV3, AAV4, AAV5, AAV6, AAV7, AAV8, AAV9, AAV10, or AAV11). In some embodiments, the vector is for protein expression in a bacterial system such as E. coli.

As used herein, the term "expression," or "protein expression" refers to the translation of a transcribed RNA molecule into a protein molecule. Protein expression may be characterized by its temporal, spatial, developmental, or morphological qualities as well as by quantitative or qualitative indications. In some embodiments, the protein or proteins are expressed such that the proteins are configured, e.g., are positioned, for dimerization in the presence of a ligand.

As used herein, "fusion proteins" or "chimeric proteins" are proteins created through the joining of two or more genes that originally coded for separate proteins or portions of proteins. The fusion proteins can also be made up of specific protein domains from two or more separate proteins. Translation of this fusion gene can result in a single or multiple polypeptides with functional properties derived from each of the original proteins. Recombinant fusion proteins can be created artificially by recombinant DNA technology for use in biological research or therapeutics. Such methods for creating fusion proteins are known to those skilled in the art. Some fusion proteins combine whole peptides and therefore can contain all domains, especially functional domains, of the original proteins. However, other fusion proteins, especially those that are non-naturally occurring, combine only portions of coding sequences and therefore do not maintain the original functions of the parental genes that formed them.

As used herein, the term "regulatory element" refers to a DNA molecule having gene regulatory activity, e.g., one that has the ability to affect the transcription and/or translation of an operably linked transcribable DNA molecule. Regulatory elements such as promoters (e.g. an MND promoter, such as, without limitation, the MND promoter including the nucleic acid sequence of SEQ ID NO: 33), leaders, introns, and transcription termination regions are DNA molecules that have gene regulatory activity and play an integral part in the overall expression of genes in living cells. Isolated regulatory elements, such as promoters, that function in plants are therefore useful for modifying plant phenotypes through the methods of genetic engineering.

As used herein, the term "operably linked" refers to a first molecule joined to a second molecule, wherein the molecules are so arranged that the first molecule affects the function of the second molecule. The two molecules may be part of a single contiguous molecule and may be adjacent. For example, a promoter is operably linked to a transcribable DNA molecule if the promoter modulates transcription of the transcribable DNA molecule of interest in a cell.

"Dimeric chemical-induced signaling complex," "dimeric CISC," or "dimer" as used herein refers to two components of a CISC, which may or may not be fusion protein complexes that join together. "Dimerization" refers to the process of the joining together of two separate entities into a single entity, for example in response to binding of the entities to a ligand (for example, rapamycin). In some embodiments, a ligand or agent stimulates dimerization. In some embodiments, dimerization refers to homodimerization, or the joining of two identical entities, such as two identical CISC components. In some embodiments, dimerization refers to heterodimerization, of the joining of two different entities, such as two different and distinct CISC components. In some embodiments, the dimerization of the CISC components results in a cellular signaling pathway. In some embodiments, the dimerization of the CISC components allows for the selective expansion of a cell or a population of cells. Additional CISC systems can include a CISC gibberellin CISC dimerization system, or a SLF-TMP CISC dimerization system. Other chemically inducible dimerization (CID) systems and component parts may be used.

As used herein, "chemical-induced signaling complex" or "CISC" refers to an engineered complex that initiates a signal into the interior of a cell as a direct outcome of ligand-induced dimerization. A CISC may be a homodimer (dimerization of two identical components) or a heterodimer (dimerization of two distinct components). Thus, as used herein the term "homodimer" refers to a dimer of two protein components described herein with identical amino acid sequences. The term "heterodimer" refers to a dimer of two protein components described herein with non-identical amino acid sequences.

The CISC may be a synthetic complex as described herein in greater detail. "Synthetic" as used herein refers to a complex, protein, dimer, or composition, as described herein, which is not natural, or that is not found in nature. In some embodiments, an IL2R-CISC refers to a signaling complex that involves interleukin-2 receptor components. In some embodiments, an IL2/15-CISC refers to a signaling complex that involves receptor signaling subunits that are shared by interleukin-2 (IL2) and interleukin-15 (IL15). In some embodiments, an IL7-CISC refers to a signaling complex that involves an interleukin-7 receptor components. A CISC may thus be termed according to the component parts that make up the components of a given CISC. One of skill in the art will recognize that the component parts of the chemical-induced signaling complex may be composed of a natural or a synthetic component useful for incorporation into a CISC. Thus, the examples provided herein are not intended to be limiting.

As used herein, "cytokine receptor" refers to receptor molecules that recognize and bind to cytokines. In some embodiments, cytokine receptor encompasses modified cytokine receptor molecules (e.g., "variant cytokine receptors"), including those with substitutions, deletions, and/or additions to the cytokine receptor amino acid and/or nucleic acid sequence. Thus, it is intended that the term encompass wild-type, as well as, recombinant, synthetically-produced, and variant cytokine receptors. In some embodiments, the cytokine receptor is a fusion protein, including an extracellular binding domain, a hinge domain, a transmembrane domain, and a signaling domain. In some embodiments, the components of the receptor (that is, the domains of the receptor) are natural or synthetic. In some embodiments, the domains are human derived domains.

"FKBP" as used herein, is a FK506 binding protein domain. FKBP refers to a family of proteins that have prolyl isomerase activity and are related to the cyclophilins in function, though not in amino acid sequence. FKBPs have been identified in many eukaryotes from yeast to humans and function as protein folding chaperones for proteins containing proline residues. Along with cyclophilin, FKBPs belong to the immunophilin family. The term FKBP includes, for example, FKBP12 as well as, proteins encoded by the genes AIP; AIPL1; FKBP1A; FKBP1B; FKBP2; FKBP3; FKBP5; FKBP6; FKBP7; FKBP8; FKBP9; FKBP9L; FKBP10; FKBP11; FKBP14; FKBP15; FKBP52; and/or LOC541473; including homologs thereof and functional protein fragments thereof.

"FRB" as used herein, is a FKBP rapamycin binding domain. FRB domains are polypeptide regions (protein "domains") that are configured to form a tripartite complex with an FKBP protein and rapamycin or rapalog thereof. FRB domains are present in a number of naturally occurring proteins, including mTOR proteins (also referred to in the literature as FRAP, RAPT 1, or RAFT) from human and other species; yeast proteins including Tor1 and/or Tor2; and a *Candida* FRAP homolog. Both FKBP and FRB are major constituents in the mammalian target of rapamycin (mTOR) signaling.

A "naked FKBP rapamycin binding domain polypeptide" or a "naked FRB domain polypeptide" (which can also be referred to as an "FKBP rapamycin binding domain polypeptide" or an "FRB domain polypeptide") refers to a polypeptide consisting of the amino acids of an FRB domain, or refers to a protein wherein about 90%, 91%, 92%, 93%, 94%, 95%, 96%, 97%, 98%, 99%, or 100% of the amino acids of the protein are amino acids of an FRB domain. In general, such protein has the ability to bind interact with the rapalog AP21967 as well as rapamycin. The FRB domain can be expressed as a 12 kDa soluble protein (Chen, J. et al. (1995). *Proc. Natl. Acad. Sci. U.S.A.*, 92(11):4947-4951). The FRB domain forms a four helix bundle, a common structural motif in globular proteins. Its overall dimensions are 30 Å by 45 Å by 30 Å, and all four helices) have short underhand connections similar to the cytochrome b562 fold (Choi, J. et al. (1996). *Science*, 273(5272):239-242). In some embodiments, the naked FRB domain includes the amino acids of SEQ ID NO: 1

```
(MEMWHEGLEEASRLYFGERNVKGMFEVLEPLHAMMERGPQTLKETSFN
QAYGRDLMEAQEWCRKYMKSGNVKDLTQAWDLYYHVERRISK)
or
                                           SEQ ID NO: 2
(MEMWHEGLEEASRLYFGERNVKGMFEVLEPLHAMMERGPQTLKETSFN
QAYGRDLMEAQEWCRKYMKSGNVKDLLQAWDLYYHVFRRISK).
```

As used herein, the term "extracellular binding domain" refers to a domain of a complex that is outside of the cell, and which is configured to bind to a specific atom or molecule. In some embodiments, the extracellular binding domain of a CISC is a FKBP domain or a functional derivative thereof. In some embodiments, the extracellular binding domain is an FRB domain or a functional derivative thereof. In some embodiments, the extracellular binding domain is configured to bind a ligand or agent, thereby stimulating dimerization of two CISC components. In some embodiments, the extracellular binding domain is configured to bind to a cytokine receptor modulator.

As used herein, the term "cytokine receptor modulator" refers to an agent, which modulates the phosphorylation of a downstream target of a cytokine receptor, the activation of a signal transduction pathway associated with a cytokine receptor, and/or the expression of a particular protein such as a cytokine. Such an agent may directly or indirectly modulate the phosphorylation of a downstream target of a cytokine receptor, the activation of a signal transduction pathway associated with a cytokine receptor, and/or the expression of a particular protein such as a cytokine. Thus, examples of cytokine receptor modulators include, but are not limited to, cytokines, fragments of cytokines, fusion proteins and/or antibodies or binding portions thereof that immuno-specifically bind to a cytokine receptor or a fragment thereof. Further, examples of cytokine receptor modulators include, but are not limited to, peptides, polypeptides (e.g., soluble cytokine receptors), fusion proteins and/or antibodies or binding portions thereof that immuno-specifically bind to a cytokine or a fragment thereof.

As used herein, the term "activate" refers to an increase in at least one biological activity of a protein of interest. Similarly, the term "activation" refers to a state of a protein of interest being in a state of increased activity. The term "activatable" refers to the ability of a protein of interest to become activated in the presence of a signal, an agent, a ligand, a compound, or a stimulus. In some embodiments, a dimer, as described herein, is activated in the presence of a signal, an agent, a ligand, a compound, or a stimulus, and becomes a signaling competent dimer. As used herein, the term "signaling competent" refers to the ability or configuration of the dimer so as to be capable of initiating or sustaining a downstream signaling pathway.

As used herein, the term "hinge domain" refers to a domain that links the extracellular binding domain to the transmembrane domain, and may confer flexibility to the extracellular binding domain. In some embodiments, the hinge domain positions the extracellular domain close to the plasma membrane to minimize the potential for recognition by antibodies or binding fragments thereof. In some embodiments, the extracellular binding domain is located N-terminal to the hinge domain. In some embodiments, the hinge domain may be natural or synthetic.

As used herein, the term "transmembrane domain" or "TM domain" refers to a domain that is stable in a membrane, such as in a cell membrane. The terms "transmembrane span," "integral protein," and "integral domain" are also used herein. In some embodiments, the hinge domain and the extracellular domain is located N-terminal to the transmembrane domain. In some embodiments, the transmembrane domain is a natural or a synthetic domain. In some embodiments, the transmembrane domain is an IL-2 transmembrane domain.

As used herein, the term "signaling domain" refers to a domain of the fusion protein or CISC component that is involved in a signaling cascade inside the cell, such as a mammalian cell. A signaling domain refers to a signaling moiety that provides to cells, such as T-cells, a signal which, in addition to the primary signal provided by for instance the CD3 zeta chain of the TCR/CD3 complex, mediates a cellular response, such as a T-cell response, including, but not limited to, activation, proliferation, differentiation, and/or cytokine secretion. In some embodiments, the signaling domain is N-terminal to the transmembrane domain, the hinge domain, and the extracellular domain. In some embodiments, the signaling domain is a synthetic or a natural domain. In some embodiments, the signaling domain is a concatenated cytoplasmic signaling domain. In some embodiments, the signaling domain is a cytokine signaling domain. In some embodiments, the signaling domain is an antigen signaling domain. In some embodiments, the signaling domain is an interleukin-2 receptor subunit gamma (IL2Rγ or IL2Rg) domain. In some embodiments, the signaling domain is an interleukin-2 receptor subunit beta (IL2Rβ or IL2Rb) domain or a truncated IL2Rβ domain (such as the truncated IL2Rβ domain including the amino acid sequence of SEQ ID NO: 5). In some embodiments, binding of an agent or ligand to the extracellular binding domain causes a signal transduction through the signaling domain by the activation of a signaling pathway, as a result of dimerization of the CISC components. As used herein, the term "signal transduction" refers to the activation of a signaling pathway by a ligand or an agent binding to the extracellular domain. Activation of a signal is a result of the binding of the extracellular domain to the ligand or agent, resulting in CISC dimerization.

As used herein, the term "IL2Rb" or "IL2Rβ" refers to an interleukin-2 receptor subunit beta. Similarly, the term "IL2Rg" or "IL2Rγ" refers to an interleukin-2 receptor subunit gamma, and the term "IL2Ra" or "IL2Rα" refers to an interleukin-2 receptor subunit alpha. The IL-2 receptor has three forms, or chains, alpha, beta, and gamma, which are also subunits for receptors for other cytokines. IL2Rβ and IL2Rγ are members of the type I cytokine receptor family. "IL2R" as used herein refers to interleukin-2 receptor, which is involved in T cell-mediated immune responses. IL2R is involved in receptor-mediated endocytosis and transduction of mitogenic signals from interleukin 2. Similarly, the term "IL-2/15R" refers to a receptor signaling subunit that is shared by IL-2 and IL-15, and may include a subunit alpha (IL2/15Ra or IL2/15Rα), beta (IL2/15Rb or IL2/15Rβ, or gamma (IL2/15Rg or IL2/15Rγ).

In some embodiments, a chemical-induced signaling complex is a heterodimerization activated signaling complex including two components. In some embodiments, the first component includes an extracellular binding domain that is one part of a heterodimerization pair, an optional hinge domain, a transmembrane domain, and one or more concatenated cytoplasmic signaling domains. In some embodiments, the second component includes an extracellular binding domain that is the other part of a heterodimerization pair, an optional hinge domain, a transmembrane domain, and one or more concatenated cytoplasmic signaling domains. Thus, in some embodiments, there are two distinct modification events. In some embodiments, the two CISC components are expressed in a cell, such as a mammalian cell. In some embodiments, the cell, such as a mammalian cell, or a population of cells, such as a population of mammalian cells, is contacted with a ligand or agent that causes heterodimerization, thereby initiating a signal. In some embodiments, a homodimerization pair dimerize, whereby a single CISC component is expressed in a cell, such as a mammalian cell, and the CISC components homodimerize to initiate a signal.

As used herein, the term "ligand" or "agent" refers to a molecule that has a desired biological effect. In some embodiments, a ligand is recognized by and bound by an extracellular binding domain, forming a tripartite complex including the ligand and two binding CISC components. Ligands include, but are not limited to, proteinaceous molecules, including, but not limited to, peptides, polypeptides, proteins, post-translationally modified proteins, antibodies, binding portions thereof; small molecules (less than 1000 Daltons), inorganic or organic compounds; and nucleic acid molecules including, but not limited to, double-stranded or single-stranded DNA, or double-stranded or single-stranded RNA (e.g., antisense, RNAi, etc.), aptamers, as well as, triple helix nucleic acid molecules. Ligands can be derived or obtained from any known organism (including, but not limited to, animals (e.g., mammals (human and non-human mammals)), plants, bacteria, fungi, and protista, or viruses) or from a library of synthetic molecules. In some embodiments, the ligand is a protein, an antibody or functional derivative thereof, a small molecule, or a drug. In some embodiments, the ligand is rapamycin or a rapamycin analog (rapalogs). In some embodiments, the rapalog includes variants of rapamycin having one or more of the following modifications relative to rapamycin: demethylation, elimination or replacement of the methoxy at C7, C42 and/or C29; elimination, derivatization or replacement of the hydroxy at C13, C43 and/or C28; reduction, elimination or derivatization of the ketone at C14, C24 and/or C30; replacement of the 6-membered pipecolate ring with a 5-membered prolyl ring; and alternative substitution on the cyclohexyl ring or replacement of the cyclohexyl ring with a substituted cyclopentyl ring. Thus, in some embodiments, the rapalog is everolimus, merilimus, novolimus, pimecrolimus, ridaforolimus, tacrolimus, temsirolimus, umirolimus, zotarolimus, CCI-779, C20-methallylrapamycin, C16-(S)-3-methylindolerapamycin, C16-iRap, AP21967, sodium mycophenolic acid, benidipine hydrochloride, AP23573, or AP1903, or metabolites, derivatives, and/or combinations of any thereof. In some embodiments, the ligand is an IMID-class drug (e.g. thalidomide, pomalidomide, lenalidomide or related analogues).

As used herein, the term "simultaneous binding" refers to the binding of the ligand by two or more CISC components at the same time or, in some cases, at substantially the same time, to form a multicomponent complex, including the CISC components and the ligand component, and resulting in subsequent signal activation. Simultaneous binding requires that the CISC components are configured spatially to bind a single ligand, and also that both CISC components are configured to bind to the same ligand, including to different moieties on the same ligand.

As used herein, the term "selective expansion" refers to an ability of a desired cell, such as a mammalian cell, or a desired population of cells, such as a population of mammalian cells, to expand. In some embodiments, selective expansion refers to the generation or expansion of a pure population of cells, such as mammalian cells, that have undergone two genetic modification events. One component of a dimerization CISC is part of one modification and the other component is the other modification. Thus, one component of the heterodimerizing CISC is associated with each genetic modification. Exposure of the cells to a ligand allows for selective expansion of only the cells, such as mammalian cells, having both desired modifications. Thus, in some embodiments, the only cells, such as mammalian cells, that will be able to respond to contact with a ligand are those that express both components of the heterodimerization CISC.

As used herein, "host cell" includes any cell type, such as a mammalian cell, that is susceptible to transformation, transfection, or transduction, with a nucleic acid construct or vector. In some embodiments, the host cell, such as a mammalian cell, is a T cell or a T regulatory cell ($T_{reg}$). T-cells" or "T lymphocytes" as used herein can be from any mammalian, e.g., primate, species, including monkeys, dogs, and humans. In some embodiments, the T-cells are allogeneic (from the same species but different donor) as the recipient subject; in some embodiments the T-cells are autologous (the donor and the recipient are the same); in some embodiments the T-cells are syngeneic (the donor and the recipients are different but are identical twins). In some embodiments, the host cell, such as a mammalian cell, is a hematopoietic stem cell. In some embodiments, the host cell is a CD34+, CD8+, or a CD4+ cell. In some embodiments, the host cell is a CD8+ T cytotoxic lymphocyte cell selected from the group consisting of naïve CD8+ T cells, central memory CD8+ T cells, effector memory CD8+ T cells, and bulk CD8+ T cells. In some embodiments, the host cell is a CD4+ T helper lymphocyte cell selected from the group consisting of naïve CD4+ T cells, central memory CD4+ T cells, effector memory CD4+ T cells, and bulk CD4+ T cells. As used herein, the term "population of cells" refers to a group of cells, such as mammalian cells, including more than one cell. In some embodiments, a cell, such as a mammalian cell, is manufactured, wherein the cell includes the protein sequence as described herein or an expression vector that encodes the protein sequence as described herein.

"Cytotoxic T lymphocyte" (CTL), as used herein, refers to a T lymphocyte that expresses CD8 on the surface thereof (e.g., a CD8+ T-cell). In some embodiments, such cells are, for example, "memory" T-cells (TM cells) that are antigen-experienced. In some embodiments, a cell for fusion protein secretion is provided. In some embodiments, the cell is a cytotoxic T lymphocyte. "Central memory" T-cell (or "TCM") as used herein, refers to an antigen experienced CTL that expresses CD62L, CCR-7 and/or CD45RO on the surface thereof, and does not express or has decreased expression of CD45RA, as compared to naïve cells. In some embodiments, a cell for fusion protein secretion is provided. In some embodiments, the cell is a central memory T-cell (TCM). In some embodiments, the central memory cells are positive for expression of CD62L, CCR7, CD28, CD127, CD45RO, and/or CD95, and may have decreased expression of CD54RA, as compared to naïve cells. "Effector memory" T-cell (or "TEM") as used herein refers to an antigen experienced T-cell that does not express or has decreased expression of CD62L on the surface thereof, as compared to central memory cells, and does not express or has a decreased expression of CD45RA, as compared to naïve cell. In some embodiments, a cell for fusion protein secretion is provided. In some embodiments, the cell is an effector memory T-cell. In some embodiments, effector memory cells are negative for expression of CD62L and/or CCR7, as compared to naïve cells or central memory cells, and may have variable expression of CD28 and/or CD45RA.

"Naïve T-cells" as used herein, refers to a non-antigen experienced T lymphocyte that expresses CD62L and/or CD45RA, and does not express CD45RO−, as compared to central or effector memory cells. In some embodiments, a cell, such as a mammalian cell, for fusion protein secretion is provided. In some embodiments, the cell, such as a mammalian cell, is a naïve T-cell. In some embodiments, naïve CD8+ T lymphocytes are characterized by the expression of phenotypic markers of naïve T-cells including CD62L, CCR7, CD28, CD127, and/or CD45RA.

"Effector" T-cells as used herein, refers to antigen experienced cytotoxic T lymphocyte cells that do not express or have decreased expression of CD62L, CCR7, and/or CD28, and are positive for granzyme B and/or perforin, as compared to central memory or naïve T-cells. In some embodiments, a cell, such as a mammalian cell, for fusion protein secretion is provided. In some embodiments, the cell, such as a mammalian cell, is an effector T-cell. In some embodiments, the cell, such as a mammalian cell, does not express or have decreased expression of CD62L, CCR7, and/or CD28, and are positive for granzyme B and/or perforin, as compared to central memory or naïve T-cells.

As used herein, the term "transformed" or "transfected" refers to a cell, such as a mammalian cell, tissue, organ, or organism into which a foreign polynucleotide molecule, such as a construct, has been introduced. The introduced polynucleotide molecule may be integrated into the genomic DNA of the recipient cell, such as a mammalian cell, tissue, organ, or organism such that the introduced polynucleotide molecule is inherited by subsequent progeny. A "transgenic" or "transfected" cell, such as a mammalian cell, or organism also includes progeny of the cell or organism and progeny produced from a breeding program employing such a transgenic organism as a parent in a cross and exhibiting an altered phenotype resulting from the presence of a foreign polynucleotide molecule. The term "transgenic" refers to a bacteria, fungi, or plant containing one or more heterologous nucleic acid molecules.

"Transduction," as used herein, refers to virus-mediated (for example a lentivirus or adeno-associated virus) gene transfer into cells, such as mammalian cells.

As used herein, a "subject" or an "individual" refers to an animal that is the object of treatment, observation or experiment. "Animal" includes cold- and warm-blooded vertebrates and invertebrates such as fish, shellfish, reptiles and, in particular, mammals. "Mammal" includes, without limitation, mice, rats, rabbits, guinea pigs, dogs, cats, sheep, goats, cows, horses, primates, such as monkeys, chimpanzees, and apes, and, in particular, humans. In some embodiments, the subject is human.

A "marker sequence," as described herein, encodes a protein that is used for selecting or tracking a protein or cell, such as a mammalian cell, that has a protein of interest. In the embodiments described herein, the fusion protein provided can include a marker sequence that can be selected in experiments, such as flow cytometry.

"Percent (%) amino acid sequence identity" with respect to the CISC sequences or other polypeptide sequences (for example, a naked FRB domain polypeptide sequence) identified herein is defined as the percentage of amino acid residues in a candidate sequence that are identical with the amino acid residues in the reference sequence for each of the extracellular binding domain, hinge domain, transmembrane domain, and/or the signaling domain, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over the full-length of the sequences being compared. For example, % amino acid sequence identity values generated using the WU-BLAST-2 computer program (Altschul, S. F. et al. (1996). *Methods in Enzymol.*, 266:460-480) uses several search parameters, most of which are set to the default values. Those that are not set to default values (e.g., the adjustable parameters) are set with the following values: overlap span=1, overlap fraction=0.125, word threshold (T)=11 and scoring matrix=BLOSUM62. In some embodiments of the CISC, the CISC includes an extracellular binding domain, a hinge domain, a transmembrane domain, and a signaling domain, wherein each domain includes a natural, synthetic, or a mutated or truncated form of the native domain. In some embodiments, a mutated or truncated form of any given domain includes an amino acid sequence with 100%, 95%, 90%, 85% sequence identity, or a percent sequence identity that is within a range defined by any two of the aforementioned percentages to a sequence set forth in a sequence provided herein.

"CISC variant polypeptide sequence" or "CISC variant amino acid sequence" as used herein refers to a protein sequence as defined below having at least 80%, 85%, 90%, 95%, 98% or 99% amino acid sequence identity (or a percentage amino acid sequence identity within a range defined by any two of the aforementioned percentages) with the protein sequences provided herein, or a specifically derived fragment thereof, such as protein sequence for an extracellular binding domain, a hinge domain, a transmembrane domain and/or a signaling domain. Ordinarily, a CISC variant polypeptide or fragment thereof will have at least or at least about 80% amino acid sequence identity, at least or at least about 81% amino acid sequence identity, at least or at least about 82% amino acid sequence identity, at least or at least about 83% amino acid sequence identity, at least or at least about 84% amino acid sequence identity, at least or at least about 85% amino acid sequence identity, at least or at least about 86% amino acid sequence identity, at least or at least about 87% amino acid sequence identity, at least or at least about 88% amino acid sequence identity, at least or at least about 89% amino acid sequence identity, at least or at least about 90% amino acid sequence identity, at least or at least about 91% amino acid sequence identity, at least or at least about 92% amino acid sequence identity, at least or at least about 93% amino acid sequence identity, at least or at least about 94% amino acid sequence identity, at least or at least about 95% amino acid sequence identity, at least or at least about 96% amino acid sequence identity, at least or at least about 97% amino acid sequence identity, at least or at least about 98% amino acid sequence identity, and at least or at least about 99% amino acid sequence identity with the amino acid sequence or a derived fragment thereof. Variants do not encompass the native protein sequence.

"Naked FRB domain variant polypeptide sequence" or "Naked FRB domain variant amino acid sequence" as used herein refers to a protein sequence as defined below having at least or at least about 80%, about 85%, about 90%, about 95%, about 98% or about 99% amino acid sequence identity (or a percentage amino acid sequence identity within a range defined by any two of the aforementioned percentages) with the protein sequences provided herein (for example, SEQ ID NO: 1 or SEQ ID NO: 2), or a specifically derived fragment thereof, such as protein sequence for an extracellular binding domain, a hinge domain, a transmembrane domain and/or a signaling domain. Ordinarily, a Naked FRB domain variant polypeptide or fragment thereof will have at least or at least about 80% amino acid sequence identity, at least or at least about 81% amino acid sequence identity, at least or at least about 82% amino acid sequence identity, at least or at least about 83% amino acid sequence identity, at least or at least about 84% amino acid sequence identity, at least or at least about 85% amino acid sequence identity, at least or at least about 86% amino acid sequence identity, at least or at least about 87% amino acid sequence identity, at least or at least about 88% amino acid sequence identity, at least or at least about 89% amino acid sequence identity, at least or at least about 90% amino acid sequence identity, at least or at least about 91% amino acid sequence identity, at least or at least about 92% amino acid sequence identity, at least or at least about 93% amino acid sequence identity, at least or at least about 94% amino acid sequence identity, at least or at least about 95% amino acid sequence identity, at least or at least about 96% amino acid sequence identity, at least or at least about 97% amino acid sequence identity, at least or at least about 98% amino acid sequence identity and yet at least or at least about 99% amino acid sequence identity with the amino acid sequence or a derived fragment thereof. Variants do not encompass the native protein sequence.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "comprising at least." When used in the context of a process, the term "comprising" means that the process includes at least the recited steps, but may include additional steps. When used in the context of a compound, composition or device, the term "comprising" means that the compound, composition or device includes at least the recited features or components, but may also include additional features or components.

CISC

The one or more protein sequence can have a first and a second sequence. In some embodiments, a first sequence encodes a first CISC component that can include a first extracellular binding domain or functional derivative thereof, a hinge domain, a transmembrane domain, and a signaling domain or functional derivative thereof. In some embodiments, a second sequence encodes a second CISC component that can include a second extracellular binding domain or a functional derivative thereof, a hinge domain, a transmembrane domain, and a signaling domain or portions thereof. In some embodiments, the first and second CISC components may be positioned such that when expressed, they dimerize in the presence of a ligand. In some embodiments, the first and second CISC components may be positioned such that when expressed, they dimerize in the presence of a ligand simultaneously.

In some embodiments, a protein sequence or sequences for heterodimeric two component CISC are provided. In some embodiments, the first CISC component is an IL2Rγ-CISC complex. In some embodiments, the IL2Rγ-CISC includes an amino acid sequence as set forth in SEQ ID NO:

9. Embodiments also include a nucleic acid sequence encoding the protein sequence of SEQ ID NO: 9. In some embodiments, the IL2Rγ-CISC includes an amino acid sequence as set forth in SEQ ID NO: 10. Embodiments also include a nucleic acid sequence encoding the protein sequence of SEQ ID NO: 10. In some embodiments, the IL2Rγ-CISC includes an amino acid sequence as set forth in SEQ ID NO: 11. Embodiments also include a nucleic acid sequence encoding the protein sequence of SEQ ID NO: 11. In some embodiments, the IL2Rγ-CISC includes an amino acid sequence as set forth in SEQ ID NO: 12. Embodiments also include a nucleic acid sequence encoding the protein sequence of SEQ ID NO: 12.

In some embodiments, the protein sequence for the first CISC component includes a protein sequence encoding an extracellular binding domain, a hinge domain, a transmembrane domain, or a signaling domain. Embodiments also include a nucleic acid sequence encoding the extracellular binding domain, the hinge domain, the transmembrane domain, or the signaling domain. In some embodiments, the protein sequence of the first CISC component, including the first extracellular binding domain, the hinge domain, the transmembrane domain, and/or the signaling domain includes an amino acid sequence that includes a 100%, 99%, 98%, 95%, 90%, 85%, or 80% sequence identity to the sequence set forth in SEQ ID NOs: 9, 10, 11, or 12, inclusive of all values and ranges falling within these percentages.

In some embodiments, the second CISC component is an IL2Rβ complex. In some embodiments, the IL2Rβ-CISC includes an amino acid sequence as set forth in SEQ ID NO: 13. Embodiments also include a nucleic acid sequence encoding the protein sequence of SEQ ID NO: 13. In some embodiments, the IL2Rβ-CISC includes an amino acid sequence as set forth in SEQ ID NO: 14. Embodiments also include a nucleic acid sequence encoding the protein sequence of SEQ ID NO: 14. In some embodiments, the IL2Rβ-CISC includes an amino acid sequence as set forth in SEQ ID NO: 15. Embodiments also include a nucleic acid sequence encoding the protein sequence of SEQ ID NO: 15. In some embodiments, the IL2Rβ-CISC includes an amino acid sequence as set forth in SEQ ID NO: 24. Embodiments also include a nucleic acid sequence encoding the protein sequence of SEQ ID NO: 24. In some embodiments, the second CISC component is an IL7Ra complex. In some embodiments, the IL7Rα-CISC includes an amino acid sequence as set forth in SEQ ID NO: 16, 17 or 26. Embodiments also include a nucleic acid sequence encoding the protein sequence of SEQ ID NO: 16, 17 or 26.

In other embodiments, IL2Rβ-CISC includes a truncated intracellular domain or a nucleic acid sequence encoding a truncated intracellular IL2Rβ domain. The truncated IL2Rβ domain retains the ability to activate downstream IL2 signaling upon heterodimerization with the IL2Rγ-CISC protein sequence. In some embodiments, the truncated IL2Rβ includes an amino acid sequence as set forth in SEQ ID NO: 5 (PAALGKDTIPWLGHLLVGLSGAFGFIILV-YLLINCRNTGPWLKKVLKCNTPDPSKFF SQLSSEHGGDVQKWLSSPFPSSSFSPGGLAPEISPLEV-LERDKVTQLLLQQDKVPEPA SLSLNTDAYLSLQELQ; SEQ ID NO: 5). In some embodiments, the truncated IL2Rβ domain of SEQ ID NO: 5 lacks any of 1, 2, 3, 4, 5, 6, 7, 8, 9, or 10 N-terminal amino acids. In other embodiments, the FRB-CISC having a truncated intracellular IL2Rβ domain includes an amino acid sequence as set forth in SEQ ID NO: 7

SEQ ID NO: 7
(MALPVTALLLPLALLLHAARPILWHEMWHEGLEEASRLYFGERNVKGM

FEVLEPLHAMMERGPQTLKETSFNQAYGRDLMEAQEWCRKYMKSGNVKD

LLQAWDLYYHVFRRISKPAALGKDTIPWLGHLLVGLSGAFGFIILVYLL

INCRNTGPWLKKVLKCNTPDPSKFFSQLSSEHGGDVQKWLSSP*WORFP

SSSFSPGGLAPEISPLEVLERDKVTQLLLQQDKVPEPASLSLNTDAYLS

LQELQ;).

In some embodiments, the protein sequence for the second CISC component includes a protein sequence encoding an extracellular binding domain, a hinge domain, a transmembrane domain, or a signaling domain. Embodiments also include a nucleic acid sequence encoding the extracellular binding domain, the hinge domain, the transmembrane domain, or the signaling domain of the second CISC component. In some embodiments, the protein sequence of the second CISC component, including the second extracellular binding domain, the hinge domain, the transmembrane domain, and/or the signaling domain (including in some embodiments a truncated IL2Rβ signaling domain) includes an amino acid sequence that includes a 100%, 99%, 98%, 95%, 90%, 85%, or 80% sequence identity to the sequence set forth in SEQ ID NOs: 5, 8, 13, 14, 15, 16, or 17, inclusive of all values and ranges falling within these percentages.

In some embodiments, the protein sequence may include a linker. In some embodiments, the linker includes 1, 2, 3, 4, 5, 6, 7, 8, 9 or 10 amino acids, such as glycines, or a number of amino acids, such as glycine, within a range defined by any two of the aforementioned numbers. In some embodiments, the glycine spacer includes at least 3 glycines. In some embodiments, the glycine spacer includes a sequence set forth in SEQ ID NO: 18 (GGGS; SEQ ID NO: 18), SEQ ID NO: 19 (GGGSGGG; SEQ ID NO: 19), SEQ ID NO: 20 (GGG; SEQ ID NO: 20), SEQ ID NO: 21 (GGS; SEQ ID NO: 21), SEQ ID NO: 22 (GGSP; SEQ ID NO: 22), or SEQ ID NO: 31 (PAAL; SEQ ID NO: 31). Embodiments also include a nucleic acid sequence encoding SEQ ID NOs: 18-22 and 31. In some embodiments, the transmembrane domain is located N-terminal to the signaling domain, the hinge domain is located N-terminal to the transmembrane domain, the linker is located N-terminal to the hinge domain, and the extracellular binding domain is located N-terminal to the linker.

In some embodiments, a protein sequence or sequences for homodimeric two component CISC are provided. In some embodiments, the first CISC component is an IL2Rγ-CISC complex. In some embodiments, the IL2Rγ-CISC includes an amino acid sequence as set forth in SEQ ID NO: 23. Embodiments also include a nucleic acid sequence encoding the protein sequence of SEQ ID NO: 23.

In some embodiments, the protein sequence for the first CISC component includes a protein sequence encoding an extracellular binding domain, a hinge domain, a transmembrane domain, or a signaling domain. Embodiments also include a nucleic acid sequence encoding the extracellular binding domain, the hinge domain, the transmembrane domain, or the signaling domain. In some embodiments, the protein sequence of the first CISC component, including the first extracellular binding domain, the hinge domain, the transmembrane domain, and/or the signaling domain includes an amino acid sequence that includes a 100%, 99%, 98%, 95%, 90%, 85%, or 80% sequence identity to the sequence set forth in SEQ ID NO: 23 inclusive of all values and ranges falling within these percentages.

In some embodiments, the second CISC component is an IL2Rβ complex or an IL2Rα complex. In some embodiments, the IL2Rβ-CISC includes an amino acid sequence as set forth in SEQ ID NO: 24. Embodiments also include a nucleic acid sequence encoding the protein sequence of SEQ ID NO: 24.

In some embodiments, the IL2Rα-CISC includes an amino acid sequence as set forth in SEQ ID NO: 25. Embodiments also include a nucleic acid sequence encoding the protein sequence of SEQ ID NO: 25.

In some embodiments, the protein sequence for the second CISC component includes a protein sequence encoding an extracellular binding domain, a hinge domain, a transmembrane domain, or a signaling domain. Embodiments also include a nucleic acid sequence encoding the extracellular binding domain, the hinge domain, the transmembrane domain, or the signaling domain of the second CISC component. In some embodiments, the protein sequence of the second CISC component, including the second extracellular binding domain, the hinge domain, the transmembrane domain, and/or the signaling domain includes an amino acid sequence that includes a 100%, 99%, 98%, 95%, 90%, 85%, or 80% sequence identity to the sequence set forth in SEQ ID NO: 24 or SEQ ID NO: 25, inclusive of all values and ranges falling within these percentages.

In some embodiments, the protein sequence may include a linker. In some embodiments, the linker includes 1, 2, 3, 4, 5, 6, 7, 8, 9 or 10 amino acids, such as glycines, or a number of amino acids, such as glycine, within a range defined by any two of the aforementioned numbers. In some embodiments, the glycine spacer includes at least 3 glycines. In some embodiments, the glycine spacer includes a sequence set forth in SEQ ID NO: 18 (GGGS; SEQ ID NO: 18), SEQ ID NO: 19 (GGGSGGG; SEQ ID NO: 19), SEQ ID NO: 20 (GGG; SEQ ID NO: 20), SEQ ID NO: 21 (GGS; SEQ ID NO: 21), SEQ ID NO: 22 (GGSP; SEQ ID NO: 22), or SEQ ID NO: 31 (PAAL; SEQ ID NO: 31). Embodiments also include a nucleic acid sequence encoding SEQ ID NOs: 18-22 and 31. In some embodiments, the transmembrane domain is located N-terminal to the signaling domain, the hinge domain is located N-terminal to the transmembrane domain, the linker is located N-terminal to the hinge domain, and the extracellular binding domain is located N-terminal to the linker.

In some embodiments, the sequences for the homodimerizing two component CISC incorporate FKBP F36V domain for homodimerization with the ligand AP1903.

In some embodiments is provided a protein sequence or sequences for single component homodimerization CISC. In some embodiments, the single component CISC is an IL7Rα-CISC complex. In some embodiments, the IL7Rα-CISC includes an amino acid sequence as set forth in SEQ ID NO: 26. Embodiments also include a nucleic acid sequence encoding the protein sequence of SEQ ID NO: 26.

In some embodiments, the single component CISC is an MPL-CISC complex. In some embodiments, the MPL-CISC includes an amino acid sequence as set forth in SEQ ID NO: 27. Embodiments also include a nucleic acid sequence encoding the protein sequence of SEQ ID NO: 27.

In some embodiments, the protein sequence for the single component CISC includes a protein sequence encoding an extracellular binding domain, a hinge domain, a transmembrane domain, or a signaling domain. Embodiments also include a nucleic acid sequence encoding the extracellular binding domain, the hinge domain, the transmembrane domain, or the signaling domain. In some embodiments, the protein sequence of the first CISC component, including the first extracellular binding domain, the hinge domain, the transmembrane domain, and/or the signaling domain includes an amino acid sequence that includes a 100%, 99%, 98%, 95%, 90%, 85%, or 80% sequence identity to the sequence set forth in SEQ ID NO: 26 or SEQ ID NO: 27 or has a sequence identity that is within a range defined by any two of the aforementioned percentages.

In some embodiments, the sequences for the homodimerizing single component CISC incorporate FKBP F36V domain for homodimerization with the ligand AP1903.

Vectors

A variety of vector combinations can be constructed to provide for efficient transduction and transgene expression. In some embodiments, the vector is a viral vector. In other embodiments, the vectors can include a combination of viral vectors and plasmid vectors. Other viral vectors include foamy virus, adenoviral vectors, adeno-associated viral (AAV) vectors, retroviral vectors, and/or lentiviral vectors. In some embodiments, the vector is a lentiviral vector. In some embodiments, the vector is a foamy viral vector, adenoviral vectors, retroviral vectors or lentiviral vectors. In some embodiments, the vector is for protein expression in a bacterial system, such as *E. coli*. In other embodiments, a first vector can encode a first CISC component including a first extracellular binding domain or functional derivative thereof, a hinge domain, a transmembrane domain, and a signaling domain or functional derivative thereof while a second vector can encode a second CISC component including a second extracellular binding domain or a functional derivative thereof, a hinge domain, a transmembrane domain, and a signaling domain or portions thereof.

A vector can have one or more promoters for driving expression of DNA sequence in the vector (for example, a DNA sequence encoding a naked FRB domain or a component of a CISC). A "promoter" is a region of DNA that initiates transcription of a specific gene. The promoters can be located near the transcription start site of a gene, on the same strand and upstream on the DNA (the 5' region of the sense strand). The promoter can be a conditional, inducible or a constitutive promoter. The promoter can be specific for bacterial, mammalian or insect cell protein expression. In some embodiments, wherein a nucleic acid encoding a fusion protein is provided, the nucleic acid further includes a promoter sequence. In some embodiments, the promoter is specific for bacterial, mammalian or insect cell protein expression. In some embodiments, the promoter is a conditional, inducible or a constitutive promoter. In some embodiments, the promoter is an MND promoter (a synthetic promoter that contains the U3 region of a modified MoMuLV LTR with myeloproliferative sarcoma virus enhancer). In some embodiments, the MND promoter includes the nucleic acid sequence of SEQ ID NO: 33.

"Conditional" or "inducible" as used herein refers to a nucleic acid construct that includes a promoter that provides for gene expression in the presence of an inducer and does not substantially provide for gene expression in the absence of the inducer.

"Constitutive" as used herein refer to the nucleic acid construct that includes a promoter that is constitutive, and thus provides for expression of a polypeptide that is continuously produced.

In some embodiments, the inducible promoter has a low level of basal activity. In some embodiments, wherein a lentiviral vector is used, the level of basal activity in uninduced cells is 20%, 15%, 10%, 5%, 4%, 3%, 2%, 1% or less (but not zero) or within a range defined by any two of the aforementioned values, as compared to when cells are induced to express the gene. The level of basal activity can be determined by measuring the amount of the expression of the transgene (e.g. marker gene) in the absence of the inducer (e.g. drug) using flow cytometry. In some embodiments described herein a marker protein (such as mCherry) is used for determination of expression.

In some embodiments, the inducible promoter provides for a high level of induced activity, as compared to uninduced or basal activity. In some embodiments, the level of activity in the induced state is 2, 4, 6, 8, 9 or 10 fold or greater than the activity level in the uninduced state or within a range defined by any two of the aforementioned values. In some embodiments, transgene expression under control of the inducible promoter is turned off in the absence of a transactivator in less than 10, 8, 6, 4, 2, or 1 days excluding 0 days or within a range defined by any two of the aforementioned time periods.

In some embodiments, an inducible promoter is designed and/or modified to provide for a low level of basal activity, a high level of inducibility, and/or a short time for reversibility.

In some embodiments, the expression vector includes a nucleic acid encoding the protein sequence of one or more of SEQ ID NOs: 1, 2, 5, 7, 9, 10, 11, 12, 13, 14, 15, 16 or 17. In some embodiments, the expression vector includes a nucleic acid sequence as set forth in SEQ ID NO: 28. SEQ ID NO: 28 encodes the protein sequences as set forth in SEQ ID NOs: 12 and 16.

In some embodiments, the expression vector is a variant of SEQ ID NO: 28 as set forth in SEQ ID NO: 29. SEQ ID NO: 29 encodes the protein sequences as set forth in SEQ ID NOs: 10 and 14.

In some embodiments, the expression vector is a variant of SEQ ID NO: 28 as set forth in SEQ ID NO: 30. SEQ ID NO: 30 encodes the protein sequences as set forth in SEQ ID NOs: 11 and 15.

In some embodiments, the expression vector includes a nucleic acid having at least 80%, 85%, 90%, 95%, 98% or 99% nucleic acid sequence identity (or a percentage nucleic acid sequence identity within a range defined by any two of the aforementioned percentages) with the nucleotide sequences provided herein, or a specifically derived fragment thereof. In some embodiments, the expression vector includes a promoter. In some embodiments, the expression vector includes the nucleic acid encoding a fusion protein. In some embodiments, the vector is RNA or DNA.

Naked FRB Domain

Provided herein are naked FKBP-rapamycin binding (FRB) domain polypeptides for intracellular expression. In some non-limiting embodiments, the naked FRB domain polypeptides are co-expressed with one or more protein sequences of a first and second CISC component, described more thoroughly herein. The naked FRB domain polypeptides can include an amino acid sequence that shares a 100%, 99%, 98%, 95%, 90%, 85%, or 80% sequence identity to the sequence set forth in SEQ ID NOs: 1 or 2, inclusive of all values and ranges falling within these percentages.

Systems for Genome Editing

Provided herein are systems for genome editing in a cell to express a naked FRB domain polypeptide as described herein, and optionally to further express a CISC as described herein, such as by targeted integration of a nucleic acid encoding the naked FRB domain polypeptide and optionally further encoding the CISC into the genome of the cell. The disclosures also provide, inter alia, systems for use in selectively activating and/or expanding a population of genetically modified cells, such as for preparing a population of cells selectively enriched for the genetically modified cells.

In some embodiments, provided herein is a system including i) a deoxyribonucleic acid (DNA) endonuclease or nucleic acid encoding the DNA endonuclease; ii) a guide RNA (gRNA) including a spacer sequence complementary to a target sequence within a target genomic locus in a cell, or nucleic acid encoding the gRNA; and iii) a donor template including a donor cassette including a nucleic acid sequence encoding a naked FKBP-rapamycin binding (FRB) domain polypeptide, wherein the DNA endonuclease, gRNA, and donor template are configured such that a complex formed by association of the DNA endonuclease with the gRNA is capable of promoting targeted integration of the donor cassette into the target genomic locus in a cell to generate a genetically modified cell capable of expressing the naked FRB domain polypeptide.

In some embodiments, according to any of the systems described herein, the gRNA includes a spacer sequence that is complementary to a sequence within a FOXP3 locus, AAVS1 locus, or a TCRa (TRAC) locus in the cell. In some embodiments, the gRNA includes a spacer sequence from any one of SEQ ID NOs: 40-57, or a variant thereof having no more than 3 mismatches compared to any one of SEQ ID NOs: 40-57.

"Cas endonuclease" or "Cas nuclease" as used herein includes but is not limited to, for example, an RNA-guided DNA endonuclease enzyme associated with the CRISPR (Clustered Regularly Interspaced Short Palindromic Repeats) adaptive immunity system. Herein, "Cas endonuclease" refers to both naturally-occurring and recombinant Cas endonucleases. In some embodiments, according to any of the systems described herein, the Cas DNA endonuclease is a Cas9 endonuclease. In some embodiments, the Cas9 endonuclease is from *Streptococcus pyogenes* (spCas9). In some embodiments, the Cas9 is from *Staphylococcus lugdunensis* (SluCas9).

In some embodiments, according to any of the systems described herein, the system includes a nucleic acid encoding the DNA endonuclease. In some embodiments, the nucleic acid encoding the DNA endonuclease is codon-optimized for expression in a host cell. In some embodiments, the nucleic acid encoding the DNA endonuclease is codon-optimized for expression in a human cell. In some embodiments, the nucleic acid encoding the DNA endonuclease is DNA, such as a DNA plasmid. In some embodiments, the nucleic acid encoding the DNA endonuclease is RNA, such as mRNA.

In some embodiments, according to any of the systems described herein, the donor template is configured such that the donor cassette is capable of being integrated into a genomic locus targeted by a gRNA in the system by homology directed repair (HDR). In some embodiments, the donor cassette is flanked on both sides by homology arms corresponding to sequences in the targeted genomic locus. In some embodiments, the homology arms are at least at or about 0.2 kb (such as at least at or about any of 0.3 kb, 0.4 kb, 0.5 kb, 0.6 kb, 0.7 kb, 0.8 kb, 0.9 kb, 1 kb, or greater) in length. In some embodiments, the homology arms are at least at or about 0.4 kb, e.g., 0.45 kb, 0.6 kb, or 0.8 kb, in length. Exemplary homology arms further include homology arms from a donor template having the sequence of SEQ ID NO: 32. Exemplary donor templates include donor templates having the sequence of SEQ ID NOs: 3-4, 8, 28-30, 32, and 37-39. In some embodiments, the donor template is encoded in an Adeno Associated Virus (AAV) vector. In some embodiments, the AAV vector is an AAV2, AAV5, or AAV6 vector. In some embodiments, the AAV vector is an AAV6 vector.

In some embodiments, according to any of the systems described herein, the donor template is configured such that the donor cassette is capable of being integrated into a genomic locus targeted by a gRNA in the system by non-homologous end joining (NHEJ). In some embodiments, the donor cassette is flanked on one or both sides by a gRNA target site. In some embodiments, the donor cassette is flanked on both sides by a gRNA target site. In some embodiments, the gRNA target site is a target site for a gRNA in the system. In some embodiments, the gRNA target site of the donor template is the reverse complement of a cell genome gRNA target site for a gRNA in the system. In some embodiments, the donor template is encoded in an Adeno Associated Virus (AAV) vector. In some embodiments, the AAV vector is an AAV2, AAV5, or AAV6 vector. In some embodiments, the AAV vector is an AAV6 vector.

In some embodiments, according to any of the systems described herein, the DNA endonuclease or nucleic acid encoding the DNA endonuclease is formulated in a liposome or lipid nanoparticle. In some embodiments, the liposome or lipid nanoparticle also includes the gRNA. In some embodiments, the liposome or lipid nanoparticle is a lipid nanoparticle. In some embodiments, the system includes a lipid nanoparticle including nucleic acid encoding the DNA endonuclease and the gRNA. In some embodiments, the nucleic acid encoding the DNA endonuclease is an mRNA encoding the DNA endonuclease.

In some embodiments, according to any of the systems described herein, the DNA endonuclease is associated with the gRNA in a ribonucleoprotein (RNP) complex.

Genome Editing

Provided herein are methods for genetically modifying a host cell or organism to express any of the naked FRB domain polypeptides disclosed herein and optionally the chemically induced signaling complex polypeptides disclosed herein via gene editing. In some aspects, gene editing is performed using a CRISPR/Cas system.

CRISPR Endonuclease System

A CRISPR (Clustered Regularly Interspaced Short Palindromic Repeats) genomic locus can be found in the genomes of many prokaryotes (e.g., bacteria and archaea). In prokaryotes, the CRISPR locus encodes products that function as a type of immune system to help defend the prokaryotes against foreign invaders, such as virus and phage. There are three stages of CRISPR locus function: integration of new sequences into the CRISPR locus, expression of CRISPR RNA (crRNA), and silencing of foreign invader nucleic acid. Five types of CRISPR systems (e.g., Type I, Type II, Type III, Type U, and Type V) have been identified.

A CRISPR locus includes a number of short repeating sequences referred to as "repeats." When expressed, the repeats can form secondary hairpin structures (e.g., hairpins) and/or have unstructured single-stranded sequences. The repeats usually occur in clusters and frequently diverge between species. The repeats are regularly interspaced with unique intervening sequences referred to as "spacers," resulting in a repeat-spacer-repeat locus architecture. The spacers are identical to or have high homology with known foreign invader sequences. A spacer-repeat unit encodes a crisprRNA (crRNA), which is processed into a mature form of the spacer-repeat unit. A crRNA has a "seed" or spacer sequence that is involved in targeting a target nucleic acid (in the naturally occurring form in prokaryotes, the spacer sequence targets the foreign invader nucleic acid). A spacer sequence is located at the 5' or 3' end of the crRNA.

A CRISPR locus also has polynucleotide sequences encoding CRISPR-Associated (Cas) genes. Cas genes encode endonucleases involved in the biogenesis and the interference stages of crRNA function in prokaryotes. Some Cas genes have homologous secondary and/or tertiary structures.

A genome-targeting nucleic acid interacts with a site-directed polypeptide (e.g., a nucleic acid-guided nuclease such as Cas9), thereby forming a complex. The genome-targeting nucleic acid (e.g. gRNA) guides the site-directed polypeptide to a target nucleic acid.

As stated previously, in some embodiments the site-directed polypeptide and genome-targeting nucleic acid can each be administered separately to a cell or a subject. On the other hand, in some other embodiments the site-directed polypeptide can be pre-complexed with one or more guide RNAs, or one or more crRNA together with a tracrRNA. The pre-complexed material can then be administered to a cell or a subject. Such pre-complexed material is known as a ribonucleoprotein particle (RNP).

Type II CRISPR Systems crRNA biogenesis in a Type II CRISPR system in nature requires a trans-activating CRISPR RNA (tracrRNA). The tracrRNA is modified by endogenous RNase III, and then hybridizes to a crRNA repeat in the pre-crRNA array. Endogenous RNase III is recruited to cleave the pre-crRNA. Cleaved crRNAs are subjected to exoribonuclease trimming to produce the mature crRNA form (e.g., 5' trimming). The tracrRNA remains hybridized to the crRNA, and the tracrRNA and the crRNA associate with a site-directed polypeptide (e.g., Cas9). The crRNA of the crRNA-tracrRNA-Cas9 complex guides the complex to a target nucleic acid to which the crRNA can hybridize. Hybridization of the crRNA to the target nucleic acid activates Cas9 for targeted nucleic acid cleavage. The target nucleic acid in a Type II CRISPR system is referred to as a protospacer adjacent motif (PAM). In nature, the PAM is essential to facilitate binding of a site-directed polypeptide (e.g., Cas9) to the target nucleic acid. Type II systems (also referred to as Nmeni or CASS4) are further subdivided into Type II-A (CASS4) and II-B (CASS4a). Jinek, M. et al. (2012). *Science,* 337(6096):816-821 showed that the CRISPR/Cas9 system is useful for RNA-programmable genome editing, and international patent application publication number WO 2013/176772 provides numerous examples and applications of the CRISPR/Cas endonuclease system for site-specific gene editing.

Type V CRISPR Systems

Type V CRISPR systems have several important differences from Type II systems. For example, Cpf1 is a single RNA-guided endonuclease that, in contrast to Type II systems, lacks tracrRNA. In fact, Cpf1-associated CRISPR arrays are processed into mature crRNAS without the requirement of an additional trans-activating tracrRNA. The Type V CRISPR array is processed into short mature crRNAs of 42-44 nucleotides in length, with each mature crRNA beginning with 19 nucleotides of direct repeat followed by 23-25 nucleotides of spacer sequence. In contrast, mature crRNAs in Type II systems start with 20-24 nucleotides of spacer sequence followed by at or about 22 nucleotides of direct repeat. Also, Cpf1 utilizes a T-rich protospacer-adjacent motif such that Cpf1-crRNA complexes efficiently cleave target DNA preceded by a short T-rich PAM, which is in contrast to the G-rich PAM following the target DNA for Type II systems. Thus, Type V systems cleave at a point that is distant from the PAM, while Type II systems cleave at a point that is adjacent to the PAM. In addition, in contrast to Type II systems, Cpf1 cleaves DNA via a staggered DNA double-stranded break with a 4 or 5 nucleotide 5' overhang. Type II systems cleave via a blunt double-stranded break. Similar to Type II systems, Cpf1 contains a predicted RuvC-like endonuclease domain, but lacks a second HNH endonuclease domain, which is in contrast to Type II systems.

Site-Directed Polypeptide or DNA Endonuclease

The modifications of the target DNA due to NHEJ and/or HDR can lead to, for example, mutations, deletions, alterations, integrations, gene correction, gene replacement, gene tagging, transgene insertion, nucleotide deletion, gene disruption, translocations and/or gene mutation. The process of integrating non-native nucleic acid into genomic DNA is an example of genome editing.

A site-directed polypeptide is a nuclease used in genome editing to cleave DNA. The site-directed polypeptide can be administered to a cell or a subject as either: one or more polypeptides, or one or more mRNAs encoding the polypeptide.

In the context of a CRISPR/Cas or CRISPR/Cpf1 system, the site-directed polypeptide can bind to a guide RNA that, in turn, specifies the site in the target DNA to which the polypeptide is directed. In embodiments of CRISPR/Cas or CRISPR/Cpf1 systems herein, the site-directed polypeptide is an endonuclease, such as a DNA endonuclease. "Cas endonuclease" or "Cas nuclease" as used herein includes but is not limited to, for example, an RNA-guided DNA endonuclease enzyme associated with the CRISPR (Clustered Regularly Interspaced Short Palindromic Repeats) adaptive immunity system. Herein, "Cas endonuclease" refers to both naturally-occurring and recombinant Cas endonucleases.

In some embodiments, a site-directed polypeptide has a plurality of nucleic acid-cleaving (e.g., nuclease) domains. Two or more nucleic acid-cleaving domains can be linked together via a linker. In some embodiments, the linker has a flexible linker. Linkers can have 1, 2, 3, 4, 5, 6, 7, 8, 9, 10, 11, 12, 13, 14, 15, 16, 17, 18, 19, 20, 21, 22, 23, 24, 25, 30, 35, 40 or more amino acids in length.

Naturally-occurring wild-type Cas9 enzymes have two nuclease domains, a HNH nuclease domain and a RuvC domain. Herein, the "Cas9" refers to both naturally-occurring and recombinant Cas9s. Cas9 enzymes contemplated herein have a HNH or HNH-like nuclease domain, and/or a RuvC or RuvC-like nuclease domain.

HNH or HNH-like domains have a McrA-like fold. HNH or HNH-like domains has two antiparallel β-strands and an α-helix. HNH or HNH-like domains has a metal binding site (e.g., a divalent cation binding site). HNH or HNH-like domains can cleave one strand of a target nucleic acid (e.g., the complementary strand of the crRNA targeted strand).

RuvC or RuvC-like domains have an RNaseH or RNaseH-like fold. RuvC/RNaseH domains are involved in a diverse set of nucleic acid-based functions including acting on both RNA and DNA. The RNaseH domain has 5 β-strands surrounded by a plurality of α-helices. RuvC/RNaseH or RuvC/RNaseH-like domains have a metal binding site (e.g., a divalent cation binding site). RuvC/RNaseH or RuvC/RNaseH-like domains can cleave one strand of a target nucleic acid (e.g., the non-complementary strand of a double-stranded target DNA).

In some embodiments, the site-directed polypeptide has an amino acid sequence having at least 10%, at least 15%, at least 20%, at least 30%, at least 40%, at least 50%, at least 60%, at least 70%, at least 75%, at least 80%, at least 85%, at least 90%, at least 95%, at least 99%, or 100% amino acid sequence identity to a wild-type exemplary site-directed polypeptide (e.g., Cas9 from S. pyogenes, US 2014/0068797 Sequence ID No. 8 or Sapranauskas, R. et al. (2011). Nucl. Acids Res., 39(21):9275-9282, and various other site-directed polypeptides).

In some embodiments, the site-directed polypeptide has an amino acid sequence having at least 10%, at least 15%, at least 20%, at least 30%, at least 40%, at least 50%, at least 60%, at least 70%, at least 75%, at least 80%, at least 85%, at least 90%, at least 95%, at least 99%, or 100% amino acid sequence identity to the nuclease domain of a wild-type exemplary site-directed polypeptide (e.g., Cas9 from S. pyogenes, supra).

In some embodiments, a site-directed polypeptide has at least 70, 75, 80, 85, 90, 95, 97, 99, or 100% identity to a wild-type site-directed polypeptide (e.g., Cas9 from S. pyogenes, supra) over 10 contiguous amino acids. In some embodiments, a site-directed polypeptide has at most: 70, 75, 80, 85, 90, 95, 97, 99, or 100% identity to a wild-type site-directed polypeptide (e.g., Cas9 from S. pyogenes, supra) over 10 contiguous amino acids. In some embodiments, a site-directed polypeptide has at least: 70, 75, 80, 85, 90, 95, 97, 99, or 100% identity to a wild-type site-directed polypeptide (e.g., Cas9 from S. pyogenes, supra) over 10 contiguous amino acids in a HNH nuclease domain of the site-directed polypeptide. In some embodiments, a site-directed polypeptide has at most: 70, 75, 80, 85, 90, 95, 97, 99, or 100% identity to a wild-type site-directed polypeptide (e.g., Cas9 from S. pyogenes, supra) over 10 contiguous amino acids in a HNH nuclease domain of the site-directed polypeptide. In some embodiments, a site-directed polypeptide has at least: 70, 75, 80, 85, 90, 95, 97, 99, or 100% identity to a wild-type site-directed polypeptide (e.g., Cas9 from S. pyogenes, supra) over 10 contiguous amino acids in a RuvC nuclease domain of the site-directed polypeptide. In some embodiments, a site-directed polypeptide has at most: 70, 75, 80, 85, 90, 95, 97, 99, or 100% identity to a wild-type site-directed polypeptide (e.g., Cas9 from S. pyogenes, supra) over 10 contiguous amino acids in a RuvC nuclease domain of the site-directed polypeptide.

In some embodiments, the site-directed polypeptide has a modified form of a wild-type exemplary site-directed polypeptide. The modified form of the wild-type exemplary site-directed polypeptide has a mutation that reduces the nucleic acid-cleaving activity of the site-directed polypeptide. In some embodiments, the modified form of the wild-type exemplary site-directed polypeptide has less than 90%, less than 80%, less than 70%, less than 60%, less than 50%, less than 40%, less than 30%, less than 20%, less than 10%, less than 5%, or less than 1% of the nucleic acid-cleaving activity of the wild-type exemplary site-directed polypeptide (e.g., Cas9 from S. pyogenes, supra). The modified form of the site-directed polypeptide can have no substantial nucleic acid-cleaving activity. When a site-directed polypeptide is a modified form that has no substantial nucleic acid-cleaving activity, it is referred to herein as "enzymatically inactive."

In some embodiments, the modified form of the site-directed polypeptide has a mutation such that it can induce a single-strand break (SSB) on a target nucleic acid (e.g., by cutting only one of the sugar-phosphate backbones of a double-strand target nucleic acid). In some embodiments, the mutation results in less than 90%, less than 80%, less than 70%, less than 60%, less than 50%, less than 40%, less than 30%, less than 20%, less than 10%, less than 5%, or less than 1% of the nucleic acid-cleaving activity in one or more of the plurality of nucleic acid-cleaving domains of the wild-type site directed polypeptide (e.g., Cas9 from *S. pyogenes*, supra). In some embodiments, the mutation results in one or more of the plurality of nucleic acid-cleaving domains retaining the ability to cleave the complementary strand of the target nucleic acid, but reducing its ability to cleave the non-complementary strand of the target nucleic acid. In some embodiments, the mutation results in one or more of the plurality of nucleic acid-cleaving domains retaining the ability to cleave the non-complementary strand of the target nucleic acid, but reducing its ability to cleave the complementary strand of the target nucleic acid. For example, residues in the wild-type exemplary *S. pyogenes* Cas9 polypeptide, such as Asp10, His840, Asn854 and Asn856, are mutated to inactivate one or more of the plurality of nucleic acid-cleaving domains (e.g., nuclease domains). In some embodiments, the residues to be mutated correspond to residues Asp10, His840, Asn854 and Asn856 in the wild-type exemplary *S. pyogenes* Cas9 polypeptide (e.g., as determined by sequence and/or structural alignment). Non-limiting examples of mutations include D10A, H840A, N854A or N856A. One skilled in the art will recognize that mutations other than alanine substitutions are suitable.

In some embodiments, a D10A mutation is combined with one or more of H840A, N854A, or N856A mutations to produce a site-directed polypeptide substantially lacking DNA cleavage activity. In some embodiments, a H840A mutation is combined with one or more of D10A, N854A, or N856A mutations to produce a site-directed polypeptide substantially lacking DNA cleavage activity. In some embodiments, a N854A mutation is combined with one or more of H840A, D10A, or N856A mutations to produce a site-directed polypeptide substantially lacking DNA cleavage activity. In some embodiments, a N856A mutation is combined with one or more of H840A, N854A, or D10A mutations to produce a site-directed polypeptide substantially lacking DNA cleavage activity. Site-directed polypeptides that have one substantially inactive nuclease domain are referred to as "nickases".

In some embodiments, variants of RNA-guided endonucleases, for example Cas9, can be used to increase the specificity of CRISPR-mediated genome editing. For example, wild type Cas9 is generally guided by a single guide RNA designed to hybridize with a specified ~20 nucleotide sequence in the target sequence (such as an endogenous genomic locus). However, several mismatches can be tolerated between the guide RNA and the target locus, effectively reducing the length of required homology in the target site to, for example, as little as 13 nt of homology, and thereby resulting in elevated potential for binding and double-strand nucleic acid cleavage by the CRISPR/Cas9 complex elsewhere in the target genome—also known as off-target cleavage. Because nickase variants of Cas9 each only cut one strand, in order to create a double-strand break it is necessary for a pair of nickases to bind in close proximity and on opposite strands of the target nucleic acid, thereby creating a pair of nicks, which is the equivalent of a double-strand break. This requires that two separate guide RNAs—one for each nickase—must bind in close proximity and on opposite strands of the target nucleic acid. This requirement essentially doubles the minimum length of homology needed for the double-strand break to occur, thereby reducing the likelihood that a double-strand cleavage event will occur elsewhere in the genome, where the two guide RNA sites—if they exist—are unlikely to be sufficiently close to each other to enable formation of the double-strand break. As described in the art, nickases can also be used to promote HDR versus NHEJ. HDR can be used to introduce selected changes into target sites in the genome through the use of specific donor sequences that effectively mediate the desired changes. Descriptions of various CRISPR/Cas systems for use in gene editing can be found, e.g., in international patent application publication number WO 2013/176772, and in Sander J. D. et al. (2014). *Nat. Biotechnol.*, 32(4):347-355, and references cited therein.

In some embodiments, the site-directed polypeptide (e.g., variant, mutated, enzymatically inactive and/or conditionally enzymatically inactive site-directed polypeptide) targets nucleic acid. In some embodiments, the site-directed polypeptide (e.g., variant, mutated, enzymatically inactive and/or conditionally enzymatically inactive endoribonuclease) targets DNA. In some embodiments, the site-directed polypeptide (e.g., variant, mutated, enzymatically inactive and/or conditionally enzymatically inactive endoribonuclease) targets RNA.

In some embodiments, the site-directed polypeptide has one or more non-native sequences (e.g., the site-directed polypeptide is a fusion protein).

In some embodiments, the site-directed polypeptide has an amino acid sequence having at least 15% amino acid identity to a Cas9 from a bacterium (e.g., *S. pyogenes*), a nucleic acid binding domain, and two nucleic acid cleaving domains (such as a HNH domain and a RuvC domain).

In some embodiments, the site-directed polypeptide has an amino acid sequence having at least 15% amino acid identity to a Cas9 from a bacterium (e.g., *S. pyogenes*), and two nucleic acid cleaving domains (such as a HNH domain and a RuvC domain).

In some embodiments, the site-directed polypeptide has an amino acid sequence having at least 15% amino acid identity to a Cas9 from a bacterium (e.g., *S. pyogenes*), and two nucleic acid cleaving domains, wherein one or both of the nucleic acid cleaving domains have at least 50% amino acid identity to a nuclease domain from Cas9 from a bacterium (e.g., *S. pyogenes*).

In some embodiments, the site-directed polypeptide has an amino acid sequence having at least 15% amino acid identity to a Cas9 from a bacterium (e.g., *S. pyogenes*), two nucleic acid cleaving domains (such as a HNH domain and a RuvC domain), and non-native sequence (for example, a nuclear localization signal) or a linker linking the site-directed polypeptide to a non-native sequence.

In some embodiments, the site-directed polypeptide has an amino acid sequence having at least 15% amino acid identity to a Cas9 from a bacterium (e.g., *S. pyogenes*), two nucleic acid cleaving domains (such as a HNH domain and a RuvC domain), wherein the site-directed polypeptide has a mutation in one or both of the nucleic acid cleaving domains that reduces the cleaving activity of the nuclease domains by at least 50%.

In some embodiments, the site-directed polypeptide has an amino acid sequence having at least 15% amino acid identity to a Cas9 from a bacterium (e.g., *S. pyogenes*), and two nucleic acid cleaving domains (such as a HNH domain and a RuvC domain), wherein one of the nuclease domains has mutation of aspartic acid 10, and/or wherein one of the nuclease domains has mutation of histidine 840, and wherein the mutation reduces the cleaving activity of the nuclease domain(s) by at least 50%.

In some embodiments, the one or more site-directed polypeptides, e.g. DNA endonucleases, include two nickases that together effect one double-strand break at a specific locus in the genome, or four nickases that together effect two double-strand breaks at specific loci in the genome. Alternatively, one site-directed polypeptide, e.g. DNA endonuclease, affects one double-strand break at a specific locus in the genome.

In some embodiments, a polynucleotide encoding a site-directed polypeptide can be used to edit genome. In some of such embodiments, the polynucleotide encoding a site-directed polypeptide is codon-optimized according to methods standard in the art for expression in the cell containing the target DNA of interest. For example, if the intended target nucleic acid is in a human cell, a human codon-optimized polynucleotide encoding Cas9 is contemplated for use for producing the Cas9 polypeptide.

Cas Genes/Polypeptides and Protospacer Adjacent Motifs

Figure 1:
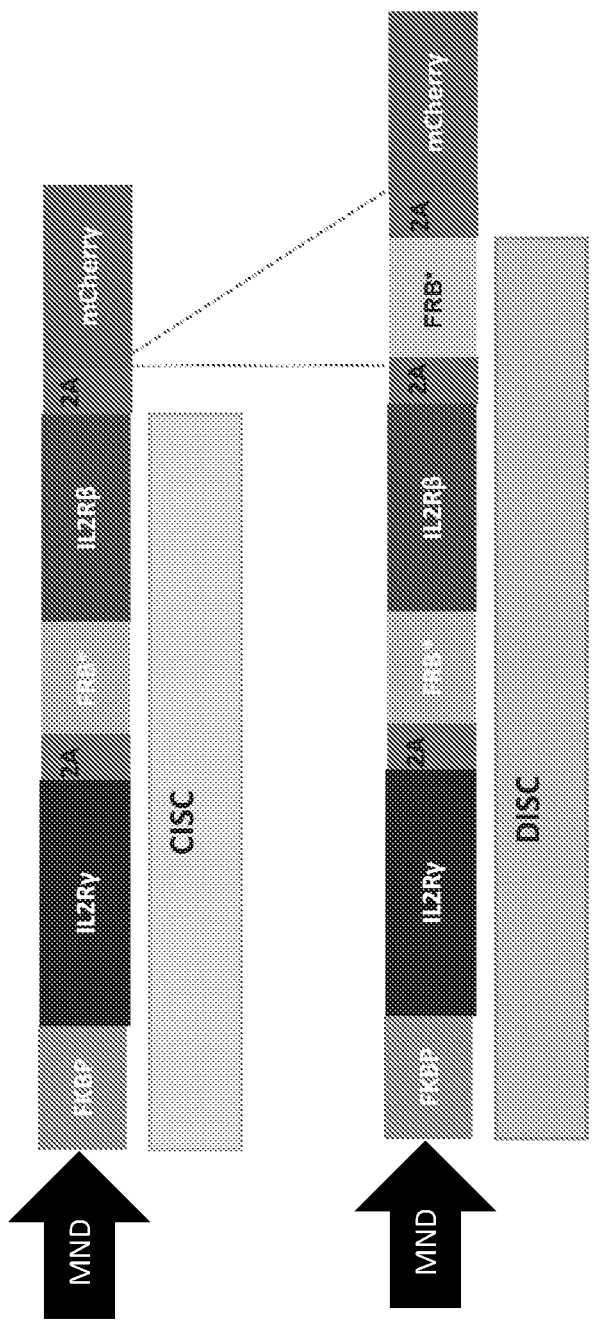
FIG. 1 is a schematic diagram of a lentiviral construct to express an intracellular naked "decoy" FRB (FKBP12 rapamycin binding domain). Constructs that express the extra FRB* domain along with the CISC were designated as "decoy-CISC," or "DISC." The asterisk in the figure denotes this sequence has a point mutation rendering it capable of interacting with the rapalog AP21967 as well as rapamycin (T2098L relative to mTOR amino acid sequence; (Bayle, J. H. et al. (2006). *Chem. Biol.*, 13(1):99-107).
Figure 5:
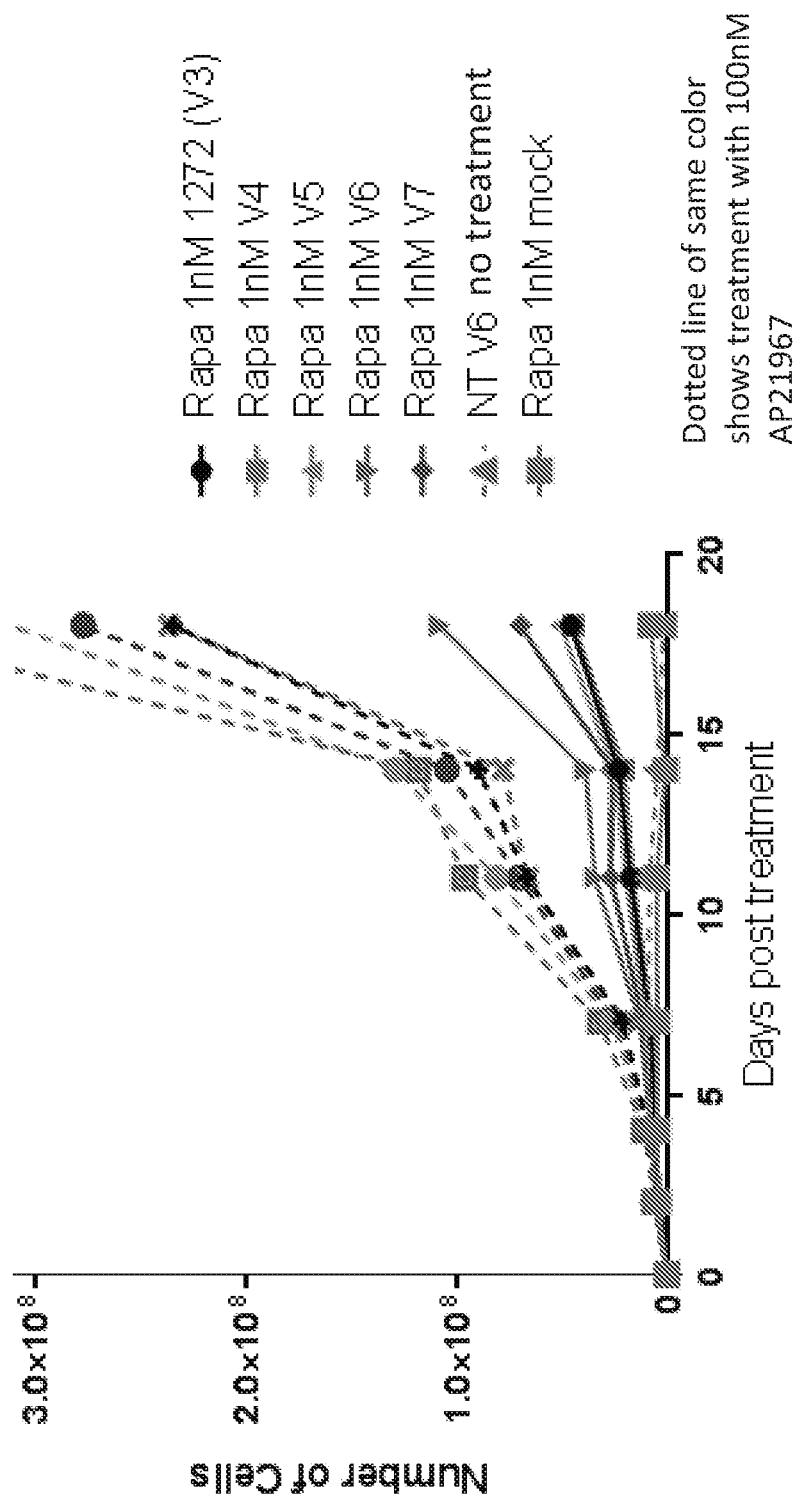
FIG. 5 is a graph showing the numerical expansion of lentivirus-transduced T cells over several weeks in culture with the indicated media additive shown in legend at right.

Exemplary CRISPR/Cas polypeptides include the Cas9 polypeptides in FIG. 1 of Fonfara I. et al. (2014). *Nucl. Acids Res.*, 42(4):2577-2590 (incorporated by reference herein). The CRISPR/Cas gene naming system has undergone extensive rewriting since the Cas genes were discovered. FIG. 5 of Fonfara, et al. (2014) provides PAM sequences for the Cas9 polypeptides from various species.

Nucleic Acids

Genome-Targeting Nucleic Acids or Guide RNAs

The present disclosure provides a genome-targeting nucleic acid that can direct the activities of an associated polypeptide (e.g., a site-directed polypeptide or DNA endonuclease) to a specific target sequence (for example, a gene of interest) within a target nucleic acid. In some embodiments, the genome-targeting nucleic acid is an RNA. A genome-targeting RNA is referred to as a "guide RNA" or "gRNA" herein. A guide RNA has at least a spacer sequence that hybridizes to a target nucleic acid sequence of interest and a CRISPR repeat sequence. In Type II systems, the gRNA also has a second RNA called the tracrRNA sequence. In the Type II guide RNA (gRNA), the CRISPR repeat sequence and tracrRNA sequence hybridize to each other to form a duplex. In the Type V guide RNA (gRNA), a CRISPR repeat RNA (crRNA) forms a duplex. In both systems, the duplex binds a site-directed polypeptide such that the guide RNA and site-direct polypeptide form a complex. The genome-targeting nucleic acid provides target specificity to the complex by virtue of its association with the site-directed polypeptide. The genome-targeting nucleic acid thus directs the activity of the site-directed polypeptide.

In some embodiments, the genome-targeting nucleic acid is a double-molecule guide RNA. In some embodiments, the genome-targeting nucleic acid is a single-molecule guide RNA. A double-molecule guide RNA has two strands of RNA. The first strand has in the 5' to 3' direction, an optional spacer extension sequence, a spacer sequence and a minimum CRISPR repeat sequence. The second strand has a minimum tracrRNA sequence (complementary to the minimum CRISPR repeat sequence), a 3' tracrRNA sequence and an optional tracrRNA extension sequence. A single-molecule guide RNA (sgRNA) in a Type II system has, in the 5' to 3' direction, an optional spacer extension sequence, a spacer sequence, a minimum CRISPR repeat sequence, a single-molecule guide linker, a minimum tracrRNA sequence, a 3' tracrRNA sequence and an optional tracrRNA extension sequence. The optional tracrRNA extension may have elements that contribute additional functionality (e.g., stability) to the guide RNA. The single-molecule guide linker links the minimum CRISPR repeat and the minimum tracrRNA sequence to form a hairpin structure. The optional tracrRNA extension has one or more hairpins. A single-molecule guide RNA (sgRNA) in a Type V system has, in the 5' to 3' direction, a minimum CRISPR repeat sequence and a spacer sequence.

By way of illustration, guide RNAs used in the CRISPR/Cas/Cpf1 system, or other smaller RNAs can be readily synthesized by chemical means as illustrated below and described in the art. While chemical synthetic procedures are continually expanding, purifications of such RNAs by procedures such as high performance liquid chromatography (HPLC, which avoids the use of gels such as PAGE) tends to become more challenging as polynucleotide lengths increase significantly beyond a hundred or so nucleotides. One approach used for generating RNAs of greater length is to produce two or more molecules that are ligated together. Much longer RNAs, such as those encoding a Cas9 or Cpf1 endonuclease, are more readily generated enzymatically. Various types of RNA modifications can be introduced during or after chemical synthesis and/or enzymatic generation of RNAs, e.g., modifications that enhance stability, reduce the likelihood or degree of innate immune response, and/or enhance other attributes, as described in the art.

Spacer Extension Sequence

In some embodiments of genome-targeting nucleic acids, a spacer extension sequence can modify activity, provide stability and/or provide a location for modifications of a genome-targeting nucleic acid. A spacer extension sequence can modify on- or off-target activity or specificity. In some embodiments, a spacer extension sequence is provided. A spacer extension sequence can have a length of more than 1, 5, 10, 15, 20, 25, 30, 35, 40, 45, 50, 60, 70, 80, 90, 100, 120, 140, 160, 180, 200, 220, 240, 260, 280, 300, 320, 340, 360, 380, 400, 1000, 2000, 3000, 4000, 5000, 6000, or 7000 or more nucleotides. A spacer extension sequence can have a length of or about 1, 5, 10, 15, 20, 25, 30, 35, 40, 45, 50, 60, 70, 80, 90, 100, 120, 140, 160, 180, 200, 220, 240, 260, 280, 300, 320, 340, 360, 380, 400, 1000, 2000, 3000, 4000, 5000, 6000, or 7000 or more nucleotides. A spacer extension sequence can have a length of less than 1, 5, 10, 15, 20, 25, 30, 35, 40, 45, 50, 60, 70, 80, 90, 100, 120, 140, 160, 180, 200, 220, 240, 260, 280, 300, 320, 340, 360, 380, 400, 1000, 2000, 3000, 4000, 5000, 6000, 7000 or more nucleotides. In some embodiments, a spacer extension sequence is less than 10 nucleotides in length. In some embodiments, a spacer extension sequence is between 10-30 nucleotides in length. In some embodiments, a spacer extension sequence is between 30-70 nucleotides in length.

In some embodiments, the spacer extension sequence has another moiety (e.g., a stability control sequence, an endoribonuclease binding sequence, a ribozyme). In some embodiments, the moiety decreases or increases the stability of a nucleic acid targeting nucleic acid. In some embodiments, the moiety is a transcriptional terminator segment (e.g., a transcription termination sequence). In some embodiments, the moiety functions in a eukaryotic cell. In some embodiments, the moiety functions in a prokaryotic cell. In some embodiments, the moiety functions in both eukaryotic and prokaryotic cells. Non-limiting examples of suitable moieties include: a 5' cap (e.g., a 7-methylguanylate cap (m7 G)), a riboswitch sequence (e.g., to allow for regulated stability and/or regulated accessibility by proteins and protein complexes), a sequence that forms a dsRNA duplex (e.g., a hairpin), a sequence that targets the RNA to a subcellular location (e.g., nucleus, mitochondria, chloroplasts, and the like), a modification or sequence that provides for tracking (e.g., direct conjugation to a fluorescent molecule, conjugation to a moiety that facilitates fluorescent detection, a sequence that allows for fluorescent detection, etc.), and/or a modification or sequence that provides a binding site for proteins (e.g., proteins that act on DNA, including transcriptional activators, transcriptional repressors, DNA methyltransferases, DNA demethylases, histone acetyltransferases, histone deacetylases, and the like).

Spacer Sequence

The spacer sequence hybridizes to a sequence in a target nucleic acid of interest. The spacer of a genome-targeting nucleic acid interacts with a target nucleic acid in a sequence-specific manner via hybridization (e.g., base pairing). The nucleotide sequence of the spacer thus varies depending on the sequence of the target nucleic acid of interest.

In a CRISPR/Cas system herein, the spacer sequence is designed to hybridize to a target nucleic acid that is located 5' of a PAM of the Cas enzyme (for example, a Cas9 enzyme) used in the system. The spacer can perfectly match the target sequence or can have mismatches. Each Cas enzyme has a particular PAM sequence that it recognizes in a target DNA. For example, Streptococcus pyogenes Cas9 recognizes in a target nucleic acid a PAM that has the sequence 5'-NRG-3', where R has either A or G, where N is any nucleotide and N is immediately 3' of the target nucleic acid sequence targeted by the spacer sequence.

In some embodiments, the target nucleic acid sequence has 20 nucleotides. In some embodiments, the target nucleic acid has less than 20 nucleotides. In some embodiments, the target nucleic acid has more than 20 nucleotides. In some embodiments, the target nucleic acid has at least: 5, 10, 15, 16, 17, 18, 19, 20, 21, 22, 23, 24, 25, 30 or more nucleotides. In some embodiments, the target nucleic acid has at most: 5, 10, 15, 16, 17, 18, 19, 20, 21, 22, 23, 24, 25, 30 or more nucleotides. In some embodiments, the target nucleic acid sequence has 20 bases immediately 5' of the first nucleotide of the PAM. For example, in a sequence having 5'-NNNNNNNNNNNNNNNNNNNNNRG-3', the target nucleic acid has the sequence that corresponds to the Ns, wherein N is any nucleotide, and the underlined NRG sequence (R is G or A) is the S. pyogenes Cas9 PAM. In some embodiments, the PAM sequence used in the compositions and methods of the present disclosure as a sequence recognized by S.p. Cas 9 is NGG.

In some embodiments, the spacer sequence that hybridizes to the target nucleic acid has a length of at least or at least about 6 nucleotides (nt). The spacer sequence can be at least or at least about 6 nt, about 10 nt, about 15 nt, about 18 nt, about 19 nt, about 20 nt, about 25 nt, about 30 nt, about 35 nt or about 40 nt, from or from about 6 nt to or to about 80 nt, from or from about 6 nt to or to about 50 nt, from or from about 6 nt to or to about 45 nt, from or from about 6 nt to or to about 40 nt, from or from about 6 nt to or to about 35 nt, from or from about 6 nt to or to about 30 nt, from or from about 6 nt to or to about 25 nt, from or from about 6 nt to or to about 20 nt, from or from about 6 nt to or to about 19 nt, from or from about 10 nt to or to about 50 nt, from or from about 10 nt to or to about 45 nt, from or from about 10 nt to or to about 40 nt, from or from about 10 nt to or to about 35 nt, from or from about 10 nt to or to about 30 nt, from or from about 10 nt to or to about 25 nt, from or from about 10 nt to or to about 20 nt, from or from about 10 nt to or to about 19 nt, from or from about 19 nt to or to about 25 nt, from or from about 19 nt to or to about 30 nt, from or from about 19 nt to or to about 35 nt, from or from about 19 nt to or to about 40 nt, from or from about 19 nt to or to about 45 nt, from or from about 19 nt to or to about 50 nt, from or from about 19 nt to or to about 60 nt, from or from about 20 nt to or to about 25 nt, from or from about 20 nt to or to about 30 nt, from or from about 20 nt to or to about 35 nt, from or from about 20 nt to or to about 40 nt, from or from about 20 nt to or to about 45 nt, from or from about 20 nt to or to about 50 nt, or from or from about 20 nt to or to about 60 nt. In some embodiments, the spacer sequence has 20 nucleotides. In some embodiments, the spacer has 19 nucleotides. In some embodiments, the spacer has 18 nucleotides. In some embodiments, the spacer has 17 nucleotides. In some embodiments, the spacer has 16 nucleotides. In some embodiments, the spacer has 15 nucleotides.

In some embodiments, the percent complementarity between the spacer sequence and the target nucleic acid is at least or at least about 30%, at least or at least about 40%, at least or at least about 50%, at least or at least about 60%, at least or at least about 65%, at least or at least about 70%, at least or at least about 75%, at least or at least about 80%, at least or at least about 85%, at least or at least about 90%, at least or at least about 95%, at least or at least about 97%, at least or at least about 98%, at least or at least about 99%, or 100%. In some embodiments, the percent complementarity between the spacer sequence and the target nucleic acid is at most or at most about 30%, at most or at most about 40%, at most or at most about 50%, at most or at most about 60%, at most or at most about 65%, at most or at most about 70%, at most or at most about 75%, at most or at most about 80%, at most or at most about 85%, at most or at most about 90%, at most or at most about 95%, at most or at most about 97%, at most or at most about 98%, at most or at most about 99%, or about 100%. In some embodiments, the percent complementarity between the spacer sequence and the target nucleic acid is 100% over the six contiguous 5'-most nucleotides of the target sequence of the complementary strand of the target nucleic acid. In some embodiments, the percent complementarity between the spacer sequence and the target nucleic acid is at least 60% over or over about 20 contiguous nucleotides. In some embodiments, the length of the spacer sequence and the target nucleic acid can differ by 1 to 6 nucleotides, which can be thought of as a bulge or bulges.

In some embodiments, the spacer sequence is designed or chosen using a computer program. The computer program can use variables, such as predicted melting temperature, secondary structure formation, predicted annealing temperature, sequence identity, genomic context, chromatin accessibility, % GC, frequency of genomic occurrence (e.g., of sequences that are identical or are similar but vary in one or more spots as a result of mismatch, insertion or deletion), methylation status, presence of SNPs, and the like.

Minimum CRISPR Repeat Sequence

In some embodiments, a minimum CRISPR repeat sequence is a sequence with at least or at least about 30%, about 40%, about 50%, about 60%, about 65%, about 70%, about 75%, about 80%, about 85%, about 90%, about 95%, or 100% sequence identity to a reference CRISPR repeat sequence (e.g., crRNA from S. pyogenes).

In some embodiments, a minimum CRISPR repeat sequence has nucleotides that can hybridize to a minimum tracrRNA sequence in a cell. The minimum CRISPR repeat sequence and a minimum tracrRNA sequence form a duplex, e.g. a base-paired double-stranded structure. Together, the minimum CRISPR repeat sequence and the minimum tracrRNA sequence bind to the site-directed polypeptide. At least a part of the minimum CRISPR repeat sequence hybridizes to the minimum tracrRNA sequence. In some embodiments, at least a part of the minimum CRISPR repeat sequence has at least or at least about 30%, about 40%, about 50%, about 60%, about 65%, about 70%, about 75%, about 80%, about 85%, about 90%, about 95%, or 100% complementary to the minimum tracrRNA sequence. In some embodiments, at least a part of the minimum CRISPR repeat sequence has at most or at most about 30%, about 40%, about 50%, about 60%, about 65%, about 70%, about 75%, about 80%, about 85%, about 90%, about 95%, or 100% complementary to the minimum tracrRNA sequence.

The minimum CRISPR repeat sequence can have a length from or from about 7 nucleotides to or to about 100 nucleotides. For example, the length of the minimum CRISPR repeat sequence is from or from about 7 nucleotides (nt) to or to about 50 nt, from or from about 7 nt to or to about 40 nt, from or from about 7 nt to or to about 30 nt, from or from about 7 nt to or to about 25 nt, from or from about 7 nt to or to about 20 nt, from or from about 7 nt to or to about 15 nt, from or from about 8 nt to or to about 40 nt, from or from about 8 nt to or to about 30 nt, from or from about 8 nt to or to about 25 nt, from or from about 8 nt to or to about 20 nt, from or from about 8 nt to or to about 15 nt, from or from about 15 nt to or to about 100 nt, from or from about 15 nt to or to about 80 nt, from or from about 15 nt to or to about 50 nt, from or from about 15 nt to or to about 40 nt, from or from about 15 nt to or to about 30 nt, or from or from about 15 nt to or to about 25 nt. In some embodiments, the minimum CRISPR repeat sequence is approximately 9 nucleotides in length. In some embodiments, the minimum CRISPR repeat sequence is approximately 12 nucleotides in length.

In some embodiments, the minimum CRISPR repeat sequence is at least or at least about 60% identical to a reference minimum CRISPR repeat sequence (e.g., wild-type crRNA from *S. pyogenes*) over a stretch of at least 6, 7, or 8 contiguous nucleotides. For example, the minimum CRISPR repeat sequence is at least or at least about 65% identical, at least or at least about 70% identical, at least or at least about 75% identical, at least or at least about 80% identical, at least or at least about 85% identical, at least or at least about 90% identical, at least or at least about 95% identical, at least or at least about 98% identical, at least or at least about 99% identical or 100% identical to a reference minimum CRISPR repeat sequence over a stretch of at least 6, 7, or 8 contiguous nucleotides.

Minimum tracrRNA Sequence

In some embodiments, a minimum tracrRNA sequence is a sequence with at least or at least about 30%, about 40%, about 50%, about 60%, about 65%, about 70%, about 75%, about 80%, about 85%, about 90%, about 95%, or 100% sequence identity to a reference tracrRNA sequence (e.g., wild type tracrRNA from *S. pyogenes*).

In some embodiments, a minimum tracrRNA sequence has nucleotides that hybridize to a minimum CRISPR repeat sequence in a cell. A minimum tracrRNA sequence and a minimum CRISPR repeat sequence form a duplex, e.g. a base-paired double-stranded structure. Together, the minimum tracrRNA sequence and the minimum CRISPR repeat bind to a site-directed polypeptide. At least a part of the minimum tracrRNA sequence can hybridize to the minimum CRISPR repeat sequence. In some embodiments, the minimum tracrRNA sequence is at least or at least about 30%, about 40%, about 50%, about 60%, about 65%, about 70%, about 75%, about 80%, about 85%, about 90%, about 95%, or 100% complementary to the minimum CRISPR repeat sequence.

The minimum tracrRNA sequence can have a length from or from about 7 nucleotides to or to about 100 nucleotides. For example, the minimum tracrRNA sequence can be from or from about 7 nucleotides (nt) to or to about 50 nt, from or from about 7 nt to or to about 40 nt, from or from about 7 nt to or to about 30 nt, from or from about 7 nt to or to about 25 nt, from or from about 7 nt to or to about 20 nt, from or from about 7 nt to or to about 15 nt, from or from about 8 nt to or to about 40 nt, from or from about 8 nt to or to about 30 nt, from or from about 8 nt to or to about 25 nt, from or from about 8 nt to or to about 20 nt, from or from about 8 nt to or to about 15 nt, from or from about 15 nt to or to about 100 nt, from or from about 15 nt to or to about 80 nt, from or from about 15 nt to or to about 50 nt, from or from about 15 nt to or to about 40 nt, from or from about 15 nt to or to about 30 nt or from or from about 15 nt to or to about 25 nt long. In some embodiments, the minimum tracrRNA sequence is approximately 9 nucleotides in length. In some embodiments, the minimum tracrRNA sequence is approximately 12 nucleotides. In some embodiments, the minimum tracrRNA consists of tracrRNA nt 23-48 described in Jinek M. et al. (2012). *Science,* 337(6096):816-821.

In some embodiments, the minimum tracrRNA sequence is at least or at least about 60% identical to a reference minimum tracrRNA (e.g., wild type, tracrRNA from *S. pyogenes*) sequence over a stretch of at least 6, 7, or 8 contiguous nucleotides. For example, the minimum tracrRNA sequence is at least or at least about 65% identical, about 70% identical, about 75% identical, about 80% identical, about 85% identical, about 90% identical, about 95% identical, about 98% identical, about 99% identical or 100% identical to a reference minimum tracrRNA sequence over a stretch of at least 6, 7, or 8 contiguous nucleotides.

In some embodiments, the duplex between the minimum CRISPR RNA and the minimum tracrRNA has a double helix. In some embodiments, the duplex between the minimum CRISPR RNA and the minimum tracrRNA has at least or at least about 1, 2, 3, 4, 5, 6, 7, 8, 9, or 10 or more nucleotides. In some embodiments, the duplex between the minimum CRISPR RNA and the minimum tracrRNA has at most or at most about 1, 2, 3, 4, 5, 6, 7, 8, 9, or 10 or more nucleotides.

In some embodiments, the duplex has a mismatch (e.g., the two strands of the duplex are not 100% complementary). In some embodiments, the duplex has at least or at least about 1, 2, 3, 4, or 5 or mismatches. In some embodiments, the duplex has at most or at most about 1, 2, 3, 4, or 5 or mismatches. In some embodiments, the duplex has no more than 2 mismatches.

3' tracrRNA Sequence

In some embodiments, a 3' tracrRNA sequence has a sequence with at least or at least about 30%, about 40%, about 50%, about 60%, about 65%, about 70%, about 75%, about 80%, about 85%, about 90%, about 95%, or 100% sequence identity to a reference tracrRNA sequence (e.g., a tracrRNA from *S. pyogenes*).

In some embodiments, the 3' tracrRNA sequence has a length from or from about 6 nucleotides to or to about 100 nucleotides. For example, the 3' tracrRNA sequence can have a length from or from about 6 nucleotides (nt) to or to about 50 nt, from or from about 6 nt to or to about 40 nt, from or from about 6 nt to or to about 30 nt, from or from about 6 nt to or to about 25 nt, from or from about 6 nt to or to about 20 nt, from or from about 6 nt to or to about 15 nt, from or from about 8 nt to or to about 40 nt, from or from about 8 nt to or to about 30 nt, from or from about 8 nt to or to about 25 nt, from or from about 8 nt to or to about 20 nt, from or from about 8 nt to or to about 15 nt, from or from about 15 nt to or to about 100 nt, from or from about 15 nt to or to about 80 nt, from or from about 15 nt to or to about 50 nt, from or from about 15 nt to or to about 40 nt, from or from about 15 nt to or to about 30 nt, or from or from about 15 nt to or to about 25 nt. In some embodiments, the 3' tracrRNA sequence has a length of approximately 14 nucleotides.

In some embodiments, the 3' tracrRNA sequence is at least or at least about 60% identical to a reference 3' tracrRNA sequence (e.g., wild type 3' tracrRNA sequence from *S. pyogenes*) over a stretch of at least 6, 7, or 8 contiguous nucleotides. For example, the 3' tracrRNA sequence is at least or at least about 60% identical, about 65% identical, about 70% identical, about 75% identical, about 80% identical, about 85% identical, about 90% identical, about 95% identical, about 98% identical, about 99% identical, or 100% identical, to a reference 3' tracrRNA sequence (e.g., wild type 3' tracrRNA sequence from *S. pyogenes*) over a stretch of at least 6, 7, or 8 contiguous nucleotides.

In some embodiments, a 3' tracrRNA sequence has more than one duplexed region (e.g., hairpin, hybridized region). In some embodiments, a 3' tracrRNA sequence has two duplexed regions.

In some embodiments, the 3' tracrRNA sequence has a stem loop structure. In some embodiments, a stem loop structure in the 3' tracrRNA has at least 1, 2, 3, 4, 5, 6, 7, 8, 9, 10, 15 or 20 or more nucleotides. In some embodiments, the stem loop structure in the 3' tracrRNA has at most 1, 2, 3, 4, 5, 6, 7, 8, 9 or 10 or more nucleotides. In some embodiments, the stem loop structure has a functional moiety. For example, the stem loop structure can have an aptamer, a ribozyme, a protein-interacting hairpin, a CRISPR array, an intron, or an exon. In some embodiments, the stem loop structure has at least or at least about 1, 2, 3, 4, or 5 or more functional moieties. In some embodiments, the stem loop structure has at most or at most about 1, 2, 3, 4, or 5 or more functional moieties.

In some embodiments, the hairpin in the 3' tracrRNA sequence has a P-domain. In some embodiments, the P-domain has a double-stranded region in the hairpin.

tracrRNA Extension Sequence

In some embodiments, a tracrRNA extension sequence can be provided whether the tracrRNA is in the context of single-molecule guides or double-molecule guides. In some embodiments, a tracrRNA extension sequence has a length from or from about 1 nucleotide to or to about 400 nucleotides. In some embodiments, a tracrRNA extension sequence has a length of more than 1, 5, 10, 15, 20, 25, 30, 35, 40, 45, 50, 60, 70, 80, 90, 100, 120, 140, 160, 180, 200, 220, 240, 260, 280, 300, 320, 340, 360, 380, or 400 nucleotides. In some embodiments, a tracrRNA extension sequence has a length from or from about 20 to or to about 5000 or more nucleotides. In some embodiments, a tracrRNA extension sequence has a length of more than 1000 nucleotides. In some embodiments, a tracrRNA extension sequence has a length of less than 1, 5, 10, 15, 20, 25, 30, 35, 40, 45, 50, 60, 70, 80, 90, 100, 120, 140, 160, 180, 200, 220, 240, 260, 280, 300, 320, 340, 360, 380, 400 or more nucleotides. In some embodiments, a tracrRNA extension sequence can have a length of less than 1000 nucleotides. In some embodiments, a tracrRNA extension sequence has less than 10 nucleotides in length. In some embodiments, a tracrRNA extension sequence is 10-30 nucleotides in length. In some embodiments, tracrRNA extension sequence is 30-70 nucleotides in length.

In some embodiments, the tracrRNA extension sequence has a functional moiety (e.g., a stability control sequence, ribozyme, endoribonuclease binding sequence). In some embodiments, the functional moiety has a transcriptional terminator segment (such as a transcription termination sequence). In some embodiments, the functional moiety has a total length from or from about 10 nucleotides (nt) to or to about 100 nucleotides, from or from about 10 nt to or to about 20 nt, from or from about 20 nt to or to about 30 nt, from or from about 30 nt to or to about 40 nt, from or from about 40 nt to or to about 50 nt, from or from about 50 nt to or to about 60 nt, from or from about 60 nt to or to about 70 nt, from or from about 70 nt to or to about 80 nt, from or from about 80 nt to or to about 90 nt, or from or from about 90 nt to or to about 100 nt, from or from about 15 nt to or to about 80 nt, from or from about 15 nt to or to about 50 nt, from or from about 15 nt to or to about 40 nt, from or from about 15 nt to or to about 30 nt, or from or from about 15 nt to or to about 25 nt. In some embodiments, the functional moiety functions in a eukaryotic cell. In some embodiments, the functional moiety functions in a prokaryotic cell. In some embodiments, the functional moiety functions in both eukaryotic and prokaryotic cells.

Non-limiting examples of suitable tracrRNA extension functional moieties include a 3' poly-adenylated tail, a riboswitch sequence (e.g., to allow for regulated stability and/or regulated accessibility by proteins and protein complexes), a sequence that forms a dsRNA duplex (e.g., a hairpin), a sequence that targets the RNA to a subcellular location (e.g., nucleus, mitochondria, chloroplasts, and the like), a modification or sequence that provides for tracking (e.g., direct conjugation to a fluorescent molecule, conjugation to a moiety that facilitates fluorescent detection, a sequence that allows for fluorescent detection, etc.), and/or a modification or sequence that provides a binding site for proteins (e.g., proteins that act on DNA, including transcriptional activators, transcriptional repressors, DNA methyltransferases, DNA demethylases, histone acetyltransferases, histone deacetylases, and the like). In some embodiments, a tracrRNA extension sequence has a primer binding site or a molecular index (e.g., barcode sequence). In some embodiments, the tracrRNA extension sequence has one or more affinity tags.

Bulges

In some embodiments, there is a "bulge" in the duplex between the minimum CRISPR RNA and the minimum tracrRNA. The bulge is an unpaired region of nucleotides within the duplex. In some embodiments, the bulge contributes to the binding of the duplex to the site-directed polypeptide. A bulge has, on one side of the duplex, an unpaired 5'-XXXY-3' where X is any purine and Y has a nucleotide that can form a wobble pair with a nucleotide on the opposite strand, and an unpaired nucleotide region on the other side of the duplex. The number of unpaired nucleotides on the two sides of the duplex can be different.

In one example, the bulge has an unpaired purine (e.g., adenine) on the minimum CRISPR repeat strand of the bulge. In some embodiments, a bulge has an unpaired 5'-AAGY-3' of the minimum tracrRNA sequence strand of the bulge, where Y has a nucleotide that can form a wobble pairing with a nucleotide on the minimum CRISPR repeat strand.

In some embodiments, a bulge on the minimum CRISPR repeat side of the duplex has at least 1, 2, 3, 4, or 5 or more unpaired nucleotides. In some embodiments, a bulge on the minimum CRISPR repeat side of the duplex has at most 1, 2, 3, 4, or 5 or more unpaired nucleotides. In some embodiments, a bulge on the minimum CRISPR repeat side of the duplex has 1 unpaired nucleotide.

In some embodiments, a bulge on the minimum tracrRNA sequence side of the duplex has at least 1, 2, 3, 4, 5, 6, 7, 8, 9, or 10 or more unpaired nucleotides. In some embodiments, a bulge on the minimum tracrRNA sequence side of the duplex has at most 1, 2, 3, 4, 5, 6, 7, 8, 9, or 10 or more unpaired nucleotides. In some embodiments, a bulge on a second side of the duplex (e.g., the minimum tracrRNA sequence side of the duplex) has 4 unpaired nucleotides.

In some embodiments, a bulge has at least one wobble pairing. In some embodiments, a bulge has at most one wobble pairing. In some embodiments, a bulge has at least one purine nucleotide. In some embodiments, a bulge has at least 3 purine nucleotides. In some embodiments, a bulge sequence has at least 5 purine nucleotides. In some embodiments, a bulge sequence has at least one guanine nucleotide. In some embodiments, a bulge sequence has at least one adenine nucleotide.

Hairpins

In various embodiments, one or more hairpins are located 3' to the minimum tracrRNA in the 3' tracrRNA sequence.

In some embodiments, the hairpin starts at least or at least about 1, 2, 3, 4, 5, 6, 7, 8, 9, 10, 15, or 20 or more nucleotides 3' from the last paired nucleotide in the minimum CRISPR repeat and minimum tracrRNA sequence duplex. In some embodiments, the hairpin can start at most or at most about 1, 2, 3, 4, 5, 6, 7, 8, 9 or 10 or more nucleotides 3' of the last paired nucleotide in the minimum CRISPR repeat and minimum tracrRNA sequence duplex.

In some embodiments, a hairpin has at least or at least about 1, 2, 3, 4, 5, 6, 7, 8, 9, 10, 15, or 20 or more consecutive nucleotides. In some embodiments, a hairpin has at most or at most about 1, 2, 3, 4, 5, 6, 7, 8, 9, 10, 15, or more consecutive nucleotides.

In some embodiments, a hairpin has a CC dinucleotide (such as two consecutive cytosine nucleotides).

In some embodiments, a hairpin has duplexed nucleotides (e.g., nucleotides in a hairpin, hybridized together). For example, a hairpin has a CC dinucleotide that is hybridized to a GG dinucleotide in a hairpin duplex of the 3' tracrRNA sequence.

One or more of the hairpins can interact with guide RNA-interacting regions of a site-directed polypeptide.

In some embodiments, there are two or more hairpins, and in some embodiments there are three or more hairpins.

Single-Molecule Guide Linker Sequence

In some embodiments, the linker sequence of a single-molecule guide nucleic acid has a length from or from about 3 nucleotides to or to about 100 nucleotides. In Jinek, M. et al. (2012). Science, 337(6096):816-821) for example, a simple 4 nucleotide "tetraloop" (-GAAA-) was used. An illustrative linker has a length from or from about 3 nucleotides (nt) to or to about 90 nt, from or from about 3 nt to or to about 80 nt, from or from about 3 nt to or to about 70 nt, from or from about 3 nt to or to about 60 nt, from or from about 3 nt to or to about 50 nt, from or from about 3 nt to or to about 40 nt, from or from about 3 nt to or to about 30 nt, from or from about 3 nt to or to about 20 nt, from or from about 3 nt to or to about 10 nt. For example, the linker can have a length from or from about 3 nt to or to about 5 nt, from or from about 5 nt to or to about 10 nt, from or from about 10 nt to or to about 15 nt, from or from about 15 nt to or to about 20 nt, from or from about 20 nt to or to about 25 nt, from or from about 25 nt to or to about 30 nt, from or from about 30 nt to or to about 35 nt, from or from about 35 nt to or to about 40 nt, from or from about 40 nt to or to about 50 nt, from or from about 50 nt to or to about 60 nt, from or from about 60 nt to or to about 70 nt, from or from about 70 nt to or to about 80 nt, from or from about 80 nt to or to about 90 nt, or from or from about 90 nt to or to about 100 nt. In some embodiments, the linker of a single-molecule guide nucleic acid is between 4 and 40 nucleotides. In some embodiments, a linker is at least or at least about 100, 500, 1000, 1500, 2000, 2500, 3000, 3500, 4000, 4500, 5000, 5500, 6000, 6500, or 7000 or more nucleotides. In some embodiments, a linker is at most or at most about 100, 500, 1000, 1500, 2000, 2500, 3000, 3500, 4000, 4500, 5000, 5500, 6000, 6500, or 7000 or more nucleotides.

Linkers can have any of a variety of sequences, although in some embodiments, the linker will not have sequences that have extensive regions of homology with other portions of the guide RNA, which might cause intramolecular binding that could interfere with other functional regions of the guide. In Jinek et al. (2012). Science, 337(6096):816-821, a simple 4 nucleotide sequence -GAAA- was used but numerous other sequences, including longer sequences can likewise be used.

In some embodiments, the linker sequence has a functional moiety. For example, the linker sequence can have one or more features, including an aptamer, a ribozyme, a protein-interacting hairpin, a protein binding site, a CRISPR array, an intron, or an exon. In some embodiments, the linker sequence has at least or at least about 1, 2, 3, 4, or 5 or more functional moieties. In some embodiments, the linker sequence has at most or at most about 1, 2, 3, 4, or 5 or more functional moieties.

Donor DNA or Donor Template

Site-directed polypeptides, such as a DNA endonuclease, can introduce double-strand breaks or single-strand breaks in nucleic acids, e.g., genomic DNA. The double-strand break can stimulate a cell's endogenous DNA-repair pathways (e.g., homology-dependent repair (HDR) or non-homologous end joining or alternative non-homologous end joining (A-NHEJ) or microhomology-mediated end joining (MMEJ). NHEJ can repair cleaved target nucleic acid without the need for a homologous template. This can sometimes result in small deletions or insertions (indels) in the target nucleic acid at the site of cleavage, and can lead to disruption or alteration of gene expression. HDR, which is also known as homologous recombination (HR) can occur when a homologous repair template, or donor, is available.

The homologous donor template has sequences that are homologous to sequences flanking the target nucleic acid cleavage site. The sister chromatid is generally used by the cell as the repair template. However, for the purposes of genome editing, the repair template is often supplied as an exogenous nucleic acid, such as a plasmid, duplex oligonucleotide, single-strand oligonucleotide, double-stranded oligonucleotide, or viral nucleic acid. With exogenous donor templates, it is common to introduce an additional nucleic acid sequence (such as a transgene) or modification (such as a single or multiple base change or a deletion) between the flanking regions of homology so that the additional or altered nucleic acid sequence also becomes incorporated into the target locus. MMEJ results in a genetic outcome that is similar to NHEJ in that small deletions and insertions can occur at the cleavage site. MMEJ makes use of homologous sequences of a few base pairs flanking the cleavage site to drive a favored end-joining DNA repair outcome. In some instances, it can be possible to predict likely repair outcomes based on analysis of potential microhomologies in the nuclease target regions.

Thus, in some cases, homologous recombination is used to insert an exogenous polynucleotide sequence into the target nucleic acid cleavage site. An exogenous polynucleotide sequence is termed a donor polynucleotide (or donor or donor sequence or donor template) herein. In some embodiments, the donor polynucleotide, a portion of the donor polynucleotide, a copy of the donor polynucleotide, or a portion of a copy of the donor polynucleotide is inserted into the target nucleic acid cleavage site. In some embodiments, the donor polynucleotide is an exogenous polynucleotide sequence, e.g., a sequence that does not naturally occur at the target nucleic acid cleavage site.

When an exogenous DNA molecule is supplied in sufficient concentration inside the nucleus of a cell in which the double strand break occurs, the exogenous DNA can be inserted at the double strand break during the NHEJ repair process and thus can be stably maintained in the genome, e.g., become a permanent addition to the genome. These exogenous DNA molecules are referred to as donor templates in some embodiments. If the donor template contains a coding sequence for a gene of interest or a genomic site of interest optionally together with relevant regulatory sequences such as promoters, enhancers, polyA sequences and/or splice acceptor sequences, the gene of interest can be expressed from the integrated copy in the genome resulting in permanent expression for the life of the cell. Moreover, the integrated copy of the donor DNA template can be transmitted to the daughter cells when the cell divides.

In the presence of sufficient concentrations of a donor DNA template that contains flanking DNA sequences with homology to the DNA sequence either side of the double strand break (referred to as homology arms), the donor DNA template can be integrated via the HDR pathway. The homology arms act as substrates for homologous recombination between the donor template and the sequences either side of the double strand break. This can result in an error free insertion of the donor template in which the sequences either side of the double strand break are not altered from that in the un-modified genome.

Supplied donors for editing by HDR vary markedly but generally contain the intended sequence with small or large flanking homology arms to allow annealing to the genomic DNA. The homology regions flanking the introduced genetic changes can be 30 bp or smaller, or as large as a multi-kilobase cassette that can contain promoters, cDNAs, etc. Both single-stranded and double-stranded oligonucleotide donors can be used. These oligonucleotides range in size from less than 100 nt to over many kb, though longer ssDNA can also be generated and used. Double-stranded donors are often used, including PCR amplicons, plasmids, and mini-circles. In general, it has been found that an AAV vector (though the gene editing methods disclosed herein are not limited to as such) is a very effective means of delivery of a donor template, though the packaging limits for individual donors is <5 kb. Active transcription of the donor increased HDR three-fold, indicating the inclusion of promoter can increase conversion. Conversely, CpG methylation of the donor can decrease gene expression and HDR.

In some embodiments, the donor DNA can be supplied with the nuclease or independently by a variety of different methods, for example by transfection, nanoparticle, microinjection, or viral transduction. A range of tethering options can be used to increase the availability of the donors for HDR in some embodiments. Examples include attaching the donor to the nuclease, attaching to DNA binding proteins that bind nearby, or attaching to proteins that are involved in DNA end binding or repair.

In addition to genome editing by MET or HDR, site-specific gene insertions can be conducted that use both the NEED pathway and HR. A combination approach can be applicable in certain settings, possibly including intron/exon borders. NHEJ can prove effective for ligation in the intron, while the error-free HDR can be better suited in the coding region.

Nucleic Acid Encoding Site-Directed Polypeptide or DNA Endonuclease

In some embodiments, the methods of genome edition and compositions therefore can use a nucleic acid sequence (or oligonucleotide) encoding a site-directed polypeptide or DNA endonuclease. The nucleic acid sequence encoding the site-directed polypeptide can be DNA or RNA. If the nucleic acid sequence encoding the site-directed polypeptide is RNA, it can be covalently linked to a gRNA sequence or exist as a separate sequence. In some embodiments, a peptide sequence of the site-directed polypeptide or DNA endonuclease can be used instead of the nucleic acid sequence thereof.

Gene Editing Vectors

In another aspect, the present disclosure provides a nucleic acid having a nucleotide sequence encoding a genome-targeting nucleic acid of the disclosure, a site-directed polypeptide of the disclosure, and/or any nucleic acid or proteinaceous molecule necessary to carry out the embodiments of the methods of the disclosure. In some embodiments, such a nucleic acid is a vector (e.g., a recombinant expression vector).

Expression vectors contemplated include, but are not limited to, viral vectors based on vaccinia virus, poliovirus, adenovirus, adeno-associated virus, SV40, herpes simplex virus, human immunodeficiency virus, retrovirus (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus) and other recombinant vectors. Other vectors contemplated for eukaryotic target cells include, but are not limited to, the vectors pXT1, pSG5, pSVK3, pBPV, pMSG, and pSVLSV40 (Pharmacia). Additional vectors contemplated for eukaryotic target cells include, but are not limited to, the vectors pCTx-1, pCTx-2, and pCTx-3. Other vectors can be used so long as they are compatible with the host cell.

In some embodiments, a vector has one or more transcription and/or translation control elements. Depending on the host/vector system utilized, any of a number of suitable transcription and translation control elements, including constitutive and inducible promoters, transcription enhancer elements, transcription terminators, etc. can be used in the expression vector. In some embodiments, the vector is a self-inactivating vector that either inactivates the viral sequences or the components of the CRISPR machinery or other elements.

Non-limiting examples of suitable eukaryotic promoters (e.g., promoters functional in a eukaryotic cell) include those from cytomegalovirus (CMV) immediate early, herpes simplex virus (HSV) thymidine kinase, early and late SV40, long terminal repeats (LTRs) from retrovirus, human elongation factor-1 promoter (EF1), a hybrid construct having the cytomegalovirus (CMV) enhancer fused to the chicken beta-actin promoter (CAG), murine stem cell virus promoter (MSCV), phosphoglycerate kinase-1 locus promoter (PGK), and mouse metallothionein-I. In further embodiments, the promoter is an MND promoter (for example, the MND promoter including the nucleic acid sequence of SEQ ID NO: 33).

For expressing small RNAs, including guide RNAs used in connection with Cas endonuclease, various promoters such as RNA polymerase III promoters, including for example U6 and H1, can be advantageous. Descriptions of and parameters for enhancing the use of such promoters are known in art, and additional information and approaches are regularly being described; see, e.g., Ma, H. et al. (2014). *Mol. Ther.—Nucleic Acids* 3:e161, doi:10.1038/mtna.2014.12.

The expression vector can also contain a ribosome binding site for translation initiation and a transcription terminator. The expression vector can also include appropriate sequences for amplifying expression. The expression vector can also include nucleotide sequences encoding non-native tags (e.g., histidine tag, hemagglutinin tag, green fluorescent protein, etc.) that are fused to the site-directed polypeptide, thus resulting in a fusion protein.

In some embodiments, a promoter is an inducible promoter (e.g., a heat shock promoter, tetracycline-regulated promoter, steroid-regulated promoter, metal-regulated promoter, estrogen receptor-regulated promoter, etc.). In some embodiments, a promoter is a constitutive promoter (e.g., CMV promoter, UBC promoter). In some embodiments, the promoter is a spatially restricted and/or temporally restricted promoter (e.g., a tissue specific promoter, a cell type specific promoter, etc.). In some embodiments, a vector does not have a promoter for at least one gene to be expressed in a host cell if the gene is going to be expressed, after it is inserted into a genome, under an endogenous promoter present in the genome.

In some embodiments, the vector contains one or more nucleic acid sequences encoding one or more components of a CISC (such as any of the CISC polypeptides disclosed herein including a CISC polypeptide including a truncated ILR2β intracellular signaling domain). The gene editing vectors disclosed herein can also contain a nucleic acid sequence encoding any of the naked FRB domain polypeptides disclosed herein. In some embodiments, the vector includes the nucleic acid sequence of SEQ ID NO: 3. In further embodiments, the vector includes the nucleic acid sequence of SEQ ID NO: 8.

Complexes of a Genome-Targeting Nucleic Acid and a Site-Directed Polypeptide

A genome-targeting nucleic acid interacts with a site-directed polypeptide (e.g., a nucleic acid-guided nuclease such as Cas9), thereby forming a complex. The genome-targeting nucleic acid (e.g., gRNA) guides the site-directed polypeptide to a target nucleic acid.

As stated previously, in some embodiments the site-directed polypeptide and genome-targeting nucleic acid can each be administered separately to a cell or a subject. On the other hand, in some other embodiments the site-directed polypeptide can be pre-complexed with one or more guide RNAs, or one or more crRNA together with a tracrRNA. The pre-complexed material can then be administered to a cell or a subject. Such pre-complexed material is known as a ribonucleoprotein particle (RNP).

Method of Making a Cell that Expresses a Naked FRB Domain Polypeptide and/or a CISC Component In some embodiments described herein, it may be desired to introduce a protein sequence or an expression vector into a host cell, such as a mammalian cell, e.g., a lymphocyte, to be used for rapamycin-regulated cytokine signaling and/or for the selective expansion of cells that express the dimeric CISC components and an intracellularly expressed naked FRB domain polypeptide. For example, the dimeric CISC can allow for cytokine signaling in cells that have introduced CISC components for transmitting signals to the interior of a cell, such as a mammalian cell, upon contact with a ligand while the intracellularly expressed naked FRB domain polypeptide confers resistance to the adverse effects of rapamycin to the cell. In addition, the selective expansion of cells, such as mammalian cells, can be controlled to select for only those cells that have undergone two specific genetic modification events (such as genetic modification events mediated by a CRISPR/Cas system), as described herein. Preparation of these cells can be carried out in accordance with known techniques that will be apparent to those skilled in the art based upon the present disclosure.

In some embodiments, a method of making a CISC-bearing cell, such as a mammalian cell, is provided, wherein the cell expresses a dimeric CISC and an intracellularly expressed naked FRB domain polypeptide. The method can include delivering to a cell, such as a mammalian cell, the protein sequence of any one of the embodiments or embodiments described herein or the expression vector of the embodiments or embodiments described herein and delivering to the cell, such as a mammalian cell. In some embodiments, the protein sequence includes a first and a second sequence. In other embodiments, the protein sequence includes a first, a second, a third, and a fourth sequence. In some embodiments, the first sequence encodes for a first CISC component including a first extracellular binding domain, a hinge domain, a linker of a specified length, wherein the length is optimized, a transmembrane domain, and a signaling domain. In some embodiments, the second sequence encodes for a second CISC component including a second extracellular binding domain, a hinge domain, a linker of a specified length, wherein the length is optimized, a transmembrane domain, and a signaling domain. In some embodiments, the spacer is 1, 2, 3, 4, 5, 6, 7, 8, 9, 10, 11, 12, 13, 14 or 15 amino acids in length or a length within a range defined by any two of the aforementioned lengths. In some embodiments, the signaling domain includes an interleukin-2 signaling domain, such as an IL2Rβ (including a truncated IL2Rβ) or an IL2Rγ domain. In some embodiments, the extracellular binding domain is a binding domain that binds to rapamycin or a rapalog, including FKBP or FRB or a functional derivative thereof. In some embodiments, the cell is a CD8+ or a CD4+ cell. In some embodiments, the cell is a CD8+ T cytotoxic lymphocyte cell selected from the group consisting of naïve CD8+ T-cells, central memory CD8+ T-cells, effector memory CD8+ T-cells and bulk CD8+ T-cells. In some embodiments, the cell is a CD4+ T helper lymphocyte cell that is selected from the group consisting of naïve CD4+ T-cells, central memory CD4+ T-cells, effector memory CD4+ T-cells, and bulk CD4+ T-cells. In some embodiments, the cell is a precursor T-cell. In some embodiments, the cell is a stem cell. In some embodiments, the cell is a hematopoietic stem cell. In some embodiments, the cell is a B cell. In some embodiments, the cell is a neuronal stem cell. In some embodiments, the cell is an NK cell.

Genetically Modified Cells and Cell Populations

In one aspect, the disclosures herein provide a method of editing a genome in a cell, thereby creating a genetically modified cell. In some aspects, a population of genetically modified cells are provided. A genetically modified cell therefore includes a cell that has at least one genetic modification introduced by genome editing (e.g., by using a CRISPR/Cas system). In some embodiments, the genetically modified cell is a genetically modified lymphocytic cell, e.g. a T cell such as a human CD4+ T cell. A genetically modified cell having an integrated nucleic acid encoding a naked FRB domain polypeptide and optionally further encoding a CISC is contemplated herein.

The compositions described herein provide for genetically modified host cells, such as mammalian cells, which include the protein sequences or the expression vectors as set forth and described herein. Accordingly, provided herein are cells, such as mammalian cells, for dimeric CISC expression as well as intracellularly expressed naked FRB domain expression, wherein the cell includes the protein sequences of any one of the embodiments described herein or the expression vector of anyone of the embodiments described herein. In some embodiments, the cell is a bacterial cell or a mammalian cell, such as a lymphocyte. In some embodiments, the cell is *E. coli*. In some embodiments, the cell is an insect cell that permits protein expression. In some embodiments, the cell is a lymphocyte.

In some embodiments, the host cells are precursor T cells or T regulatory cells. In some embodiments, the cells are stem cells, such as hematopoietic stem cells. In some embodiments, the cell is a NK cell. In some embodiments, the cells are CD34+, CD8+, and/or CD4+ T lymphocytes. In some embodiments, the cell is a B cell. In some embodiments, the cell is a neuronal stem cell.

In some embodiments, the host cells are CD8+ T cytotoxic lymphocyte cells, which may include naïve CD8+ T cells, central memory CD8+ T cells, effector memory CD8+ T cells, or bulk CD8+ T cells. In some embodiments, the cells are CD4+ T helper lymphocyte cells, which may include naïve CD4+ T cells, central memory CD4+ T cells, effector memory CD4+ T cells, or bulk CD4+ T cells.

The lymphocytes (T lymphocytes) can be collected in accordance with known techniques and enriched or depleted by known techniques such as affinity binding to antibodies such as flow cytometry and/or immunomagnetic selection. After enrichment and/or depletion steps, in vitro expansion of the desired T lymphocytes can be carried out in accordance with known techniques or variations thereof that will be apparent to those skilled in the art. In some embodiments, the T cells are autologous T cells obtained from a subject.

For example, the desired T cell population or subpopulation can be expanded by adding an initial T lymphocyte population to a culture medium in vitro, and then adding to the culture medium feeder cells, such as non-dividing peripheral blood mononuclear cells (PBMC), (e.g., such that the resulting population of cells contains at least 5, 10, 20, or 40 or more PBMC feeder cells for each T lymphocyte in the initial population to be expanded); and incubating the culture (e.g. for a time sufficient to expand the numbers of T cells). The non-dividing feeder cells can include gamma-irradiated PBMC feeder cells. In some embodiments, the PBMC are irradiated with gamma rays in the range of 3000 to 3600 rads to prevent cell division. In some embodiments, the PBMC are irradiated with gamma rays of 3000, 3100, 3200, 3300, 3400, 3500 or 3600 rads or any value of rads between any two endpoints of any of the listed values to prevent cell division. The order of addition of the T cells and feeder cells to the culture media can be reversed if desired. The culture can generally be incubated under conditions of temperature and the like that are suitable for the growth of T lymphocytes. For the growth of human T lymphocytes, for example, the temperature will generally be at least or at least about 25° C., at least or at least about 30° C., at least or at least about 37° C. In some embodiments, the temperature for the growth of human T lymphocytes is about 22, about 24, about 26, about 28, about 30, about 32, about 34, about 36, about 37° C., or any other temperature between any two endpoints of any of the listed values.

After isolation of T lymphocytes both cytotoxic and helper T lymphocytes can be sorted into naïve, memory, and effector T cell subpopulations either before or after expansion.

CD8+ cells can be obtained by using standard methods. In some embodiments, CD8+ cells are further sorted into naïve, central memory, and effector memory cells by identifying cell surface antigens that are associated with each of those types of CD8+ cells. In some embodiments, memory T cells are present in both CD62L+ and CD62L− subsets of CD8+ peripheral blood lymphocytes. PBMC are sorted into CD62L−CD8+ and CD62L+CD8+ fractions after staining with anti-CD8 and anti-CD62L antibodies. In some embodiments, the expression of phenotypic markers of central memory TCM include CD45RO, CD62L, CCR7, CD28, CD3, and/or CD127 and are negative or low for granzyme B. In some embodiments, central memory T cells are CD45RO+, CD62L+, and/or CD8+ T cells. In some embodiments, effector $T_E$ are negative for CD62L, CCR7, CD28, and/or CD127, and positive for granzyme B and/or perforin. In some embodiments, naïve CD8+ T lymphocytes are characterized by the expression of phenotypic markers of naïve T cells including CD62L, CCR7, CD28, CD3, CD127, and/or CD45RA.

CD4+ T helper cells are sorted into naïve, central memory, and effector cells by identifying cell populations that have cell surface antigens. CD4+ lymphocytes can be obtained by standard methods. In some embodiments, naïve CD4+ T lymphocytes are CD45RO−, CD45RA+, CD62L+, and/or CD4+ T cells. In some embodiments, central memory CD4+ cells are CD62L+ and/or CD45RO+. In some embodiments, effector CD4+ cells are CD62L− and/or CD45RO−.

Whether a cell, such as a mammalian cell, or cell population, such as a population of mammalian cells, is selected for expansion depends upon whether the cell or population of cells has undergone two distinct genetic modification events. In some embodiments, the genetic modification events are mediated by a CRISPR/Cas system. In some embodiments, the genetic modification events are mediated by a CRISPR/Cas9 system. If a cell, such as a mammalian cell, or a population of cells, such as a population of mammalian cells, has undergone one or fewer genetic modification events, then the addition of a ligand will result in no dimerization. However, if the cell, such as a mammalian cell, or the population of cells, such as a population of mammalian cells, has undergone two genetic modification events, then the addition of the ligand will result in dimerization of the CISC component, and subsequent signaling cascade. Thus, a cell, such as a mammalian cell, or a population of cells, such as a population of mammalian cells, may be selected based on its response to contact with the ligand. In some embodiments, the ligand may be added in an amount of 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10, 11, 12, 13, 14, 15, 20, 25, 30, 35, 40, 45, 50, 55, 60, 65, 70, 75, 80, 85, 90, 95, or 100 nM or a concentration within a range defined by any two of the aforementioned values.

In some embodiments, a cell, such as a mammalian cell, or a population of cells, such as a population of mammalian cells, may be positive for the dimeric CISC as well as the intracellularly expressed naked FRB domain polypeptide based on the expression of a marker as a result of a signaling pathway. Thus, a cell population positive for the dimeric CISC may be determined by flow cytometry using staining with a specific antibody for the surface marker and an isotype matched control antibody. In some embodiments, the marker is a fluorescent or light-emitting protein, such as GFP or mCherry. In some embodiments, the marker is a low affinity nerve growth factor receptor (LNGFR).

In some embodiments, the cell is not a germ cell.

Method of Activating a Signal in the Interior of a Cell

In some embodiments, a method of activating a signal in the interior of a cell, such as a mammalian cell, is provided. The method can include providing a cell, such as a mammalian cell, as described herein, wherein the cell includes a protein sequence as set forth herein or an expression vector as set forth herein. In some embodiments, the method further includes expressing the protein sequence encoding a dimeric CISC as described herein, or expression the vector as described herein. In some embodiments, the method includes contacting the cell, such as a mammalian cell, with a ligand, which causes the first and second CISC components to dimerize, which transduces a signal into the interior of the cell. In some embodiments, the ligand is rapamycin or rapalog. In some embodiments an effective amount of a ligand for inducing dimerization is provided an amount of 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10, 11, 12, 13, 14, 15, 20, 25, 30, 35, 40, 45, 50, 55, 60, 65, 70, 75, 80, 85, 90, 95, or 100 nM or a concentration within a range defined by any two of the aforementioned values.

In some embodiments, the ligand or agent used in the approaches described herein for chemical induction of the signaling complex may include: rapamycin (including analogues, derivatives, and including pharmaceutically acceptable salts thereof. Rapamycin may include sirolimus (Rapamune®), (3S,6R,7E,9R,10R,12R,14S,15E,17E,19E,21S, 23S,26R,27R,34aS)-9,10,12,13,14,21,22,23,24,25,26,27, 32,33,34,34a-hexadecahydro-9,27-dihydroxy-3-[(1R)-2-[(1S,3R,4R)-4-hydroxy-3-methoxycyclohexyl]-1-methylethyl]-10,21-dimethoxy-6,8,12,14,20,26-hexamethyl-23,27-epoxy-3H-pyrido[2,1-c][1,4] oxaazacyclohentriacontine-1,5,11,28,29 (4H,6H,31H)-pentone); everolimus (including analogues, derivatives, and including pharmaceutically acceptable salts thereof. Everolimus may include RAD001, Zortress, Certican, Afinitor, Votubia, 42-O-(2-hydroxyethyl)rapamycin, (1R,9S,12S, 15R,16E,18R,19R,21R,23S,24E,26E,28E,30S,32S,35R)-1, 18-dihydroxy-12-[(2R)-1-[(1S,3R,4R)-4-(2-hydroxyethoxy)-3-methoxycyclohexyl]propan-2-yl]-19,30-dimethoxy-15,17,21,23,29,35-hexamethyl-11,36-dioxa-4-azatricyclo[30.3.1.0$^{4,9}$]hexatriaconta-16,24,26,28-tetraene-2,3,10,14,20-pentone); merilimus (including analogues, derivatives, and including pharmaceutically acceptable salts thereof. Merilimus may include SAR943, 42-O-(tetrahydrofuran-3-yl)rapamycin (Merilimus-1); 42-O-(oxetan-3-yl)rapamycin (Merilimus-2), 42-O-(tetrahydropyran-3-yl)rapamycin (Merilimus-3), 42-O-(4-methyl, tetrahydrofuran-3-yl)rapamycin, 42-O-(2,5,5-trimethyl, tetrahydrofuran-3-yl) rapamycin, 42-O-(2,5-diethyl-2-methyl, tetrahydrofuran-3-yl)rapamycin, 42-O-(2H-Pyran-3-yl, tetrahydro-6-methoxy-2-methyl)rapamycin, or 42-O-(2H-Pyran-3-yl, tetrahydro-2, 2-dimethyl-6-phenyl)rapamycin); novolimus (including analogues, derivatives, and including pharmaceutically acceptable salts thereof. Novolimus may include 16-O-demethyl rapamycin); pimecrolimus (including analogues, derivatives, and including pharmaceutically acceptable salts thereof. Pimecrolimus may include Elidel®, (3S,4R,5S,8R, 9E,12S,14S,15R,16S,18R,19R,26aS)-3-((E)-2-((1R,3R, 4S)-4-chloro-3 methoxycyclohexyl)-1-methylvinyl)-8-ethyl 5,6,8,11,12,13,14,15,16,17,18,19,24,26,26ahexadecahydro-5,19-epoxy-3H-pyrido(2,1-c)(1,4)oxaazacyclotricosine-1, 17,20,21 (4H,23H)-tetrone 33-epi-chloro-33-desoxyascomycin); ridaforolimus (including analogues, derivatives, and including pharmaceutically acceptable salts thereof. Ridaforolimus may include AP23573, MK-8669, deforolimus, (1R,9S,12S,15R,16E,18R,19R,21R,23S,24E,26E,28E, 30S,32S,35R)-12-((1R)-2-((1S,3R,4R)-4-((Dimethylphosphinoyl)oxy)-3-methoxycyclohexyl)-1-methylethyl)-1,18-dihydroxy-19,30-dimethoxy15,17,21,23,29,35-hexamethyl-11,36-dioxa-4-azatricyclo(30.3.1.04,9)hexatriaconta-16,24, 26,28-tetraene-2,3,10,14,20-pentone); tacrolimus (including analogues, derivatives, and including pharmaceutically acceptable salts thereof. Tacrolimus may include FK-506, fujimycin, Prograf®, Advagraf®, protopic, 3S-[3R*[E(1S*, 3S*,4S*)],4S*,5R*,8S*,9E,12R*,14R*,15S*,16R*,18S*, 19S*,26aR*5,6,8,11,12,13,14,15,16,17,18,19, 24,25,26, 26a-hexadecahydro-5,19-dihydroxy-3-[2-(4-hydroxy-3-methoxycyclohexyl)-1-methylethenyl]-14,16-dimethoxy-4, 10,12,18-tetramethyl-8-(2-propenyl)-15,19-epoxy-3H-pyrido[2,1-c] [1,4] oxaazacyclotricosine-1,7,20,21 (4H, 23H)-tetrone, monohydrate); temsirolimus (including analogues, derivatives, and including pharmaceutically acceptable salts thereof. Temsirolimus may include CCI-779, CCL-779, Torisel®, (1R,2R,4S)-4-{(2R)-2-[(3S,6R, 7E,9R,10R,12R,14S,15E,17E,19E,21 S,23 S,26R,27R, 34aS)-9,27-dihydroxy-10,21-dimethoxy-6,8,12,14,20,26-hexamethyl-1,5,11,28,29-pentaoxo-1,4,5,6,9,10,11,12,13, 14,21,22,23,24,25,26,27,28,29,31,32,33,34,34a-tetracosahydro-3H-23,27-epoxypyrido[2,1-c][1,4] oxaazacyclohentriacontin-3-yl]propyl}-2-methoxycyclohexyl 3-hydroxy-2-(hydroxymethyl)-2-methylpropanoate); umirolimus (including analogues, derivatives, and including pharmaceutically acceptable salts thereof. Umirolimus may include Biolimus, Biolimus A9, BA9, TRM-986, 42-O-(2-ethoxyethyl)rapamycin; zotarolimus (including analogues, derivatives, and including pharmaceutically acceptable salts thereof. Zotarolimus may include ABT-578, (42S)-42-deoxy-42-(1H-tetrazol-1-yl)-rapamycin); C20-methallylrapamycin (including analogues, derivatives, and including pharmaceutically acceptable salts thereof. C20-methallylrapamycin may include C20-Marap); C16-(S)-3-methylindolerapamycin (including analogues, derivatives, and including pharmaceutically acceptable salts thereof. C16-(S)-3-methylindolerapamycin may include C16-iRap); AP21967 (including analogues, derivatives, and including pharmaceutically acceptable salts thereof. AP21967 may include C-16-(S)-7-methylindolerapamycin); sodium mycophenolic acid (including analogues, derivatives, and including pharmaceutically acceptable salts thereof. Sodium mycophenolic acid may include CellCept®, Myfortic, (4E)-6-(4-Hydroxy-6-methoxy-7-methyl-3-oxo-1,3-dihydro-2-benzofuran-5-yl)-4-methylhex-4-enoic acid); benidipine hydrochloride (including analogues, derivatives, and including pharmaceutically acceptable salts thereof). Benidipine hydrochloride may include Coniel); or AP1903 (including analogues, derivatives, and including pharmaceutically acceptable salts thereof. AP1903 may include rimiducid, [(1R)-3-(3,4-dimethoxyphenyl)-1-[3-[2-[2-[[2-[3-[(1R)-3-(3,4-dimethoxyphenyl)-1-[(2S)-1-[(2S)-2-(3,4,5-trimethoxyphenyl)butanoyl]piperidine-2-carbonyl] oxypropyl]phenoxy]acetyl]amino]ethylamino]-2-oxoethoxy]phenyl]propyl] (2S)-1-[(2S)-2-(3,4,5-trimethoxyphenyl)butanoyl]piperidine-2-carboxylate); or any combinations thereof.

In some embodiments, the ligand used in these approaches is rapamycin or a rapalog, including, for example, everolimus, CCI-779, C20-methallylrapamycin, C16-(S)-3-methylindolerapamycin, C16-iRap, AP21967, sodium mycophenolic acid, benidipine hydrochloride, AP23573, or AP1903, or metabolites, derivatives, and/or combinations of any thereof. Additional useful rapalogs may include, for example, variants of rapamycin having one or more of the following modifications relative to rapamycin: demethylation, elimination or replacement of the methoxy at C7, C42 and/or C29; elimination, derivatization or replacement of the hydroxy at C13, C43 and/or C28; reduction, elimination or derivatization of the ketone at C14, C24 and/or C30; replacement of the 6-membered pipecolate ring with a 5-membered prolyl ring; and/or alternative substitution on the cyclohexyl ring or replacement of the cyclohexyl ring with a substituted cyclopentyl ring. Additional useful rapalogs may include novolimus, pimecrolimus, ridaforolimus, tacrolimus, temsirolimus, umirolimus, or zotarolimus, or metabolites, derivatives, and/or combinations of any thereof. In some embodiments, the ligand is an IMID-class drug (e.g. thalidomide, pomalidomide, lenalidomide or related analogues).

In some embodiments, detecting a signal in the interior of the cell, such as a mammalian cell, can be achieved by a method of detecting a marker that is the result of a signaling pathway. Thus, for example, a signal may be detected by determining the levels of Akt or other signaling marker in a cell, such as a mammalian cell, through a process of Western blot, flow cytometry, or other protein detection and quantification method. Markers for detection may include, for example, JAK, Akt, STAT, NF-κ, MAPK, PI3K, JNK, ERK, or Ras, or other cellular signaling markers that are indicative of a cellular signaling event.

In some embodiments, transduction of a signal affects cytokine signaling. In some embodiments, transduction of the signal affects IL2R signaling. In some embodiments, transduction of the signal affects phosphorylation of a downstream target of a cytokine receptor. In some embodiments, the method of activating a signal induces proliferation in CISC-expressing cells, such as mammalian cells, and a concomitant anti-proliferation in non-CISC expressing cells.

For cellular signaling to take place, not only must cytokine receptors dimerize or heterodimerize, but they must be in the proper configuration for a conformational change to take place (Kim, M. J. et al. (2007). *J. Biol. Chem.*, 282 (19):14253-14261). Thus, dimerization in conjunction with the correct conformational positioning of signaling domains are desired processes for appropriate signaling, because receptor dimerization or heterodimerization alone is insufficient to drive receptor activation. The chemical-induced signaling complexes described herein are generally in the correct orientation for downstream signaling events to occur.

Method of Selective Expansion of Cell Populations

In some embodiments, a method of selectively expanding a population of cells, such as mammalian cells, is provided herein. In some embodiments, the method includes providing a cell, such as a mammalian cell, as described herein, wherein the cell includes a protein sequence as set forth herein or an expression vector as set forth herein. In some embodiments, the method further includes expressing the protein sequence encoding a naked FRB domain polypeptide and/or a dimeric CISC as described herein, or expression the vector as described herein. In some embodiments, the method includes contacting the cell, such as a mammalian cell, with a ligand, which causes the first and second CISC components to dimerize, which transduces a signal into the interior of the cell. In some embodiments, the ligand is rapamycin or rapalog (such as any of the rapamycin or rapalog compounds disclosed herein). In some embodiments an effective amount of a ligand provided for inducing dimerization is an amount of 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10, 11, 12, 13, 14, 15, 20, 25, 30, 35, 40, 45, 50, 55, 60, 65, 70, 75, 80, 85, 90, 95, or 100 nM or a concentration within a range defined by any two of the aforementioned values.

In some embodiments, the ligand used is rapamycin or a rapalog, including, for example, everolimus, CCI-779, C20-methallylrapamycin, C16-(S)-3-methylindolerapamycin, C16-iRap, AP21967, sodium mycophenolic acid, benidipine hydrochloride, or AP23573, AP1903, or metabolites, derivatives, and/or combinations of any thereof. Additional useful rapalogs may include, for example, variants of rapamycin having one or more of the following modifications relative to rapamycin: demethylation, elimination or replacement of the methoxy at C7, C42 and/or C29; elimination, derivatization or replacement of the hydroxy at C13, C43 and/or C28; reduction, elimination or derivatization of the ketone at C14, C24 and/or C30; replacement of the 6-membered pipecolate ring with a 5-membered prolyl ring; and/or alternative substitution on the cyclohexyl ring or replacement of the cyclohexyl ring with a substituted cyclopentyl ring. Additional useful rapalogs may include novolimus, pimecrolimus, ridaforolimus, tacrolimus, temsirolimus, umirolimus, or zotarolimus, or metabolites, derivatives, and/ or combinations of any thereof.

In some embodiments, the selective expansion of a population of cells, such as mammalian cells, takes place only when two distinct genetic modification events have taken place (such as a genetic modification mediated by a CRISPR/Cas9 system). One genetic modification event is one component of the dimeric chemical-induced signaling complex, and the other genetic modification event is the other component of the dimeric chemical-induced signaling complex. When both events take place within the population of cells, such as a population of mammalian cells, the chemical-induced signaling complex components dimerize in the presence of a ligand, resulting in an active chemical-induced signaling complex and generation of a signal into the interior of the cells.

Methods for Genome Editing

In some embodiments, provided herein is a method of editing the genome of a cell, in particular, editing the cell genome to allow for expression of i) a naked FRB domain polypeptide within the cytoplasm of the cell, and optionally ii) one or more polypeptide components of a dimerization activatable chemical-induced signaling complex (CISC), wherein the signaling-competent CISC is capable of producing a stimulatory signal in a signaling pathway that promotes survival and/or proliferation of the cell.

In one aspect, provided herein is a method of editing the genome of a cell, the method including providing to the cell i) a deoxyribonucleic acid (DNA) endonuclease or nucleic acid encoding the DNA endonuclease; ii) a guide RNA (gRNA) including a spacer sequence complementary to a target sequence within a target genomic locus in a cell, or nucleic acid encoding the gRNA; and iii) a donor template including a donor cassette including a nucleic acid sequence encoding a naked FKBP-rapamycin binding (FRB) domain polypeptide, wherein the DNA endonuclease, gRNA, and donor template are configured such that a complex formed by association of the DNA endonuclease with the gRNA is capable of promoting targeted integration of the donor cassette into the target genomic locus in a cell to generate a genetically modified cell capable of expressing the naked FRB domain polypeptide.

In one aspect, provided herein is a method of editing the genome of a cell, the method including providing to the cell a) a gRNA directed to a gene or genomic sequence of interest b) a RGEN or a nucleic acid encoding the RGEN according to any of the embodiments described herein, c) a nucleic acid encoding a naked FRB domain and d) one or more donor templates including nucleic acids encoding i) a first CISC component including a first extracellular binding domain or functional derivative thereof, a hinge domain, a transmembrane domain, and a signaling domain or functional derivative thereof or functional derivative thereof; and i) a second CISC component including a second extracellular binding domain or functional derivative thereof, a hinge domain, a transmembrane domain, and a signaling domain or functional derivative thereof, wherein the first CISC component and the second CISC component are configured, e.g. are positioned, such that when expressed by a T cell, they dimerize in the presence of a ligand (for example, rapamycin) to create a signaling competent CISC capable of producing a downstream signal (such as a survival signal or a proliferation signal). In some embodiments, one of the CISC components includes a truncated IL2Rβ intracellular signaling domain.

In some embodiments, according to any of the methods of editing the genome of a cell described herein, one or more nucleic acids encoding the first CISC component including a first extracellular binding domain or functional derivative thereof, a hinge domain, a transmembrane domain, and a signaling domain or functional derivative thereof or functional derivative thereof; and i) a second CISC component including a second extracellular binding domain or functional derivative thereof, a hinge domain, a transmembrane domain, and a signaling domain or functional derivative thereof, wherein the one or more nucleic acids encoding the first CISC component and the second CISC component are expressed in one or more vectors. The extracellular binding domain can also include an endoplasmic reticulum signal sequence to target the protein to the extracellular space. In some embodiments, the vectors include the nucleic acid sequences according to one or more of SEQ ID NOs.: 3, 8, 28, 29, and 30.

In some embodiments, according to any of the methods of editing the genome of a cell described herein, the RGEN is selected from the group consisting of a Cas1, Cas1B, Cas2, Cas3, Cas4, Cas5, Cas6, Cas7, Cas8, Cas9 (also known as Csn1 and Csx12), Cas100, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, and Cpf1 endonuclease, or a functional derivative thereof. In some embodiments, the RGEN is Cas 9. In some embodiments, the nucleic acid encoding the RGEN is a ribonucleic acid (RNA) sequence. In some embodiments, the RNA sequence encoding the RGEN is linked to the first gRNA or the second gRNA via a covalent bond. In some embodiments, the RGEN is pre-complexed with the first gRNA and/or the second gRNA, forming an RNP complex, prior to the provision to the cell. In some embodiments, the RGEN is pre-complexed with the first gRNA and/or the second gRNA at a molar ratio of gRNA to RGEN between 1:1 to 20:1, respectively.

Targeted Integration

In some embodiments, the methods provided herein allow for integration of a sequence encoding a naked FRB domain polypeptide or a functional derivative thereof at a specific location in a host genome, a process which is referred to as "targeted integration". In some embodiments, targeted integration is enabled to generate a double-stranded break in the genomic DNA by using a sequence-specific nuclease, such as a site-directed polypeptide, for example a DNA endonuclease (e.g., a nucleic acid-guided nuclease such as Cas9).

The CRISPR-Cas system used in some embodiments has the advantage that a large number of genomic targets can be rapidly screened to identify an optimal CRISPR-Cas design. The CRISPR-Cas system uses an RNA molecule referred to as a single guide RNA (sgRNA) that targets an associated Cas nuclease (for example the Cas9 nuclease) to a specific sequence in DNA. This targeting occurs by Watson-Crick based pairing between the sgRNA and the sequence of the genome within the approximately 20 bp targeting sequence of the sgRNA. Once bound at a target site, the Cas nuclease cleaves both strands of the genomic DNA creating a double-strand break. The only requirement for designing a sgRNA to target a specific DNA sequence is that the target sequence must contain a protospacer adjacent motif (PAM) sequence at the 3' end of the sgRNA sequence that is complementary to the genomic sequence. In the case of the Cas9 nuclease, the PAM sequence is NRG (where R is A or G, and N is any base), or the more restricted PAM sequence NGG. Therefore, sgRNA molecules that target any region of the genome can be designed in silico by locating the 20 bp sequence adjacent to all PAM motifs. PAM motifs occur on average very 15 bp in the genome of eukaryotes. However, sgRNA designed by in silico methods will generate double-strand breaks in cells with differing efficiencies and it is not possible to predict the cutting efficiencies of a series of sgRNA molecule using in silico methods. Because sgRNA can be rapidly synthesized in vitro this enables the rapid screening of all potential sgRNA sequences in a given genomic region to identify the sgRNA that results in the most efficient cutting. Generally, when a series of sgRNAs within a given genomic region are tested in cells, a range of cleavage efficiencies between 0 and 90% is observed. In silico algorithms as well as laboratory experiments can also be used to determine the off-target potential of any given sgRNA. While a perfect match to the 20 bp recognition sequence of a sgRNA will primarily occur only once in most eukaryotic genomes there will be a number of additional sites in the genome with one or more base pair mismatches to the sgRNA. These sites can be cleaved at variable frequencies which are often not predictable based on the number or location of the mismatches. Cleavage at additional off-target sites that were not identified by the in silico analysis can also occur. Thus, screening a number of sgRNA in a relevant cell type to identify sgRNA that have the most favorable off-target profile is a critical component of selecting an optimal sgRNA for therapeutic use. A favorable off-target profile takes into account not only the number of actual off-target sites and the frequency of cutting at these sites, but also the location in the genome of these sites. For example, off-target sites close to or within functionally important genes, particularly oncogenes or anti-oncogenes would be considered as less favorable than sites in intergenic regions with no known function. Thus, the identification of an optimal sgRNA cannot be predicted simply by in silico analysis of the genomic sequence of an organism but requires experimental testing. While in silico analysis can be helpful in narrowing down the number of guides to test it cannot predict guides that have high on-target cutting or predict guides with low desirable off-target cutting. Experimental data indicates that the cutting efficiency of sgRNA that each has a perfect match to the genome in a region of interest (such as the fibrinogen-a intron 1) varies from no cutting to >90% cutting and is not predictable by any known algorithm. The ability of a given sgRNA to promote cleavage by a Cas enzyme can relate to the accessibility of that specific site in the genomic DNA which can be determined by the chromatin structure in that region. While the majority of the genomic DNA in a quiescent differentiated cell exists in highly condensed heterochromatin, regions that are actively transcribed exists in more open chromatin states that are known to be more accessible to large molecules such as proteins like the Cas protein. Even within actively transcribed genes some specific regions of the DNA are more accessible than others due to the presence or absence of bound transcription factors or other regulatory proteins. Predicting sites in the genome or within a specific genomic locus or region of a genomic locus is not possible and therefore would need to be determined experimentally in a relevant cell type. Once some sites are selected as potential sites for insertion, it can be possible to add some variations to such a site, e.g., by moving a few nucleotides upstream or downstream from the selected sites, with or without experimental tests.

In some embodiments, gRNAs that can be used in the methods disclosed herein include a spacer sequence that is complementary to a sequence within a FOXP3 locus, AAVS1 locus, or a TCRa (TRAC) locus in the cell. In some embodiments, gRNAs that can be used in the methods disclosed herein one or more spacer sequences from the nucleotide sequence of any one of SEQ ID NOs: 40-57 or any derivatives thereof having at least or at least about 85% nucleotide sequence identity to the nucleotide sequence of any one of SEQ ID NOs: 40-57.

Nucleic Acid Modifications

In some embodiments, polynucleotides introduced into cells have one or more modifications that can be used individually or in combination, for example, to enhance activity, stability, or specificity, alter delivery, reduce innate immune responses in host cells, or for other enhancements, as further described herein and known in the art.

In certain embodiments, modified polynucleotides are used in the CRISPR/Cas9/Cpf1 system, in which case the guide RNAs (either single-molecule guides or double-molecule guides) and/or a DNA or an RNA encoding a Cas or Cpf1 endonuclease introduced into a cell can be modified, as described and illustrated below. Such modified polynucleotides can be used in the CRISPR/Cas9/Cpf1 system to edit any one or more genomic loci.

Using the CRISPR/Cas9/Cpf1 system for purposes of non-limiting illustrations of such uses, modifications of guide RNAs can be used to enhance the formation or stability of the CRISPR/Cas9/Cpf1 genome editing complex having guide RNAs, which can be single-molecule guides or double-molecule, and a Cas or Cpf1 endonuclease. Modifications of guide RNAs can also or alternatively be used to enhance the initiation, stability, or kinetics of interactions between the genome editing complex with the target sequence in the genome, which can be used, for example, to enhance on-target activity. Modifications of guide RNAs can also or alternatively be used to enhance specificity, e.g., the relative rates of genome editing at the on-target site as compared to effects at other (off-target) sites.

Modifications can also or alternatively be used to increase the stability of a guide RNA, e.g., by increasing its resistance to degradation by ribonucleases (RNases) present in a cell, thereby causing its half-life in the cell to be increased. Modifications enhancing guide RNA half-life can be particularly useful in embodiments in which a Cas or Cpf1 endonuclease is introduced into the cell to be edited via an RNA that needs to be translated to generate endonuclease, because increasing the half-life of guide RNAs introduced at the same time as the RNA encoding the endonuclease can be used to increase the time that the guide RNAs and the encoded Cas or Cpf1 endonuclease co-exist in the cell.

Modifications can also or alternatively be used to decrease the likelihood or degree to which RNAs introduced into cells elicit innate immune responses. Such responses, which have been well characterized in the context of RNA interference (RNAi), including small-interfering RNAs (siRNAs), as described below and in the art, tend to be associated with reduced half-life of the RNA and/or the elicitation of cytokines or other factors associated with immune responses.

One or more types of modifications can also be made to RNAs encoding an endonuclease that are introduced into a cell, including, without limitation, modifications that enhance the stability of the RNA (such as by increasing its degradation by RNAses present in the cell), modifications that enhance translation of the resulting product (such as the endonuclease), and/or modifications that decrease the likelihood or degree to which the RNAs introduced into cells elicit innate immune responses.

Combinations of modifications, such as the foregoing and others, can likewise be used. In the case of CRISPR/Cas9/Cpf1, for example, one or more types of modifications can be made to guide RNAs (including those exemplified above), and/or one or more types of modifications can be made to RNAs encoding Cas endonuclease (including those exemplified above).

By way of illustration, guide RNAs used in the CRISPR/Cas9/Cpf1 system, or other smaller RNAs can be readily synthesized by chemical means, enabling a number of modifications to be readily incorporated, as illustrated below and described in the art. While chemical synthetic procedures are continually expanding, purifications of such RNAs by procedures such as high performance liquid chromatography (HPLC, which avoids the use of gels such as PAGE) tends to become more challenging as polynucleotide lengths increase significantly beyond a hundred or so nucleotides. One approach used for generating chemically-modified RNAs of greater length is to produce two or more molecules that are ligated together. Much longer RNAs, such as those encoding a Cas9 endonuclease, are more readily generated enzymatically. While fewer types of modifications are generally available for use in enzymatically produced RNAs, there are still modifications that can be used to, e.g., enhance stability, reduce the likelihood or degree of innate immune response, and/or enhance other attributes, as described further below and in the art; and new types of modifications are regularly being developed.

By way of illustration of various types of modifications, especially those used frequently with smaller chemically synthesized RNAs, modifications can have one or more nucleotides modified at the 2' position of the sugar, in some embodiments a 2'-O-alkyl, 2'-O-alkyl-O-alkyl, or 2'-fluoro-modified nucleotide. In some embodiments, RNA modifications include 2'-fluoro, 2'-amino, or 2' O-methyl modifications on the ribose of pyrimidines, abasic residues, or an inverted base at the 3' end of the RNA. Such modifications are routinely incorporated into oligonucleotides and these oligonucleotides have been shown to have a higher Tm (such as higher target binding affinity) than 2'-deoxyoligonucleotides against a given target.

A number of nucleotide and nucleoside modifications have been shown to make the oligonucleotide into which they are incorporated more resistant to nuclease digestion than the native oligonucleotide; these modified oligos survive intact for a longer time than unmodified oligonucleotides. Specific examples of modified oligonucleotides include those having modified backbones, for example, phosphorothioates, phosphotriesters, methyl phosphonates, short chain alkyl or cycloalkyl intersugar linkages or short chain heteroatomic or heterocyclic intersugar linkages. Some oligonucleotides are oligonucleotides with phosphorothioate backbones and those with heteroatom backbones, particularly CH2-NH—O—CH2, CH, ~N(CH3)~O~CH2 (known as a methylene(methylimino) or MMI backbone), CH2-O—N (CH3)-CH2, CH2-N(CH3)-N(CH3)-CH2 and O—N(CH3)-CH2-CH2 backbones, wherein the native phosphodiester backbone is represented as O—P—O—CH); amide backbones (see De Mesmaeker, A. et al. (1995). *Acc. Chem. Res.*, 28:366-374); morpholino backbone structures (see Summerton and Weller, U.S. Pat. No. 5,034,506); peptide nucleic acid (PNA) backbone (where the phosphodiester backbone of the oligonucleotide is replaced with a polyamide backbone, the nucleotides being bound directly or indirectly to the aza nitrogen atoms of the polyamide backbone, see Nielsen, P. E. et al. (1991). *Science*, 254 (5037):1497-1500). Phosphorus-containing linkages include, but are not limited to, phosphorothioates, chiral phosphorothioates, phosphorodithioates, phosphotriesters, aminoalkylphosphotriesters, methyl and other alkyl phosphonates having 3' alkylene phosphonates and chiral phosphonates, phosphinates, phosphoramidates having 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2; see U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050.

Morpholino-based oligomeric compounds are described in Braasch, D. A. et al. (2002). *Biochemistry*, 41(14):4503-4510; Genesis, Volume 30, Issue 3, (2001); Heasman, J. (2002). *Dev. Biol.*, 243(2):209-214; Nasevicius, A. et al. (2000). *Nat. Genet.*, 26(2):216-220; Lacerra, G. et al. (2000). *Proc. Natl. Acad. Sci. U.S.A.*, 97(17):9591-9596; and U.S. Pat. No. 5,034,506, issued Jul. 23, 1991.

Cyclohexenyl nucleic acid oligonucleotide mimetics are described in Wang, J. et al. (2000). *J. Am. Chem. Soc.*, 122(36):8595-8602.

Modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These have those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S, and CH2 component parts; see U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

One or more substituted sugar moieties can also be included, e.g., one of the following at the 2' position: OH, SH, SCH$_3$, F, OCN, OCH$_3$, OCH$_3$O(CH$_2$)n CH$_3$, O(CH$_2$)n NH$_2$, or O(CH$_2$)n CH$_3$, where n is from 1 to or to about 10; C1 to C10 lower alkyl, alkoxyalkoxy, substituted lower alkyl, alkaryl, or aralkyl; Cl; Br; CN; CF$_3$; OCF$_3$; O-, S-, or N-alkyl; O-, S-, or N-alkenyl; SOCH$_3$; SO$_2$CH$_3$; ONO$_2$; NO$_2$; N$_3$; NH$_2$; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. In some embodiments, a modification includes 2'-methoxyethoxy (2'-O—CH$_2$CH$_2$OCH$_3$, also known as 2'-O-(2-methoxyethyl)) (Martin, P. et al. (1995). *Helv. Chim. Acta*, 78(2):486-504). Other modifications include 2'-methoxy (2'-0-CH$_3$), 2'-propoxy (2'-OCH$_2$CH$_2$CH$_3$) and 2'-fluoro (2'-F). Similar modifications can also be made at other positions on the oligonucleotide, particularly the 3' position of the sugar on the 3' terminal nucleotide and the 5' position of 5' terminal nucleotide. Oligonucleotides can also have sugar mimetics, such as cyclobutyls in place of the pentofuranosyl group.

In some embodiments, both a sugar and an internucleoside linkage, such as the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, for example, an aminoethylglycine backbone. The nucleobases are retained and are bound directly or indirectly to aza nitrogen atoms of the amide portion of the backbone. Representative United States patents that teach the preparation of PNA compounds have, but are not limited to, U.S. Pat. Nos. 5,539,082; 5,714,331; and 5,719,262. Further teaching of PNA compounds can be found in Nielsen, P. E. et al. (1991). *Science*, 254(5037):1497-1500.

In some embodiments, guide RNAs can also include, additionally or alternatively, nucleobase (often referred to in the art simply as "base") modifications or substitutions. As used herein, "unmodified" or "natural" nucleobases include adenine (A), guanine (G), thymine (T), cytosine (C), and uracil (U). Modified nucleobases include nucleobases found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, as well as synthetic nucleobases, e.g., 2-aminoadenine, 2-(methylamino)adenine, 2-(imidazolylalkyl)adenine, 2-(aminoalklyamino)adenine, or other heterosubstituted alkyladenines, 2-thiouracil, 2-thiothymine, 5-bromouracil, 5-hydroxymethyluracil, 8-azaguanine, 7-deazaguanine, N6 (6-aminohexyl)adenine, and 2,6-diaminopurine. Kornberg, A. et al. (1980). *DNA Replication* ($2^{nd}$ ed., pp. 75-77). San Francisco, CA: W. H. Freeman & Co.; Gebeyehu, G. et al. (1987). *Nucl Acids Res.*, 15(11): 4513-4534. A "universal" base known in the art, e.g., inosine, can also be included. 5-Me-C substitutions have been shown to increase nucleic acid duplex stability by 0.6-1.2° C. (Sanghvi, Y. S. (1993). *Antisense Research and Applications*, (pp. 276-278). Crooke, S. T. and Lebleu, B., (Eds.), Boca Raton, FL: CRC Press) and are embodiments of base substitutions.

In some embodiments, modified nucleobases include other synthetic and natural nucleobases, such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudo-uracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylquanine and 7-methyladenine, 8-azaguanine and 8-azaadenine, 7-deazaguanine and 7-deazaadenine, and 3-deazaguanine and 3-deazaadenine.

Further, nucleobases include those disclosed in U.S. Pat. No. 3,687,808; those disclosed in Kroschwitz, J. (1990). *Concise Encyclopedia of Polymer Science And Engineering*, (pp. 858-859) New York, NY: Wiley; those disclosed by Englisch, U. et al. (1991). *Angewandte Chemie International Edition*, 30(6):613-722; and those disclosed by Sanghvi, Y. S. (1993). Chapter 15, *Antisense Research and Applications*, (pp. 289-302), Crooke, S. T. and Lebleu, B. (Eds), Boca Raton, FL: CRC Press. Certain of these nucleobases are particularly useful for increasing the binding affinity of the oligomeric compounds of the disclosure. These include 5-substituted pyrimidines, 6-azapyrimidines and N-2, N-6 and 0-6 substituted purines, having 2-aminopropyladenine, 5-propynyluracil and 5-propynylcytosine. 5-methylcytosine substitutions have been shown to increase nucleic acid duplex stability by 0.6-1.2° C. (Sanghvi, Y. S. (1993). *Antisense Research and Applications*, (pp. 276-278). Crooke, S. T. and Lebleu, B., (Eds.), Boca Raton, FL: CRC Press) and are embodiments of base substitutions, even more particularly when combined with 2'-O-methoxyethyl sugar modifications. Modified nucleobases are described in U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,596,091; 5,614,617; 5,681,941; 5,750,692; 5,763,588; 5,830,653; 6,005,096; and U.S. Patent Application Publication 2003/0158403.

In some embodiments, the guide RNAs and/or mRNA (or DNA) encoding an endonuclease are chemically linked to one or more moieties or conjugates that enhance the activity, cellular distribution, or cellular uptake of the oligonucleotide. Such moieties include, but are not limited to, lipid moieties such as a cholesterol moiety (Letsinger, R. L. et al. (1989). *Proc. Natl. Acad. Sci. U.S.A.,* 86(17):6553-6556); cholic acid (Manoharan, M. et al. (1994). *Bioorg. Med. Chem. Let.,* 4(8):1053-1060); a thioether, e.g., hexyl-S-tritylthiol (Manoharan, M. et al. (1992). *Ann. N.Y. Acad. Sci.,* 660(1):306-309; and Manoharan, M. et al. (1993). *Bioorg. Med. Chem. Let.,* 3(12):2765-2770); a thiocholesterol (Oberhauser, B. et al. (1992). *Nucl. Acids Res.,* 20(3):533-538); an aliphatic chain, e.g., dodecandiol or undecyl residues (Kabanov, A. V. et al. (1990). *FEBS Lett.,* 259(2):327-330 and Svinarchuk, F. P. et al. (1993). *Biochimie,* 75(1-2):49-54); a phospholipid, e.g., di-hexadecyl-rac-glycerol or triethylammonium 1,2-di-O-hexadecyl-rac-glycero-3-H-phosphonate (Manoharan et al. (1995). *Tetrahedron Lett.,* 36(21):3651-3654 and Shea, R. G. et al. (1990). *Nucl. Acids Res.,* 18(13):3777-3783); a polyamine or a polyethylene glycol chain (Manohoran, M. et al. (1995). *Nucleos. Nucleot. Nucl.,* 14(3-5): 969-973); adamantane acetic acid (Manoharan, M. et al. (1995). *Tetrahedron Lett.,* 36(21):3651-3654); a palmityl moiety (Mishra, R. K. et al. (1995). *Biochim. Biophys. Acta,* 1264(2):229-237); or an octadecylamine or hexylamino-carbonyl-t oxycholesterol moiety (Crooke, S. T. et al. (1996). *J. Pharmacol. Exp. Ther.,* 277(2):923-937). See also U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599, 928; and 5,688,941.

In some embodiments, sugars and other moieties can be used to target proteins and complexes having nucleotides, such as cationic polysomes and liposomes, to particular sites. For example, hepatic cell directed transfer can be mediated via asialoglycoprotein receptors (ASGPRs); see, e.g., Hu, J. et al. (2014). *Protein Pept. Lett.,* 21(10):1025-1030. Other systems known in the art and regularly developed can be used to target biomolecules of use in the present case and/or complexes thereof to particular target cells of interest.

In some embodiments, these targeting moieties or conjugates can include conjugate groups covalently bound to functional groups, such as primary or secondary hydroxyl groups. Conjugate groups of the disclosure include intercalators, reporter molecules, polyamines, polyamides, polyethylene glycols, polyethers, groups that enhance the pharmacodynamic properties of oligomers, and groups that enhance the pharmacokinetic properties of oligomers. Exemplary conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this disclosure, include groups that improve uptake, enhance resistance to degradation, and/or strengthen sequence-specific hybridization with the target nucleic acid. Groups that enhance the pharmacokinetic properties, in the context of this disclosure, include groups that improve uptake, distribution, metabolism, or excretion of the compounds of the present disclosure. Representative conjugate groups are disclosed in International Patent Application No. PCT/US92/09196, filed Oct. 23, 1992, and U.S. Pat. No. 6,287,860, which are incorporated herein by reference. Conjugate moieties include, but are not limited to, lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxy cholesterol moiety. See, e.g., U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737;

4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

Longer polynucleotides that are less amenable to chemical synthesis and are generally produced by enzymatic synthesis can also be modified by various means. Such modifications can include, for example, the introduction of certain nucleotide analogs, the incorporation of particular sequences or other moieties at the 5' or 3' ends of molecules, and other modifications. By way of illustration, the mRNA encoding Cas9 is approximately 4 kb in length and can be synthesized by in vitro transcription. Modifications to the mRNA can be applied to, e.g., increase its translation or stability (such as by increasing its resistance to degradation with a cell), or to reduce the tendency of the RNA to elicit an innate immune response that is often observed in cells following introduction of exogenous RNAs, particularly longer RNAs such as that encoding Cas9.

Numerous such modifications have been described in the art, such as polyA tails, 5' cap analogs (e.g., Anti Reverse Cap Analog (ARCA) or m7G(5')ppp(5')G (mCAP)), modified 5' or 3' untranslated regions (UTRs), use of modified bases (such as Pseudo-UTP, 2-Thio-UTP, 5-Methylcytidine-5'-Triphosphate (5-Methyl-CTP) or N6-Methyl-ATP), or treatment with phosphatase to remove 5' terminal phosphates. These and other modifications are known in the art, and new modifications of RNAs are regularly being developed.

There are numerous commercial suppliers of modified RNAs, including for example, TriLink Biotech, AxoLabs, Bio-Synthesis Inc., Dharmacon and many others. As described by TriLink, for example, 5-methyl-CTP can be used to impart desirable characteristics, such as increased nuclease stability, increased translation or reduced interaction of innate immune receptors with in vitro transcribed RNA. 5-methylcytidine-5'-triphosphate (5-methyl-CTP), N6-methyl-ATP, as well as pseudo-UTP and 2-thio-UTP, have also been shown to reduce innate immune stimulation in culture and in vivo while enhancing translation, as illustrated in publications by Kormann et al. (2011) and Warren et al. (2010) referred to below.

It has been shown that chemically modified mRNA delivered in vivo can be used to achieve improved therapeutic effects; see, e.g., Kormann, M. S. D. et al. (2011). *Nat. Biotechnol.,* 29:154-157. Such modifications can be used, for example, to increase the stability of the RNA molecule and/or reduce its immunogenicity. Using chemical modifications such as pseudo-U, N6-methyl-A, 2-thio-U, and 5-methyl-C, it was found that substituting just one quarter of the uridine and cytidine residues with 2-thio-U and 5-methyl-C respectively resulted in a significant decrease in toll-like receptor (TLR) mediated recognition of the mRNA in mice. By reducing the activation of the innate immune system, these modifications can be used to effectively increase the stability and longevity of the mRNA in vivo; see, e.g., Kormann et al. (2011).

It has also been shown that repeated administration of synthetic messenger RNAs incorporating modifications designed to bypass innate anti-viral responses can reprogram differentiated human cells to pluripotency. See, e.g., Warren, L. et al. (2010). *Cell Stem Cell,* 7(5):618-630. Such modified mRNAs that act as primary reprogramming proteins can be an efficient means of reprogramming multiple human cell types. Such cells are referred to as induced pluripotency stem cells (iPSCs), and it was found that enzymatically synthesized RNA incorporating 5-methyl-CTP, pseudo-UTP, and an Anti Reverse Cap Analog (ARCA) could be used to effectively evade the cell's antiviral response; see, e.g., Warren et al. (2010).

Other modifications of polynucleotides described in the art include, for example, the use of polyA tails, the addition of 5' cap analogs (such as m7G(5')ppp(5')G (mCAP)), modifications of 5' or 3' untranslated regions (UTRs), or treatment with phosphatase to remove 5' terminal phosphates—and new approaches are regularly being developed.

A number of compositions and techniques applicable to the generation of modified RNAs for use herein have been developed in connection with the modification of RNA interference (RNAi), including small-interfering RNAs (siRNAs). siRNAs present particular challenges in vivo because their effects on gene silencing via mRNA interference are generally transient, which can require repeat administration. In addition, siRNAs are double-stranded RNAs (dsRNA) and mammalian cells have immune responses that have evolved to detect and neutralize dsRNA, which is often a by-product of viral infection. Thus, there are mammalian enzymes such as PKR (dsRNA-responsive kinase), and potentially retinoic acid-inducible gene I (RIG-I), that can mediate cellular responses to dsRNA, as well as Toll-like receptors (such as TLR3, TLR7, and TLR8) that can trigger the induction of cytokines in response to such molecules; see, e.g., the reviews by Angart, P. et al. (2013). *Pharmaceuticals,* 6(4):440-468; Kanasty, R. L. et al. (2012). *Mol. Ther.,* 20(3):513-524; Burnett, J. C. et al. (2011). *Biotechnol. J.,* 6(9):1130-1146; Judge, A. D. (2008). *Hum. Gene Ther.,* 19(2):111-124; and references cited therein.

A large variety of modifications have been developed and applied to enhance RNA stability, reduce innate immune responses, and/or achieve other benefits that can be useful in connection with the introduction of polynucleotides into human cells, as described herein; see, e.g., the reviews by Whitehead, K. A. et al. (2011). *Ann. Rev. Chem. Biomolec. Eng.,* 2:77-96; Gaglione, M. et al. (2010). *Mini Rev. Med. Chem.,* 10(7):578-595; Chernolovskaya, E. L. et al. (2010). *Curr. Opin. Mol Ther.,* 12(2):158-167; Deleavey, G. G. et al. (2009). *Curr. Protoc. Nucleic Acid Chem.,* 39(1):16.3.1-16.3.22; Behlke, M. A. (2008). *Oligonucleotides,* 18(4):305-319; Fucini, R. V. et al. (2012). *Nucleic Acid Ther.,* 22(3):205-210; Bremsen, J. B. et al. (2012). *Front. Genet.,* 3:154.

As noted above, there are a number of commercial suppliers of modified RNAs, many of which have specialized in modifications designed to improve the effectiveness of siRNAs. A variety of approaches are offered based on various findings reported in the literature. For example, Dharmacon notes that replacement of a non-bridging oxygen with sulfur (phosphorothioate, PS) has been extensively used to improve nuclease resistance of siRNAs, as reported by Kole, R. (2012). *Nat. Rev. Drug Disc.,* 11(2):125-140. Modifications of the 2'-position of the ribose have been reported to improve nuclease resistance of the internucleotide phosphate bond while increasing duplex stability (Tm), which has also been shown to provide protection from immune activation. A combination of moderate PS backbone modifications with small, well-tolerated 2'-substitutions (2'-O-methyl, 2'-fluoro, 2'-hydro) have been associated with highly stable siRNAs for applications in vivo, as reported by Soutschek, J. et al. (2004). *Nature,* 432:173-178; and 2'-O-methyl modifications have been reported to be effective in improving stability as reported by Volkov, A. A. et al. (2009). *Oligonucleotides,* 19:191-202. With respect to decreasing the induction of innate immune responses, modifying specific sequences with 2'-O-methyl, 2'-fluoro, 2'-hydro have been reported to reduce TLR7/TLR8 interaction while generally preserving silencing activity; see, e.g., Judge, A. D. et al. (2006). *Mol. Ther.*, 13:494-505; and Cekaite, L. et al. (2007). *J. Mol. Biol.*, 365(1):90-108. Additional modifications, such as 2-thiouracil, pseudouracil, 5-methylcytosine, 5-methyluracil, and N6-methyladenosine have also been shown to minimize the immune effects mediated by TLR3, TLR7, and TLR8; see, e.g., Kariko, K. et al. (2005). *Immunity*, 23(2):165-175.

As is also known in the art, and commercially available, a number of conjugates can be applied to polynucleotides, such as RNAs, for use herein that can enhance their delivery and/or uptake by cells, including for example, cholesterol, tocopherol and folic acid, lipids, peptides, polymers, linkers, and aptamers; see, e.g., the review by Winkler, J. (2013). *Ther. Deliv.*, 4(7):791-809, and references cited therein.

Delivery

In some embodiments, any nucleic acid molecules used in the methods provided herein, e.g., a nucleic acid encoding a genome-targeting nucleic acid of the disclosure and/or a site-directed polypeptide, are packaged into or on the surface of delivery vehicles for delivery to cells. Delivery vehicles contemplated include, but are not limited to, nanospheres, liposomes, quantum dots, nanoparticles, polyethylene glycol particles, hydrogels, and micelles. As described in the art, a variety of targeting moieties can be used to enhance the preferential interaction of such vehicles with desired cell types or locations.

Introduction of the complexes, polypeptides, and nucleic acids of the disclosure into cells can occur by viral or bacteriophage infection, transfection, conjugation, protoplast fusion, lipofection, electroporation, nucleofection, calcium phosphate precipitation, polyethyleneimine (PEI)-mediated transfection, DEAE-dextran mediated transfection, liposome-mediated transfection, particle gun technology, calcium phosphate precipitation, direct micro-injection, nanoparticle-mediated nucleic acid delivery, and the like.

In embodiments, guide RNA polynucleotides (RNA or DNA) and/or endonuclease polynucleotide(s) (RNA or DNA) can be delivered by viral or non-viral delivery vehicles known in the art. Alternatively, endonuclease polypeptide(s) can be delivered by viral or non-viral delivery vehicles known in the art, such as electroporation or lipid nanoparticles. In some embodiments, the DNA endonuclease can be delivered as one or more polypeptides, either alone or pre-complexed with one or more guide RNAs, or one or more crRNA together with a tracrRNA.

In embodiments, polynucleotides can be delivered by non-viral delivery vehicles including, but not limited to, nanoparticles, liposomes, ribonucleoproteins, positively charged peptides, small molecule RNA-conjugates, aptamer-RNA chimeras, and RNA-fusion protein complexes. Some exemplary non-viral delivery vehicles are described in Peer, D. et al. (2011). *Gene Ther.*, 18:1127-1133 (which focuses on non-viral delivery vehicles for siRNA that are also useful for delivery of other polynucleotides).

In embodiments, polynucleotides, such as guide RNA, sgRNA, and mRNA encoding an endonuclease, can be delivered to a cell or a subject by a lipid nanoparticle (LNP).

While several non-viral delivery methods for nucleic acids have been tested both in animal models and in humans the most well developed system is lipid nanoparticles. Lipid nanoparticles (LNP) are generally composed of an ionizable cationic lipid and 3 or more additional components, generally cholesterol, DOPE, and a polyethylene glycol (PEG) containing lipid. The cationic lipid can bind to the positively charged nucleic acid forming a dense complex that protects the nucleic from degradation. During passage through a micro fluidics system the components self-assemble to form particles in the size range of 50 to 150 nM in which the nucleic acid is encapsulated in the core complexed with the cationic lipid and surrounded by a lipid bilayer like structure. After endocytosis, the LNPs are present in endosomes. The encapsulated nucleic acid undergoes a process of endosomal escape mediate by the ionizable nature of the cationic lipid. This delivers the nucleic acid into the cytoplasm where mRNA can be translated into the encoded protein. Thus, in some embodiments encapsulation of gRNA and mRNA encoding Cas9 into an LNP is used to efficiently deliver both components to cells after IV injection. After endosomal escape the Cas9 mRNA is translated into Cas9 protein and can form a complex with the gRNA. In some embodiments, inclusion of a nuclear localization signal into the Cas9 protein sequence promotes translocation of the Cas9 protein/gRNA complex to the nucleus. Alternatively, the small gRNA crosses the nuclear pore complex and form complexes with Cas9 protein in the nucleus. Once in the nucleus the gRNA/Cas9 complex scan the genome for homologous target sites and generate double-strand breaks preferentially at the desired target site in the genome. The half-life of RNA molecules in vivo is generally short, on the order of hours to days. Similarly, the half-life of proteins tends to be short, on the order of hours to days. Thus, in some embodiments, delivery of the gRNA and Cas9 mRNA using an LNP can result in only transient expression and activity of the gRNA/Cas9 complex. This can provide the advantage of reducing the frequency of off-target cleavage and thus minimize the risk of genotoxicity in some embodiments. LNP are generally less immunogenic than viral particles. While many humans have preexisting immunity to AAV there is no pre-existing immunity to LNP. In additional and adaptive immune response against LNP is unlikely to occur which enables repeat dosing of LNP.

Several different ionizable cationic lipids have been developed for use in LNP. These include C12-200 (Love, K. T. et al. (2010). *Proc. Nat. Acad. Sci. U.S.A.*, 107(5):1864-1869), MC3, LN16, MD1 among others. In one type of LNP a GalNac moiety is attached to the outside of the LNP and acts as a ligand for uptake via the asialyloglycoprotein receptor. Any of these cationic lipids are used to formulate LNP for delivery of gRNA and Cas9 mRNA to cells.

In some embodiments, an LNP refers to any particle having a diameter of less than 1000 nm, 500 nm, 250 nm, 200 nm, 150 nm, 100 nm, 75 nm, 50 nm, or 25 nm. Alternatively, a nanoparticle can range in size from 1-1000 nm, 1-500 nm, 1-250 nm, 25-200 nm, 25-100 nm, 35-75 nm, or 25-60 nm.

LNPs can be made from cationic, anionic, or neutral lipids. Neutral lipids, such as the fusogenic phospholipid DOPE or the membrane component cholesterol, can be included in LNPs as 'helper lipids' to enhance transfection activity and nanoparticle stability. Limitations of cationic lipids include low efficacy owing to poor stability and rapid clearance, as well as the generation of inflammatory or anti-inflammatory responses. LNPs can also have hydrophobic lipids, hydrophilic lipids, or both hydrophobic and hydrophilic lipids.

Any lipid or combination of lipids that are known in the art can be used to produce an LNP. Examples of lipids used to produce LNPs are: DOTMA, DOSPA, DOTAP, DMRIE, DC-cholesterol, DOTAP-cholesterol, GAP-DMORIE-DPyPE, and GL67A-DOPE-DMPE-polyethylene glycol (PEG). Examples of cationic lipids are: 98N12-5, C12-200, DLin-KC2-DMA (KC2), DLin-MC3-DMA (MC3), XTC, MD1, and 7C1. Examples of neutral lipids are: DPSC, DPPC, POPC, DOPE, and SM. Examples of PEG-modified lipids are: PEG-DMG, PEG-CerC14, and PEG-CerC20.

In embodiments, the lipids can be combined in any number of molar ratios to produce an LNP. In addition, the polynucleotide(s) can be combined with lipid(s) in a wide range of molar ratios to produce an LNP.

In embodiments, the site-directed polypeptide and genome-targeting nucleic acid can each be administered separately to a cell or a subject. On the other hand, the site-directed polypeptide can be pre-complexed with one or more guide RNAs, or one or more crRNA together with a tracrRNA. The pre-complexed material can then be administered to a cell or a subject. Such pre-complexed material is known as a ribonucleoprotein particle (RNP).

RNA can form specific interactions with RNA or DNA. While this property is exploited in many biological processes, it also comes with the risk of promiscuous interactions in a nucleic acid-rich cellular environment. One solution to this problem is the formation of ribonucleoprotein particles (RNPs), in which the RNA is pre-complexed with an endonuclease. Another benefit of the RNP is protection of the RNA from degradation.

In some embodiments, the endonuclease in the RNP can be modified or unmodified. Likewise, the gRNA, crRNA, tracrRNA, or sgRNA can be modified or unmodified. Numerous modifications are known in the art and can be used.

The endonuclease and sgRNA can be generally combined in a 1:1 molar ratio. Alternatively, the endonuclease, crRNA, and tracrRNA can be generally combined in a 1:1:1 molar ratio. However, a wide range of molar ratios can be used to produce an RNP.

Gene editing components can be delivered to the nucleus of the cell via several mechanisms. These mechanisms can be generally categorized into viral and non-viral delivery. For many applications, a combination of viral and non-viral delivery can be used.

In some embodiments, a recombinant adeno-associated virus (AAV) vector can be used for delivery. Strategies, techniques, and systems suitable for manufacturing rAAV particles, in which an AAV genome to be packaged that includes the polynucleotide to be delivered, rep, and cap genes, and helper virus functions are provided to a cell are known in the art. Production of rAAV generally requires that the following components are present within a single cell (denoted herein as a packaging cell): a rAAV genome, AAV rep and cap genes separate from (such as not in) the rAAV genome, and helper virus functions. Common approaches to generate rAAV include transient transfection, insect-baculovirus dual infection, and insect-baculovirus single infection. Further information in this regard can be found in, for example, Ayuso, E. et al. (2010). *Curr. Gene Ther.*, 10(6): 423-436; Mietzsch, M. et al. (2014). *Hum. Gene Ther.*, 25(3):212-222; Mietzsch, M. et al. (2015). *Hum. Gene Ther.*, 26(10):688-697; and Mietzsch, M. et al. (2017). *Hum. Gene Ther. Method*, 28(1):15-22.

Generally, the AAV rep and cap genes can be from any AAV serotype for which recombinant virus can be derived, and can be from a different AAV serotype than the rAAV genome ITRs, including, but not limited to, AAV serotypes AAV-1, AAV-2, AAV-3, AAV-4, AAV-5, AAV-6, AAV-7, AAV-8, AAV-9, AAV-10, AAV-11, AAV-12, AAV-13, and AAV rh.74. Further, different naturally occurring and/or synthetic serotypes of the virus may be used to target specific tissue types. Production of pseudotyped rAAV is disclosed in, for example, international patent application publication number WO 01/83692. Table 1A lists AAV serotype and Genbank Accession No. of some selected AAVs.

TABLE 1A

| AAV Serotype | Genbank Accession No. |
| --- | --- |
| AAV-1 | NC_002077.1 |
| AAV-2 | NC_001401.2 |
| AAV-3 | NC_001729.1 |
| AAV-3B | AF028705.1 |
| AAV-4 | NC_001829.1 |
| AAV-5 | NC_006152.1 |
| AAV-6 | AF028704.1 |
| AAV-7 | NC_006260.1 |
| AAV-8 | NC_006261.1 |
| AAV-9 | AX753250.1 |
| AAV-10 | AY631965.1 |
| AAV-11 | AY631966.1 |
| AAV-12 | DQ813647.1 |
| AAV-13 | EU285562.1 |

In some embodiments, a method of generating a packaging cell involves creating a cell line that stably expresses all of the necessary components for AAV particle production. For example, a plasmid (or multiple plasmids) having a rAAV genome lacking AAV rep and cap genes, AAV rep and cap genes separate from the rAAV genome, and a selectable marker, such as a neomycin resistance gene, are integrated into the genome of a cell. AAV genomes have been introduced into bacterial plasmids by procedures such as GC tailing (Samulski, R. J. et al. (1982). *Proc. Natl. Acad. Sci. U.S.A.*, 79(6):2077-2081), addition of synthetic linkers containing restriction endonuclease cleavage sites (Laughlin, C. A. et al. (1983). *Gene*, 23(1):65-73) or by direct, blunt-end ligation (Senapathy, P. (1984). *J. Biol. Chem.*, 259:4661-4666). The packaging cell line is then infected with a helper virus, such as adenovirus. The advantages of this method are that the cells are selectable and are suitable for large-scale production of rAAV. Other examples of suitable methods employ adenovirus or baculovirus, rather than plasmids, to introduce rAAV genomes and/or rep and cap genes into packaging cells.

General principles of rAAV production are reviewed in, for example, Carter, B. J. (1992). *Curr. Opin. Biotechnol.*, 3(5):533-539; and Muzyczka, M. (1992). *Curr. Topics Microbial. Immunol.*, 158:97-129. Various approaches are described in Tratschin, J. D. et al. (1984). *Mol. Cell. Biol.*, 4(10):2072-2081; Hermonat, P. L. et al. (1984). *Proc. Natl. Acad. Sci. U.S.A.*, 81(2):6466-6470; Tratschin, J. D. et al. (1985). *Mol. Cell. Biol.*, 5(11):3251-3260; McLaughlin, S. K. et al. (1988). *J. Virol.*, 62(6):1963-1973; and Lebkowski, J. S. et al. (1988). *Mol. Cell. Biol.*, 8(10):3988-3996. Samulski, R. J. et al. (1989). *J. Virol.*, 63(9):3822-3828); U.S. Pat. No. 5,173,414; WO 95/13365 and corresponding U.S. Pat. No. 5,658,776; WO 95/13392; WO 96/17947; PCT/US98/18600; WO 97/09441 (PCT/US96/14423); WO 97/08298 (PCT/US96/13872); WO 97/21825 (PCT/US96/20777); WO 97/06243 (PCT/FR96/01064); WO 99/11764; Perrin, P. et al. (1995) *Vaccine*, 13(13):1244-1250; Paul, R. W. et al. (1993). *Hum. Gene Ther.*, 4(5):609-615; Clark, K. R. et al. (1996) *Gene Ther.*, 3(12):1124-1132; U.S. Pat. Nos. 5,786,211; 5,871,982; and 6,258,595.

AAV vector serotypes can be matched to target cell types. For example, the following exemplary cell types can be transduced by the indicated AAV serotypes among others. For example, the serotypes of AAV vectors suitable to liver tissue/cell type include, but not limited to, AAV3, AAV5, AAV8, and AAV9. In some cases, an AAV serotype is selected for low immunogenicity in a population or in the individual to be treated.

In addition to adeno-associated viral vectors, other viral vectors can be used. Such viral vectors include, but are not limited to, lentivirus, alphavirus, enterovirus, pestivirus, baculovirus, herpesvirus, Epstein Barr virus, papovavirus, poxvirus, vaccinia virus, and herpes simplex virus.

In some embodiments, Cas9 mRNA, sgRNA targeting one or two loci in fibrinogen-α genes, and donor DNA are each separately formulated into lipid nanoparticles, or are all co-formulated into one lipid nanoparticle, or co-formulated into two or more lipid nanoparticles.

In some embodiments, Cas9 mRNA is formulated in a lipid nanoparticle, while sgRNA and donor DNA are delivered in an AAV vector. In some embodiments, Cas9 mRNA and sgRNA are co-formulated in a lipid nanoparticle, while donor DNA is delivered in an AAV vector.

Options are available to deliver the Cas9 nuclease as a DNA plasmid, as mRNA or as a protein. The guide RNA can be expressed from the same DNA, or can be delivered as an RNA. The RNA can be chemically modified to alter or improve its half-life and/or decrease the likelihood or degree of immune response. The endonuclease protein can be complexed with the gRNA prior to delivery. Viral vectors allow efficient delivery; split versions of Cas9 and smaller orthologs of Cas9 can be packaged in AAV, as can donors for HDR. A range of non-viral delivery methods also exist that can deliver each of these components, or non-viral and viral methods can be employed in tandem. For example, nanoparticles can be used to deliver the protein and guide RNA, while AAV can be used to deliver a donor DNA.

In some embodiments that are related to delivering genome-editing components for therapeutic treatments, at least two components are delivered into the nucleus of a cell to be transformed, e.g., lymphocytes, a sequence-specific nuclease (such as a site-directed polypeptide, e.g., DNA endonuclease, for example a nucleic acid-guided nuclease), and a DNA donor template. In some embodiments, the donor DNA template is packaged into an Adeno Associated Virus (AAV) with tropism for lymphocytes. In some embodiments, the AAV is selected from the serotypes AAV8, AAV9, AAVrh10, AAV5, AAV6, or AAV-DJ. In some embodiments, the AAV packaged DNA donor template is administered to a subject, e.g., a patient, first by peripheral IV injection followed by administration of the sequence-specific nuclease (e.g., a DNA endonuclease). The advantage of delivering an AAV packaged donor DNA template first is that the delivered donor DNA template will be stably maintained in the nucleus of the transduced cells which allows for the subsequent administration of the sequence-specific nuclease (e.g., a DNA endonuclease) which will create a double-strand break in the genome with subsequent integration of the DNA donor by HDR or NHEJ. It is desirable in some embodiments that the sequence-specific nuclease (e.g., a DNA endonuclease) remain active in the target cell only for the time required to promote targeted integration of the transgene at sufficient levels for the desired therapeutic effect. If the sequence-specific nuclease (e.g., a DNA endonuclease) remains active in the cell for an extended duration this will result in an increased frequency of double-strand breaks at off-target sites. Generally, the frequency of off-target cleavage is a function of the off-target cutting efficiency multiplied by the time over which the nuclease is active. Delivery of a sequence-specific nuclease (e.g., a DNA endonuclease) in the form of an mRNA results in a short duration of nuclease activity in the range of hours to a few days because the mRNA and the translated protein are short lived in the cell. Thus, delivery of the sequence-specific nuclease (e.g., a DNA endonuclease) into cells that already contain the donor template is expected to result in the highest possible ratio of targeted integration relative to off-target integration. In addition, AAV mediated delivery of a donor DNA template to the nucleus of cells after peripheral i.v. injection takes time, generally on the order of one to fourteen days, because the virus must infect the cell, escape the endosomes, transit to the nucleus, and undergo conversion of the single-stranded AAV genome to a double-stranded DNA molecule by host components. Thus, in at least some embodiments, delivery of a donor DNA template to the nucleus is completed before supplying the CRISPR-Cas components because these nuclease components are generally active for about one to three days.

In some embodiments, the sequence-specific nuclease (e.g., a DNA endonuclease) is CRISPR-Cas9 which is composed of a sgRNA directed to a DNA sequence within intron 1 of the fibrinogen-α gene together with a Cas9 nuclease. In some embodiments, the Cas9 nuclease is delivered as a mRNA encoding the Cas9 protein operably fused to one or more nuclear localization signals (NLS). In some embodiments, the sgRNA and the Cas9 mRNA are delivered to the cells by packaging into a lipid nanoparticle. In some embodiments, the lipid nanoparticle contains the lipid C12-200 (Love, K. T. et al. (2010). *Proc. Nat. Acad. Sci. U.S.A.*, 107(5):1864-1869). In some embodiments, the ratio of the sgRNA to the Cas9 mRNA that is packaged in the LNP is 1:1 (mass ratio) to result in maximal DNA cleavage in vivo in mice. In alternative embodiments, different mass ratios of the sgRNA to the Cas9 mRNA that is packaged in the LNP can be used, for example, 10:1, 9:1, 8:1, 7:1, 6:1, 5:1, 4:1, 3:1, or 2:1 or reverse ratios. In some embodiments, the Cas9 mRNA and the sgRNA are packaged into separate LNP formulations and the Cas9 mRNA containing LNP is delivered to the subject about 1 to about 8 hours before the LNP containing the sgRNA to allow optimal time for the Cas9 mRNA to be translated prior to delivery of the sgRNA.

In some embodiments, an LNP formulation encapsulating a gRNA and a Cas9 mRNA ("the LNP-nuclease formulation") is administered to a subject, e.g., a patient, that previously was administered a DNA donor template packaged into an AAV. In some embodiments, the LNP-nuclease formulation is administered to the subject within one day to twenty eight days or within seven days to twenty eight days or within seven days to fourteen days after administration of the AAV-donor DNA template. The effective timing of delivery of the LNP-nuclease formulation relative to the AAV-donor DNA template can be determined using the techniques known in the art, e.g., studies done in animal models including mice and monkeys.

In some embodiments, a DNA-donor template is delivered to the cells of a subject, e.g., a patient, using a non-viral delivery method. While some subjects (generally 30%) have pre-existing neutralizing antibodies directed to most commonly used AAV serotypes that prevent the efficacious gene delivery by the AAV, more subjects may be treatable with a non-viral delivery method. Several non-viral delivery methodologies have been known in the field. In particular lipid nanoparticles (LNP) are known to efficiently deliver their encapsulated cargo to the cytoplasm of cells after intravenous injection in animals and humans. These LNP are actively taken up by the cells through a process of receptor mediated endocytosis.

In some embodiments, to promote nuclear localization of a donor template, DNA sequence that can promote nuclear localization of plasmids, e.g., a 366 bp region of the simian virus 40 (SV40) origin of replication and early promoter, can be added to the donor template. Other DNA sequences that bind to cellular proteins can also be used to improve nuclear entry of DNA.

In some embodiments, the level of expression or activity of an introduced POI (e.g., FVIII) coding sequence is measured in the blood of a subject, e.g., a patient, following the first administration of an LNP-nuclease formulation, e.g., containing gRNA and Cas9 nuclease or mRNA encoding Cas9 nuclease, after the AAV-donor DNA template. If the POI level is not sufficient to cure the disease as defined for example as POI levels of at least 5 to 50%, in particular 5 to 20% of normal levels, then a second or third administration of the LNP-nuclease formulation can be given to promote additional targeted integration into the fibrinogen-α intron 1 site. The feasibility of using multiple doses of the LNP-nuclease formulation to obtain the desired therapeutic levels of POI can be tested and optimized using techniques known in the art, e.g., tests using animal models, including mouse models and monkey models.

In some embodiments, according to any of the methods described herein including administration of i) an AAV-donor DNA template including a donor cassette and ii) an LNP-nuclease formulation to a subject, an initial dose of the LNP-nuclease formulation is administered to the subject within one day to twenty eight days after administration of the AAV-donor DNA template to the subject. In some embodiments, the initial dose of the LNP-nuclease formulation is administered to the subject after a sufficient time to allow delivery of the donor DNA template to the nucleus of a target cell. In some embodiments, the initial dose of the LNP-nuclease formulation is administered to the subject after a sufficient time to allow conversion of the single-stranded AAV genome to a double-stranded DNA molecule in the nucleus of a target cell. In some embodiments, one or more (such as 2, 3, 4, 5, or more) additional doses of the LNP-nuclease formulation are administered to the subject following administration of the initial dose. In some embodiments, one or more doses of the LNP-nuclease formulation are administered to the subject until a target level of targeted integration of the donor cassette and/or a target level of expression of the donor cassette is achieved. In some embodiments, the method further includes measuring the level of targeted integration of the donor cassette and/or the level of expression of the donor cassette following each administration of the LNP-nuclease formulation, and administering an additional dose of the LNP-nuclease formulation if the target level of targeted integration of the donor cassette and/or the target level of expression of the donor cassette is not achieved. In some embodiments, the amount of at least one of the one or more additional doses of the LNP-nuclease formulation is the same as the initial dose. In some embodiments, the amount of at least one of the one or more additional doses of the LNP-nuclease formulation is less than the initial dose. In some embodiments, the amount of at least one of the one or more additional doses of the LNP-nuclease formulation is more than the initial dose.

Therapeutic Approach

In one aspect, provided herein is a gene therapy approach for treating a subject by adoptive cell therapy with cells edited according to any of the methods described herein. For example, in some embodiments, the disorder or health condition is an autoimmune disease (e.g., IPEX syndrome) or a disorder that results from organ transplant (e.g., GVHD), and the edited cells have a Treg phenotype. In some embodiments, the gene therapy approach integrates a nucleic acid including a sequence encoding a naked FRB domain polypeptide and a CISC into the genome of a relevant cell type in a subject and thereby provides a stable treatment, e.g., a treatment that ameliorates one or more symptoms of the disorder or health condition for an extended period of time, and/or provides a permanent cure or amelioration of the disorder or health condition. In some embodiments, a cell type subject to the gene therapy approach in which to integrate the sequence encoding a naked FRB domain polypeptide and a CISC is a lymphocytic cell, e.g., a CD4+ T cell.

In some embodiments, an ex vivo cell-based therapy is performed using a lymphocytic cell that is isolated from a subject, e.g., an autologous CD4+ T cell derived from cord blood. Next, the chromosomal DNA of these cells is edited using the systems, compositions, and methods described herein. Finally, the edited cells are implanted into the subject.

One advantage of an ex vivo cell therapy approach is the ability to conduct a comprehensive analysis of the therapeutic prior to administration. All nuclease-based therapeutics have some level of off-target effects. Performing gene correction ex vivo allows one to fully characterize the corrected cell population prior to implantation. Aspects of the disclosure include sequencing the entire genome of the corrected cells to ensure that the off-target cuts, if any, are in genomic locations associated with minimal risk to the subject. Furthermore, populations of specific cells, including clonal populations, can be isolated prior to implantation.

Another embodiment of such methods is an in vivo based therapy. In this method, the chromosomal DNA of the cells in the subject is corrected using the systems, compositions, and methods described herein. In some embodiments, the cells are lymphocytic cells, e.g., CD4+ cells, such as T cells.

An advantage of in vivo gene therapy is the ease of therapeutic production and administration. The same therapeutic approach and therapy can be used to treat more than one subject, for example a number of subjects who share the same or similar genotype or allele. In contrast, ex vivo cell therapy generally uses a subject's own cells, which are isolated, manipulated, and returned to the same subject.

More embodiments concern a genetically modified cell in which the genome of the cell is edited by one of the methods described herein for use in inhibiting or treating a disease or condition associated with FOXP3, such as an inflammatory disease or an autoimmune disease. Additional embodiments concern use of a genetically modified cell in which the genome of the cell is edited by any one of the methods herein as a medicament.

Implanting Cells into a Subject

In some embodiments, the ex vivo methods of the disclosure involve implanting the genome-edited cells into a subject who is in need of such method. This implanting step can be accomplished using any method of implantation known in the art. For example, the genetically modified cells can be injected directly in the subject's blood or otherwise administered to the subject.

In some embodiments, the methods disclosed herein include administering, which can be interchangeably used with "introducing" and "transplanting," genetically modified, therapeutic cells into a subject, by a method or route that results in at least partial localization of the introduced cells at a desired site such that a desired effect(s) is produced. The therapeutic cells or their differentiated progeny can be administered by any appropriate route that results in delivery to a desired location in the subject where at least a portion of the implanted cells or components of the cells remain viable. The period of viability of the cells after administration to a subject can be as short as a few hours, e.g., twenty-four hours, to a few days, to as long as several years, or even the life time of the subject, such as long-term engraftment.

When provided prophylactically, the therapeutic cells described herein can be administered to a subject in advance of any symptom of a disease or condition to be treated. Accordingly, in some embodiments the prophylactic administration of a genetically modified stem cell population serves to prevent the occurrence of symptoms of the disease or condition.

When provided therapeutically in some embodiments, genetically modified stem cells are provided at (or after) the onset of a symptom or indication of a disease or condition, e.g., upon the onset of disease or condition.

For use in the various embodiments described herein, an effective amount of therapeutic cells, e.g., genome-edited stem cells, can be at least 102 cells, at least $5\times10^2$ cells, at least $10^3$ cells, at least $5\times10^3$ cells, at least $10^4$ cells, at least $5\times10^4$ cells, at least $10^5$ cells, at least $2\times10^5$ cells, at least $3\times10^5$ cells, at least $4\times10^5$ cells, at least $5\times10^5$ cells, at least $6\times10^5$ cells, at least $7\times10^5$ cells, at least $8\times10^5$ cells, at least $9\times10^5$ cells, at least $1\times10^6$ cells, at least $2\times10^6$ cells, at least $3\times10^6$ cells, at least $4\times10^6$ cells, at least $5\times10^6$ cells, at least $6\times10^6$ cells, at least $7\times10^6$ cells, at least $8\times10^6$ cells, at least $9\times10^6$ cells, or multiples thereof. The therapeutic cells can be derived from one or more donors or can be obtained from an autologous source. In some embodiments described herein, the therapeutic cells are expanded in culture prior to administration to a subject in need thereof.

In embodiments, the delivery of a therapeutic cell composition (e.g., a composition including a plurality of cells according to any of the cells described herein) into a subject by a method or route results in at least partial localization of the cell composition at a desired site. A cell composition can be administered by any appropriate route that results in effective treatment in the subject, e.g., administration results in delivery to a desired location in the subject where at least a portion of the composition delivered, e.g., at least $1\times10^4$ cells, is delivered to the desired site for a period of time. Modes of administration include injection, infusion, instillation, or ingestion. "Injection" includes, without limitation, intravenous, intramuscular, intra-arterial, intrathecal, intraventricular, intracapsular, intraorbital, intracardiac, intradermal, intraperitoneal, transtracheal, subcutaneous, subcuticular, intraarticular, subcapsular, subarachnoid, intraspinal, intracerebrospinal, and intrasternal injection and infusion. In some embodiments, the route is intravenous. For the delivery of cells, administration by injection or infusion can be made.

In one embodiment, the cells are administered systemically, in other words a population of therapeutic cells are administered other than directly into a target site, tissue, or organ, such that it enters, instead, the subject's circulatory system and, thus, is subject to metabolism and other like processes.

The efficacy of a treatment having a composition for the treatment of a disease or condition can be determined by the skilled clinician. However, a treatment is considered effective treatment if any one or all of the signs or symptoms or markers of disease are improved or ameliorated. Efficacy can also be measured by failure of an individual to worsen as assessed by hospitalization or need for medical interventions (e.g., progression of the disease is halted or at least slowed). Methods of measuring these indicators are known to those of skill in the art and/or described herein. Treatment includes any treatment of a disease in an individual or an animal (some non-limiting examples include a human, or a mammal) and includes: (1) inhibiting the disease, e.g., arresting, or slowing the progression of symptoms; or (2) relieving the disease, e.g., causing regression of symptoms; and (3) preventing or reducing the likelihood of the development of symptoms.

Compositions

In one aspect, the present disclosure provides compositions for carrying out the methods disclosed herein. A composition can include one or more of the following: a genome-targeting nucleic acid (e.g., a gRNA); a site-directed polypeptide (e.g., a DNA endonuclease) or a nucleotide sequence encoding the site-directed polypeptide; and a polynucleotide to be inserted (e.g., a donor template) to effect the desired genetic modification of the methods disclosed herein.

In some embodiments, a composition has a nucleotide sequence encoding a genome-targeting nucleic acid (e.g., a gRNA).

In some embodiments, a composition has a site-directed polypeptide (e.g. DNA endonuclease). In some embodiments, a composition has a nucleotide sequence encoding the site-directed polypeptide.

In some embodiments, a composition has a polynucleotide (e.g., a donor template) to be inserted into a genome.

In some embodiments, a composition has (i) a nucleotide sequence encoding a genome-targeting nucleic acid (e.g., a gRNA) and (ii) a site-directed polypeptide (e.g., a DNA endonuclease) or a nucleotide sequence encoding the site-directed polypeptide.

In some embodiments, a composition has (i) a nucleotide sequence encoding a genome-targeting nucleic acid (e.g., a gRNA) and (ii) a polynucleotide (e.g., a donor template) to be inserted into a genome.

In some embodiments, a composition has (i) a site-directed polypeptide (e.g., a DNA endonuclease) or a nucleotide sequence encoding the site-directed polypeptide and (ii) a polynucleotide (e.g., a donor template) to be inserted into a genome.

In some embodiments, a composition has (i) a nucleotide sequence encoding a genome-targeting nucleic acid (e.g., a gRNA), (ii) a site-directed polypeptide (e.g., a DNA endonuclease) or a nucleotide sequence encoding the site-directed polypeptide and (iii) a polynucleotide (e.g., a donor template) to be inserted into a genome.

In some embodiments of any of the above compositions, the composition has a single-molecule guide genome-targeting nucleic acid. In some embodiments of any of the above compositions, the composition has a double-molecule genome-targeting nucleic acid. In some embodiments of any of the above compositions, the composition has two or more double-molecule guides or single-molecule guides. In some embodiments, the composition has a vector that encodes the nucleic acid targeting nucleic acid. In some embodiments, the genome-targeting nucleic acid is a DNA endonuclease, in particular, a Cas9.

In some embodiments, a composition can include one or more gRNAs that can be used for genome-edition, in particular, insertion of a sequence encoding a naked FRB domain polypeptide and a CISC into a genome of a cell. The one or more gRNAs can target a genomic site at, within, or near the endogenous FOXP3 gene. Therefore, in some embodiments, the one or more gRNAs can have a spacer sequence complementary to a genomic sequence at, within, or near a FOXP3 gene.

In some embodiments, a gRNA for a composition includes a spacer sequence selected from any one of SEQ ID NOs: 40-57, and variants thereof having at least or at least about 50%, about 55%, about 60%, about 65%, about 70%, about 75%, about 80%, about 85%, about 90% or about 95% identity or homology to any one of SEQ ID NOs: 40-57. In some embodiments, the variants of gRNA for the kit include a spacer sequence having at least or at least about 85% homology to any one of SEQ ID NOs: 40-57.

In some embodiments, a gRNA for a composition has a spacer sequence that is complementary to a target site in the genome. In some embodiments, the spacer sequence is 15 bases to 20 bases in length. In some embodiments, a complementarity between the spacer sequence to the genomic sequence is at least about 80%, at least about 85%, at least about 90%, at least about 95%, at least about 96%, at least about 97%, at least about 98%, at least about 99% or at least about 100%.

In some embodiments, a composition can have a DNA endonuclease or a nucleic acid encoding the DNA endonuclease and/or a donor template having a nucleic acid sequence encoding a naked FRB domain polypeptide and a CISC. In some embodiments, the nucleic acid sequence encoding a naked FRB domain polypeptide and a CISC has at least or at least about 70% sequence identity, e.g., at least or at least about 75%, 80%, 85%, 90%, 92%, 93%, 94%, 95%, 96%, 97%, 98%, 99% or greater sequence identity, to a sequence according to SEQ ID NOs: 3-4, 8, 28-30, 32, and 37-39. In some embodiments, the nucleic acid sequence encoding a naked FRB domain polypeptide and a CISC has at least or at least about 70% sequence identity, e.g., at least or at least about 75%, 80%, 85%, 90%, 92%, 93%, 94%, 95%, 96%, 97%, 98%, 99% or greater sequence identity, to a sequence according to SEQ ID NO: 32. In some embodiments, the DNA endonuclease is a Cas9. In some embodiments, the nucleic acid encoding the DNA endonuclease is DNA or RNA.

In some embodiments, one or more of any nucleic acids for the kit can be encoded in an Adeno Associated Virus (AAV) vector. Therefore, in some embodiments, a gRNA can be encoded in an AAV vector. In some embodiments, a nucleic acid encoding a DNA endonuclease can be encoded in an AAV vector. In some embodiments, a donor template can be encoded in an AAV vector. In some embodiments, two or more nucleic acids can be encoded in a single AAV vector. Thus, in some embodiments, a gRNA sequence and a DNA endonuclease-encoding nucleic acid can be encoded in a single AAV vector.

In some embodiments, a composition can have a liposome or a lipid nanoparticle. Therefore, in some embodiments, any compounds (e.g., a DNA endonuclease or a nucleic acid encoding thereof, gRNA, and donor template) of the composition can be formulated in a liposome or lipid nanoparticle. In some embodiments, one or more such compounds are associated with a liposome or lipid nanoparticle via a covalent bond or non-covalent bond. In some embodiments, any of the compounds can be separately or together contained in a liposome or lipid nanoparticle. Therefore, in some embodiments, each of a DNA endonuclease or a nucleic acid encoding thereof, gRNA, and donor template is separately formulated in a liposome or lipid nanoparticle. In some embodiments, a DNA endonuclease is formulated in a liposome or lipid nanoparticle with gRNA. In some embodiments, a DNA endonuclease or a nucleic acid encoding thereof, gRNA, and donor template are formulated in a liposome or lipid nanoparticle together.

In some embodiments, a composition described above further has one or more additional reagents, where such additional reagents are selected from a buffer, a buffer for introducing a polypeptide or polynucleotide into a cell, a wash buffer, a control reagent, a control vector, a control RNA polynucleotide, a reagent for in vitro production of the polypeptide from DNA, adaptors for sequencing and the like. A buffer can be a stabilization buffer, a reconstituting buffer, a diluting buffer, or the like. In some embodiments, a composition can also include one or more components that can be used to facilitate or enhance the on-target binding or the cleavage of DNA by the endonuclease, or improve the specificity of targeting.

In some embodiments, any components of a composition are formulated with pharmaceutically acceptable excipients such as carriers, solvents, stabilizers, adjuvants, diluents, etc., depending upon the particular mode of administration and dosage form. In embodiments, guide RNA compositions are generally formulated to achieve a physiologically compatible pH, and range from a pH of or about 3 to a pH of or about 11, from a pH of or about 3 to or to about pH 7, depending on the formulation and route of administration. In some embodiments, the pH is adjusted to a range from or from about pH 5.0 to or to about pH 8. In some embodiments, the composition has a therapeutically effective amount of at least one compound as described herein, together with one or more pharmaceutically acceptable excipients. Optionally, the composition can have a combination of the compounds described herein, or can include a second active ingredient useful in the treatment or prevention of bacterial growth (for example and without limitation, anti-bacterial or anti-microbial agents), or can include a combination of reagents of the disclosure. In some embodiments, gRNAs are formulated with other one or more nucleic acids, e.g., nucleic acid encoding a DNA endonuclease and/or a donor template. Alternatively, a nucleic acid encoding a DNA endonuclease and a donor template, separately or in combination with other nucleic acids, are formulated with the method described above for gRNA formulation.

Suitable excipients can include, for example, carrier molecules that include large, slowly metabolized macromolecules such as proteins, polysaccharides, polylactic acids, polyglycolic acids, polymeric amino acids, amino acid copolymers, and inactive virus particles. Other exemplary excipients include antioxidants (for example and without limitation, ascorbic acid), chelating agents (for example and without limitation, EDTA), carbohydrates (for example and without limitation, dextrin, hydroxyalkylcellulose, and hydroxyalkylmethylcellulose), stearic acid, liquids (for example and without limitation, oils, water, saline, glycerol, and ethanol), wetting or emulsifying agents, pH buffering substances, and the like.

In some embodiments, any compounds (e.g., a DNA endonuclease or a nucleic acid encoding thereof, gRNA, and donor template) of a composition can be delivered into a cell via transfection, such as chemical transfection (e.g., lipofection) or electroporation. In some embodiments, a DNA endonuclease can be pre-complexed with a gRNA, forming a ribonucleoprotein (RNP) complex, prior to the provision to the cell. In some embodiments, the RNP complex is delivered into the cell via transfection. In such embodiments, the donor template is delivered into the cell via transfection.

In some embodiments, a composition refers to a therapeutic composition having therapeutic cells that are used in an ex vivo treatment method.

In embodiments, therapeutic compositions contain a physiologically tolerable carrier together with the cell composition, and optionally at least one additional bioactive agent as described herein, dissolved or dispersed therein as an active ingredient. In some embodiments, the therapeutic composition is not substantially immunogenic when administered to a mammal or human subject for therapeutic purposes, unless so desired.

In general, the genetically modified, therapeutic cells described herein are administered as a suspension with a pharmaceutically acceptable carrier. One of skill in the art will recognize that a pharmaceutically acceptable carrier to be used in a cell composition will not include buffers, compounds, cryopreservation agents, preservatives, or other agents in amounts that substantially interfere with the viability of the cells to be delivered to the subject. A formulation having cells can include e.g., osmotic buffers that permit cell membrane integrity to be maintained, and optionally, nutrients to maintain cell viability or enhance engraftment upon administration. Such formulations and suspensions are known to those of skill in the art and/or can be adapted for use with the progenitor cells, as described herein, using routine experimentation.

In some embodiments, a cell composition can also be emulsified or presented as a liposome composition, provided that the emulsification procedure does not adversely affect cell viability. The cells and any other active ingredient can be mixed with one or more excipients that are pharmaceutically acceptable and compatible with the active ingredient, and in amounts suitable for use in the therapeutic methods described herein.

Additional agents included in a cell composition can include pharmaceutically acceptable salts of the components therein. Pharmaceutically acceptable salts include the acid addition salts (formed with the free amino groups of the polypeptide) that are formed with inorganic acids, such as, for example, hydrochloric or phosphoric acids, or such organic acids as acetic, tartaric, mandelic, and the like. Salts formed with the free carboxyl groups can also be derived from inorganic bases, such as, for example, sodium, potassium, ammonium, calcium, or ferric hydroxides, and such organic bases as isopropylamine, trimethylamine, 2-ethylamino ethanol, histidine, procaine, and the like.

Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active compound used in the cell compositions that is effective in the treatment of a particular disorder or condition will depend on the nature of the disorder or condition, and can be determined by known clinical techniques.

Kits and Systems

Also provided herein are kits and systems including the cells, expression vectors, and protein sequences provided and described herein as well as written instructions for making and using the same. Thus, for example, provided herein is a kit including one or more of: a protein sequence as described herein; an expression vector as described herein; and/or a cell as described herein. Also provided is a system for selectively activation a signal into an interior of a rapamycin resistant cell, the system including a cell as described herein, wherein the cell includes an expression vector as described herein including a nucleic acid encoding a protein sequence as described herein.

Some embodiments provide a kit that contains one or more components of a CRISPR/Cas system for genome editing described herein.

In some embodiments, a kit can have one or more additional therapeutic agents that can be administered simultaneously or in sequence with the other kit components for a desired purpose, e.g., genome edition or cell therapy.

In some embodiments, a kit can further include instructions for using the components of the kit to practice the methods. The instructions for practicing the methods are generally recorded on a suitable recording medium. For example, the instructions can be printed on a substrate, such as paper or plastic, etc. The instructions can be present in the kits as a package insert, in the labeling of the container of the kit or components thereof (such as associated with the packaging or subpackaging), etc. The instructions can be present as an electronic storage data file present on a suitable computer readable storage medium, e.g. CD-ROM, diskette, flash drive, etc. In some instances, the actual instructions are not present in the kit, but means for obtaining the instructions from a remote source (e.g., via the internet), can be provided. An example of this embodiment is a kit that includes a web address where the instructions can be viewed and/or from which the instructions can be downloaded. As with the instructions, this means for obtaining the instructions can be recorded on a suitable substrate.

With respect to the use of plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those of skill within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.).

Any of the features of an embodiment of the first through eleventh aspects is applicable to all aspects and embodiments identified herein. Moreover, any of the features of an embodiment of the first through eleventh aspects is independently combinable, partly or wholly with other embodiments described herein in any way, e.g., one, two, or three or more embodiments may be combinable in whole or in part. Further, any of the features of an embodiment of the first through eleventh aspects may be made optional to other aspects or embodiments. Although described above in terms of various exemplary embodiments and implementations, it should be understood that the various features, aspects and functionality described in one or more of the individual embodiments are not limited in their applicability to the particular embodiment with which they are described, but instead may be applied, alone or in various combinations, to one or more of the other embodiments of the present application, whether or not such embodiments are described and whether or not such features are presented as being a part of a described embodiment. Thus, the breadth and scope of the present application should not be limited by any of the above-described exemplary embodiments.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

Some embodiments of the disclosures provided herewith are further illustrated by the following non-limiting examples.

EXAMPLES

The practice of the present invention will employ, unless otherwise indicated, conventional techniques of molecular biology, microbiology, cell biology, biochemistry, nucleic acid chemistry, and immunology, which are well known to those skilled in the art. Such techniques are explained fully in the literature, such as Sambrook, J., & Russell, D. W. (2012). *Molecular Cloning: A Laboratory Manual* ($4^{th}$ ed.). Cold Spring Harbor, NY: Cold Spring Harbor Laboratory and Sambrook, J., & Russel, D. W. (2001). *Molecular Cloning: A Laboratory Manual* ($3^{rd}$ ed.). Cold Spring Harbor, NY: Cold Spring Harbor Laboratory (jointly referred to herein as "Sambrook"); Ausubel, F. M. (1987). *Current Protocols in Molecular Biology* New York, NY: Wiley (including supplements through 2014); Mullis, K. B., Ferré, F. & Gibbs, R. (1994). *PCR: The Polymerase Chain Reaction*, Boston: Birkhauser Publisher; Harlow, E., & Lane, D. (1999). *Antibodies: A Laboratory Manual* ($2^{nd}$ ed.). New York, NY: Cold Spring Harbor Laboratory Press; Beaucage, S. L. et al. (2000). *Current Protocols in Nucleic Acid Chemistry*, New York, NY: Wiley, (including supplements through 2014); and Makrides, S. C. (2003). *Gene Transfer and Expression in Mammalian Cells* Amsterdam, NL: Elsevier Sciences B.V.).

Example 1: Generation and Characterization of DISC Construct

This Example describes the creation and testing of a CISC-encoding lentiviral construct to intracellularly express a naked "decoy" FRB domain in the cytoplasm of host cells.

IL-2 signal modulating-CISC-containing lentiviral constructs were modified with an additional naked FRB* domain located 3' of the CISC chimeric receptor proteins (FIG. 1). Constructs that express the additional naked FRB* domain along with the CISC were designated as "decoy-CISC," or "DISC." Without being bound to theory, it is believed that the naked FRB domain will compete with the endogenous FRB domain of mTOR for binding to rapamycin, thereby resulting in rapamycin-mediated intracellular signaling via the CISC but without the attendant cytotoxicity associated with rapamycin's effects on host cells, thereby overcoming the problem of inhibition of proliferation.

As shown in FIG. 2, FKBP domain-containing proteins are naturally expressed in the cytoplasm of cells, and mTOR contains an FRB domain. In the absence of rapamycin, the CISC subunits do not dimerize, and intracellular mTOR signals normally (left panel). In the presence of rapamycin, the CISC subunits dimerize and provide intracellular signals, however mTOR signals are inhibited, limiting cell growth (middle); in DISC cells where the naked FRB domain is co-expressed, intracellular signals are still provided by rapamycin induced dimerization, but many of the mTOR proteins can still signal as intracellular rapamycin is bound by the intracellularly expressed naked FRB and endogenous FKBP polypeptides.

The novel DISC construct was then tested to determine how it performed with respect to the maintenance of host cell growth and viability in comparison to CISC constructs that do not express a naked intracellular FRB domain. In brief, isolated CD4+ T cells were activated for sixty one hours, resulting in $1.9 \times 10^7$ total cells after isolation. Lentivirus transduction was then performed without beads (1 million cells/500 μL/well, 10 μl of Construct #1272 (CISC-only construct)/10 μl of DN-1272 (DISC-containing construct) (2 wells/LV) with protamine sulfate 4 μg/ml in a 24-well dish. Spinoculation was performed at 800 g for 30 minutes at 32° C. Medium (1.5 mL) was then added after a five hour incubation. The transduced T cells were incubated at 37° C. for 48 hours with cytokines (IL-2 50 ng/ml, IL-7 5 ng/ml, and IL-15 5 ng/ml) followed by verification of transduction efficiency. Following this, 1 million cells/well were plated in a 24 well dish with 2 mL media. Following this, the T cells were treated with rapamycin (0.1 nM, 1 nM, and 10 nM), the rapalog AP21967 (100 nM) or IL-2 (50 ng/mL) with media being changed every two days. Also included in this experiment was a 'no-treatment" group with just media. The T cells were then assessed for viability and mCherry positive signal.

Figure 3:
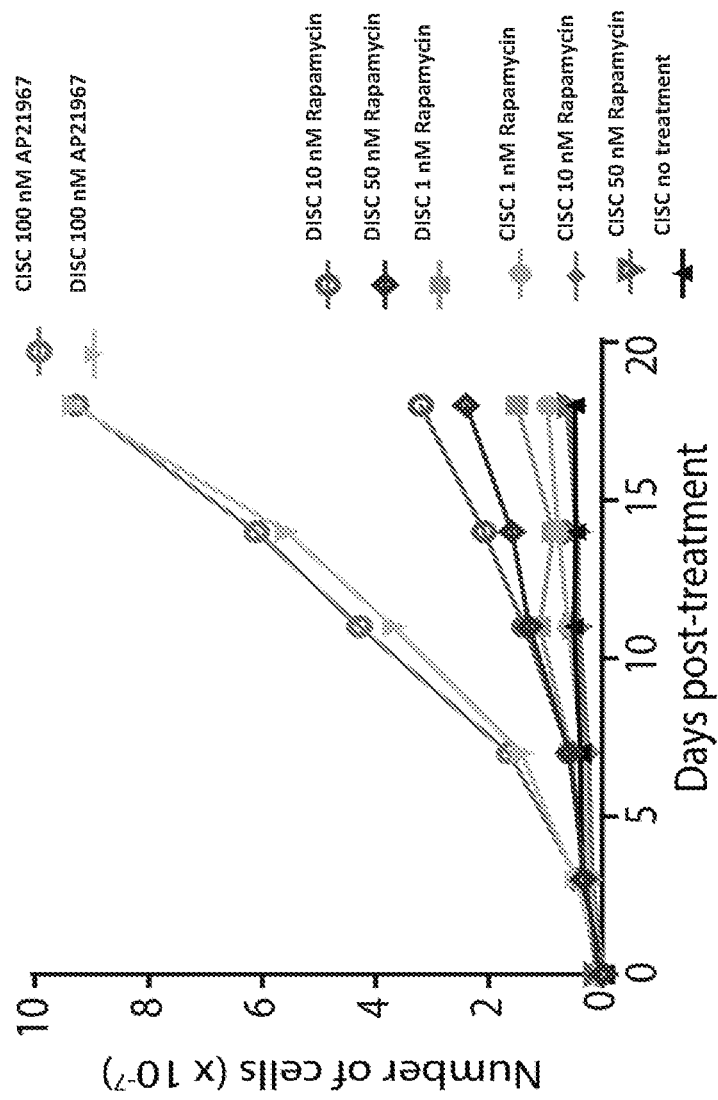
FIG. 3 depicts a graph comparing the expansion of T cells that express CISC versus DISC constructs in cells cultured in the presence of rapamycin or the rapalog AP21967. The DISC construct promotes improved T cell expansion compared with cells transduced with CISC-only constructs at all doses of rapamycin tested.

As shown in FIG. 3, in the presence of rapamycin, T cells expressing the DISC expand better than those expressing the CISC at all doses. This result demonstrates that the DISC construct can remediate the negative effects that rapamycin or rapamycin-related compounds have on the growth and viability of host cells, which is a proof of concept for the DISC construct. Both CISC and DISC constructs expand equally well in the presence of the rapalog AP21967 because the rapalog does not bind endogenous mTor.

Example 2: Modified CISC Components of the DISC

This Example describes the creation of modified receptor proteins of the CISC component of the DISC construct. Computer based protein modeling predicts that spacing between the two receptor proteins of the CISC components of the DISC construct might not be optimal. As such, several additional constructs were made to test whether changing the length of certain sections of the chimeric receptor proteins (e.g., the interface between the extracellular domains and the transmembrane domains) will increase growth signals.

Figure 4:
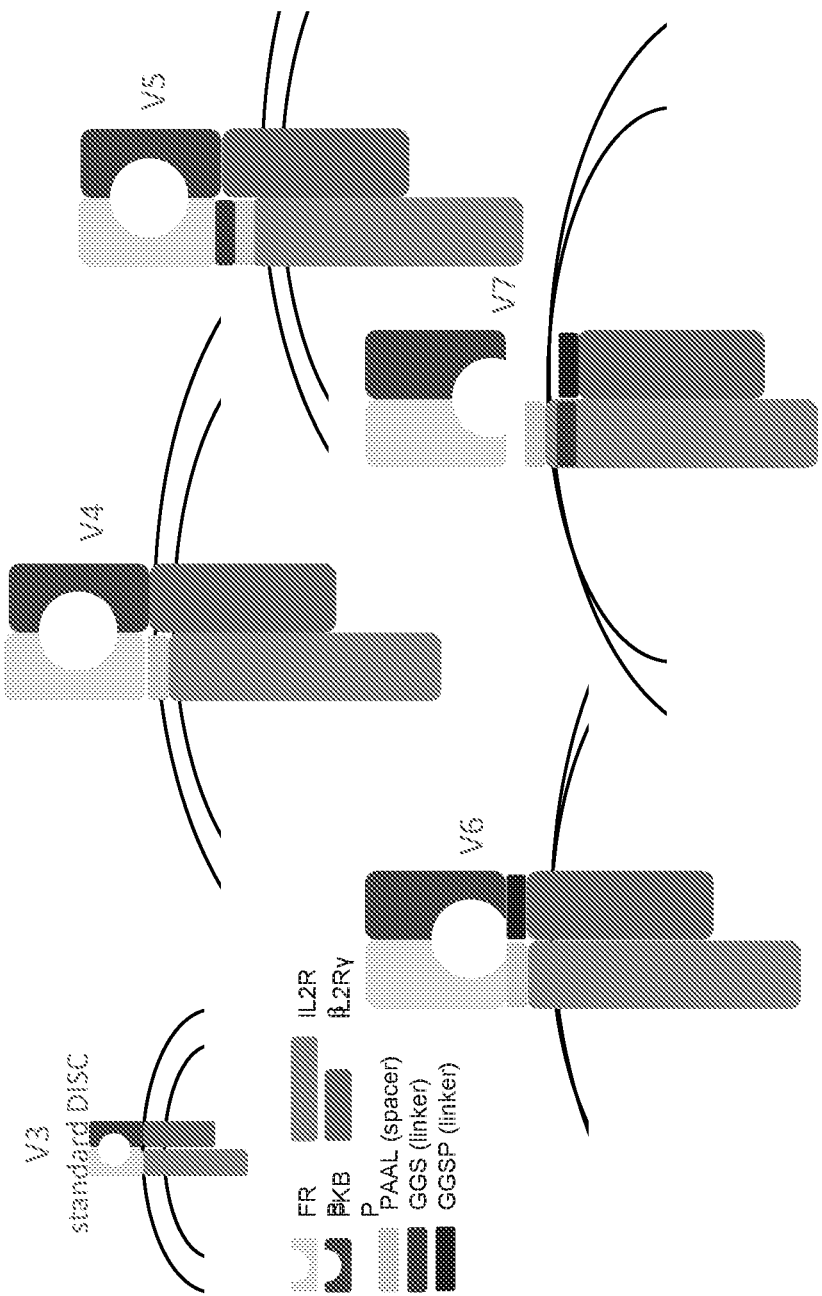
FIG. 4 is a conceptual diagram showing significant amino acid changes introduced in the various iterations of the CISC construct that was tested. Four additional pairs (V4-V7) of FRB-IL2Rβ/FKBP-IL2Rγ receptor proteins were created that contained one or more of a PAAL spacer amino acid sequence and/or GGS or GGSP linker amino acid sequences. The additional spacer and linker amino acid sequences were located either at the interface between the extracellular FRB/FKBP and IL2Rβ/IL2Rγ domains or within the IL2Rβ domain.

Various amino acid additions were used to create versions 4 through 7 (V4-V7) to see whether this improved T cell expansion with Rapamycin. Four additional pairs (V4-V7) of FRB-IL2Rβ/FKBP-IL2Rγ receptor proteins were created that contained one or more of a PAAL spacer amino acid sequence and/or GGS or GGSP linker amino acid sequences. The additional spacer and linker amino acid sequences were located either at the interface between the extracellular FRB/FKBP and IL2Rβ/IL2Rγ domains or within the IL2Rβ domain (FIG. 4). V3 standard DISC has FRB, FKBP, IL2Rβ, IL2Rγ; V4 has FRB, FKBP, IL2Rβ, IL2Rγ and a PAAL spacer at the N-terminus of the IL2Rβ; V5 has FRB, FKBP, IL2Rβ, IL2Rγ, GGS linker and PAAL spacer in which the IL2Rβ has the linker and the PAAL spacer at the N terminus; V6 has the FRB, FKBP, IL2Rβ, IL2Rγ, PAAL spacer and GGSP linker, in which the PAAL spacer is at the N terminus of the IL2Rβ and the GGSP linker is at the N terminus of the IL2Rγ; V7 has FRB, FKBP, IL2Rβ, IL2Rγ in which the IL2Rβ has a GGS linker and PAAL spacer while the IL2Rγ includes the GGSP linker.

Once constructed, the new DISC constructs (V4-V7) were tested to determine whether they improved cellular proliferation and viability in the presence of rapamycin compared to the originally-created DISC construct described in Example 1. The timeline of the procedure used to test these novel DISC architectures in primary human T cells is as follows. PBMC3 were thaw for approximately twenty four hours before CD4 isolation and CD3/CD28 bead stimulation. After approximately sixty one hours, beads were removed. Lentiviral spinnoculation was performed at 800×g in a volume of 500 μL, followed by additional of 1.5 mL media supplemented with cytokines. Transduced cells were split into 4 treatment cohorts: (1) 1 nM rapamycin, (2) 50 ng/mL IL-2, (3) 100 nM AP21967, and (4) no treatment; and growth of transduced cells was monitored by flow cytometry for the co-expressed mCherry and counting total cell numbers after two days, four days, eleven days, fifteen days, and twenty days.

The results of flow cytometry studies are shown in Table 1 below, where T cell expansion was determined after 48 hours following treatment with rapamycin. Percentage of cells with mCherry co-expression is shown, and indicates similar transduction efficiency of the constructs in each cohort. As shown in Table 1B below, each of the modified DISC constructs exhibited similar transduction efficiency compared to the original DISC construct (V3).

TABLE 1B

| DISC construct | % mCherry co-expression |
| --- | --- |
| V3 (original) | 9.92 |
| V4 | 11.8 |
| V5 | 10.6 |
| V6 | 12.9 |
| V7 | 11.0 |
| Mock | 0.67 |

Figure 6:
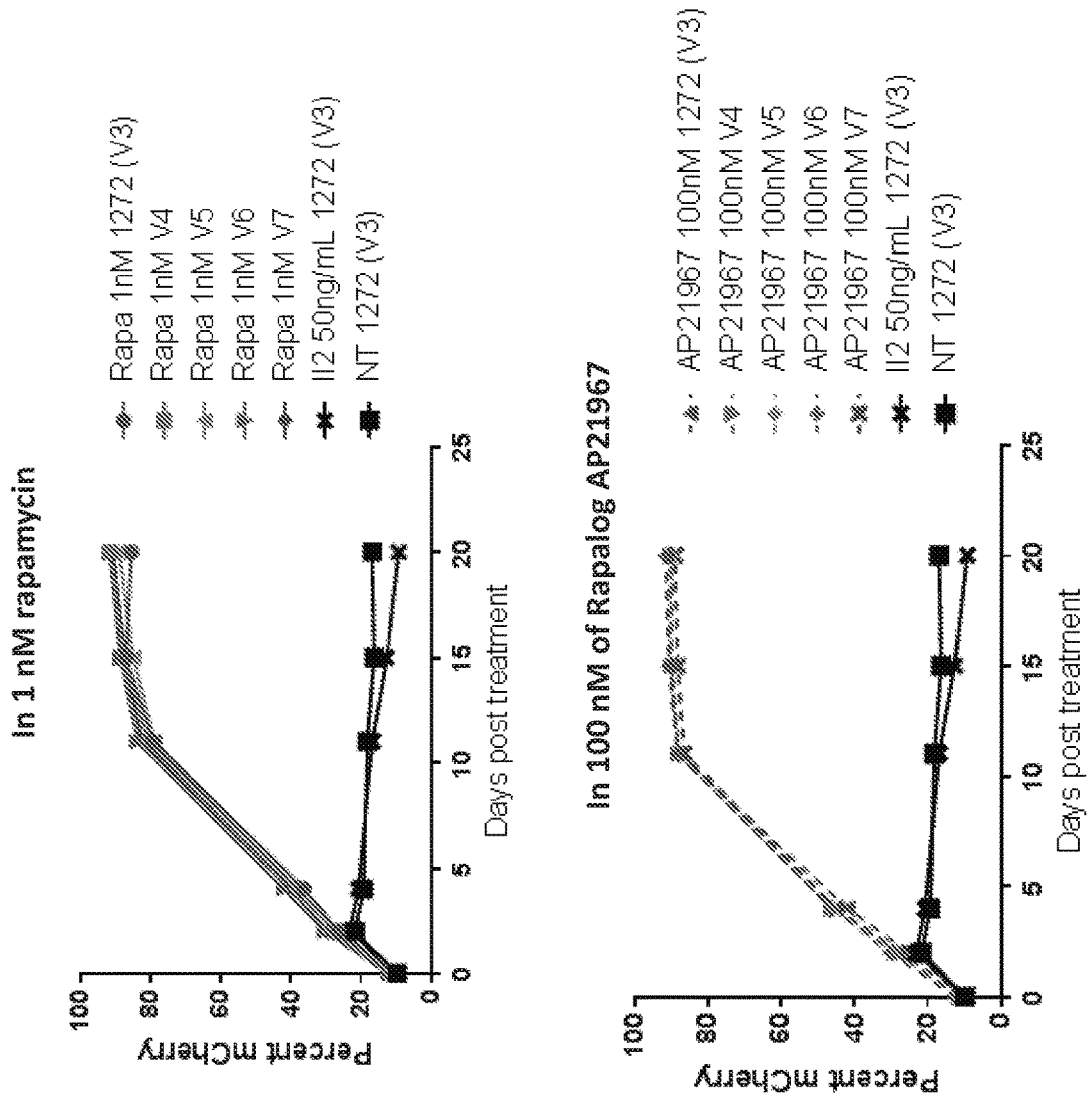
FIG. 6 depicts two graphs showing enrichment of lentivirus-transduced T cells (read out as percentage of mCherry$^+$ cells) over time in culture with rapamycin (top) or the rapalog AP21967 (bottom).

Similarly, as exemplified in FIG. 5, identical numbers of cells at all time points were observed with all versions of the DISC up to twenty days post treatment with 1 nM rapamycin. Finally, as detailed in FIG. 6, measurements of the percent enrichment of lentivirus transduced T cells over time in culture with rapamycin or rapalog treatment indicated that the percentage of cells that were mCherry+ was similar in all LV treatment groups compared to IL-2- or non-treated (NT) controls. Thus, this Example shows that all tested versions of the modified DISC constructs performed similarly with respect to transduction efficiency, cell growth and expansion, and enrichment of transduced cells.

Example 3: Generation and Characterization of a μDISC Construct

One problem that can arise in gene editing is that there are limitations on the amount of material that can be packaged into a delivery vector, e.g., virus. This Example describes modification of the IL2Rβ cytoplasmic component of one half of a CISC binding pair engineered into T cells to control proliferation with rapamycin treatment. The modification is a truncation of the IL2Rβ domain that retains its ability to activate downstream IL2 signaling events in response to heterodimerization following binding to rapamycin.

Figure 7:
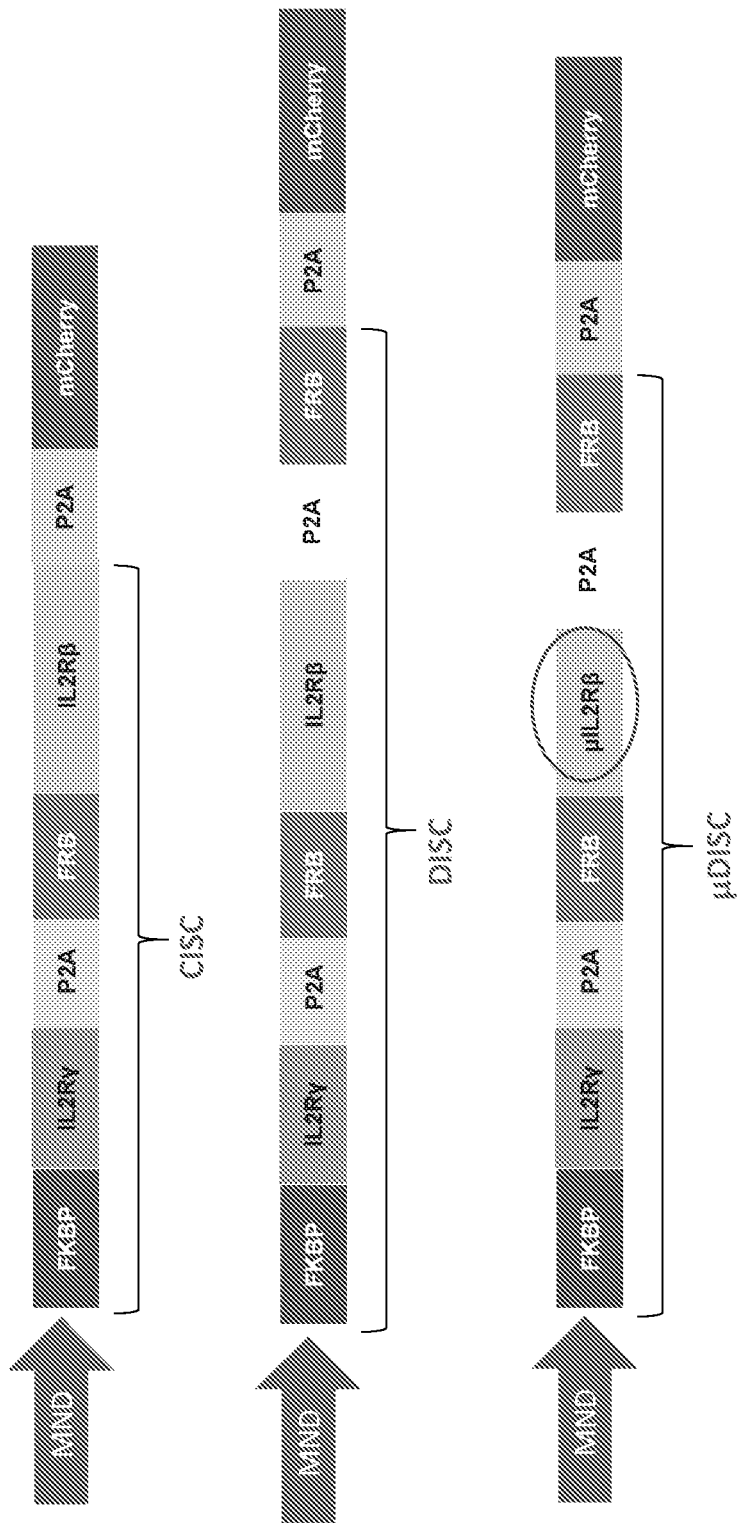
FIG. 7 is a conceptual diagram showing lentiviral constructs used to directly compare rapamycin-induced T cell expansion with the DISC and μDISC constructs (the original CISC construct is included as a reference).

The modification was made to decrease the amount of genetic material that must be packaged into the viruses used to deliver the CISC and/or DISC components to a host cell. The modification was based on a previous report (Lord, J. D. et al. (2000). *J. Immunol.*, 164(5):2533-2541, incorporated by reference herein) that identified essential signaling domains within IL2Rβ. This information was then used to delete non-essential amino acids from the IL2Rβ domain. The construct that was created to incorporate this truncated IL2Rβ domain as well as the intracellularly expressed naked FRB domain described in Example 1 was referred to as the "micro-DISC" or "μDISC" (FIG. 7).

The original CISC construct, the DISC construct from Example 1, and the μDISC construct were then tested to determine the respective ability of each to induce T cell expansion following transduction into cells and treatment with rapamycin. The timeline of the procedure used to test the novel μDISC construct in primary human T cells is as follows. PBMC were thaw for approximately two hours before CD4 isolation and CD3/CD28 bead stimulation. After approximately twenty four hours, beads were removed. Lentiviral transduction was performed with approximately 1 million cells, using the following contracts: V3 CISC, V3 DICS, and V3 μDISC. Transduced cells were then expanded for approximately one day, and split into three treatment cohorts: (1) 1 nM rapamycin, (2) 5 nM rapamycin, (3) 10 nM rapamycin. Approximately 0.4 million cells were used for each treatment. Growth of transduced cells was monitored by flow cytometry for the co-expressed mCherry and counting total cell numbers.

The viral transduction efficiencies are shown in Table 2 below, where similar viral transduction efficiencies were observed in T cells transduced with both the DISC and μDISC constructs in the presence of 10 nM rapamycin. Percentage of cells with mCherry co-expression is shown, and indicates similar transduction efficiency of the constructs in each cohort.

TABLE 2

| CISC/DISC construct | % mCherry co-expression |
| --- | --- |
| CISC | 55.7 |
| DISC | 46.3 |
| μDISC | 36.9 |
| Mock | 1.32 |

Figure 8:
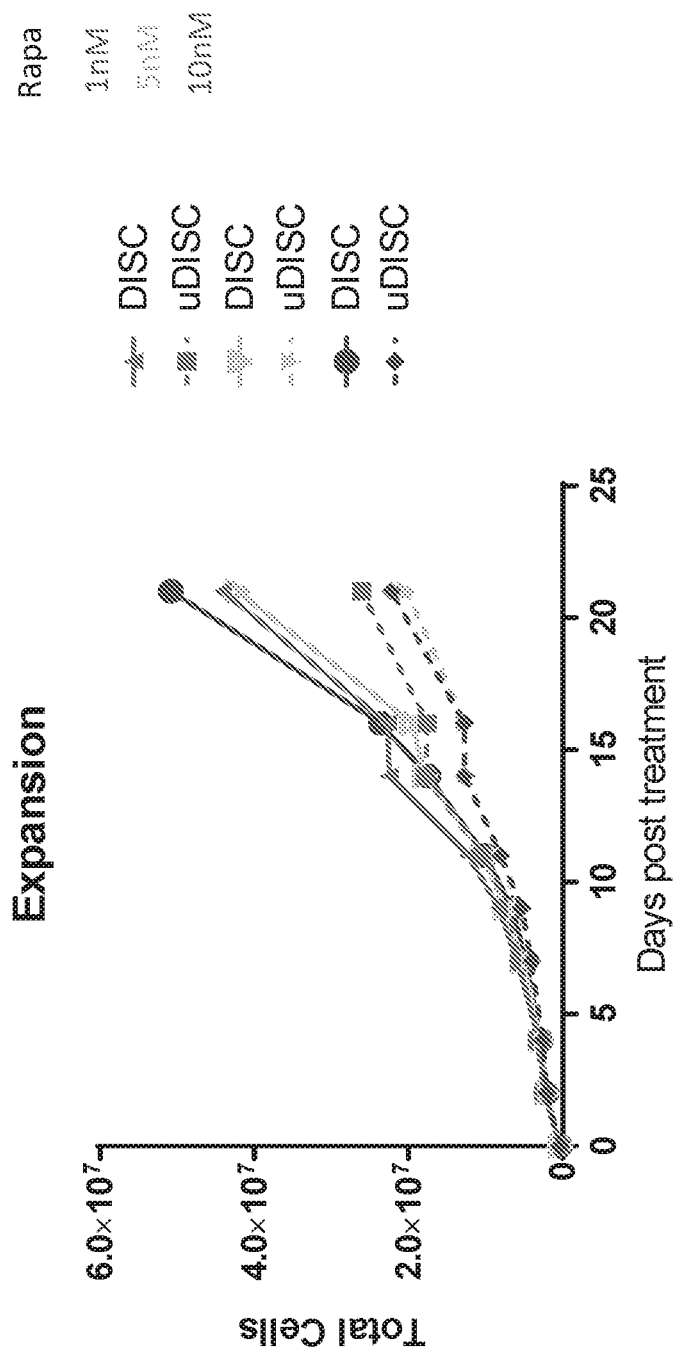
FIG. 8 is a graph showing the numbers of lentiviral-transduced T cells (mCherry+) over days in culture with the indicated concentrations of rapamycin.

FIG. 8 shows that T cells transduced with the μDISC construct expanded similarly, albeit slightly less than the full-length DISC construct, under all concentrations of rapamycin used. These results indicated that the μDISC construct provides sufficient IL2R signals for T cell growth and expansion.

Figure 9:
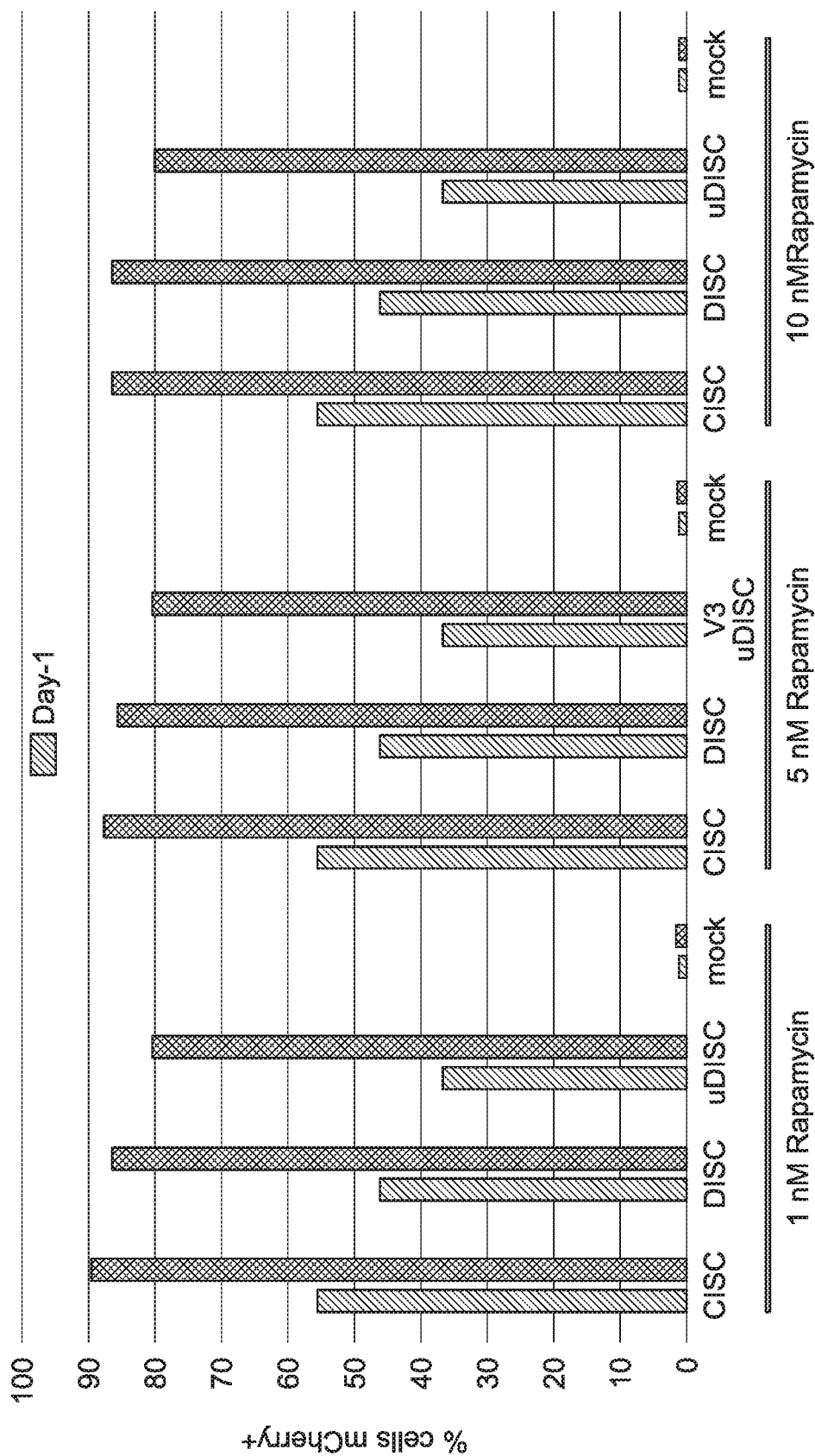
FIG. 9 is a graph showing enrichment of lentiviral-transduced T cells (read out as percentage of mCherry+ cells) after nine days in culture with rapamycin at varying doses.
Figure 10:
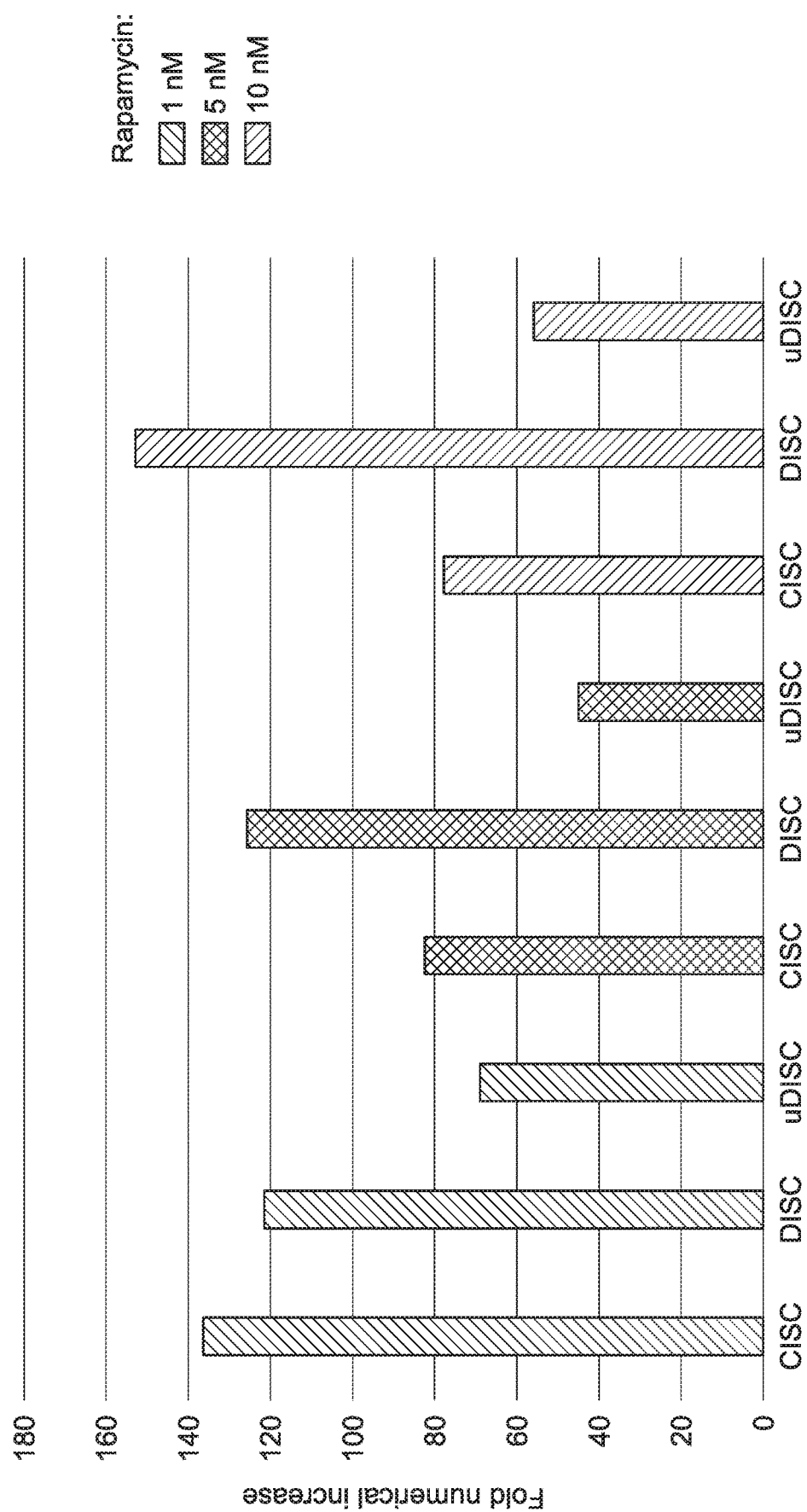
FIG. 10 is a graph showing fold numerical expansion of lentiviral-transduced (mCherry$^+$) T cells after twenty one days in culture with rapamycin at varying doses. Fold increase was calculated as the number of mCherry+ cells on Day 21 divided by the number of mCherry+ cells on Day 0. As shown on the x-axis from left to right are cells treated with rapamycin (first three bars), cells treated with 5 nM of rapamycin (bars 4-6) and cells treated with 10 nM of rapamycin (bars 7-9).

As shown in FIG. 9 and following nine days of culture, the percentage of cells that were mCherry+ was similar in the cells treated with the DISC and CISC lentiviral construct. T cells transduced with the μDISC construct produced slightly less mCherry+ (~80% vs 90%), but were still highly enriched. FIG. 10 shows the fold numerical expansion of LV transduced (mCherry+) cells after twenty one days in culture with rapamycin at varying doses. As such, this Example demonstrates that comparable levels of rapamycin-mediated T cell expansion can be achieved in cells transduced with the μDISC construct. The μDISC has the added benefit of having additional space for packaging of further genetic elements or markers into viruses used for gene transfer experiments or therapeutic treatments.

Figure 11:
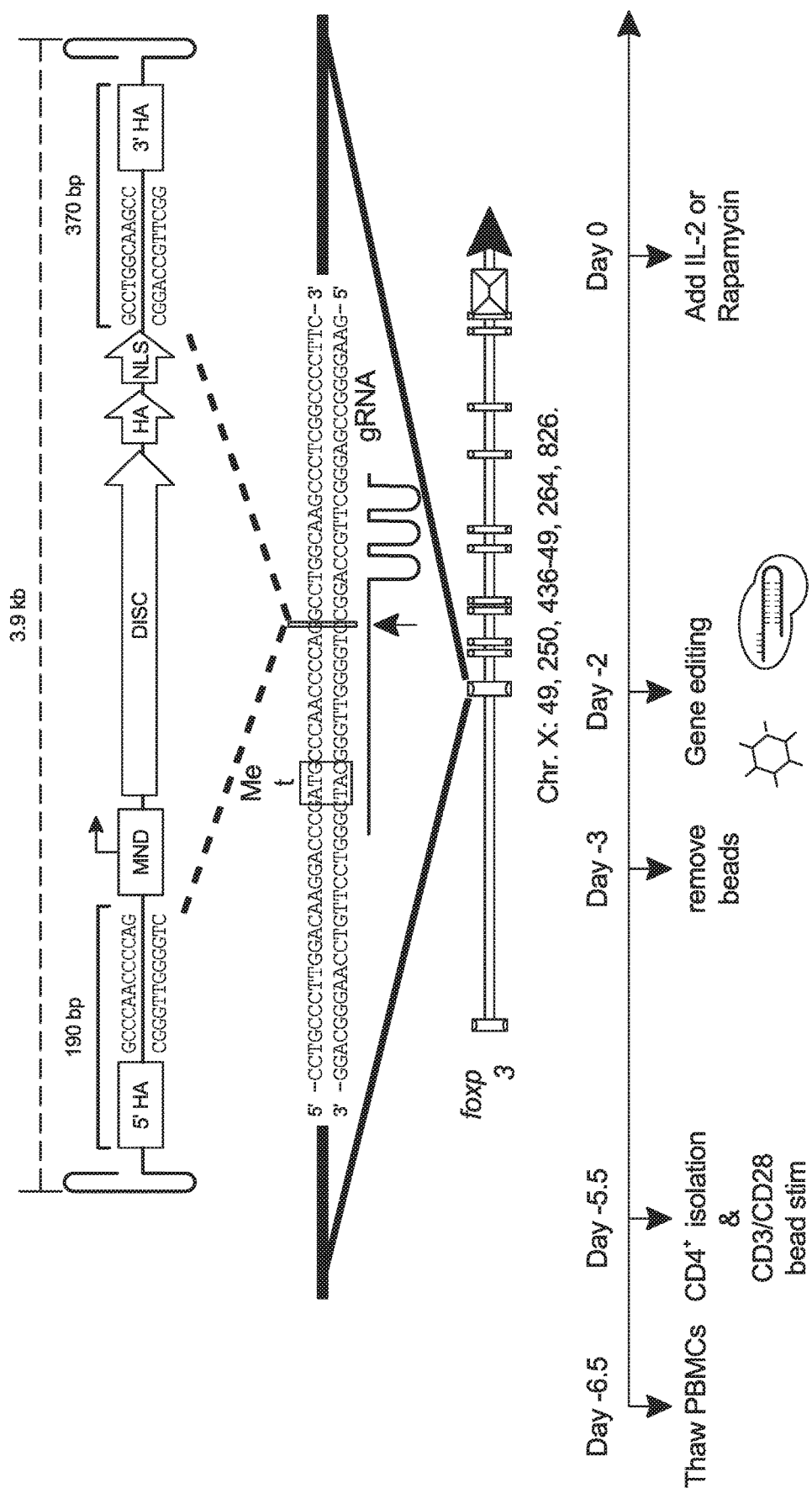
FIG. 11 is a diagram outlining the experimental protocol used in gene editing experiments to insert a DISC construct into the endogenous FOXP3 gene. An AAV6 donor template (top) and gene editing procedure using CRISPR/CAS9 RNP and AAV6 delivered donor template (bottom) for introducing an ectopic promoter driving DISC expression upstream of endogenous FOXP3 is shown. gRNA=guide RNA; 5' and 3' HA=human FOXP3 homology arms.

Example 4: Generation and Characterization of Cells with Targeted Integration of DISC Constructs at the FOXP3 Locus This Example illustrates the use of gene editing technology to knock-in a construct encoding the DISC and a promoter upstream of the endogenous FOXP3 (Forkhead box P3) locus in CD4+ T cells. FIG. 11 schematically shows the experimental protocol used in this experiment. In brief, a CRISPR/CAS9 ribonucleoprotein containing a guide RNA (gRNA) specific for a locus 5' of exon 1 of FOXP3 was used in combination with an adeno-associated virus 6 (AAV6) donor template for FOXP3 gene editing The gRNA included a spacer having the sequence of SE ID NO:58. An ectopic MND promoter was introduced to drive DISC expression upstream of endogenous FOXP3. Expression of FOXP3 was designed to be in-frame with an N-terminal hemagglutinin (HA) epitope tag and nuclear localization sequence to generate a chimeric protein.

As shown in Table 3 below, edited $T_{reg}$ cells expressing the DISC described above were selectively expanded in cultures containing rapamycin or AP21967. In this experiment, cells were labelled with APC-labeled anti-HA tag and PE-anti-FOXP3+ T cells after culture in media alone or with IL-2, rapamycin, or rapalog AP21967. The percentage of double positive cells (expressing HA-FOXP3) in each cohort is shown.

TABLE 3

| | 7 day post-treatment | | |
| --- | --- | --- | --- |
| Treatment | Mock | DISC/HA-FOXP3 | 15 day post-treatment DISC/HA-FOXP3 |
| No treatment | 0.025% | 4.33% | 6.16% |
| 50 ng/mL IL-2 | 0.010% | 4.92% | 2.12% |
| 10 nM Rapamycin | 0.022% | 47.6% | 85.6% |
| 100 nM AP21967 | 0.033% | 45.7% | 82.1% |

Moreover, as shown in Table 4 below, when assayed for the presence of regulatory T cell markers, the DISC-expressing edited Treg cells were phenotypically consistent to what would be expected for this type of cell by virtue of expressing T cell markers FOXP3, CTLA, LAG3, and ICOS, comparatively high amounts of CD25, and comparatively low amounts of CD127. The percentage of single positive cells (expressing only T cell marker) and double positive cells (expressing T cell marker and FOXP3) in each cohort is shown.

TABLE 4

| | CD25+ | | CD 127+ | | CTLA4+ | | LAG3+ | | ICOS+ | |
| --- | --- | --- | --- | --- | --- | --- | --- | --- | --- | --- |
| Treatment | FOXP3+ | FOXP3− | FOXP3+ | FOXP3− | FOXP3+ | FOXP3− | FOXP3+ | FOXP3− | FOXP3+ | FOXP3− |
| No Treatment | 0.88 | 1.35 | 0.56 | 0.90 | 0.25 | 3.26 | 0.31 | 0.37 | 0.14 | 0.20 |
| IL-2 50 ng/mL | 3.98 | 8.50 | 0.26 | 8.84 | 3.17 | 1.33 | 1.85 | 3.43 | 3.32 | 0.40 |
| Papamycin 10 nM | 28.9 | 14.5 | 1.47 | 40.8 | 15.5 | 29.4 | 7.86 | 33.3 | 38.2 | 2.38 |
| AP21967 100 nM | 22.5 | 20.4 | 1.63 | 40.3 | 13.6 | 30.8 | 8.81 | 31.5 | 36.8 | 2.99 |

Figure 12:
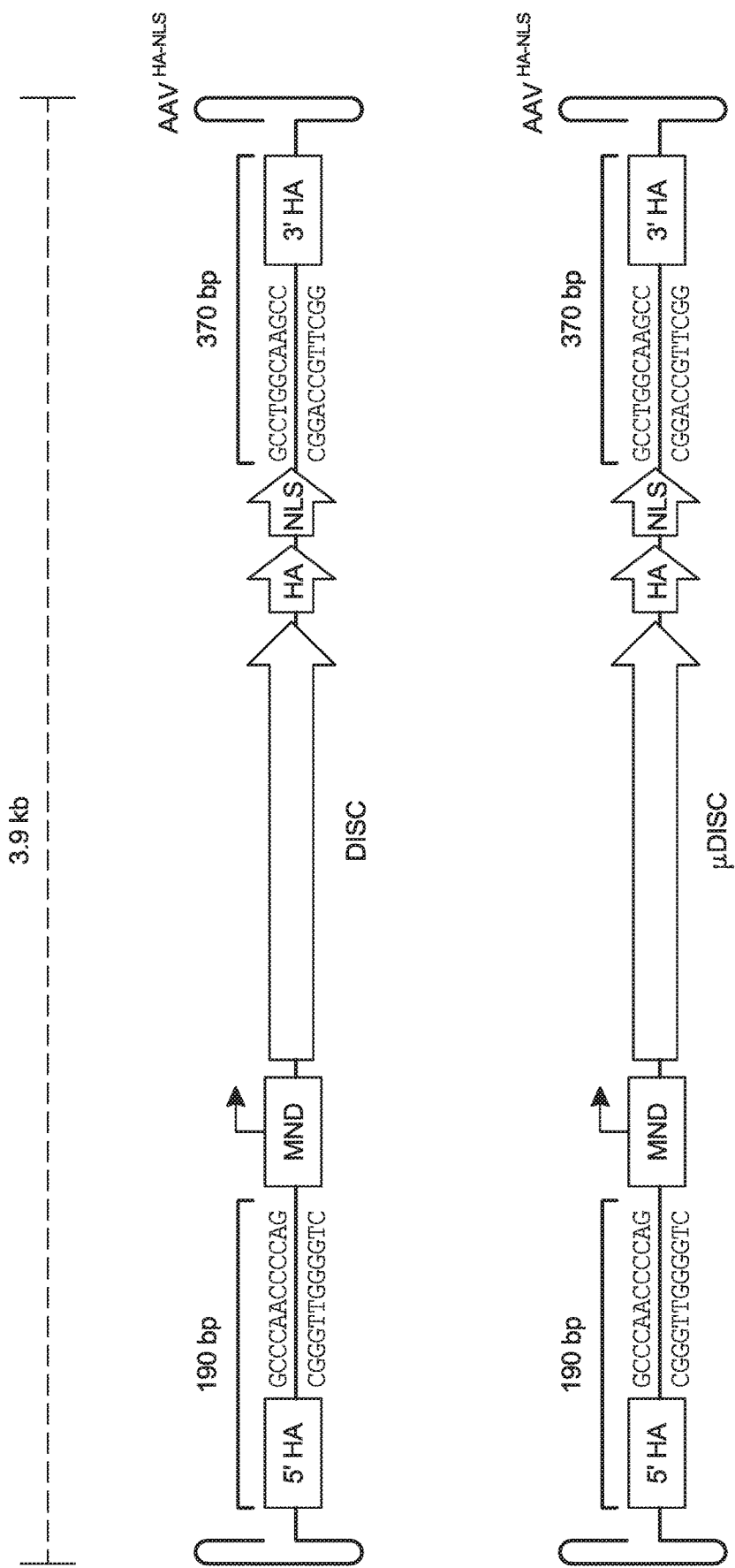
FIG. 12 shows schematic diagrams illustrating the experimental designs used in gene editing experiments to insert a DISC construct into the endogenous FOXP3 gene in T regulatory T cells. The MND promoter drives DISC/μDISC expression upstream of HA-tagged endogenous FOXP3. 5' and 3' homology arms at either end are human FOXP3 homology.

Endogenous genes in CD4+ T cells were then edited using the μDISC construct described in Example 3 or the DISC construct inserted in the constructs shown in FIG. 12. For these experiments, the MND promoter drove DISC/μDISC expression upstream of HA-tagged endogenous FOXP3 gene.

As shown in Table 5 below, the μDISC and DISC edited $T_{reg}$ cells are similarly preferentially enriched in the presence of rapamycin. As expected, IL-2 or media alone did not enrich the HA-FOXP3 expressing fraction. In Table 5, the percentage of double positive cells (edited cells expressing DISC/μDISC and HA-FOXP3) in each cohort is shown.

TABLE 5

| Treatment | | DISC | μDISC |
| --- | --- | --- | --- |
| Day 0 | | 24.9 | 12.6 |
| Day 7 | No treatment | 7.70 | 4.55 |
| | 50 ng/mL IL-2 | 18.1 | 12.1 |
| | 1 nM Rapamycin | 68.7 | 59.4 |

These data demonstrate that both the DISC and μDISC constructs can be used for editing genes in T cells as well as to make their expansion dependent on the presence of rapamycin.

Example 5: Optimization of DISC Cell Expansion

This Example describes the experiments performed with DISC constructs to preferentially expand the edTreg cells relative to unedited cells in the same culture. The rational of these experiments was to boost T cell expansion once rapamycin enriched population had been achieved. Generally, after editing primary human CD4+ T cells using DISC FOXP3 AAV donor templates, the result is a mixed population of cells: cells successfully edited (DISC edTreg) and cells that have not been edited. FOXP3 expressing Treg cells grow more slowly in culture relative to conventional T cells. Thus, in the presence of IL-2 the percentage of Treg cells in a mixed culture will rapidly decline. Culturing the mixed cell population with rapamycin and no IL-2 can result in an enrichment for the edited cells. However, without a TCR signal the total cell number increases slowly. Therefore, it would be useful to add anti-CD3/CD28 beads during expansion to provide a TCR signal. However, the addition of beads after editing may activate unedited cells that are also present, causing them to secrete IL-2 and thus removing the selective advantage of the rapamycin treatment for DISC edTregs in media without recombinant IL-2. In this scenario, cells without FOXP3 expression may outgrow the DISC edTreg that express FOXP3. Therefore, several trials were performed to optimize the number and enrichment (%) of DISC edTreg. As described in more detail below, these optimization trials were conducted using two different protocols: a two-phase expansion protocol and a three-phase expansion protocol.

Two-Phase Expansion Protocol

Figure 13A:
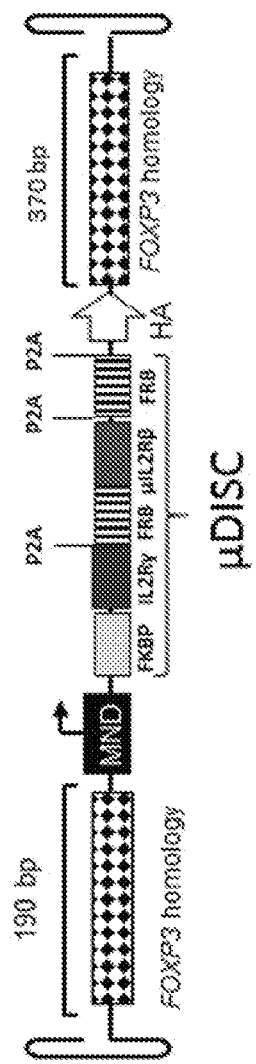
FIG. 13A is a diagram showing the structure of an AAV construct used in two-phase expansion protocol designed to improve expansion of CD4+ T cells successfully edited using DISC (edTreg), where the MND promoter drives cell-surface expression of the micro-DISC and intracellular expression of HA-tagged FOXP3.

In a two-phase expansion protocol, cell expansion was conducted in two phases: Expansion Phase 1 tested rapamycin selection with or without IL-2 (50 ng/mL) in the recovery media, followed by Expansion Phase 2, addition of anti-CD3/CD28 beads, and removal of IL-2 from media. Generally, CD4 T cells were isolated at Day-4 from human PBMCs cultured in T cell media with 50 µg/mL IL-2 and anti-human CD3/CD28 beads. At Day-1, CD3/CD28 beads were removed. During Expansion Phase 1 (Days 0-9), gene editing was performed with CRISPR/Cas9 RNPs and AAV6 (an exemplary construct is shown in FIG. 13A). Cells were divided into three expansion cohorts as described below. Flow cytometry was performed at Day 2 to assess gene editing. At Day 9, cells were further divided into two expansion cohorts to test bead and antibody CD3/CD28 stimulation. Upon completion of Expansion Phase 2 (Day 16), flow cytometry was then performed to assess enrichment and expansion of edited cells.

For this experiment, a construct expressing the µDISC (with a shortened IL2Rβ sequence, and an HA-tag fusion with FOXP3) was used. The structure of the AAV construct used in this experiment is presented in FIG. 13A, where the MND promoter drives cell-surface expression of the microDISC and intracellular expression of HA-tagged FOXP3.

Without being bound to theory, it is believed that Expansion Phase 1 promotes selective enrichment of DISC edTreg/ µDISC edTreg in rapamycin, which allows edited cells to out-compete unedited cells prior to Expansion Phase 2, where CD3/CD28 stimulation will result in an expansion in the number of DISC edTreg. Generally, Expansion Phase 1 includes homology-dependent repair (HDR), DISC expression, recovery from electroporation, and CD4+ T cell expansion. The following cohorts tested rapamycin or rapalog with or without IL-2 (50 ng/mL) in the recovery media: (1) rapamycin with 50 ng/mL IL-2; (2) rapalog with 50 ng/mL IL-2; and (3) rapamycin without IL-2.

During Expansion Phase 2, a second CD3/CD28 stimulation was tested to improve the number of DISC edTreg. The following cohorts tested both CD3/CD28 expander beads vs. soluble anti-CD3/CD28 antibodies: (1) none (no beads/no antibody); (2) T cell expander beads; and (3) soluble CD3/CD8 antibodies. In this experiment, haft of the media was removed and replenished with the same volume of media containing twice the concentration of rapamycin, rapalog, or IL-2 on days three, six, eight, ten, thirteen, and fifteen.

Figure 13B:
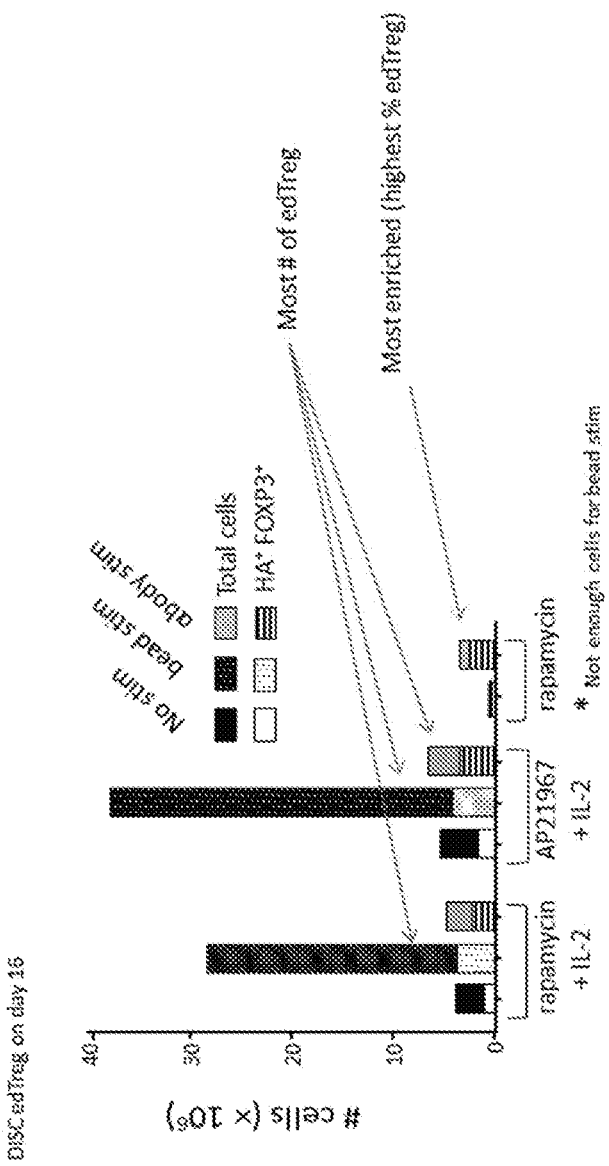
FIG. 13B summarizes the results of a two-phase expansion experiments described herein, where Expansion Phase 1 Cell conditions are indicated along the X axis. Expansion Phase 2 conditions are also indicated.

The result of this experiment is presented in FIG. 13B, where it was observed that cells receiving bead stimulation during Expansion Phase 2 resulted in the highest total number of cells, as well as highest numbers of µDISC edTreg, as determined by flow cytometry read-out for HA+ FOXP3+ cells. Soluble antibody stimulation also improved expansion, but to a lesser extent. Although the presence of IL-2 in the media during Expansion Phase 1 improved final cell numbers, the numbers of unedited cells were higher relative to the edited cells, thus limiting the amount of IL2 in Phase 1 was important. The cohort with the highest percentage of µDISC edTreg did not receive IL-2 during Expansion Phase 1, but were bead stimulated during Expansion Phase 2, as there were not enough cells for the bead stimulation condition. Conclusions drawn from these experiments include: (1) limiting IL-2 in the media prior to bead expansion could improve enrichment of µDISC edTreg; (2) IL-2 after editing improved the total cell yield; and (3) anti-CD3/CD28 beads improved cell expansion vs. use of soluble CD3 and CD28 antibodies or no stimulation.

Three-Phase Expansion Protocol

A three-phase expansion protocol was designed to test whether limiting IL-2 immediately after editing, rather than eliminating IL-2 entirely, would improve the enrichment and cell yield. Compared to the two-phase expansion protocol described above, the inclusion of an additional short expansion phase (Expansion Phase 0; Days 0-3), immediately post-editing, in a three-phase expansion protocol was designed to allow cell recovery and DISC expression in media containing varying amounts of IL-2 (or rapamycin or rapalog only). Recovered cells after Expansion Phase 0 were then transferred to the G-Rex flask and expanded in rapamycin (Expansion Phase 1; Days 3-10) to allow DISC edTreg enrichment, followed by addition of anti-CD3/CD28 beads (Expansion Phase 2; Days 10-15). The same AAV construct as shown in FIG. 13A was used in this experiment.

Flow cytometry was performed on Day 3 after intracellular staining with anti-FOXP3 and anti-HA tag (HA tag was fused in-frame with FOXP3 to create a fusion protein), which illustrate a direct correlation of IL-2 concentration in post-editing Expansion Phase 0 with the percentage of µDISC edTreg cells. The results are shown in Table 6 below. Successfully edited cells are HA+ FOXP3+ (see, Q2). HA-FOXP3+ naturally occurring tTreg and/or activated T cells that upregulate FOXP3 expression are also shown (see, Q1).

TABLE 6

| Day-3 flow cytometry | Q1 | Q2 | Q3 | Q4 |
| --- | --- | --- | --- | --- |
| Mock edited | 15.40 | 1.03 | 4.08 | 79.50 |
| 50 µg/mL IL-2 | 4.42 | 16.40 | 2.88 | 76.30 |
| 5 µg/mL IL-2 | 2.71 | 8.24 | 3.61 | 85.20 |
| 0.5 µg/mL IL-2 | 1.59 | 6.54 | 5.44 | 86.4 |
| Media only | 0.68 | 5.46 | 1.32 | 92.50 |
| 10 nM rapamycin | 0.38 | 6.41 | 1.48 | 91.70 |
| 100 nM AP21967 | 0.39 | 11.90 | 1.74 | 86.00 |

It was observed that editing rates directly correlated with IL-2 levels, indicating that the IL-2 signal during the 3-day post-editing expansion phase (Phase 0) improved HDR outcome. In addition, it was observed that rapamycin did not rescue editing rates in the absence of IL-2 at this time point.

After Expansion Phase 1 (Day 10), successfully edited cells were assessed by flow cytometry. The results of flow cytometry showing the enrichment of µDISC edTreg after Expansion Phase 1 (Day 10) are shown in Table 7 below.

TABLE 7

| Day-10 flow cytometry | Q1 | Q2 | Q3 | Q4 |
| --- | --- | --- | --- | --- |
| Mock edited | 6.10 | 0.00 | 0.078 | 93.8 |
| 50 µg/mL IL-2 | 2.59 | 23.8 | 2.45 | 71.2 |
| 5 µg/mL IL-2 | 0.53 | 50.0 | 5.18 | 44.3 |
| 0.5 µg/mL IL-2 | 0.46 | 58.3 | 9.10 | 32.2 |
| Media only | 0.26 | 53.6 | 15.2 | 30.9 |
| 10 nM rapamycin | 0.44 | 70.1 | 9.31 | 20.1 |
| 100 nM AP21967 | 0.59 | 80.5 | 5.54 | 13.3 |

Successfully edited cells HA+ FOXP3+ are indicated in column Q2. HA-FOXP3+ naturally occurring tTreg are only present when cells received 50 ng/mL IL-2 during Expansion Phase 0 (includes mock edited). Flow cytometry on Day 10 showed that cells cultured in higher doses of IL-2 during Expansion Phase 0 were less enriched for DISC edTreg, likely because some IL-2 media from Expansion Phase 0 carried over into the Expansion Phase 1 media. In this experiment, cells that were cultured in rapamycin throughout, or with rapalog AP21967, had the highest enrichment rates.

The results of flow cytometry performed on Day 15, such as upon completion of Expansion Phase 2, showing the enrichment levels of µDISC edTreg after Expansion Phase 2, are shown in Table 8 below.

TABLE 8

| Day-15 flow cytometry | Q1 | Q2 | Q3 | Q4 |
|---|---|---|---|---|
| Mock edited | 3.20 | 0.12 | 1.04 | 95.6 |
| 50 µg/mL IL-2 | 3.97 | 24.0 | 7.77 | 64.3 |
| 5 µg/mL IL-2 | 1.54 | 68.2 | 2.81 | 27.4 |
| 0.5 µg/mL IL-2 | 0.46 | 72.9 | 5.37 | 21.3 |
| Media only | 1.12 | 60.1 | 4.49 | 34.3 |
| 10 nM rapamycin | 1.08 | 75.6 | 7.56 | 15.7 |
| 100 nM AP21967 | 0.33 | 84.1 | 4.93 | 10.7 |

While enrichment improved for each of the IL-2 and rapamycin cohorts after Expansion Phase 2, cells that were cultured in higher doses of IL-2 during the Expansion Phase 0 remained less-enriched for DISC edTreg here, while cells cultured in rapamycin or rapalog AP21967 during Expansion Phase 0 had the highest enrichment rates even at Day 15.

Figures 14A, 14B:
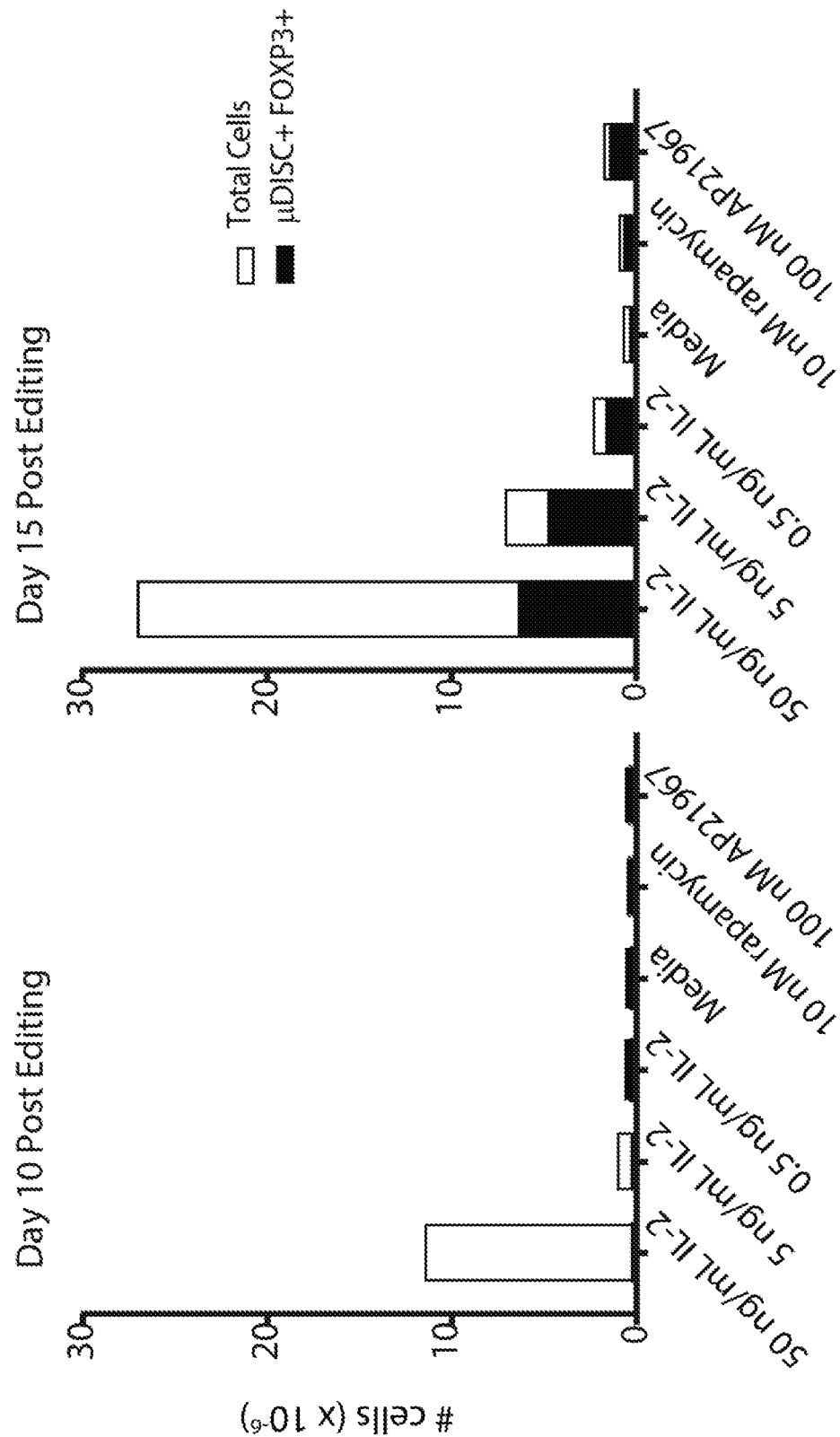
FIGS. 14A-14B graphically summarizes the number of μDISC edTreg relative to total number of cells in culture ten days and fifteen days post editing. Expansion Phase 0 culturing conditions are indicated along the X axis. The number of total cells in the culture are indicated in white, while the number successfully edited (HA+/μDISC+ and FOXP3+) are indicated in black. Based upon these findings, the optimal conditions for μDISC edTreg production were chosen as the second condition from left, which corresponds to the use of 5 ng/ml IL-2 during Expansion Phase 0.

As shown in FIGS. 14A and 14B, cell counts after Expansion Phases 1 and 2 (day 10 and 15 post-editing, respectively, showed that the highest number of HA+ (labeled as µDISC+ here) FOXP3+ edited cells were obtained when 50 ng/mL IL-2 was present in the media during Expansion Phase 0. However, this condition also had the lowest enrichment rate (%) relative to unedited cells. Culturing cells in 5 ng/mL IL-2 during Expansion Phase 0 had slightly fewer µDISC edTreg, but this population included nearly 70% of the total cells. It was therefore concluded that the use of 5 ng/mL IL-2 during Expansion Phase 0 best optimized the total yield of µDISC edTreg without markedly reducing overall cell µDISC edTreg purity.

Using a Three-Phase Expansion Protocol for µDISC FOXP3 cDNA edTreg

In a subsequent experiment, a similar three-phase expansion protocol was tested using a different rAAV6 donor construct for editing that has a potential application for treatment of subjects with, e.g., IPEX (immune dysregulation, polyendocrinopathy, enteropathy, X-linked). The rAAV6 donor construct used in this experiment included coding sequences for, from N- to C-terminal orientation, HA tag-FOXP3 cDNA-µDISC. After integration, the inserted construct is designed to express an HA-FOXP3 cDNA fusion protein as well as the µDISC. The inclusion of an additional short expansion phase (Expansion Phase 0; Days 0-3), immediately post-editing, was designed to allow cell recovery and DISC expression. Recovered cells after Expansion Phase 0 were then transferred to the G-rex® flask and expanded in 10 nM rapamycin to select edited cells (Expansion Phase 1; Days 3-10) and to allow DISC edTreg enrichment, followed by addition of anti-human CD3/CD28 (Expansion Phase 2; Days 10-17) for second stimulation. This is experiment, Expansion Phase 2 was extended to seventeen days to improve cell yield.

Using the above three-phase protocol, an increased expansion of µDISC FOXP3 cDNA edTreg compared to expansion of unedited cells was achieved. In particular, a 26-fold expansion of the number of edited cells from Day 3 to Day 17 was achieved, with approximately 78% enrichment of edited cells at the Day 17 time point (data not shown). It was observed that the starting editing rates were about 10% which may reflect the larger packaging size of the AAV donor for this study.

Compilation of Expansion of Cells Using Optimized DISC Expansion

Subsequently, a candidate clinical AAV donor was tested for editing and expansion using the optimized three-phase expansion protocol discussed above, which was designed to determine expansion of DISC edTreg compared to expansion of unedited cells after a three-phase expansion protocol. In this experiment, the donor AAV was designed for use in multiple autoimmune applications, in which full-length DISC elements and endogenous FOXP3 are under control of an upstream MND promoter. AAV donor with HA tag fused to endogenous FOXP3 (AAV donor template #3187; SEQ ID NO: 38) or without the HA tag (AAV donor template #3195; SEQ ID NO: 39). Editing using these AAV donors resulted in expression of the full-length DISC elements and endogenous FOXP3 expression under control of an upstream MND promoter. The first test vector (AAV donor template #3187; Test 1) utilized an AAV construct that included an HA tag fused to endogenous FOXP3; the next three tests (Test 2, Test 3, and Test 4) used a more clinically relevant, which was an AAV donor without an HA tag (AAV donor template #3195). In this experiment, the inclusion of an additional short expansion phase (Expansion Phase 0; Days 0-3; in the presence of 5 ng/mL IL-2), immediately post-editing, was designed to allow cell recovery and DISC expression. Recovered cells after Expansion Phase 0 were then transferred to the G-Rex flask and expanded in the presence of 10 nM rapamycin to select edited cells (Expansion Phase 1; Days 3-10) and to allow DISC edTreg enrichment, followed by flow cytometry and addition of anti-CD3/CD28 beads (Expansion Phase 2; Days 10-17; in the presence of 10 nM rapamycin). At Day 17, upon completion of Expansion Phase 2, flow cytometry was performed, and cells were counted and frozen.

It was observed that the average fold expansion of edited cells (with or without HA tag) from Day 3 to when bead activation started (day 10-13) was 2±1.6-fold; average fold expansion during bead activation (from days 10-13 to days 16-20-fold) was 20.5±5.9-fold (mean of 4 experiments with 2 donors±s.d.) (data not shown). Because the starting Day 3 editing rates (such as percentage of double positive FOXP3+ P2A+ cells) were about twice as high as the experiments shown above, these experiments consistently generated final products with very high purity (93.5±2.4%) within the live cell gate at completion of the third phase expansion.

Example 6: Effect of Rapamycin on µDISC GFP edTreg Expansion or Survival In Vivo This Example describes experiments performed to test the capacity of edTreg cells expressing a µDISC construct to be expanded in vivo by rapamycin treatment. This is an important concept, as engineered T cells or expanded natural Tregs often do not expand into patients sufficiently. There are also conditions under which it is not desirable to expand Tregs, for example, in some cases of infection. Therefore, a useful feature of engineered cells provided herein having Treg features is the ability to exert control on expansion in vivo. Experiments were carried out to determine whether rapamycin could increase the number of μDISC edTregs in vivo using a humanized mouse model, which included human cells transferred into immune-incompetent NOD-scid-IL2RgNULL (NSG) mice. For these experiments, cells were edited using an AAV donor to drive cis-linked expression of the μDISC and endogenous FOXP3 from the MND promoter. This AAV donor template incorporates a GFP fusion protein at the N-terminal of endogenous FOXP3. The GFP-labeled FOXP3 fusion protein was used to facilitate the ability to detect gene-edited cells within the in vivo cell samples. In the three-phase expansion protocol used in this study, CD4+ cells were cultured with anti-CD3/CD28 expander beads in 50 ng/mL IL-2 at Day −4. The beads were then removed at Day −1. Immediately post-editing, Expansion Phase 0 (Days 0-3) was carried out in the presence of 5 ng/mL IL-2. In the three-phase expansion protocol used in this experiment, the timing of Expansion Phase 0 flow cytometry was on Day 2. Recovered cells after Expansion Phase 0 were then transferred to the G-rex® flask and expanded in the presence of 10 nM rapamycin to select edited cells (Expansion Phase 1; Days 3-9) and to allow DISC edTreg enrichment, followed by flow cytometry and addition of anti-CD3/CD28 beads (Expansion Phase 2; Days 9-16; in the presence of 10 nM rapamycin). Flow cytometry was performed at Days 2, 9, 12, and 16 to monitor edited GFP+FOXP3+ cell expansion. As shown in Table 9 below, it was observed that the final cell product was >80% GFP+ edited cell by Day 16, and the edited cells had expanded over 20-fold.

TABLE 9

| Timepoint | Day 2 | Day 9 | Day 12 | Day 16 |
| --- | --- | --- | --- | --- |
| edited GFP+ FOXP3+ cell | 22% | 79% | 88% | 89% |

At Day 16, upon completion of Expansion Phase 2, cells were used in intravenous injection, as described below.

NSG mice were pre-treated with rapamycin in order to saturate rapamycin binding proteins and provide rapamycin in serum. As shown in Table 10 below, some of the mice were then irradiated (irradiation=200 cGy), mimicking irradiation that is used in an in vivo immunosuppression assay.

TABLE 10

|  | rapamycin | irradiation | # mice |
| --- | --- | --- | --- |
| Mock edited | − | + | 3 |
| μDISC edTreg | − | + | 5 |
| μDISC edTreg | + | + | 5 |
| μDISC edTreg | − | − | 5 |
| μDISC edTreg | + | − | 7 |

The μDISC GFP edTregs (or mock-edited cells) were then injected i.v. according to the following general procedure. Starting from Day −4, intraperitoneal (i.p.) injection of rapamycin 0.1 mg/kg was carried out every other day until Day 21. At Day 0, irradiation was performed and μDISC edTreg was i.v. injected. Peripheral blood samples were collected to either test for rapamycin levels (Day 2) or for flow cytometry (Days 7, 14, 21, and 28) to track the phenotype and number of transferred human T cells including GFP+ edTreg cells.

To illustrates expansion of μDISC GFP edTreg in rapamycin treated vs. vehicle, flow cytometry results from peripheral blood seven days post-transfer into NSG are shown in Table 11 below (Gate: live, hCD45+, hCD4+), where human T cell markers and GFP+ are shown for a representative mouse from each cohort.

TABLE 11

|  | Radiation (200 Gy) | | No Radiation | |
| --- | --- | --- | --- | --- |
|  | Vehicle | rapamycin | Vehicle | rapamycin |
| CD25+ GFP+ edTreg cells | 44.8 | 82.6 | 35.1 | 79.9 |
| CD25− GFP+ edTreg cells | 28.2 | 5.52 | 39.7 | 8.37 |
| CD127+ GFP+ edTreg cells | 0.44 | 0.50 | 0.71 | 0.57 |
| CD127− GFP+ edTreg cells | 71.9 | 87.6 | 74.1 | 88.2 |

Figure 15A:
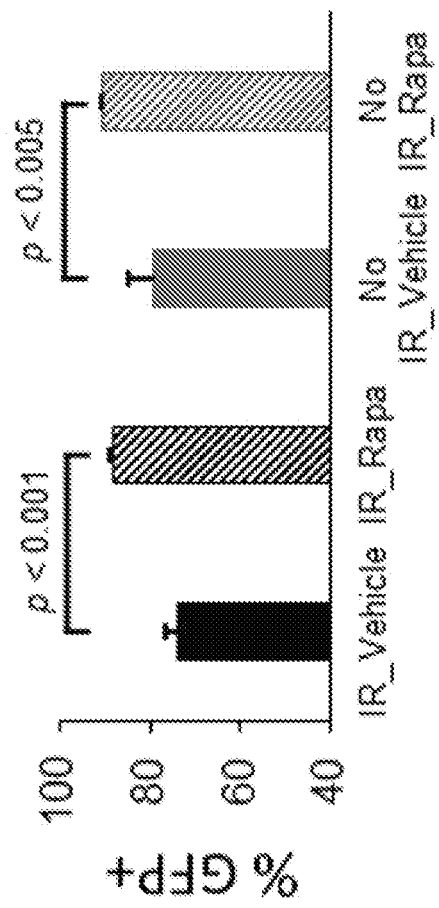
FIGS. 15A-15B summarize the results of flow cytometry experiments performed to illustrate expansion of μDISC GFP edTreg in rapamycin treated vs. vehicle at seven days post-transfer into NSG. The chart average±s.d. of the % GFP+ (FIG. 15A) or number of GFP+ cells in the 75 μL peripheral blood sample (FIG. 15B). IR=irradiation; Rapa=rapamycin, 0.1 mg/kg i.p. every two days throughout experiment. P value was obtained using a Student's T test. In each figure, the two left bars represent samples with irradiation, and the two right bars represent samples with no irradiation.
Figure 15B:
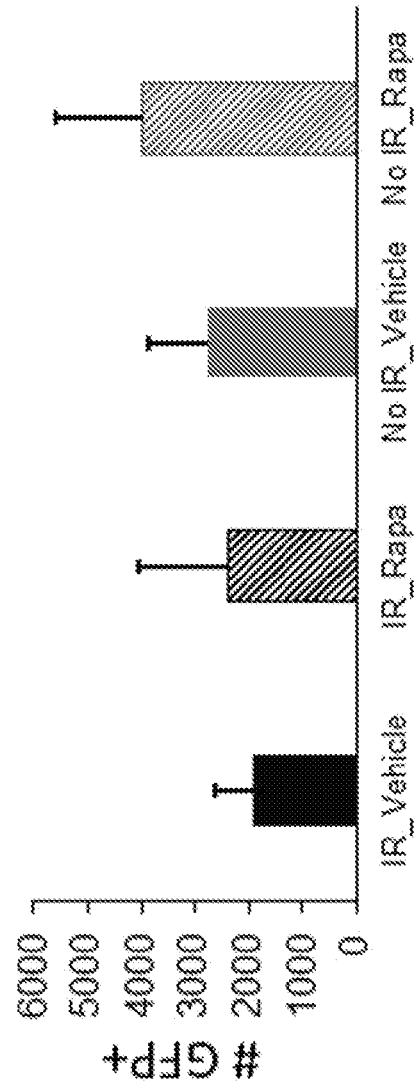

The results of flow cytometry experiments performed to illustrate expansion of μDISC GFP edTreg in rapamycin treated vs. vehicle at seven days post-transfer into NSG are also summarized in FIGS. 15A-15B. In these figures, the chart average±s.d. of the percentage of GFP+ cells (FIG. 15A) or number of GFP+ cells in the 75 μL peripheral blood sample (FIG. 15B).

Figure 16A:
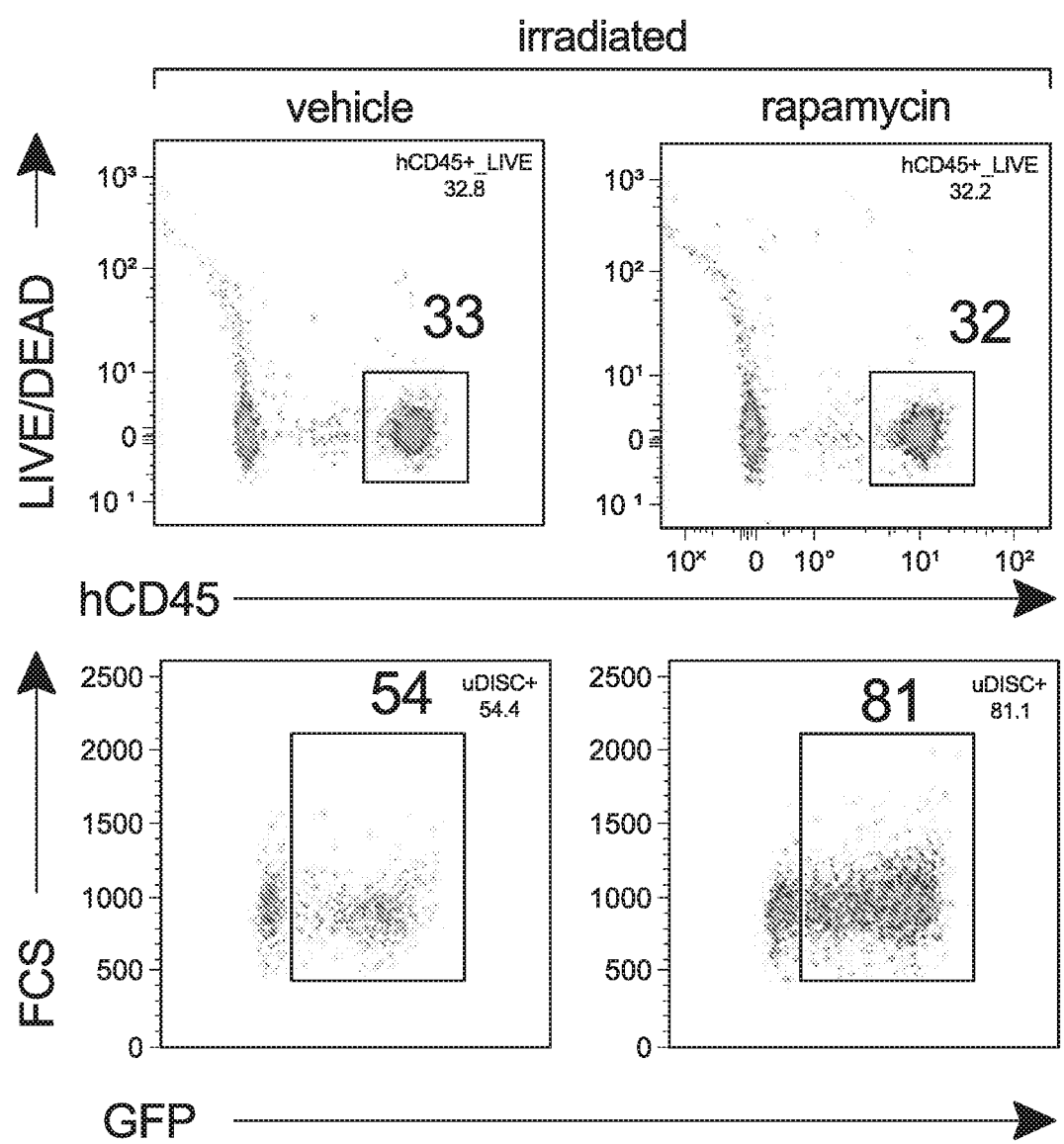
FIGS. 16A-16B summarize the results of experiments performed to illustrate expansion of μDISC GFP edTreg in rapamycin treated vs. vehicle at fourteen days post-transfer into NSG. Flow cytometry plots show human CD45 or GFP vs. either a viability dye (Live/Dead) or forward cell scatter (FCS) in FIG. 16A for a representative mouse from each cohort. Charts to the right of FIG. 16A summarize the result for each cohort.
Figure 16B:
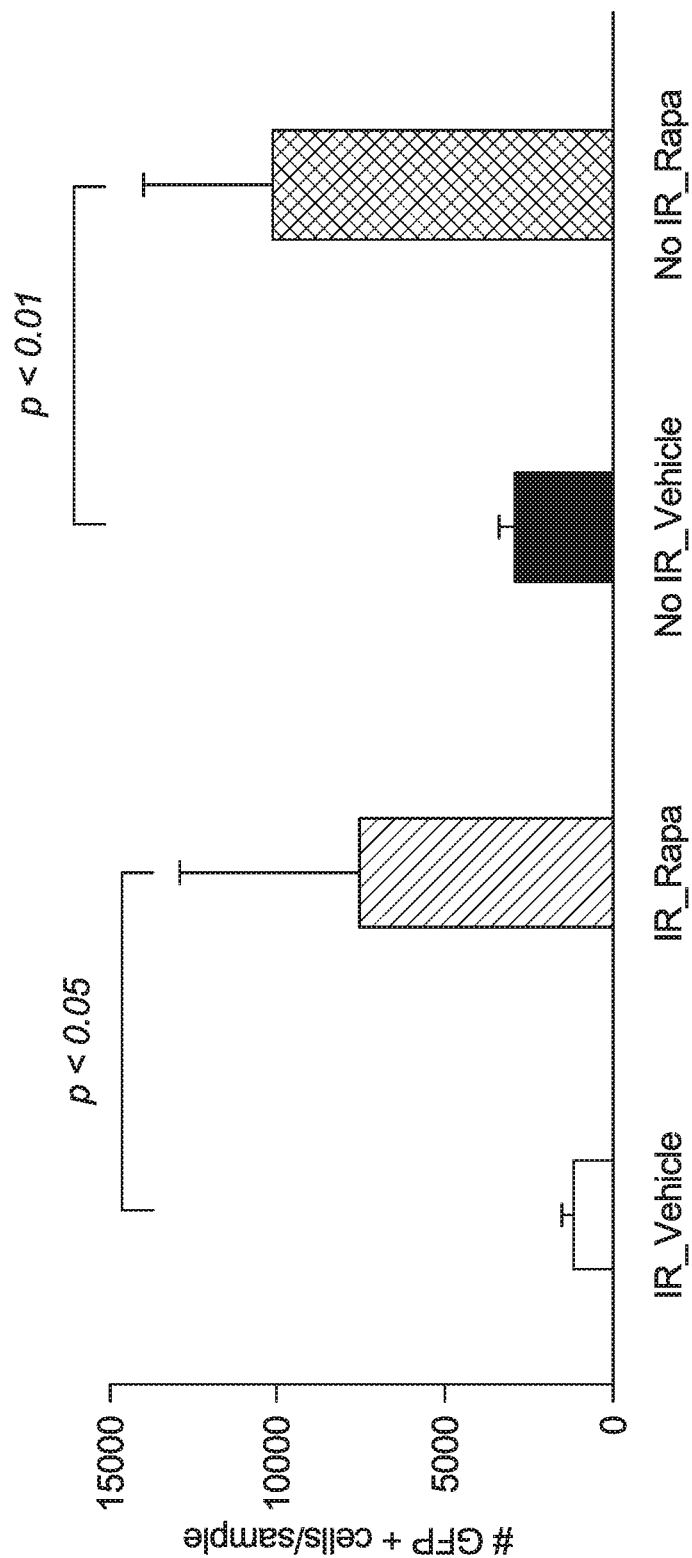

Flow cytometry results from peripheral blood fourteen days after cell transfer to mice are shown in FIGS. 16A-16B. On Day 14, peripheral blood samples were stained for human CD45, CD4, CD127, and CD25. On both days, most human CD45+CD4+ cells were GFP+. Plots on Day 7 showed that GFP+ cells were CD25+ and CD127−, as expected for Treg. The percentage of GFP+ cells, as well as the number of GFP+ cells in serum sample, was higher when mice were treated with rapamycin.

Figure 17:
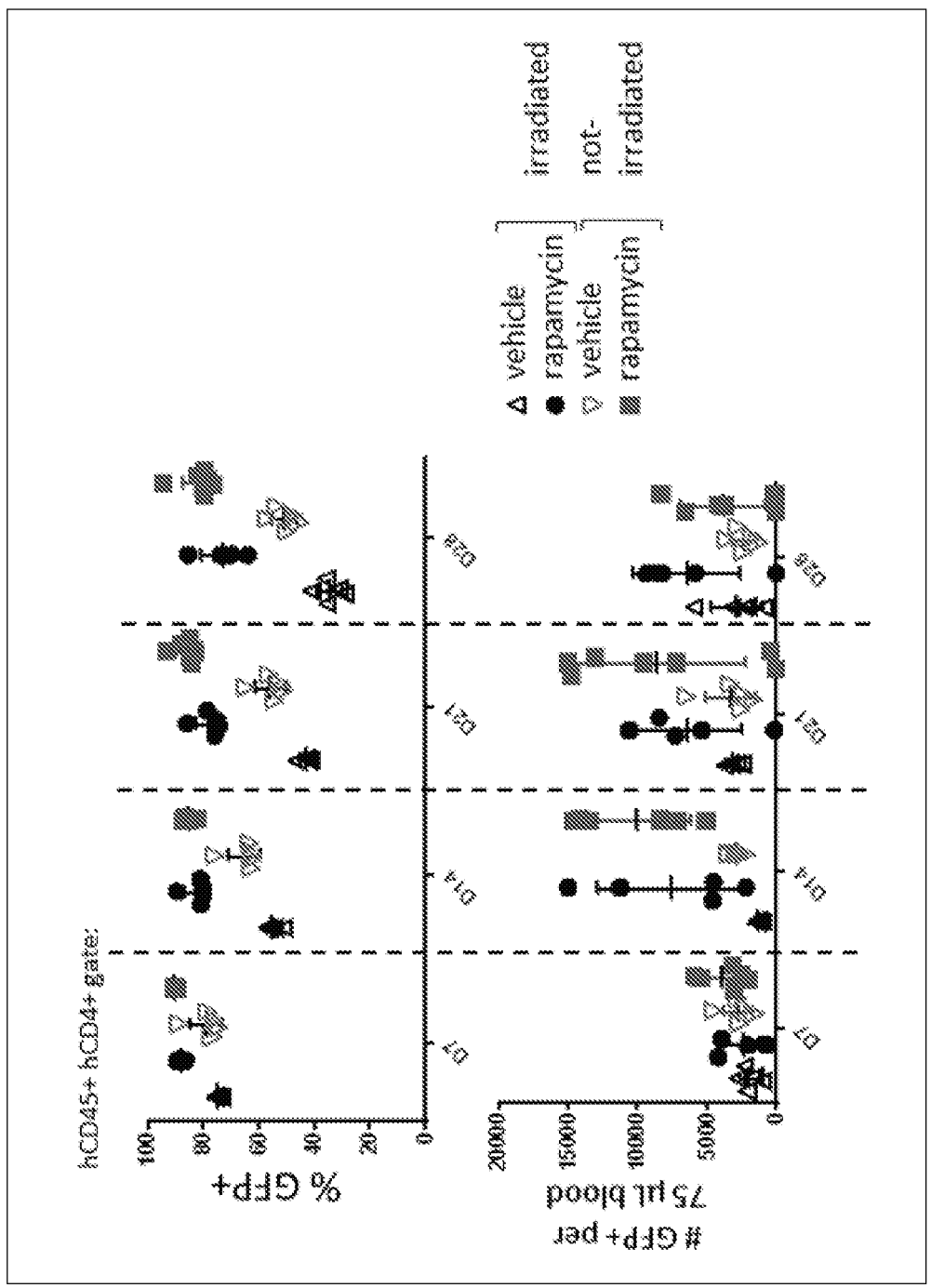
FIG. 17 summarizes the percentage (%) and number of μDISC GFP edTreg cells present in the peripheral blood of recipient mice in vivo over time in animals treated with or without rapamycin. Plots summarize flow cytometry data; each symbol represents an individual mouse, and the average±s.d. are shown by bars. % GFP in CD45+CD4+ gate is plotted at top; numbers of GFP+ cells in peripheral blood samples are plotted on the bottom.

The levels of μDISC GFP edTreg in the peripheral blood of these mice continued to be tracked weekly for a total of four weeks. The resulting percentages and numbers of GFP+ cells are summarized in the graphs in FIG. 17. A conclusion drawn from this experiment is that rapamycin treated mice had higher levels of μDISC GFP edTreg at each time point, peaking between two and three weeks after cell transfer. Irradiation slightly improved the number of cells, likely resulting from higher levels of antigen presentation by murine cells to the adoptively transferred human edTreg cells.

Taken together, the results of this study (e.g., data shown in Tables 9-11 and FIG. 17) clearly demonstrate that edTreg expressing a version of the DISC platform can be expanded in vivo using rapamycin. This provides direct evidence that these constructs and methods can be used for treatment, e.g., the platform is useful for in vivo expansion and support of DISC expressing edTreg products for treatment of autoimmune diseases.

Example 7: Testing Effect of Rapamycin on μDISC GFP edTreg Expansion or Survival In Vivo In this Example, we tested whether DISC edTreg that have been expanded in rapamycin in vitro (as part of the cell product manufacturing process outlines in our three-phase expansion protocol) have the capacity to function (e.g. suppress effector T cell immune responses) in vivo. In the model that we used to test this, human CD4 T effector cells are injected into minimally irradiated NSG mice, causing a massive inflammatory response mediated by the human T cells against mouse tissues. This inflammatory response is dependent on mouse MHC-II expression, suggesting that this model may mimic allogeneic T cell responses, such as occur in graft-vs.-host disease. Naturally occurring autologous thymic Treg and the novel edTreg products reported previously can suppress this immune response. Therefore, the AAV donor template used in this experiment was designed to generate a FOXP3 fusion protein containing an HA epitope at its N-terminus that permits tracking of successfully gene-edited cells. This AAV donor template expressed the cassette with DISC elements upstream of an HA tagged FOXP3 protein, driven off of the MND promoter (abbreviated as DISC HA ki edTreg; ki=knock-in). Following HDR, the cassette would insert into the FOXP3 locus, leading to MND-promoter mediated expression of both DISC and endogenous FOXP3. Human T cell editing and expansion were carried out using a three-phase expansion protocol, as follows. CD4+ cells were cultured with anti-CD3/CD28 expander beads in the presence of 50 ng/mL IL-2 at Day −4. The beads were then removed at Day −1. Immediately post-editing, Expansion Phase 0 (Days 0-3) was carried out in the presence of 5 ng/mL IL-2. Recovered cells after Expansion Phase 0 were then transferred to the G-Rex flask and expanded in the presence of 10 nM rapamycin to select edited cells (Expansion Phase 1; Days 3-10) and to allow DISC edTreg enrichment, followed by flow cytometry and addition of anti-CD3/CD28 beads (Expansion Phase 2; Days 9-16; in the presence of 10 nM rapamycin). Upon completion of Expansion Phase 2, cells were collected and frozen at Day 16. As shown in Table 12 below, flow cytometry was performed at Day 14 indicated that the cell product was expanded and resulted in an 18.4-fold increase in HA+FOXP3+ cells from Day 3 to Day 14, with a final cell purity of >90%.

TABLE 12

| Expansion Timepoint | Day 3 | Day 10 | Day 14 |
| --- | --- | --- | --- |
| HA+ FOXP3+ cells | 35.6% | 63.3% | 90.9% |

Further experiments were performed to test the capacity of DISC HA ki edTreg to suppress activated CD4 T effector cells in vivo. Table 13 below provides detail of the various NSG mouse cohorts indicating the T cell populations delivered by IV adoptive transfer. LNGFR edTreg were utilized as a positive control for functionally active edTreg. These edited T cells express an LNGFR epitope tag on the cell surface and a FOXP3 cDNA and were shown previously to be immunosuppressive in this model.

TABLE 13

| Cohort | 4 million Effector T | 8 million mock edited cells (AAV only) | 8 million DISC HA-edTreg | 8 million LNGFR-edTreg | # mice |
| --- | --- | --- | --- | --- | --- |
| Teff only | + | N/A | N/A | N/A | 4 |
| Teff + mock | + | + | N/A | N/A | 4 |
| Teff + mock (grown in rapamycin) | + | + | N/A | N/A | 3 |
| Teff + DISC HA edTreg | + | N/A | + | N/A | 5 |
| Teff + LNGFR edTreg | + | N/A | N/A | + | 4 |

The general procedure used in this experiment is as follows. Irradiated recipient NSG mice were infused i.v. with either DISC HA ki edTregs or mock-edited cells. After three days (to allow edTreg engraftment) CD4 T effector cells were then delivered by i.v. injection. Animals were monitored for up to fifty nine days by tracking weight and scoring for GvHD symptoms. Mice were euthanized if they reached pre-determined humane endpoints such as the loss of >20% of their body weight.

Figure 18:
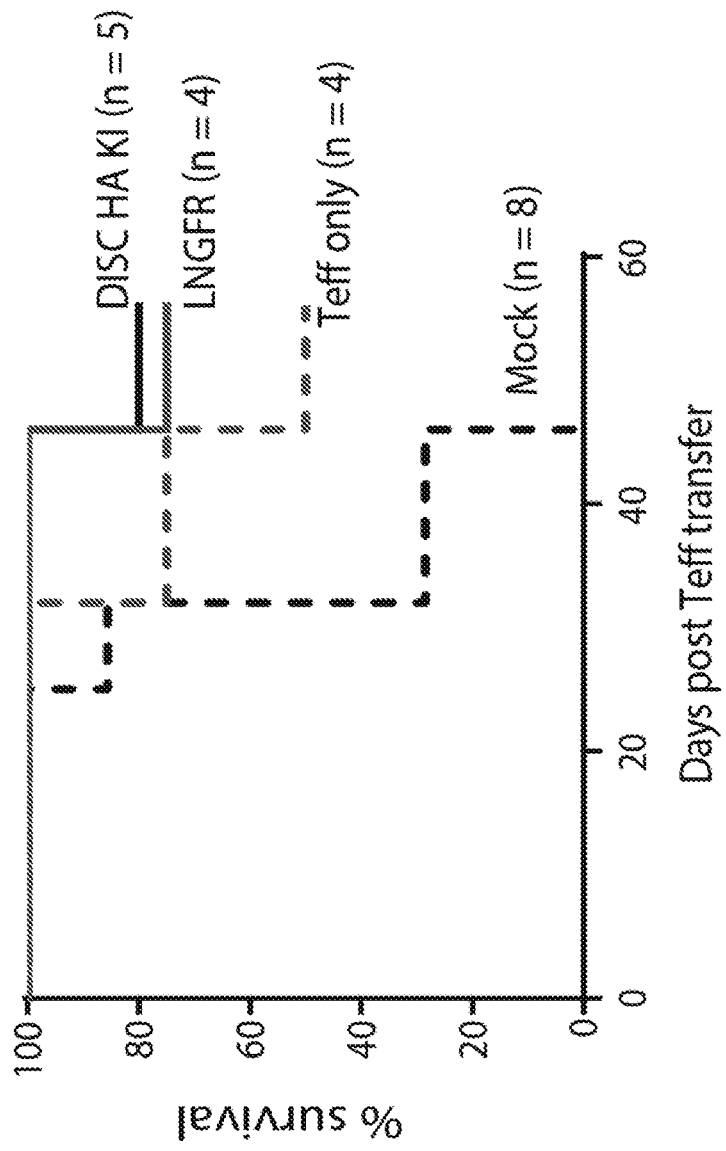
FIG. 18 shows a Kaplan-Meier survival curve of in vivo immunosuppression model. Teff=T effector only group. In these experiments, all groups received T effector cells.

It was found that mice that received mock-edited cells along with the T effector cells had the most severe outcome, with all of the mice in these cohorts dying within forty five days. This cohort fared worse than mice that received T effector cells alone due to the ability of mock-edited cells to also mount a productive inflammatory response against the murine antigens. Mice that received either LNGFR-expressing edTreg (a positive control cell verified as immunosuppressive by other groups in our laboratory) or DISC HA ki edTreg, had improved survival rates relative to both the T effector only and the mock edTreg with T effector groups, indicating the edTreg, including DISC HA ki edTreg, suppressed T effector inflammation. These combined findings clearly demonstrate that edTreg containing the DISC construct can exhibit Treg-like functional activity in vivo; thereby supporting the use of similar edited Treg products for therapy in autoimmune conditions. A Kaplan-Meier survival curve of in vivo immunosuppression model is shown in FIG. 18.

Example 8: Assessing HDR Rates of DISC edTreg Using Anti-P2A Antibody Staining or ddPCR Anti-P2A Staining to Detect Edited Cells This Example describes the development of a clinically relevant method to track DISC edTreg and measure the rates of successfully edited cells in a mixed population that does not rely upon an epitope tag or a fluorescent protein to label the edited cells. While the use of tags such as GFP or HA allow sensitive and quantitative detection of edited cells in culture or in vivo, such tags would not be used in a clinical cell product as they may mediate an immune response to the tag and/or inhibit FOXP3 function.

A new cell tracking method that we developed uses intracellular staining of the P2A ribosome skip peptide. P2A sequences were incorporated in the AAV donor sequences to separate out the coding sequences of each of the DISC elements and FOXP3 start sequence. Within HDR edited cells, a portion of the peptide sequence was introduced into edited cells at the C-terminus of DISC elements. Also used in this experiment was a P2A antibody (clone 3H4 against CGDVEENPG) that is commercially available through Novus Biologicals. The anti-P2A monoclonal antibody was labeled with a fluorophore for use in intracellular staining. As shown in Table 14 below, while some of the mock-edited cells expressed FOXP3 (an expected result as thymic Treg in this mixed population of cells express FOXP3), they did not stain with the P2A or HA tag antibodies, respectively. In this experiment, three days post-editing, cells were stained for intracellular FOXP3, HA tag, and P2A peptide. Cells edited with AAV donor template #3195, that did not include an HA tag, expressed both FOXP3 and P2A at high levels. Those cells edited with AAV donor template #3187, that introduced the HA tag, exhibited similar levels of P2A+ FOXP3+ and HA+ FOXP3+ cells, demonstrating the direct correlation between P2A staining and HA staining. Thus, use of P2A staining can permit serial assessment of manufactured edTreg and/or tracking of these cells in vivo. In Table 14 below, the percentage of double positive cells (expressing either P2A-FOXP3 or HA-FOXP3) in each cohort is shown.

TABLE 14

| AAV donor | Edited cells P2A+ FOXP3+ | Edited cells HA+ FOXP3+ |
|---|---|---|
| AAV #3195 | 42.3% | 0.10% |
| AAV #3187 | 57.2% | 59.8% |
| Mock | 0.20% | 0.20% |

A ddPCR Assay to Quantify HDR Events on a Molecular Basis

For clinical cell products, it is useful to verify a correlation between the percentage of cells expressing the gene of interest, as determined by, for example, flow cytometry, with the percentage of homology-directed repair events determined at the DNA level. As an illustration of this usefulness, FOXP3 expression can be up-regulated in effector T cells after TCR stimulation even without gene editing; additionally, an AAV template inserted in an "off target" double strand break could also express P2A labeled proteins. We therefore developed a sensitive method to quantify the percentage of FOXP3 genes that had undergone HDR events in a mixed cell population. This section describes a digital droplet PCR (ddPCR) assay developed to quantify HDR events from genomic DNA samples. Primers and probe sets were designed such that they would allow for detection of successful HDR in the target locus using the Bio-Rad® QX200™ Droplet Digital PCR System and Bio-Rad® ddPCR™ Supermix for probes. The sequences of the PCR and probe primers used are shown in Table 15 below, and the annealing temperature was 63° C.

TABLE 15

| Primer | Sequence | SEQ ID NO |
|---|---|---|
| DISC MDR FP | CGGCGACGTGGAAGAGAATC | 34 |
| DISC MDR RP | GGCTGTGGTTCAGCCTGACT | 35 |
| DISC HDR probe (FAM) | AGGCTCTCCCCGACCTCCC | 36 |

The results of HDR rates calculated by ddPCR relative to flow cytometry results by P2A antibody staining at the 10 days post-editing time point are summarized in Table 16 below.

TABLE 16

| | Edit 1 3195 | Edit 2 3195 | Edit 3 3195 | Edit 4 3195 | Edit 5 3195 | Edit 6 3195 | Edit 7 3195 | Edit 8 3195 | Edit 9 3195 | Edit 3187 | Mock |
|---|---|---|---|---|---|---|---|---|---|---|---|
| ddPCR | 68.9 | 78.8 | 72.8 | 73.1 | 61.7 | 72.0 | 74.9 | 63.8 | 64.4 | 76.1 | 0.0 |
| HDR rate | 61.3 | 69.1 | 65.0 | 67.4 | 58.3 | 63.8 | 66.6 | 55.8 | 52.9 | 67.6 | 5.26 |

In these experiments, flow cytometry of nine independent samples were evaluated at 10 days post-editing with either AAV 3195 (edits 1 through 9) or AAV 3187 or mock edited, showing intracellular staining with FOXP3 and P2A. The percentage of double positive cells (expressing P2A-FOXP3) in each cohort is shown. Genomic DNA was isolated from cells in parallel for ddPCR assay. Results of ddPCR assay are also shown. It was observed that there is a close correlation between ddPCR values and positive cells as assessed by flow cytometry (68.9 ddPCR vs 61.3 for flow cytometry, for Edit 1, etc.). Thus, ddPCR provides a second assay to track the proportion of DISC edTreg in vitro and this method correlates well with use of P2A staining by flow cytometry.

While particular embodiments of the present disclosure have been disclosed, it is to be understood that various modifications and combinations are possible and are contemplated within the true spirit and scope of the appended claims. There is no intention, therefore, of limitations to the exact abstract and disclosure herein presented.

SEQUENCES

[In addition to sequences disclosed elsewhere in the present disclosures, the following sequences are provided as they are mentioned or used in various exemplary embodiments of the disclosures, which are provided for the purpose of illustration.

| SEQ ID NO | Sequence | Description |
|---|---|---|
| 1 | MEMWHEGLEEASRLYFGERNVKGMFEVLEPLHAMMERGPQTLKETSFNQAYGRDLME AQEWCRKYMKSGNVKDLTQAWDLYYHVFRRISK | naked FRB wild-type polypeptide |
| 2 | MEMWHEGLEEASRLYFGERNVKGMFEVLEPLHAMMERGPQTLKETSFNQAYGRDLME AQEWCRKYMKSGNVKDLLQAWDLYYHVFRRISK | naked FRB mutant polypeptide |
| 3 | GAACAGAGAAACAGGAGAATATGGGCCAAACAGGATATCTGTGGTAAGCAGTTCCTG CCCCGGCTCAGGGCCAAGAACAGTTGGAACAGCAGAATATGGGCCAAACAGGATATC TGTGGTAAGCAGTTCCTGCCCCGGCTCAGGGCCAAGAACAGATGGTCCCCAGATGCG GTCCCGCCCTCAGCAGTTTCTAGAGAACCATCAGATGTTTCCAGGGTGCCCCAAGGAC CTGAAATGACCCTGTGCCTTATTTGAACTAACCAATCAGTTCGCTTCTGCTTCTGTTCG CGCGCTTCTGCTCCCCGAGCTCTATATAAGCAGAGCTCGTTTAGTGAACCGTCAGATC GCTAGCACCGGTGCCGCCACCATGCCTCTGGGCCTGCTGTGGCTGGGCCTGGCCCTGC TGGGCGCCCTGCACGCCCAGGCCGGCGTGCAGGTGGAGACAATCTCCCCAGGCGAC GGACGCACATTCCCTAAGCGGGGCCAGACCTGCGTTGTGCACTATACAGGCATGCTG GAGGATGGCAAGAAGTTTGACAGCTCCCGGGATAGAAACAAGCCATTCAAGTTTATG CTGGGCAAGCAGGAAGTGATCAGAGGCTGGGAGGAGGGCGTGGCCCAGATGTCTGT GGGCCAGAGGGCCAAGCTGACCATCAGCCCAGACTACGCCTATGGAGCAACAGGCCA CCCAGGAATCATCCCACCTCACGCCACCCTGGTGTTCGATGTGGAGCTGCTGAAGCTG GGCGAGGGATCCAACACATCAAAAGAGAACCCCTTCTGTTCGCATTGGAGGCCGTA GTCATATCTGTTGGATCCATGGGACTTATTATCTCCCTGTTGTGTGTGTACTTCTGGCT GGAACGGACTATGCCCAGGATCCCCACGCTCAAGAATCTGGAAGATCTCGTCACAGA ATACCATGGTAATTTCAGCGCCTGGAGCGGAGTCTCTAAGGGTCTGGCCGAATCCCTC CAACCCGATTATTCTGAACGGTTGTGCCTCGTATCCGAAATACCACCAAAAGGCGGGG CTCTGGGTGAGGGCCCAGGGGCGAGTCCGTGCAATAACACAGCCCGTATTGGGCCC CTCCTTGTTATACGTTGAAGCCCGAAACTGGAAGCGGAGCTACTAACTTCAGCCTGCT GAAGCAGGCTGGAGACGTGGAGGAGAACCCTGGACCTATGGCACTGCCCGTGACCG CCCTGCTGCTGCCTCTGGCCCTGCTGCTGCACGCAGCCCGGCCTATCCTGTGGCACGA GATGTGGCACGAGGGCCTGGAGGAGGCCAGCAGGCTGTATTTTGGCGAGCGCAACG TGAAGGGCATGTTCGAGGTGCTGGAGCCTCTGCACGCCATGATGGAGAGAGGCCCAC AGACCCTGAAGGAGACATCCTTTAACCAGGCCTATGGACGGGACCTGATGGAGGCAC AGGAGTGGTGCAGAAAGTACATGAAGTCTGGCAATGTGAAGGACCTGCTGCAGGCC TGGGATCTGTACTATCACGTGTTTCGGAGAATCTCCAAGGGCAAAGCACACGATTCCGT GGCTTGGGCATCTGCTCGTTGGGCTGAGTGGTGCGTTTGGTTTCATCATCTTGGTCTA TCTCTTGATCAATTGCAGAAATACAGGCCCTTGGCTGAAAAAAGTGCTCAAGTGTAAT ACCCCCGACCCAAGCAAGTTCTTCTCCCAGCTTTCTTCAGAGCATGGAGGCGATGTGC AGAAATGGCTCTCTTCACCTTTTCCCTCCTCAAGCTTCTCCCCGGGAGGGCTGGCGCCC GAGATTTCACCTCTTGAGGTACTTGAACGAGACAAGGTTACCCAACTTCTCCTTCAACA GGATAAGGTACCCGAACCTGCGAGCCTTAGCTCCAACCACTCTCTTACGAGCTGCTTC ACCAATCAGGGATACTTCTTTTTTCCACCTTCCCGATGCGCTGGAAATCGAAGCTTGTCA AGTTTACTTTACCTATGATCCATATAGCGAGGAAGATCCCGACGAAGGAGTCGCCGGT GCGCCCACGGGTTCCTCACCCCAACCTCTCCAGCCTCTCTCAGGAGATGATGCTT ATTGCACTTTTCCCAGTAGAGACGATCTCCTCCTCTTTTCTCCATCTCTTTTGGGGGAC CTTCCCCCCCTTCTACGGCACCTGGCGGGTCTGGTGCTGGCGAGGAGCGGATGCCGC CGTCCCTCCAGGAGCGAGTACCACGAGATTGGGATCCCCAGCCACTTGGACCCCCAC CCCCGGCGTACCTGACCTTGTCGATTTTCAACCTCCCCCTGAATTGGTGCTGCGAGAG GCTGGGGAGGAAGTTCCGGACGCTGGGCCGAGGGAGGGCGTGTCCTTTCCATGGAG TAGGCCTCCAGGTCAAGGCGAGTTTAGGGCTCTCAACGCGCGGCTGCCGTTGAATAC AGACGCTTATCTCTCACTGCAGGAACTGCAAGGTCAGGACCCAACACATCTTGTAGGA TCTGGTGCTACTAATTTTTCTCTTTTGAAGCAAGCTGGAGATGTTGAAGAGAACCCCG GTCCGGAGATGTGGCATGAGGGTCTGGAAGAAGCGTCTCGACTGTACTTTGGTGAGC GCAATGTGAAGGGCATGTTTGAAGTCCTCGAACCCCTTCATGCCATGATGGAACGCG GACCCCAGACCTTGAAGGAGACAAGTTTTAACCAAGCTTACGGAAGAGACCTGATGG AAGCCCAGGAATGGTGCAGGAAATACATGAAAAGCGGGAATGTGAAGGACTTGCTC CAAGCGTGGGACCTGTACTATCATGTCTTTAGGCGCATTAGTAAGGGCAGCGGCGCC ACCAACTTCAGCCTGCTGAAGCAGGCCGGCGACGTGGAGGAGAACCCCGGCCCCGTG AGCAAGGGCGAGGAGGATAACATGGCCATCATCAAGGAGTTCATGCGCTTCAAGGT GCACATGGAGGGCTCCGTGAACGGCCACGAGTTCGAGATCGAGGGCGAGGGCGAG GGCCGCCCCTACGAGGGCACCCAGACCGCCAAGCTGAAGGTGACCAAGGGTGGCCC CCTGCCCTTCGCCTGGGACATCCTGTCCCCTCAGTTCATGTACGGCTCCAAGGCCTACG TGAAGCACCCCGCCGACATCCCCGACTACTTGAAGCTGTCCTTCCCCGAGGGCTTCAA GTGGGAGCGCGTGATGAACTTCGAGGACGGCGGCGTGGTGACCGTGACCCAGGACT CCTCTCTGCAGGACGGCGAGTTCATCTACAAGGTGAAGCTGCGCGGCACCAACTTCCC CTCCGACGGCCCCGTAATGCAGAAGAAGACCATGGGCTGGGAGGCCTCCTCCGAGCG GATGTACCCCGAGGACGGCGCCCTGAAGGGCGAGATCAAGCAGAGGCTGAAGCTGA AGGACGGCGGCCACTACGACGCTGAGGTCAAGACCACCTACAAGGCCAAGAAGCCC GTGCAGCTGCCCGGCGCCTACAACGTCAACATCAAGTTGGACATCACCTCCCACAACG AGGACTACACCATCGTGGAACAGTACGAACGCGCCGAGGGCCGCCACTCCACCGGG GCATGGACGAGCTGTACAAGTGAACTAGTGTCGACAATCAACCTCTGGATTACAAAAT TTGTGAAAGATTGACTGGTATTCTTAACTATGTTGCTCCTTTTACGCTATGTGGATACG CTGCTTTAATGCCTTTGTATCATGCTATTGCTTCCCGTATGGCTTTCATTTTCTCCTCCTT GTATAAATCCTGGTTGCTGTCTCTTTATGAGGAGTTGTGGCCCGTTGTCAGGCAACGT GGCGTGGTGTGCACTGTGTTTGCTGACGCAACCCCCACTGGTTGGGGCATTGCCACCA CCTGTCAGCTCCTTTCCGGGACTTTCGCTTTCCCCCCTCCCTATTGCCACGGCGGAACTC | DISC vector DNA |

| SEQ ID NO | Sequence | Description |
|---|---|---|
| | ATCGCCGCCTGCCTTGCCCGCTGCTGGACAGGGGCTCGGCTGTTGGGCACTGACAATT<br>CCGTGGTGTTGTCGGGGAAGCTGACGTCCTTTCCATGGCTGCTCGCCTGTGTTGCCAC<br>CTGGATTCTGCGCGGGACGTCCTTCTGCTACGTCCCTTCGGCCCTCAATCCAGCGGAC<br>CTTCCTTCCCGCGGCCTGCTGCCGGCTCTGCGCCTCTTCCGCGTCTTCGCCTTCGCCC<br>TCAGACGAGTCGGATCTCCCTTTGGGCCGCCTCCCCGCCTGGA | |
| 4 | CCAGCAGCTCTCGGCAAAGACACGATTCCGTGGCTTGGGCATCTGCTCGTTGGGCTGA<br>GCGGTGCGTTTGGTTTCATCATCTTGGTCTATCTCTTGATCAATTGCAGAAATACAGGC<br>CCTTGGCTGAAAAAGTGCTCAAGTGTAATACCCCGACCCAAGCAAGTTCTTCTCCC<br>AGCTTTCTTCAGAGCATGGAGGCGATGTGCAGAAATGGCTCTCTTCACCTTTTCCCTCC<br>TCAAGCTTCTCCCCGGGAGGGCTGGCGCCCGAGATTTCACCTCTTGAGGTACTTGAAC<br>GAGACAAGGTTACCCAACTTCTCCTTCAACAGGATAAGGTACCCGAACCTGCGAGCCT<br>TAGCTTGAATACAGACGCTTATCTCTCACTGCAGGAACTGCAA | µDISC DNA (cytoplasmic tail only; codon diverged) |
| 5 | PAALGKDTIPWLGHLLVGLSGAFGFIILVYLLINCRNTGPWLKKVLKCNTPDPSKFFSQLSSE<br>HGGDVQKWLSSPFPSSSFSPGGLAPEISPLEVLERDKVTQLLLQQDKVPEPASLSLNTDAYL<br>SLQELQ | µDISC polypeptide (cytoplasmic tail only) |
| 6 | GVQVETISPGDGRTFPKRGQTCVVHYTGMLEDGKKFDSSRDRNKPFKFMLGKQEVIRG<br>WEEGVAQMSVGQRAKLTISPDYAYGATGHPGIIPPHATLVFDVELLKLGE | FKBP CISC domain |
| 7 | MALPVTALLLPLALLLHAARPILWHEMWHEGLEEASRLYFGERNVKGMFEVLEPLHAMM<br>ERGPQTLKETSFNQAYGRDLMEAQEWCRKYMKSGNVKDLLQAWDLYHVFRRISKPAA<br>LGKDTIPWLGHLLVGLSGAFGFIILVYLLINCRNTGPWLKKVLKCNTPDPSKFFSQLSSEHG<br>GDVQKWLSSPFPSSSFSPGGLAPEISPLEVLERDKVTQLLLQQDKVPEPASLSLNTDAYLSL<br>QELQ | Entire µDISC polypeptide (FRB-truncated IL2Rβ) |
| 8 | GAACAGAGAAACAGGAGAATATGGGCCAAACAGGATATCTGTGGTAAGCAGTTCCTG<br>CCCCGGCTCAGGGCCAAGAACAGTTGGAACAGCAGAATATGGGCCAAACAGGATATC<br>TGTGGTAAGCAGTTCCTGCCCCGGCTCAGGGCCAAGAACAGATGGTCCCCAGATGCG<br>GTCCCGCCCTCAGCAGTTTCTAGAGAACCATCAGATGTTTCCAGGGTGCCCCAAGGAC<br>CTGAAATGACCCTGTGCCTTATTTGAACTAACCAATCAGTTCGCTTCTCGCTTCTGTTCG<br>CGCGCTTCTGCTCCCCGAGCTCTATATAAGCAGAGCTCGTTTAGTGAACCGTCAGATC<br>GCTAGCACCGTGCCGCCACCATGCCTCTGGGCCTGCTGTGGCTGGGCCTGGCCCTGC<br>TGGGCGCCCTGCACGCCCAGGCCGGCGTGCAGGTGGAGACAATCTCCCCAGGCGAC<br>GGACGCACATTCCCTAAGCGGGGCCAGACCTGCGTTGTGCACTATACAGGCATGCTG<br>GAGGATGGCAAGAAGTTTGACAGCTCCCGGGATAGAAACAAGCCATTCAAGTTTATG<br>CTGGGCAAGCAGGAAGTGATCAGAGGCTGGGAGGAGGGCGTGGCCCAGATGTCTGT<br>GGGCCAGAGGGCCAAGCTGACCATCAGCCCAGACTACGCCTATGGAGCAACAGGCCA<br>CCCAGGAATCATCCCACCTCACGCCACCCTGGTGTTCGATGTGGAGCTGCTGAAGCTG<br>GGCGAGGGATCCAACACATCAAAAGAGAACCCCTTCGTTCGCATTGGAGGCCGTA<br>GTCATATCTGTTGGATCCATGGGACTTATTATCTCCCTGTTGTGTGTACTTCTGGCT<br>GGAACGGACTATGCCCAGGATCCCCACGCTCAAGAATCTGGAAGATCTCGTCACAGA<br>ATACCATGGTAATTTCAGCGCCTGGAGCGGAGTCTCTAAGGGTCTGGCCGAATCCCTC<br>CAACCCGATTATTCTGAACGGTTGTGCCTCGTATCCGAAATACCACCAAAAGGCGGGG<br>CTCGGGTGAGGGCCCAGGGGCGAGTCCGTGCAATAACACAGCCCGTATTGGGCCC<br>CTCCTTGTTATACGTTGAAGCCCGAAACTGGAAGCGGAGCTACTAACTTCAGCCTGCT<br>GAAGCAGGCTGGAGACGTGGAGGAGAACCCTGGACCTATGGCACTGCCCGTGACCG<br>CCCTGCTGCTGCCTCTGGCCCTGCTGCTGCACGCAGCCCGGCCTATCCTGTGGCACGA<br>GATGTGGCACGAGGGCCTGGAGGAGGCCAGCAGGCTGTATTTTGGCGAGCGCAACG<br>TGAAGGGCATGTTCGAGGTGCTGGAGCCTCTGCACGCCATGATGGAGAGAGGCCCAC<br>AGACCCTGAAGGAGACATCCTTTAACCAGGCCTATGGACGGGACCTGATGGAGGCAC<br>AGGAGTGGTGCAGAAAGTACATGAAGTCTGGCAATGTGAAGGACCTGCTGCAGGCC<br>TGGGATCTGTACTATCACGTGTTTCGGAGAATCTCCAAGGGCAAAGACACGATTCCGT<br>GGCTTGGGCATCTGCTCGTTGGGCTGAGTGGTGCGTTTGGTTTCATCATCTTGGTCTA<br>TCTCTTGATCAATTGCAGAAATACAGGCCCTTGGCTGAAAAAAGTGCTCAAGTGTAAT<br>ACCCCCGACCCAAGCAAGTTCTTCTCCCAGCTTTCTTCAGAGCATGGAGGCGATGTGC<br>AGAAATGGCTCTCTTCACCTTTTCCCTCCTCAAGCTTCTCCCCGGGAGGGCTGGCGCCC<br>GAGATTTCACCTCTTGAGGTACTTGAACGAGACAAGGTTACCCAACTTCTCCTTCAACA<br>GGATAAGGTACCCGAACCTGCGAGCCTTAGCTTGAATACAGACGCTTATCTCTCACTG<br>CAGGAACTGCAAGGATCTGGTGCTACTAATTTTTCTCTTTTGAAGCAAGCTGGAGATG<br>TTGAAGAACCCCGGTCCGGAGATGTGGCATGAGGGTCTGGAAGAAGCGTCTCGA<br>CTGTACTTTGGTGAGCGCAATGTGAAGGGCATGTTTGAAGTCCTCGAACCCCTTCATG<br>CCATGATGGAACGCGGACCCCAGACCTTGAAGGAGACAAGTTTTAACCAAGCTTACG<br>GAAGAGACCTGATGGAAGCCCAGGAATGGTGCAGGAAATACATGAAAAGCGGGAAT<br>GTGAAGGACTTGCTCCAAGCGTGGGACCTGTACTATCATGTCTTTAGGCGCATTAGTA<br>AGGGCAGCGGCGCCACCAACTTCAGCCTGCTGAAGCAGGCCGGCGACGTGGAGGAG<br>AACCCCGGCCCCGTGAGCAAGGGCGAGGAGGATAACATGGCCATCATCAAGGAGTTC<br>ATGCGCTTCAAGGTGCACATGGAGGGCTCCGTGAACGGCCACGAGTTCGAGATCGAG<br>GGCGAGGGCGAGGGCCGCCCCTACGAGGGCACCCAGACCGCCAAGCTGAAGGTGAC<br>CAAGGGTGGCCCCCTGCCCTTCGCCTGGGACATCCTGTCCCCTCAGTTCATGTACGGC<br>TCCAAGGCCTACGTGAAGCACCCCGCCGACATCCCCGACTACTTGAAGCTGTCCTTCC<br>CCGAGGGCTTCAAGTGGGAGCGCGTGATGAACTTCGAGGACGGCGGCGTGGTGACC<br>GTGACCCAGGACTCCTCTCTGCAGGACGGCGAGTTCATCTACAAGGTGAAGCTGCGC<br>GGCACCAACTTCCCCTCCGACGGCCCCGTAATGCAGAAGAAGACCATGGGCTGGGAG<br>GCCTCCTCCGAGCGGATGTACCCCGAGGACGGCGCCCTGAAGGGCGAGATCAAGCA | µDISC vector DNA |

| SEQ ID NO | Sequence | Description |
|---|---|---|
| | GAGGCTGAAGCTGAAGGACGGCGGCCACTACGACGCTGAGGTCAAGACCACCTACA<br>AGGCCAAGAAGCCCGTGCAGCTGCCCGGCGCCTACAACGTCAACATCAAGTTGGACA<br>TCACCTCCCACAACGAGGACTACACCATCGTGGAACAGTACGAACGCGCCGAGGGCC<br>GCCACTCCACCGGCGGCATGGACGAGCTGTACAAGTGAACTAGTGTCGACAATCAAC<br>CTCTGGATTACAAAATTTGTGAAAGATTGACTGGTATTCTTAACTATGTTGCTCCTTTTA<br>CGCTATGTGGATACGCTGCTTTAATGCCTTTGTATCATGCTATTGCTTCCCGTATGGCT<br>TTCATTTTCTCCTCCTTGTATAAATCCTGGTTGCTGTCTCTTTATGAGGAGTTGTGGCCC<br>GTTGTCAGGCAACGTGGCGTGGTGTGCACTGTGTTTGCTGACGCAACCCCCACTGGTT<br>GGGGCATTGCCACCACCTGTCAGCTCCTTTCCGGGACTTTCGCTTTCCCCCTCCCTATT<br>GCCACGGCGGAACTCATCGCCGCCTGCCTTGCCCGCTGCTGGACAGGGGCTCGGCTG<br>TTGGGCACTGACAATTCCGTGGTGTTGTCGGGGAAGCTGACGTCCTTTCCATGGCTGC<br>TCGCCTGTGTTGCCACCTGGATTCTGCGCGGGACGTCCTTCTGCTACGTCCCTTCGGCC<br>CTCAATCCAGCGGACCTTCCTTCCCGCGGCCTGCTGCCGGTCTGCGGCCTCTTCCGCG<br>TCTTCGCCTTCGCCCTCAGACGAGTCGGATCTCCCTTTGGGCCGCCTCCCCGCCTGGA | |
| 9 | MPLGLLWLGLALLGALHAQAGVQVETISPGDGRTFPKRGQTCVVHYTGMLEDGKKFDSS<br>RDRNKPFKFMLGKQEVIRGWEEGVAQMSVGQRAKLTISPDYAYGATGHPGIIPPHATLV<br>FDVELLKLGEGSNTSKENPFLFALEAVVISVGSMGLIISLLCVYFWLERTMPRIPTLKNLEDL<br>VTEYHGNFSAWSGVSKGLAESLQPDYSERLCLVSEIPPKGGALGEGPGASPCNQHSPYWA<br>PPCYTLKPET | IL2Rγ-CISC polypeptide |
| 10 | MPLGLLWLGLALLGALHAQAGVQVETISPGDGRTFPKRGQTCVVHYTGMLEDGKKFDSS<br>RDRNKPFKFMLGKQEVIRGWEEGVAQMSVGQRAKLTISPDYAYGATGHPGIIPPHATLV<br>FDVELLKLEGGGSQNLVIPWAPENLTLHKLSESQLELNWNNRFLNHCLEHLVQYRTDWD<br>HSWTEQSVDYRHKFSLPSVDGQKRYTFRVRSRFNPLCGSAQHWSEWSHPIHWGSNTSK<br>ENPFLFALEAVVISVGSMGLIISLLCVYFWLERTMPRIPTLKNLEDLVTEYHGNFSAWSGVS<br>KGLAESLQPDYSERLCLVSEIPPKGGALGEGPGASPCNQHSPYWAPPCYTLKPET | IL2Rγ-CISC polypeptide |
| 11 | MPLGLLWLGLALLGALHAQAGVQVETISPGDGRTFPKRGQTCVVHYTGMLEDGKKFDSS<br>RDRNKPFKFMLGKQEVIRGWEEGVAQMSVGQRAKLTISPDYAYGATGHPGIIPPHATLV<br>FDVELLKLEGQNLVIPWAPENLTLHKLSESQLELNWNNRFLNHCLEHLVQYRTDWDHSW<br>TEQSVDYRHKFSLPSVDGQKRYTFRVRSRFNPLCGSAQHWSEWSHPIHWGSNTSKENPF<br>LFALEAVVISVGSMGLIISLLCVYFWLERTMPRIPTLKNLEDLVTEYHGNFSAWSGVSKGLA<br>ESLQPDYSERLCLVSEIPPKGGALGEGPGASPCNQHSPYWAPPCYTLKPET | IL2Rγ-CISC polypeptide |
| 12 | MPLGLLWLGLALLGALHAQAGVQVETISPGDGRTFPKRGQTCVVHYTGMLEDGKKFDSS<br>RDRNKPFKFMLGKQEVIRGWEEGVAQMSVGQRAKLTISPDYAYGATGHPGIIPPHATLV<br>FDVELLKLEGGSNTSKENPFLFALEAVVISVGSMGLIISLLCVYFWLERTMPRIPTLKNLEDL<br>VTEYHGNFSAWSGVSKGLAESLQPDYSERLCLVSEIPPKGGALGEGPGASPCNQHSPYWA<br>PPCYTLKPET | IL2Rγ-CISC polypeptide |
| 13 | MALPVTALLLPLALLLHAARPILWHEMWHEGLEEASRLYFGERNVKGMFEVLEPLHAMM<br>ERGPQTLKETSFNQAYGRDLMEAQEWCRKYMKSGNVKDLLQAWDLYYHVFRRISKGKD<br>TIPWLGHLLVGLSGAFGFIILVYLLINCRNTGPWLKKVLKCNTPDPSKFFSQLSSEHGGDVQ<br>KWLSSPFPSSSFSPGGLAPEISPLEVLERDKVTQLLLQQDKVPEPASLSSNHSLTSCFTNQGY<br>FFFHLPDALEIEACQVYFTYDPYSEEDPDEGVAGAPTGSSPQPLQPLSGEDDAYCTFPSRD<br>DLLLFSPSLLGGPSPPSTAPGGSGAGEERMPPSLQERVPRDWDPQPLGPPTPGVPDLVDF<br>QPPPELVLREAGEEVPDAGPREGVSFPWSRPPGQGEFRALNARLPLNTDAYLSLQELQG<br>QDPTHLV | IL2Rβ-CISC polypeptide |
| 14 | MALPVTALLLPLALLLHAARPILWHEMWHEGLEEASRLYFGERNVKGMFEVLEPLHAMM<br>ERGPQTLKETSFNQAYGRDLMEAQEWCRKYMKSGNVKDLLQAWDLYYHVFRRISKGGS<br>KPFENLRLMAPISLQVVHVETHRCNISWEISQASHYFERHLEFEARTLSPGHTWEEAPLLTL<br>KQKQEWICLETLTPDTQYEFQVRVKPLQGEFTTWSPWSQPLAFRTKPAALGKDTIPWLG<br>HLLVGLSGAFGFIILVYLLINCRNTGPWLKKVLKCNTPDPSKFFQLSSEHGGDVQKWLSSPF<br>PSSSFSPGGLAPEISPLEVLERDKVTQLLLQQDKVPEPASLSSNHSLTSCFTNQGYFFFHLPD<br>ALEIEACQVYFTYDPYSEEDPDEGVAGAPTGSSPQPLQPLSGEDDAYCTFPSRDDLLLFSPS<br>LLGGPSPPSTAPGGSGAGEERMPPSLQERVPRDWDPQPLGPPTPGVPDLVDFQPPPELV<br>LREAGEEVPDAGPREGVSFPWSRPPGQGEFRALNARLPLNTDAYLSLQELQGQDPTHLV | IL2Rβ-CISC polypeptide |
| 15 | MALPVTALLLPLALLLHAARPILWHEMWHEGLEEASRLYFGERNVKGMFEVLEPLHAMM<br>ERGPQTLKETSFNQAYGRDLMEAQEWCRKYMKSGNVKDLLQAWDLYYHVFRRISKKPF<br>ENLRLMAPISLQVVHVETHRCNISWEISQASHYFERHLEFEARTLSPGHTWEEAPLLTLKQ<br>KQEWICLETLTPDTQYEFQVRVKPLQGEFTTWSPWSQPLAFRTKPAALGKDTIPWLGHLL<br>VGLSGAFGFIILVYLLINCRNTGPWLKKVLKCNTPDPSKFFSQLSSEHGGDVQKWLSSPFPS<br>SSFSPGGLAPEISPLEVLERDKVTQLLLQQDKVPEPASLSSNHSLTSCFTNQGYFFFHLPDAL<br>EIEACQVYFTYDPYSEEDPDEGVAGAPTGSSPQPLQPLSGEDDAYCTFPSRDDLLLFSPSLL<br>GGPSPPSTAPGGSGAGEERMPPSLQERVPRDWDPQPLGPPTPGVPDLVDFQPPPELVLR<br>EAGEEVPDAGPREGVSFPWSRPPGQGEFRALNARLPLNTDAYLSLQELQGQDPTHLV | IL2Rβ-CISC polypeptide |
| 16 | MALPVTALLLPLALLLHAARPILWHEMWHEGLEEASRLYFGERNVKGMFEVLEPLHAMM<br>ERGPQTLKETSWLGHLLVGLSGAFGFIILVYLLINCRNTGPWLKKVLKCNTPDPSKFFSQLS<br>SEHGGDVQKWLSSPFPSSSFSPGGLAPEISPLEVLERDKVTQLLLQQDKVPEPASLSSNHSL<br>TSCFTNQGYFFFHLPDALEIEACQVYFTYDPYSEEDPDEGVAGAPTGSSPQPLQPLSGEDD | IL7Rα-CISC polypeptide |

| SEQ ID NO | Sequence | Description |
|---|---|---|
| | AYCTFPSRDDLLLFSPSLLGGPSPPSTAPGGSGAGEERMPPSLQERVPRDWDPQPLGPPT<br>PGVPDLVDFQPPPELVLREAGEEVPDAGPREGVSFPWSRPPGQGEFRALNARLPLNTDA<br>YLSLQELQGQDPTHLV | |
| 17 | MALPVTALLLPLALLLHAARPILWHEMWHEGLEEASRLYFGERNVKGMFEVLEPLHAMM<br>ERGPQTLKETSFNQAYGRDLMEAQEWCRKYMKSGNVKDLLQAWDLYYHVFRRISKGEI<br>NNSSGEMDPILLTISILSFFSVALLVILACVLWKKRIKPIVWPSLPDHKKTLEHLCKKPRKNLN<br>VSFNPESFLDCQIHRVDDIQARDEVEGFLQDTFPQQLEESEKQRLGGDVQSPNCPSEDVV<br>ITPESFGRDSSLTCLAGNVSACDAPILSSSRSLDCRESGKNGPHVYQDLLLSLGTTNSTLPPP<br>FSLQSGILTLNPVAQGQPILTSLGSNQEEAYVTMSSFYQNQ | IL7Rα-CISC polypeptide |
| 18 | GGGS | Linker polypeptide |
| 19 | GGGSGGG | Linker polypeptide |
| 20 | GGG | Linker polypeptide |
| 21 | GGS | Linker polypeptide |
| 22 | GGSP | Linker polypeptide |
| 23 | MPLGLLWLGLALLGALHAQAGVQVETISPGDGRTFPKRGQTCVVHYTGMLEDGKKVDSS<br>RDRNKPFKFMLGKQEVIRGWEEGVAQMSVGQRAKLTISPDYAYGATGHPGIIPPHATLV<br>FDVELLKLEGGSNTSKENPFLFALEAVVISVGSMGLIISLLCVYFWLERTMPRIPTLKNLEDL<br>VTEYHGNFSAWSGVSKGLAESLQPDYSERLCLVSEIPPKGGALGEGPGASPCNQHSPYWA<br>PPCYTLKPET | IL2Rγ-CISC polypeptide |
| 24 | MPLGLLWLGLALLGALHAQAGVQVETISPGDGRTFPKRGQTCVVHYTGMLEDGKKVDSS<br>RDRNKPFKFMLGKQEVIRGWEEGVAQMSVGQRAKLTISPDYAYGATGHPGIIPPHATLV<br>FDVELLKLEGGKDTIPWLGHLLVGLSGAFGFIILVYLLINCRNTGPWLKKVLKCNTPDPSKFF<br>SQLSSEHGGDVQKWLSSPFFSSSFSPGGLAPEISPLEVLERDKVTQLLLQQDKVPEPASLSS<br>NHSLTSCFTNQGYFFFHLPDALEIEACQVYFTYDPYSEEDPDEGVAGAPTGSSPOPLOPLS<br>GEDDAYCTFPSRDDLLLFSPSLLGGPSPPSTAPGGSGAGEERMPPSLQERVPRDWDPQPL<br>GPPTPGVPDLVDFQPPPELVLREAGEEVPDAGPREGVSFPWSRPPGQGEFRALNARLPL<br>NTDAYLSLQELQGQDPTHLV | IL2Rβ-CISC polypeptide |
| 25 | MPLGLLWLGLALLGALHAQAGVQVETISPGDGRTFPKRGQTCVVHYTGMLEDGKKVDSS<br>RDRNKPFKFMLGKQEVIRGWEEGVAQMSVGQRAKLTISPDYAYGATGHPGIIPPHATLV<br>FDVELLKLEGEINNSSGEMDPILLTISILSFFSVALLVILACVLWKKRIKPIVWPSLPDHKKTLE<br>HLCKKPRKNLNVSFNPESFLDCQIHRVDDIQARDEVEGFLQDTFPQQLEESEKQRLGGDV<br>QSPNCPSEDVVITPESFGRDSSLTCLAGNVSACDAPILSSSRSLDCRESGKNGPHVYQDLLL<br>SLGTTNSTLPPPFSLQSGILTLNPVAQGQPILTSLGSNQEEAYVTMSSFYQNQ | IL2Rα-CISC polypeptide |
| 26 | MPLGLLWLGLALLGALHAQAGVQVETISPGDGRTFPKRGQTCVVHYTGMLEDGKKVDSS<br>RDRNKPFKFMLGKQEVIRGWEEGVAQMSVGQRAKLTISPDYAYGATGHPGIIPPHATLV<br>FDVELLKLEGEINNSSGEMDPILLTISILSFFSVALLVILACVLWKKRIKPIVWPSLPDHKKTLE<br>HLCKKPRKNLNVSFNPESFLDCQIHRVDDIQARDEVEGFLQDTFPQQLEESEKQRLGGDV<br>QSPNCPSEDVVITPESFGRDSSLTCLAGNVSACDAPILSSSRSLDCRESGKNGPHVYQDLLL<br>SLGTTNSTLPPPFSLQSGILTLNPVAQGQPILTSLGSNQEEAYVTMSSFYQNQ | IL7Rα-CISC polypeptide |
| 27 | MPLGLLWLGLALLGALHAQAGVQVETISPGDGRTFPKRGQTCVVHYTGMLEDGKKVDSS<br>RDRNKPFKFMLGKQEVIRGWEEGVAQMSVGQRAKLTISPDYAYGATGHPGIIPPHATLV<br>FDVELLKLGEETAWISLVTALHLVGLSAVLGLLLLRWQFPAHYRRLRHALWPSLPDLHRVL<br>GQYLRDTAALSPPKATVSDTCEEVEPSLLEILPKSSERTPLPLCSSQAQMDYRRLQPSCLGT<br>MPLSVCPPMAESGSCCTTHIANHSYLPLSYWQQP | MPL-CISC polypeptide |
| 28 | AGCTTAATGTAGTCTTATGCAATACTCTTGTAGTCTTGCAACATGGTAACGATGAGTTA<br>GCAACATGCCTTACAAGGAGAGAAAAAGCACCGTGCATGCCGATTGGTGGAAGTAAG<br>GTGGTACGATCGTGCCTTATTAGGAAGGCAACAGACGGGTCTGACATGGATTGGACG<br>AACCCACTGAATTGCCGCATTGCAGAGATATTGTATTTAAGTGCCTAGCTCGATACAAT<br>AAACGGGTCTCTCTGGTTAGACCAGATCTGAGCCTGGGAGCTCTCTGGCTAACTAGG<br>GAACCCACTGCTTAAGCCTCAATAAAGCTTGCCTTGAGTGCTTCAAGTAGTGTGTGCC<br>CGTCTGTTGTGTGACTCTGGTAACTAGAGATCCCTCAGACCCTTTTAGTCAGTGTGGA<br>AAATCTCTAGCAGTGGCGCCCGAACAGGGACTTGAAAGCGAAAGGGAAACCAGAGG<br>AGCTCTCTCGACGCAGGACTCGGCTTGCTGAAGCGCGCACGGCAAGAGGCGAGGGG<br>CGGCGACTGGTGAGTACGCCAAAAATTTTGACTAGCGGAGGCTAGAAGGAGAGAGA<br>TGGGTGCGAGAGCGTCAGTATTAAGCGGGGAGAATTAGATCGCGATGGGAAAAAA<br>TTCGGTTAAGGCCAGGGGGAAAGAAAAAATATAAATTAAAACATATAGTATGGGCAA<br>GCAGGGAGCTAGAACGATTCGCAGTTAATCCTGGCCTGTTAGAAACATCAGAAGGCT<br>GTAGACAAATACTGGGACAGCTACAACCATCCCTTCAGACAGGATCAGAAGAACTTA<br>GATCATTATATAATACAGTAGCAACCCTCTATTGTGTGCATCAAAGGATAGAGATAAA<br>AGACACCAAGGAAGCTTTAGACAAGATAGAGGAAGAGCAAAACAAAAGTAAGACCA<br>CCGCACAGCAAGCGGCCGCTGATCTTCAGACCTGGAGGAGGAGATATGAGGGACAA<br>TTGGAGAAGTGAATTATATAAATATAAAGTAGTAAAAATTGAACCATTAGGAGTAGC<br>ACCCACCAAGGCAAAGAGAAGAGTGGTGCAGAGAGAAAAAGAGCAGTGGGAATA<br>GGAGCTTTGTTCCTTGGGTTCTTGGGAGCAGCAGGAAGCACTATGGGCGCAGCCTCA | CISC vector DNA |

| SEQ ID NO | Sequence | Description |
|---|---|---|
| | ATGACGCTGACGGTACAGGCCAGACAATTATTGTCTGGTATAGTGCAGCAGCAGAAC<br>AATTTGCTGAGGGCTATTGAGGCGCAACAGCATCTGTTGCAACTCACAGTCTGGGGC<br>ATCAAGCAGCTCCAGGCAAGAATCCTGGCTGTGGAAAGATACCTAAAGGATCAACAG<br>CTCCTGGGGATTTGGGGTTGCTCTGGAAAACTCATTTGCACCACTGCTGTGCCTTGGA<br>ATGCTAGTTGGAGTAATAAATCTCTGGAACAGATTTGGAATCACACGACCTGGATGG<br>AGTGGGACAGAGAAATTAACAATTACACAAGCTTAATACACTCCTTAATTGAAGAATC<br>GCAAAACCAGCAAGAAAAGAATGAACAAGAATTATTGGAATTAGATAAATGGGCAA<br>GTTTGTGGAATTGGTTTAACATAACAAATTGGCTGTGGTATATAAAATTATTCATAATG<br>ATAGTAGGAGGCTTGGTAGGTTTAAGAATAGTTTTTGCTGTACTTTCTATAGTGAATA<br>GAGTTAGGCAGGGATATTCACCATTATCGTTTCAGACCCACCTCCCAACCCCGAGGGG<br>ACCCGACAGGCCCGAAGGAATAGAAGAAGAAGGTGGAGAGAGAGACAGAGACAGA<br>TCCATTCGATTAGTGAACGGATCTCGACGGTATCGGTTAACTTTTAAAAGAAAAGGGG<br>GGATTGGGGGTACAGTGCAGGGGAAAGAATAGTAGACATAATAGCAACAGACATA<br>CAAACTAAAGAATTACAAAAACAAATTACAAAAATTCAAAATTTTATCGATCACGAGA<br>CTAGCCTCGAGAAGCTTGATATCGAATTCCCACGGGGTTGGACGCGTAGGAACAGAG<br>AAACAGGAGAATATGGGCCAAACAGGATATCTGTGGTAAGCAGTTCCTGCCCCGGCT<br>CAGGGCCAAGAACAGTTGGAACAGCAGAATATGGGCCAAACAGGATATCTGTGGTA<br>AGCAGTTCCTGCCCCGGCTCAGGGCCAAGAACAGATGGTCCCCAGATGCGGTCCCGC<br>CCTCAGCAGTTTCTAGAGAACCATCAGATGTTTCCAGGGTGCCCCAAGGACCTGAAAT<br>GACCCTGTGCCTTATTTGAACTAACCAATCAGTTCGCTTCTCGCTTCTGTTCGCGCGCTT<br>CTGCTCCCCGAGCTCTATATAAGCAGAGCTCGTTTAGTGAACCGTCAGATCGCTAGCA<br>CCGGTGCCGCCACCATGCCTCTGGGCCTGCTGTGGCTGGGCCTGGCCCTGCTGGGCG<br>CCCTGCACGCCCAGGCCGGCGTGCAGGTGGAGACAATCTCCCAGGCGACGGACGCA<br>CATTCCCTAAGCGGGGCCAGACCTGCGTGGTGCACTATACAGGCATGCTGGAGGATG<br>GCAAGAAGTTTGACAGCTCCCGGGATAGAAACAAGCCATTCAAGTTTATGCTGGGCA<br>AGCAGGAAGTGATCAGAGGCTGGGAGGAGGGCGTGGCCCAGATGTCTGTGGGCCA<br>GAGGGCCAAGCTGACCATCAGCCCAGACTACGCCTATGGAGCAACAGGCCACCCAGG<br>AATCATCCCACCTCACGCCACCCTGGTGTTCGATGTGGAGCTGCTGAAGCTGGGCGAG<br>GGATCCAACACATCAAAAGAGAACCCCTTTCTGTTCGCATTGGAGGCCGTAGTCATAT<br>CTGTTGGATCCATGGGACTTATTATCTCCCTGTTGTGTGTACTTCTGGCTGGAACGG<br>ACTATGCCCAGGATCCCCACGCTCAAGAATCTGGAAGATCTCGTCACAGAATACCATG<br>GTAATTTCAGCGCCTGGAGCGGAGTCTCTAAGGGTCTGGCCGAATCCCTCCAACCCGA<br>TTATTCTGAACGGTTGTGCCTCGTATCCGAAATACCACCAAAAGGCGGGGCTCTGGGT<br>GAGGGCCCAGGGGCGAGTCCGTGCAATCAACACAGCCCGTATTGGGCCCCTCCTTGT<br>TATACGTTGAAGCCCGAAACTGGAAGCGGAGCTACTAACTTCAGCCTGCTGAAGCAG<br>GCTGGAGACGTGGAGGAGAACCCTGGACCTATGGCACTGCCCGTGACCGCCCTGCTG<br>CTGCCTCTGGCCCTGCTGCTGCACGCAGCCCGGCCTATCCTGTGGCACGAGATGTGGC<br>ACGAGGGCCTGGAGGAGGCCAGCAGGCTGTATTTTGGCGAGCGCAACGTGAAGGGC<br>ATGTTCGAGGTGCTGGAGCCTCTGCACGCCATGATGGAGAGAGGCCCACAGACCCTG<br>AAGGAGACATCCTTTAACCAGGCCTATGGACGGACCTGATGGAGGCACAGGAGTG<br>GTGCAGAAAGTACATGAAGTCTGGCAATGTGAAGGACCTGCTGCAGGCCTGGGATCT<br>GTACTATCACGTGTTTCGGAGAATCTCCAAGGGCAAAGACACGATTCCGTGGCTTGG<br>GCATCTGCTCGTTGGGCTGAGTGGTGCGTTTGGTTTCATCATCTTGGTCTATCTCTTGA<br>TCAATTGCAGAAATACAGGCCCTTGGCTGAAAAAAGTGCTCAAGTGTAATACCCCCGA<br>CCCAAGCAAGTTCTTCTCCCAGCTTTCTTCAGAGCATGGAGGCGATGTGCAGAAATGG<br>CTCTCTTCACCTTTTCCCTCCTCAAGCTTCTCCCCGGGAGGGCTGGCGCCCGAGATTTC<br>ACCTCTTGAGGTACTTGAACGAGACAAGGTTACCCAACTTCTCCTTCAACAGGATAAG<br>GTACCCGAACCTGCGAGCCTTAGCTCCAACCACTCTCTTACGAGCTGCTTCACCAATCA<br>GGGATACTTCTTTTTCCACCTTCCCGATGCGCTGGAAATCGAAGCTTGTCAAGTTTACT<br>TTACCTATGATCCATATAGCGAGGAAGATCCCGACGAAGGAGTCGCCGGTGCGCCCA<br>CGGGTTCCTCACCCCAACCTCTCCAGCCTCTCTCAGGAGAAGATGATGCTTATTGCACT<br>TTTCCCAGTAGAGACGATCTCCTCCTCTTTTCTCCATCTCTTTTGGGGGGACCTTCCCCC<br>CCTTCTACGGCACCTGGCGGGTCTGGTGCTGGCGAGGAGCGGATGCCGCCGTCCCTC<br>CAGGAGCGAGTACCACGAGATTGGGATCCCCAGCCACTTGGACCCCCCACCCCCGGC<br>GTACCTGACCTTGTCGATTTTCAACCTCCCCCTGAATTGGTGCTGCGAGAGGCTGGGG<br>AGGAAGTTCCGGACGCTGGGCCGAGGGAGGGCGTGTCCTTTCCATGGAGTAGGCCTC<br>CAGGTCAAGGCGAGTTTAGGGCTCTCAACGCGCGGCTGCCGTTGAATACAGACGCTT<br>ATCTCTCACTGCAGGAACTGCAAGGTCAGGACCCAACACATCTTGTAGGATCTGGTGC<br>TACTAATTTTTCTCTTTTGAAGCAAGCTGGAGATGTTGAAGAGAACCCTGGTCCAGTG<br>AGCAAGGGCGAGGAGCTGTTCACCGGGGTGGTGCCCATCCTGGTCGAGCTGGACGG<br>CGACGTAAACGGCCACAAGTTCAGCGTGTCCGGCGAGGGCGAGGGCGATGCCACCT<br>ACGGCAAGCTGACCCTGAAGTTCATCTGCACCACCGGCAAGCTGCCCGTGCCCTGGCC<br>CACCCTCGTGACCACCCTGACCTACGGCGTGCAGTGCTTCAGCCGCTACCCCGACCAC<br>ATGAAGCAGCACGACTTCTTCAAGTCCGCCATGCCCGAAGGCTACGTCCAGGAGCGC<br>ACCATCTTCTTCAAGGACGACGGCAACTACAAGACCCGCGCCGAGGTGAAGTTCGAG<br>GGCGACACCCTGGTGAACCGCATCGAGCTGAAGGGCATCGACTTCAAGGAGGACGG<br>CAACATCCTGGGGCACAAGCTGGAGTACAACTACAACAGCCACAACGTCTATATCATG<br>GCCGACAAGCAGAAGAACGGCATCAAGGTGAACTTCAAGATCCGCCACAACATCGAG<br>GACGGCAGCGTGCAGCTCGCCGACCACTACCAGCAGAACACCCCCATCGGCGACGGC<br>CCCGTGCTGCTGCCCGACAACCACTACCTGAGCACCCAGTCCGCCCTGAGCAAGACC<br>CCAACGAGAAGCGCGATCACATGGTCCTGCTGGAGTTCGTGACCGCCGCCGGGATCA<br>CTCTCGGCATGGACGAGCTGTACAAGTAAACTAGTGTCGACAATCAACCTCTGGATTA<br>CAAAATTTGTGAAAGATTGACTGGTATTCTTAACTATGTTGCTCCTTTTACGCTATGTG<br>GATACGCTGCTTTAATGCCTTTGTATCATGCTATTGCTTCCCGTATGGCTTTCATTTTCT<br>CCTCCTTGTATAAATCCTGGTTGCTGTCTCTTTATGAGGAGTTGTGGCCCGTTGTCAGG<br>CAACGTGGCGTGGTGTGCACTGTGTTTGCTGACGCAACCCCCACTGGTTGGGGCATTG | |

| SEQ ID NO | Sequence | Description |
|---|---|---|
| | CCACCACCTGTCAGCTCCTTTCCGGGACTTTCGCTTTCCCCCTCCCTATTGCCACGGCG<br>GAACTCATCGCCGCCTGCCTTGCCGCTGCTGGACAGGGGCTCGGCTGTTGGGCACT<br>GACAATTCCGTGGTGTTGTCGGGGAAGCTGACGTCCTTTCCATGGCTGCTCGCCTGTG<br>TTGCCACCTGGATTCTGCGCGGGACGTCCTTCTGCTACGTCCCTTCGGCCCTCAATCCA<br>GCGGACCTTCCTTCCCGCGGCCTGCTGCCGGCTCTGCGGCCTCTTCCGCGTCTTCGCCT<br>TCGCCCTCAGACGAGTCGGATCTCCCTTTGGGCGCCTCCCCGCCTGGAATTCGAGCT<br>CGGTACCTTTAAGACCAATGACTTACAAGGCAGCTGTAGATCTTAGCCACTTTTTAAAA<br>GAAAAGGGGGGACTGGAAGGGCTAATTCACTCCCAACGAAGACAAGATCTGCTTTTT<br>GCTTGTACTGGGTCTCTCTGGTTAGACCAGATCTGAGCCTGGGAGCTCTCTGGCTAAC<br>TAGGGAACCCACTGCTTAAGCCTCAATAAAGCTTGCCTTGAGTGCTTCAAGTAGTGTG<br>TGCCCGTCTGTTGTGTGACTCTGGTAACTAGAGATCCCTCAGACCCTTTTAGTCAGTGT<br>GGAAAATCTCTAGCAGTAGTAGTTCATGTCATCTTATTATTCAGTATTTATAACTTGCA<br>AAGAAATGAATATCAGAGAGTGAGAGGAACTTGTTTATTGCAGCTTATAATGGTTACA<br>AATAAAGCAATAGCATCACAAATTTCACAAATAAAGCATTTTTTTCACTGCATTCTAGT<br>TGTGGTTTGTCCAAACTCATCAATGTATCTTATCATGTCTGGCTCTAGCTATCCCGCCCC<br>TAACTCCGCCCAGTTCCGCCCATTCTCCGCCCCATGGCTGACTAATTTTTTTATTTATG<br>CAGAGGCCGAGGCCGCCTCGGCCTCTGAGCTATTCCAGAAGTAGTGAGGAGGCTTTT<br>TTGGAGGCCTAGGCTTTTGCGTCGAGACGTACCCAATTCGCCCTATAGTGAGTCGTAT<br>TACGCGCGCTCACTGGCCGTCGTTTTACAACGTCGTGACTGGGAAAACCCTGGCGTTA<br>CCCAACTTAATCGCCTTGCAGCACATCCCCCTTTCGCCAGCTGGCGTAATAGCGAAGA<br>GGCCCGCACCGATCGCCCTTCCCAACAGTTGCGCAGCCTGAATGGCGAATGGCGCGA<br>CGCGCCCTGTAGCGGCGCATTAAGCGCGGCGGGTGTGGTGGTTACGCGCAGCGTGA<br>CCGCTACACTTGCCAGCGCCCTAGCGCCCGCTCCTTTCGCTTTCTTCCCTTCCTTTCTCG<br>CCACGTTCGCCGGCTTTCCCCGTCAAGCTCTAAATCGGGGGCTCCCTTTAGGGTTCCG<br>ATTTAGTGCTTTACGGCACCTCGACCCCAAAAAACTTGATTAGGGTGATGGTTCACGT<br>AGTGGGCCATCGCCCTGATAGACGGTTTTTCGCCCTTTGACGTTGGAGTCCACGTTCTT<br>TAATAGTGGACTCTTGTTCCAAACTGGAACAACACTCAACCCTATCTCGGTCTATTCTT<br>TTGATTTATAAGGGATTTTGCCGATTTCGGCCTATTGGTTAAAAAATGAGCTGATTTAA<br>CAAAAATTTAACGCGAATTTTAACAAAATATTAACGTTTACAATTTCCCAGGTGGCACT<br>TTTCGGGGAAATGTGCGCGGAACCCCTATTTGTTTATTTTTCTAAATACATTCAAATAT<br>GTATCCGCTCATGAGACAATAACCCTGATAAATGCTTCAATAATATTGAAAAAGGAAG<br>AGTATGAGTATTCAACATTTCCGTGTCGCCCTTATTCCCTTTTTTGCGGCATTTTGCCTT<br>CCTGTTTTTGCTCACCCAGAAACGCTGGTGAAAGTAAAAGATGCTGAAGATCAGTTGG<br>GTGCACGAGTGGGTTACATCGAACTGGATCTCAACAGCGGTAAGATCCTTGAGAGTT<br>TTCGCCCCGAAGAACGTTTTCCAATGATGAGCACTTTTAAAGTTCTGCTATGTGGCGC<br>GGTATTATCCCGTATTGACGCCGGGCAAGAGCAACTCGGTCGCCGCATACACTATTCT<br>CAGAATGACTTGGTTGAGTACTCACCAGTCACAGAAAAGCATCTTACGGATGGCATGA<br>CAGTAAGAGAATTATGCAGTGCTGCCATAACCATGAGTGATAACACTGCGGCCAACTT<br>ACTTCTGACAACGATCGGAGGACCGAAGGAGCTAACCGCTTTTTTGCACAACATGGG<br>GGATCATGTAACTCGCCTTGATCGTTGGGAACCGGAGCTGAATGAAGCCATACCAAA<br>CGACGAGCGTGACACCACGATGCCTGTAGCAATGGCAACAACGTTGCGCAAACTATT<br>AACTGGCGAACTACTTACTCTAGCTTCCCGGCAACAATTAATAGACTGGATGGAGGCG<br>GATAAAGTTGCAGGACCACTTCTGCGCTCGGCCCTTCCGGCTGGCTGGTTTATTGCTG<br>ATAAATCTGGAGCCGGTGAGCGTGGGTCTCGCGGTATCATTGCAGCACTGGGGCCAG<br>ATGGTAAGCCCTCCCGTATCGTAGTTATCTACACGACGGGGAGTCAGGCAACTATGG<br>ATGAACGAAATAGACAGATCGCTGAGATAGGTGCCTCACTGATTAAGCATTGGTAACT<br>GTCAGACCAAGTTTACTCATATATACTTTAGATTGATTTAAAACTTCATTTTTAATTTAA<br>AAGGATCTAGGTGAAGATCCTTTTTGATAATCTCATGACCAAAATCCCTTAACGTGAG<br>TTTTCGTTCCACTGAGCGTCAGACCCCGTAGAAAAGATCAAAGGATCTTCTTGAGATC<br>CTTTTTTTCTGCGCGTAATCTGCTGCTTGCAAACAAAAAAACCACCGCTACCAGCGGTG<br>GTTTGTTTGCCGGATCAAGAGCTACCAACTCTTTTTCCGAAGGTAACTGGCTTCAGCA<br>GAGCGCAGATACCAAATACTGTCCTTCTAGTGTAGCCGTAGTTAGGCCACCACTTCAA<br>GAACTCTGTAGCACCGCCTACATACCTCGCTCTGCTAATCCTGTTACCAGTGGCTGCTG<br>CCAGTGGCGATAAGTCGTGTCTTACCGGGTTGGACTCAAGACGATAGTTACCGGATA<br>AGGCGCAGCGGTCGGGCTGAACGGGGGGTTCGTGCACACAGCCCAGCTTGGAGCGA<br>ACGACCTACACCGAACTGAGATACCTACAGCGTGAGCTATGAGAAAGCGCCACGCTT<br>CCCGAAGGGAGAAAGGCGGACAGGTATCCGGTAAGCGGCAGGGTCGGAACAGGAG<br>AGCGCACGAGGGAGCTTCCAGGGGGAAACGCCTGGTATCTTTATAGTCCTGTCGGGT<br>TTCGCCACCTCTGACTTGAGCGTCGATTTTTGTGATGCTCGTCAGGGGGCGGAGCCT<br>ATGGAAAAACGCCAGCAACGCGGCCTTTTTACGGTTCCTGGCCTTTTGCTGGCCTTTG<br>CTCACATGTTCTTTCCTGCGTTATCCCCTGATTCTGTGGATAACCGTATTACCGCCTTTG<br>AGTGAGCTGATACCGCTCGCCGCAGCCGAACGACCGAGCGCAGCGAGTCAGTGAGC<br>GAGGAAGCGGAAGAGCGCCCAATACGCAAACCGCCTCTCCCCGCGCGTTGGCCGATT<br>CATTAATGCAGCTGGCACGACAGGTTTCCCGACTGGAAAGCGGGCAGTGAGCGCAAC<br>GCAATTAATGTGAGTTAGCTCACTCATTAGGCACCCCAGGCTTTACACTTTATGCTTCC<br>GGCTCGTATGTTGTGTGGAATTGTGAGCGGATAACAATTTCACACAGGAAACAGCTAT<br>GACCATGATTACGCCAAGCGCGCAATTAACCCTCACTAAAGGGAACAAAAGCTGGAG<br>CTGCA | |
| 29 | AGCTTAATGTAGTCTTATGCAATACTCTTGTAGTCTTGCAACATGGTAACGATGAGTTA<br>GCAACATGCCTTACAAGGAGAGAAAAAGCACCGTGCATGCCGATTGGTGGAAGTAAG<br>GTGGTACGATCGTGCCTTATTAGGAAGGCAACAGACGGGTCTGACATGGATTGGACG<br>AACCACTGAATTGCCGCATTGCAGAGATATTGTATTTAAGTGCCTAGCTCGATACAAT<br>AAACGGGTCTCTCTGGTTAGACCAGATCTGAGCCTGGGAGCTCTCTGGCTAACTAGG<br>GAACCCACTGCTTAAGCCTCAATAAAGCTTGCCTTGAGTGCTTCAAGTAGTGTGTGCC<br>CGTCTGTTGTGTGACTCTGGTAACTAGAGATCCCTCAGACCCTTTTAGTCAGTGTGGA | CISC vector DNA |

| SEQ ID NO | Sequence | Description |
|---|---|---|
| | AAATCTCTAGCAGTGGCGCCCGAACAGGGACTTGAAAGCGAAAGGGAAACCAGAGG | |
| | AGCTCTCTCGACGCAGGACTCGGCTTGCTGAAGCGCGCACGGCAAGAGGCGAGGGG | |
| | CGGCGACTGGTGAGTACGCCAAAAATTTTGACTAGCGGAGGCTAGAAGGAGAGAGA | |
| | TGGGTGCGAGAGCGTCAGTATTAAGCGGGGGAGAATTAGATCGCGATGGGAAAAA | |
| | TTCGGTTAAGGCCAGGGGGAAAGAAAAAATATAAATTAAAACATATAGTATGGGCAA | |
| | GCAGGGAGCTAGAACGATTCGCAGTTAATCCTGGCCTGTTAGAAACATCAGAAGGCT | |
| | GTAGACAAATACTGGGACAGCTACAACCATCCCTTCAGACAGGATCAGAAGAACTTA | |
| | GATCATTATATAATACAGTAGCAACCCTCTATTGTGTGCATCAAAGGATAGAGATAAA | |
| | AGACACCAAGGAAGCTTTAGACAAGATAGAGGAAGAGCAAACAAAAGTAAGACCA | |
| | CCGCACAGCAAGCGGCCGCTGATCTTCAGACCTGGAGGAGGAGATATGAGGGACAA | |
| | TTGGAGAAGTGAATTATATAAATATAAAGTAGTAAAAATTGAACCATTAGGAGTAGC | |
| | ACCCACCAAGGCAAAGAGAAGAGTGGTGCAGAGAGAAAAAAGAGCAGTGGGAATA | |
| | GGAGCTTTGTTCCTTGGGTTCTTGGGAGCAGCAGGAAGCACTATGGGCGCAGCCTCA | |
| | ATGACGCTGACGGTACAGGCCAGACAATTATTGTCTGGTATAGTGCAGCAGCAGAAC | |
| | AATTTGCTGAGGGCTATTGAGGCGCAACAGCATCTGTTGCAACTCACAGTCTGGGGC | |
| | ATCAAGCAGCTCCAGGCAAGAATCCTGGCTGTGGAAAGATACCTAAAGGATCAACAG | |
| | CTCCTGGGGATTTGGGGTTGCTCTGGAAAACTCATTTGCACCACTGCTGTGCCTTGGA | |
| | ATGCTAGTTGGAGTAATAAATCTCTGGAACAGATTTGGAATCACACGACCTGGATGG | |
| | AGTGGGACAGAGAAATTAACAATTACACAAGCTTAATACACTCCTTAATTGAAGAATC | |
| | GCAAAACCAGCAAGAAAAGAATGAACAAGAATTATTGGAATTAGATAAATGGGCAA | |
| | GTTTGTGGAATTGGTTTAACATAACAAATTGGCTGTGGTATATAAAATTATTCATAATG | |
| | ATAGTAGGAGGCTTGGTAGGTTTAAGAATAGTTTTTGCTGTACTTTCTATAGTGAATA | |
| | GAGTTAGGCAGGGATATTCACCATTATCGTTTCAGACCCACCTCCCAACCCCGAGGGG | |
| | ACCCGACAGGCCCGAAGGAATAGAAGAAGAAGGTGGAGAGAGAGACAGAGACAGA | |
| | TCCATTCGATTAGTGAACGGATCTCGACGGTATCGGTTAACTTTTAAAAGAAAAGGGG | |
| | GGATTGGGGGGTACAGTGCAGGGGAAAGAATAGTAGACATAATAGCAACAGACATA | |
| | CAAACTAAAGAATTACAAAAACAAATTACAAAAATTCAAAATTTTATCGATCACGAGA | |
| | CTAGCCTCGAGAAGCTTGATATCGAATTCCCACGGGGTTGGACGCGTAGGAACAGAG | |
| | AAACAGGAGAATATGGGCCAAACAGGATATCTGTGGTAAGCAGTTCCTGCCCCGGCT | |
| | CAGGGCCAAGAACAGTTGGAACAGCAGAATATGGGCCAAACAGGATATCTGTGGTA | |
| | AGCAGTTCCTGCCCCGGCTCAGGGCCAAGAACAGATGGTCCCCAGATGCGGTCCCGC | |
| | CCTCAGCAGTTTCTAGAGAACCATCAGATGTTTCCAGGGTGCCCCAAGGACCTGAAAT | |
| | GACCCTGTGCCTTATTTGAACTAACCAATCAGTTCGCTTCTCGCTTCTGTTCGCGCGCTT | |
| | CTGCTCCCCGAGCTCTATATAAGCAGAGCTCGTTTAGTGAACCGTCAGATCGCTAGCA | |
| | CCGGTGCCGCCACCATGCCTCTGGGCCTGCTGTGGCTGGGCCTGGCCCTGCTGGGCG | |
| | CCCTGCACGCCCAGGCCGGCGTGCAGGTGGAGACAATCTCCCCAGGCGACGGACGCA | |
| | CATTCCCTAAGCGGGGCCAGACCTGCGTGGTGCACTATACAGGCATGCTGGAGGATG | |
| | GCAAGAAGTTTGACAGCTCCCGGGATAGAAACAAGCCATTCAAGTTTATGCTGGGCA | |
| | AGCAGGAAGTGATCAGAGGCTGGGAGGAGGGCGTGGCCCAGATGTCTGTGGGCCA | |
| | GAGGGCCAAGCTGACCATCAGCCCAGACTACGCCTATGGAGCAACAGGCCACCCAGG | |
| | AATCATCCCACCTCACGCCACCCTGGTGTTCGATGTGGAGCTGCTGAAGCTGGGCGAG | |
| | GGCGGTAGTCAGAACCTTGTGATACCATGGGCCCCAGAAAATCTCACACTTCATAAAC | |
| | TTTTCCGAATCACAACTCGAACTCAACTGGAATAACCGGTTCCTGAATCACTGTCTTGAA | |
| | CACCTGGTACAATATCGGACCGACTGGGATCACTCATGGACAGAACAATCTGTGGACT | |
| | ATAGGCACAAATTCTCACTCCCAAGCGTAGACGGCCAAAAAAGATACACTTTTCGCGT | |
| | ACGATCCGCTTTAATCCTCTCTGCGGCTCTGCTCAGCACTGGAGTGAATGGTCCCATC | |
| | CCATTCATTGGGGATCCAACACATCAAAAGAGAACCCCTTCTGTTCGCATTGGAGGC | |
| | CGTAGTCATATCTGTTGGATCCATGGGACTTATTATCTCCCTGTTGTGTGTACTTCT | |
| | GGCTGGAACGGACTATGCCCAGGATCCCCACGCTCAAGAATCTGGAAGATCTCGTCA | |
| | CAGAATACCATGGTAATTTCAGCGCCTGGAGCGGAGTCTCTAAGGGTCTGGCCGAAT | |
| | CCCTCCAACCCGATTATTCTGAACGGTTGTGCCTCGTATCCGAAATACCACCAAAAGG | |
| | CGGGGCTCTGGGTGAGGGCCCAGGGGCGAGTCCGTGCAATCAACACAGCCCGTATT | |
| | GGGCCCCTCCTTGTTATACGTTGAAGCCCGAAACTGGAAGCGGAGCTACTAACTTCAG | |
| | CCTGCTGAAGCAGGCTGGAGACGTGGAGGAGAACCCTGGACCTATGGCACTGCCCGT | |
| | GACCGCCCTGCTGCTGCCTCTGGCCCTGCTGCTGCACGCAGCCCGGCCTATCCTGTGG | |
| | CACGAGATGTGGCACGAGGGCCTGGAGGAGGCCAGCAGGCTGTATTTTGGCGAGCG | |
| | CAACGTGAAGGGCATGTTCGAGGTGCTGGAGCCTCTGCACGCCATGATGGAGAGAG | |
| | GCCCACAGACCCTGAAGGAGACATCCTTTAACCAGGCCTATGACGGGACCTGATGG | |
| | AGGCACAGGAGTGGTGCAGAAAGTACATGAAGTCTGGCAATGTGAAGGACCTGCTG | |
| | CAGGCCTGGGATCTGTACTATCACGTGTTTCGGAGAATCTCCAAGGGAGGTTCAAAAC | |
| | CTTTTGAGAACCTTAGACTGATGGCGCCCATCTCTCTGCAGGTAGTTCACGTTGAGAC | |
| | CCATAGATGCAATATAAGCTGGAAATCTCACAAGCCAGCCATTACTTTGAACGGCAT | |
| | TTGGAATTCGAGGCCCGAACACTTTCCCCCGGTCATACGTGGGAAGAAGCTCCTCTCT | |
| | TGACGCTGAAGCAGAAGCAGGAGTGGATTTGTCTGGAGACTTTGACTCCTGATACTC | |
| | AGTATGAGTTCCAAGTTCGGGTGAAACACTCCAAGGCGAGTTCACGCATGGTGCTCC | |
| | GTGGAGTCAACCGTTGGCGTTCCGCACGAAGCCCGCTGCCCTTGGCAAAGACACGAT | |
| | TCCGTGGCTTGGGCATCTGCTCGTTGGGCTGAGTGGTGCGTTTGGTTTCATCATCTTG | |
| | GTCTATCTCTTGATCAATTGCAGAAATACAGGCCCTTGGCTGAAAAAAGTGCTCAAGT | |
| | GTAATACCCCCGACCCAAGCAAGTTCTTCTCCCAGCTTTCTTCAGAGCATGGAGGCGA | |
| | TGTGCAGAAATGGCTCTCTTCACCTTTTCCCTCCTCAAGCTTCTCCCCGGGAGGCTGG | |
| | CGCCCGAGATTTCACCTCTTGAGGTACTTGAACGAGACAAGGTTACCCAACTTCTCCTT | |
| | CAACAGGATAAGGTACCCGAACCTGCGAGCCTTAGCTCCAACCACTCTCTTACGAGCT | |
| | GCTTCACCAATCAGGGATACTTCTTTTTCCACCTTCCCGATGCGCTGGAAATCGAAGCT | |
| | TGTCAAGTTTACTTTACCTATGATCCATATAGCGAGGAAGATCCCGACGAAGGGAGTCG | |
| | CCGGTGCGCCCACGGGTTCCTCACCCCAACCTCTCCAGCCTCTCTCAGGAAGATGA | |
| | TGCTTATTGCACTTTTCCCAGTAGAGACGATCTCCTCCTCTTTTCTCCATCTCTTTTGGG | |

| SEQ ID NO | Sequence | Description |
|---|---|---|
| | GGGACCTTCCCCCCCTTCTACGGCACCTGGCGGGTCTGGTGCTGGCGAGGAGCGGAT | |
| | GCCGCCGTCCCTCCAGGAGCGAGTACCACGAGATTGGGATCCCCAGCCACTTGGACC | |
| | CCCCACCCCCGGCGTACCTGACCTTGTCGATTTTCAACCTCCCCCTGAATTGGTGCTGC | |
| | GAGAGGCTGGGGAGGAAGTTCCGGACGCTGGGCCGAGGGAGGGCGTGTCCTTTCCA | |
| | TGGAGTAGGCCTCCAGGTCAAGGCGAGTTTAGGGCTCTCAACGCGCGGCTGCCGTTG | |
| | AATACAGACGCTTATCTCTCACTGCAGGAACTGCAAGGTCAGGACCCAACACATCTTG | |
| | TAGGATCTGGTGCTACTAATTTTTCTCTTTTGAAGCAAGCTGGAGATGTTGAAGAGAA | |
| | CCCTGGTCCAGTGAGCAAGGGCGAGGAGCTGTTCACCGGGGTGGTGCCCATCCTGGT | |
| | CGAGCTGGACGGCGACGTAAACGGCCACAAGTTCAGCGTGTCCGGCGAGGGCGAGG | |
| | GCGATGCCACCTACGGCAAGCTGACCCTGAAGTTCATCTGCACCACCGGCAAGCTGCC | |
| | CGTGCCCTGGCCCACCCTCGTGACCACCCTGACCTACGGCGTGCAGTGCTTCAGCCGC | |
| | TACCCCGACCACATGAAGCAGCACGACTTCTTCAAGTCCGCCATGCCCGAAGGCTACG | |
| | TCCAGGAGCGCACCATCTTCTTCAAGGACGACGGCAACTACAAGACCCGCGCCGAGG | |
| | TGAAGTTCGAGGGCGACACCCTGGTGAACCGCATCGAGCTGAAGGGCATCGACTTCA | |
| | AGGAGGACGGCAACATCCTGGGGCACAAGCTGGAGTACAACTACAACAGCCACAAC | |
| | GTCTATATCATGGCCGACAAGCAGAAGAACGGCATCAAGGTGAACTTCAAGATCCGC | |
| | CACAACATCGAGGACGGCAGCGTGCAGCTCGCCGACCACTACCAGCAGAACACCCCC | |
| | ATCGGCGACGGCCCCGTGCTGCTGCCCGACAACCACTACCTGAGCACCCAGTCCGCCC | |
| | TGAGCAAAGACCCCAACGAGAAGCGCGATCACATGGTCCTGCTGGAGTTCGTGACCG | |
| | CCGCCGGGATCACTCTCGGCATGGACGAGCTGTACAAGTAAACTAGTGTCGACAATC | |
| | AACCTCTGGATTACAAAATTTGTGAAAGATTGACTGGTATTCTTAACTATGTTGCTCCT | |
| | TTTACGCTATGTGGATACGCTGCTTTAATGCCTTTGTATCATGCTATTGCTTCCCGTATG | |
| | GCTTTCATTTTCTCCTCCTTGTATAAATCCTGGTTGCTGTCTCTTTATGAGGAGTTGTGG | |
| | CCCGTTGTCAGGCAACGTGGCTGGTGTGCACTGTGTTTGCTGACGCAACCCCCACTG | |
| | GTTGGGGCATTGCCACCACCTGTCAGCTCCTTTCCGGGACTTTCGCTTTCCCCCTCCCT | |
| | ATTGCCACGGCGGAACTCATCGCCGCCTGCCTTGCCCGCTGCTGGACAGGGGCTCGG | |
| | CTGTTGGGCACTGACAATTCCGTGGTGTTGTCGGGGAAGCTGACGTCCTTTCCATGGC | |
| | TGCTCGCCTGTGTTGCCACCTGGATTCTGCGCGGGACGTCCTTCTGCTACGTCCCTTCG | |
| | GCCCTCAATCCAGCGGACCTTCCTTCCCGCGGCCTGCTGCCGGCTCTGCGGCCTCTTCC | |
| | GCGTCTTCGCCTTCGCCCTCAGACGAGTCGGATCTCCCTTTGGGCCGCCTCCCCGCCTG | |
| | GAATTCGAGCTCGGTACCTTTAAGACCAATGACTTACAAGGCAGCTGTAGATCTTAGC | |
| | CACTTTTTAAAAGAAAAGGGGGGACTGGAAGGGCTAATTCACTCCCAACGAAGACAA | |
| | GATCTGCTTTTTGCTTGTACTGGGTCTCTCTGGTTAGACCAGATCTGAGCCTGGGAGCT | |
| | CTCTGGCTAACTAGGGAACCCACTGCTTAAGCCTCAATAAAGCTTGCCTTGAGTGCTTC | |
| | AAGTAGTGTGTGCCCGTCTGTTGTGTGACTCTGGTAACTAGAGATCCCTCAGACCCTTT | |
| | TAGTCAGTGTGGAAAATCTCTAGCAGTAGTAGTTCATGTCATCTTATTATTCAGTATTT | |
| | ATAACTTGCAAAGAAATGAATATCAGAGAGTGAGAGGAACTTGTTTATTGCAGCTTAT | |
| | AATGGTTACAAATAAAGCAATAGCATCACAAATTTCACAAATAAAGCATTTTTTTCACT | |
| | GCATTCTAGTTGTGGTTTGTCCAAACTCATCAATGTATCTTATCATGTCTGGCTCTAGCT | |
| | ATCCCGCCCCTAACTCCGCCCAGTTCCGCCCATTCTCCGCCCCATGGCTGACTAATTTTT | |
| | TTTATTTATGCAGAGGCCGAGGCCGCCTCGGCCTCTGAGCTATTCCAGAAGTAGTGAG | |
| | GAGGCTTTTTTGGAGGCCTAGGCTTTTGCGTCGAGACGTACCCAATTCGCCCTATAGT | |
| | GAGTCGTATTACGCGCGCTCACTGGCCGTCGTTTTACAACGTCGTGACTGGGAAAACC | |
| | CTGGCGTTACCCAACTTAATCGCCTTGCAGCACATCCCCCTTTCGCCAGCTGGCGTAAT | |
| | AGCGAAGAGGCCCGCACCGATCGCCCTTCCCAACAGTTGCGCAGCCTGAATGGCGAA | |
| | TGGCGCGACGCGCCCTGTAGCGGCGCATTAAGCGCGGCGGGTGTGGTGGTTACGCG | |
| | CAGCGTGACCGCTACACTTGCCAGCGCCCTAGCGCCCGCTCCTTTCGCTTTCTTCCCTT | |
| | CCTTTCTCGCCACGTTCGCCGGCTTTCCCCGTCAAGCTCTAAATCGGGGGCTCCCTTTA | |
| | GGGTTCCGATTTAGTGCTTTACGGCACCTCGACCCCAAAAAACTTGATTAGGGTGATG | |
| | GTTCACGTAGTGGGCCATCGCCCTGATAGACGGTTTTTCGCCCTTTGACGTTGGAGTC | |
| | CACGTTCTTTAATAGTGGACTCTTGTTCCAAACTGGAACAACACTCAACCCTATCTCGG | |
| | TCTATTCTTTTGATTTATAAGGGATTTTGCCGATTTCGGCCTATTGGTTAAAAAATGAG | |
| | CTGATTTAACAAAAATTTAACGCGAATTTTAACAAAATATTAACGTTTACAATTTCCCA | |
| | GGTGGCACTTTTCGGGGAAATGTGCGCGGAACCCCTATTTGTTTATTTTTCTAAATACA | |
| | TTCAAATATGTATCCGCTCATGAGACAATAACCCTGATAAATGCTTCAATAATATTGAA | |
| | AAAGGAAGAGTATGAGTATTCAACATTTCCGTGTCGCCCTTATTCCCTTTTTTGCGGCA | |
| | TTTTGCCTTCCTGTTTTTGCTCACCCAGAAACGCTGGTGAAAGTAAAAGATGCTGAAG | |
| | ATCAGTTGGGTGCACGAGTGGGTTACATCGAACTGGATCTCAACAGCGGTAAGATCC | |
| | TTGAGAGTTTTCGCCCCGAAGAACGTTTTCCAATGATGAGCACTTTTAAAGTTCTGCTA | |
| | TGTGGCGCGGTATTATCCCGTATTGACGCCGGGCAAGAGCAACTCGGTCGCCGCATA | |
| | CACTATTCTCAGAATGACTTGGTTGAGTACTCACCAGTCACAGAAAAGCATCTTACGG | |
| | ATGGCATGACAGTAAGAGAATTATGCAGTGCTGCCATAACCATGAGTGATAACACTG | |
| | CGGCCAACTTACTTCTGACAACGATCGGAGGACCGAAGGAGCTAACCGCTTTTTTGCA | |
| | CAACATGGGGGATCATGTAACTCGCCTTGATCGTTGGGAACCGGAGCTGAATGAAGC | |
| | CATACCAAACGACGAGCGTGACACCACGATGCCTGTAGCAATGGCAACAACGTTGCG | |
| | CAAACTATTAACTGGCGAACTACTTACTCTAGCTTCCCGGCAACAATTAATAGACTGGA | |
| | TGGAGGCGGATAAAGTTGCAGGACCACTTCTGCGCTCGGCCCTTCCGGCTGGCTGGT | |
| | TTATTGCTGATAAATCTGGAGCCGGTGAGCGTGGGTCTCGCGGTATCATTGCAGCACT | |
| | GGGGCCAGATGGTAAGCCCTCCCGTATCGTAGTTATCTACACGACGGGGAGTCAGGC | |
| | AACTATGATGAACGAAATAGACAGATCGCTGAGATAGGTGCCTCACTGATTAAGCA | |
| | TTGGTAACTGTCAGACCAAGTTTACTCATATATACTTTAGATTGATTTAAAACTTCATTT | |
| | TTAATTTAAAAGGATCTAGGTGAAGATCCTTTTTGATAATCTCATGACCAAAATCCCTT | |
| | AACGTGAGTTTTCGTTCCACTGAGCGTCAGACCCCGTAGAAAAGATCAAAGGATCTTC | |
| | TTGAGATCCTTTTTTTCTGCGCGTAATCTGCTGCTTGCAAACAAAAAAACCACCGCTAC | |
| | CAGCGGTGGTTTGTTTGCCGGATCAAGAGCTACCAACTCTTTTTCCGAAGGTAACTGG | |
| | CTTCAGCAGAGCGCAGATACCAAATACTGTCCTTCTAGTGTAGCCGTAGTTAGGCCAC | |

| SEQ ID NO | Sequence | Description |
|---|---|---|
| | CACTTCAAGAACTCTGTAGCACCGCCTACATACCTCGCTCTGCTAATCCTGTTACCAGT<br>GGCTGCTGCCAGTGGCGATAAGTCGTGTCTTACCGGGTTGGACTCAAGACGATAGTT<br>ACCGGATAAGGCGCAGCGGTCGGGCTGAACGGGGGGTTCGTGCACACAGCCCAGCT<br>TGGAGCGAACGACCTACACCGAACTGAGATACCTACAGCGTGAGCTATGAGAAAGCG<br>CCACGCTTCCCGAAGGGAGAAAGGCGGACAGGTATCCGGTAAGCGGCAGGGTCGGA<br>ACAGGAGAGCGCACGAGGGAGCTTCCAGGGGGAAACGCCTGGTATCTTTATAGTCCT<br>GTCGGGTTTCGCCACCTCTGACTTGAGCGTCGATTTTTGTGATGCTCGTCAGGGGGGC<br>GGAGCCTATGGAAAAACGCCAGCAACGCGGCCTTTTTACGGTTCCTGGCCTTTTGCTG<br>GCCTTTTGCTCACATGTTCTTTCCTGCGTTATCCCCTGATTCTGTGGATAACCGTATTAC<br>CGCCTTTGAGTGAGCTGATACCGCTCGCCGCAGCCGAACGACCGAGCGCAGCGAGTC<br>AGTGAGCGAGGAAGCGGAAGAGCGCCCAATACGCAAACCGCCTCTCCCCGCGCGTTG<br>GCCGATTCATTAATGCAGCTGGCACGACAGGTTTCCCGACTGGAAAGCGGGCAGTGA<br>GCGCAACGCAATTAATGTGAGTTAGCTCACTCATTAGGCACCCCAGGCTTTACACTTTA<br>TGCTTCCGGCTCGTATGTTGTGTGGAATTGTGAGCGGATAACAATTTCACACAGGAAA<br>CAGCTATGACCATGATTACGCCAAGCGCGCAATTAACCCTCACTAAAGGGAACAAAA<br>GCTGGAGCTGCA | |
| 30 | AGCTTAATGTAGTCTTATGCAATACTCTTGTAGTCTTGCAACATGGTAACGATGAGTTA<br>GCAACATGCCTTACAAGGAGAGAAAAAGCACCGTGCATGCCGATTGGTGGAAGTAAG<br>GTGGTACGATCGTGCCTTATTAGGAAGGCAACAGACGGGTCTGACATGGATTGGACG<br>AACCACTGAATTGCCGCATTGCAGAGATATTGTATTTAAGTGCCTAGCTCGATACAAT<br>AAACGGGTCTCTCTGGTTAGACCAGATCTGAGCCTGGGAGCTCTCTGGCTAACTAGG<br>GAACCCACTGCTTAAGCCTCAATAAAGCTTGCCTTGAGTGCTTCAAGTAGTGTGTGCC<br>CGTCTGTTGTGTGACTCTGGTAACTAGAGATCCCTCAGACCCTTTTAGTCAGTGTGGA<br>AAATCTCTAGCAGTGGCGCCCGAACAGGGACTTGAAAGCGAAAGGGAAACCAGAGG<br>AGCTCTCTCGACGCAGGACTCGGCTTGCTGAAGCGCGCACGGCAAGAGGCGAGGGG<br>CGGCGACTGGTGAGTACGCCAAAAATTTTGACTAGCGGAGGCTAGAAGGAGAGAGA<br>TGGGTGCGAGAGCGTCAGTATTAAGCGGGGGAGAATTAGATCGCGATGGGAAAAAA<br>TTCGGTTAAGGCCAGGGGGAAAGAAAAAATATAAATTAAAACATATAGTATGGGCAA<br>GCAGGGAGCTAGAACGATTCGCAGTTAATCCTGGCCTGTTAGAAACATCAGAAGGCT<br>GTAGACAAATACTGGGACAGCTACAACCATCCCTTCAGACAGGATCAGAAGAACTTA<br>GATCATTATATAATACAGTAGCAACCCTCTATTGTGTGCATCAAAGGATAGAGATAAA<br>AGACACCAAGGAAGCTTTAGACAAGATAGAGGAAGAGCAAACAAAAGTAAGACCA<br>CCGCACAGCAAGCGGCCGCTGATCTTCAGACCTGGAGGAGGAGATATGAGGGACAA<br>TTGGAGAAGTGAATTATATAAATATAAAGTAGTAAAAATTGAACCATTAGGAGTAGC<br>ACCCACCAAGGCAAAGAGAAGAGTGGTGCAGAGAGAAAAAAGAGCAGTGGGAATA<br>GGAGCTTTGTTCCTTGGGTTCTTGGGAGCAGCAGGAAGCACTATGGGCGCAGCCTCA<br>ATGACGCTGACGGTACAGGCCAGACAATTATTGTCTGGTATAGTGCAGCAGCAGAAC<br>AATTTGCTGAGGGCTATTGAGGCGCAACAGCATCTGTTGCAACTCACAGTCTGGGGC<br>ATCAAGCAGCTCCAGGCAAGAATCCTGGCTGTGGAAAGATACCTAAAGGATCAACAG<br>CTCCTGGGGATTTGGGGTTGCTCTGGAAAACTCATTTGCACCACTGCTGTGCCTTGGA<br>ATGCTAGTTGGAGTAATAAATCTCTGGAACAGATTTGGAATCACACGACCTGGATGG<br>AGTGGGACAGAGAAATTAACAATTACACAAGCTTAATACACTCCTTAATTGAAGAATC<br>GCAAAACCAGCAAGAAAAGAATGAACAAGAATTATTGGAATTAGATAAATGGGCAA<br>GTTTGTGGAATTGGTTTAACATAACAAATTGGCTGTGGTATATAAAATTATTCATAATG<br>ATAGTAGGAGGCTTGGTAGGTTTAAGAATAGTTTTTGCTGTACTTTCTATAGTGAATA<br>GAGTTAGGCAGGGATATTCACCATTATCGTTTCAGACCCACCTCCCAACCCCGAGGGG<br>ACCCGACAGGCCCGAAGGAATAGAAGAAGAAGGTGGAGAGAGAGACAGAGACAGA<br>TCCATTCGATTAGTGAACGGATCTCGACGGTATCGGTTAACTTTTAAAAGAAAAGGGG<br>GGATTGGGGGGTACAGTGCAGGGGAAAGAATAGTAGACATAATAGCAACAGACATA<br>CAAACTAAAGAATTACAAAAACAAATTACAAAAATTCAAAATTTTATCGATCACGAGA<br>CTAGCCTCGAGAAGCTTGATATCGAATTCCCACGGGGTTGGCGCGTAGGAACAGAG<br>AAACAGGAGAATATGGGCCAAACAGGATATCTGTGGTAAGCAGTTCCTGCCCCGGCT<br>CAGGGCCAAGAACAGTTGGAACAGCAGAATATGGGCCAAACAGGATATCTGTGGTA<br>AGCAGTTCCTGCCCCGGCTCAGGGCAAGAACAGATGGTCCCCAGATGCGGTCCCGC<br>CCTCAGCAGTTTCTAGAGAACCATCAGATGTTTCCAGGGTGCCCCAAGGACCTGAAAT<br>GACCCTGTGCCTTATTTGAACTAACCAATCAGTTCGCTTCTCGCTTCTGTTCGCGCGCTT<br>CTGCTCCCCGAGCTCTATATAAGCAGAGCTCGTTTAGTGAACCGTCAGATCGCTAGCA<br>CCGGTGCCGCCACCATGCCTCTGGGCCTGCTGTGGCTGGGCCTGGCCCTGCTGGGCG<br>CCCTGCACGCCCAGGCCGGCGTGCAGGTGGAGACAATCTCCCCAGGCGACGGACGA<br>CATTCCCTAAGCGGGGCCAGACCTGCGTGGTGCACTATACAGGCATGCTGGAGGATG<br>GCAAGAAGTTTGACAGCTCCCGGGATAGAAACAAGCCATTCAAGTTTATGCTGGGCA<br>AGCAGGAAGTGATCAGAGGCTGGGAGGAGGGCGTGGCCCAGATGTCTGTGGGCCA<br>GAGGGCCAAGCTGACCATCAGCCCCGACTACGCCTATGGAGCAACAGGCCACCCAGG<br>AATCATCCCACCTCACGCCACCCTGGTGTTCGATGTGGAGCTGCTGAAGCTGGGCGAG<br>CAAAACTTGGTGATTCCTTGGGCCCCAGAAAATCTCACGCTTCACAAGTTGTCCGAAT<br>CCCAGCTCGAGCTCAACTGGAATAATAGATTTCTTAATCATTGTTTGGAACACCTGGTT<br>CAATATAGAACGGATTGGGACCACTCATGACCGAGCAGTCAGTTGACTACCGCCAC<br>AAATTTTCACTTCCCAGCGTAGATGGGCAGAAGAGGTACACATTTAGGGTCAGATCCA<br>GGTTTAATCCTCTGTGTGGTTCTGCTCAACACTGGTCTGAGTGGAGCCATCCGATCCAC<br>TGGGGCTCAAATACCTCTAAAGAAAATCCGTTCCTCTTTGCGCTCGAAGCCGTTGTTAT<br>CAGCGTCGGAAGCATGGGACTTATCATTTCCCTTCTCTGCGTGTACTTCTGGCTGGAG<br>CGGACGATGCCGGATTCCGACGCTCAAAAACCTGGAGGACCTTGTAACAGAATAT<br>CACGGTAATTTCTCCGCTTGGAGTGGCGTATCAAAGGGGCTTGCTGAGTCCCTTCAAC<br>CGGATTACTCTGAGCGCCTCTGCTTGGTGTCCGAGATACCTCCCAAAGGAGGTGCACT<br>TGGGGAGGGGCCAGGCGCGTCCCCTTGCAATCAGCATAGTCCGTATTGGGCGCCCCC | CISC vector DNA |

| SEQ ID NO | Sequence | Description |
|---|---|---|
| | CTGTTATACCCTCAAACCGGAAACGGGAAGCGGAGCTACTAACTTCAGCCTGCTGAA<br>GCAGGCTGGAGACGTGGAGGAGAACCCTGGACCTATGGCACTGCCCGTGACCGCCCT<br>GCTGCTGCCTCTGGCCCTGCTGCTGCACGCAGCCCGGCCTATCCTGTGGCACGAGATG<br>TGGCACGAGGGCCTGGAGGAGGCCAGCAGGCTGTATTTTGGCGAGCGCAACGTGAA<br>GGGCATGTTCGAGGTGCTGGAGCCTCTGCACGCCATGATGGAGAGAGGCCCACAGA<br>CCCTGAAGGAGACATCCTTTAACCAGGCCTATGGACGGGACCTGATGGAGGCACAGG<br>AGTGGTGCAGAAAGTACATGAAGTCTGGCAATGTGAAGGACCTGCTGCAGGCCTGG<br>GATCTGTACTATCACGTGTTTCGGAGAATCTCCAAGAAACCTTTTGAGAACCTTAGACT<br>GATGGCGCCCATCTCTCTGCAGGTAGTTCACGTTGAGACCCATAGATGCAATATAAGC<br>TGGGAAATCTCACAAGCCAGCCATTACTTTGAACGGCATTTGGAATTCGAGGCCCGAA<br>CACTTTCCCCCGGTCATACGTGGGAAGAAGCTCCTCTCTTGACGCTGAAGCAGAAGCA<br>GGAGTGGATTTGTCTGGAGACTTTGACTCCTGATACTCAGTATGAGTTCCAAGTTCGG<br>GTGAAACCACTCCAAGGCGAGTTCACGACGTGGTCTCCGTGGAGTCAACCGTTGGCG<br>TTCCGCACGAAGCCCGCTGCCCTTGGCAAAGACACGATTCCGTGGCTTGGGCATCTGC<br>TCGTTGGGCTGAGTGGTGCGTTTGGTTTCATCATCTTGGTCTATCTCTTGATCAATTGC<br>AGAAATACAGGCCCTTGGCTGAAAAAAGTGCTCAAGTGTAATACCCCCGACCCAAGC<br>AAGTTCTTCTCCCAGCTTTCTTCAGAGCATGGAGGCGATGTGCAGAAATGGCTCTCTTC<br>ACCTTTTCCCTCCTCAAGCTTCTCCCCGGGAGGGCTGGCGCCCGAGATTTCACCTCTTG<br>AGGTACTTGAACGAGACAAGGTTACCCAACTTCTCCTTCAACAGGATAAGGTACCCGA<br>ACCTGCGAGCCTTAGCTCCAACCACTCTCTTACGAGCTGCTTCACCAATCAGGGATACT<br>TCTTTTTTCCACCTTCCCGATGCGCTGGAAATCGAAGCTTGTCAAGTTTACTTTACCTATG<br>ATCCATATAGCGAGGAAGATCCCGACGAAGGAGTCGCCGGTGCGCCCACGGGTTCCT<br>CACCCCAACCTCTCCAGCCTCTCTCAGGAGAAGATGATGCTTATTGCACTTTTCCCAGT<br>AGAGACGATCTCCTCCTCTTTTCTCCATCTCTTTTGGGGGACCTTCCCCCCCTTCTACG<br>GCACCTGGCGGGTCTGGTGCTGGCGAGGAGCGGATGCCGCCGTCCCTCCAGGAGCG<br>AGTACCACGAGATTGGGATCCCCAGCCACTTGGACCCCCACCCCCGGCGTACCTGAC<br>CTTGTCGATTTTCAACCTCCCCCTGAATTGGTGCTGCGAGAGGCTGGGGAGGAAGTTC<br>CGGACGCTGGGCCGAGGGAGGGCGTGTCCTTTCCATGGAGTAGGCCTCCAGGTCAA<br>GGCGAGTTTAGGGCTCTCAACGCGCGGCTGCCGTTGAATACAGACGCTTATCTCTCAC<br>TGCAGGAACTGCAAGGTCAGGACCCAACACATCTTGTAGGATCTGGTGCTACTAATTT<br>TTCTCTTTTGAAGCAAGCTGGAGATGTTGAAGAGAACCCTGGTCCAGTGAGCAAGGG<br>CGAGGAGCTGTTCACCGGGGTGGTGCCCATCCTGGTCGAGCTGGACGGCGACGTAAA<br>CGGCCACAAGTTCAGCGTGTCCGGCGAGGGCGAGGGCGATGCCACCTACGGCAAGC<br>TGACCCTGAAGTTCATCTGCACCACCGGCAAGCTGCCCGTGCCCTGGCCCACCCTCGT<br>GACCACCCTGACCTACGGCGTGCAGTGCTTCAGCCGCTACCCCGACCACATGAAGCAG<br>CACGACTTCTTCAAGTCCGCCATGCCCGAAGGCTACGTCCAGGAGCGCACCATCTTCT<br>TCAAGGACGACGGCAACTACAAGACCCGCGCCGAGGTGAAGTTCGAGGGCGACACC<br>CTGGTGAACCGCATCGAGCTGAAGGGCATCGACTTCAAGGAGGACGGCAACATCCTG<br>GGGCACAAGCTGGAGTACAACTACAACAGCCACAACGTCTATATCATGGCCGACAAG<br>CAGAAGAACGGCATCAAGGTGAACTTCAAGATCCGCCACAACATCGAGGACGGCAGC<br>GTGCAGCTCGCCGACCACTACCAGCAGAACACCCCCATCGGCGACGGCCCCGTGCTG<br>CTGCCCGACAACCACTACCTGAGCACCCAGTCCGCCCTGAGCAAAGACCCCAACGAGA<br>AGCGCGATCACATGGTCCTGCTGGAGTTCGTGACCGCCGCGGGATCACTCTCGGCAT<br>GGACGAGCTGTACAAGTAAACTAGTGTCGACAATCAACCTCTGGATTACAAAATTTGT<br>GAAAGATTGACTGGTATTCTTAACTATGTTGCTCCTTTTACGCTATGTGGATACGCTGC<br>TTTAATGCCTTTGTATCATGCTATTGCTTCCCGTATGGCTTTCATTTTCTCCTCCTTGTAT<br>AAATCCTGGTTGCTGTCTCTTTATGAGGAGTTGTGGCCCGTTGTCAGGCAACGTGGCG<br>TGGTGTGCACTGTGTTTGCTGACGCAACCCCCACTGGTTGGGGCATTGCCACCACCTG<br>TCAGCTCCTTTCCGGGACTTTCGCTTTCCCCCTCCCTATTGCCACGGCGGAACTCATCG<br>CCGCCTGCCTTGCCCGCTGCTGGACAGGGGCTCGGCTGTTGGGCACTGACAATTCCGT<br>GGTGTTGTCGGGGAAGCTGACGTCCTTTCCATGGCTGCTCGCCTGTGTTGCCACCTGG<br>ATTCTGCGCGGGACGTCCTTCTGCTACGTCCCTTCGGCCCTCAATCCAGCGGACCTTCC<br>TTCCCGCGGCCTGCTGCCGGCTCTGCGGCCTCTTCCGCGTCTTCGCCTTCGCCCTCAGA<br>CGAGTCGGATCTCCCTTTGGGCCGCCTCCCCGCCTGGAATTCGAGCTCGGTACCTTTA<br>AGACCAATGACTTACAAGGCAGCTGTAGATCTTAGCCACTTTTTAAAAGAAAAGGGG<br>GGACTGGAAGGGCTAATTCACTCCCAACGAAGACAAGATCTGCTTTTTTGCTTGTACTG<br>GGTCTCTCTGGTTAGACCAGATCTGAGCCTGGGAGCTCTCTGGCTAACTAGGGAACCC<br>ACTGCTTAAGCCTCAATAAAGCTTGCCTTGAGTGCTTCAAGTAGTGTGTGCCCGTCTGT<br>TGTGTGACTCTGGTAACTAGAGATCCCTCAGACCCTTTTAGTCAGTGTGGAAAATCTCT<br>AGCAGTAGTAGTTCATGTCATCTTATTATTCAGTATTTATAACTTGCAAAGAAATGAAT<br>ATCAGAGAGTGAGAGGAACTTGTTTATTGCAGCTTATAATGGTTACAAATAAAGCAAT<br>AGCATCACAAATTTCACAAATAAAGCATTTTTTTCACTGCATTCTAGTTGTGGTTTGTCC<br>AAACTCATCAATGTATCTTATCATGTCTGGCTCTAGCTATCCCGCCCCTAACTCCGCCCA<br>GTTCCGCCCATTCTCCGCCCCATGGCTGACTAATTTTTTTTATTTATGCAGAGGCCGAG<br>GCCGCCTCGGCCTCTGAGCTATTCCAGAAGTAGTGAGGAGGCTTTTTTGGAGGCCTAG<br>GCTTTTGCGTCGAGACGTACCCAATTCGCCCTATAGTGAGTCGTATTACGCGCGCTCA<br>CTGGCCGTCGTTTTACAACGTCGTGACTGGGAAAACCCTGGCGTTACCCAACTTAATC<br>GCCTTGCAGCACATCCCCCTTTCGCCAGCTGGCGTAATAGCGAAGAGGCCCGCACCGA<br>TCGCCCTTCCCAACAGTTGCGCAGCCTGAATGGCGAATGGCGCGACGCGCCCTGTAG<br>CGGCGCATTAAGCGCGGCGGGTGTGGTGGTTACGCGCAGCGTGACCGCTACACTTGC<br>CAGCGCCCTAGCGCCCGCTCCTTTCGCTTTCTTCCCTTCCTTTCTCGCCACGTTCGCCGG<br>CTTTCCCCGTCAAGCTCTAAATCGGGGCTCCCTTTAGGGTTCCGATTTAGTGCTTTAC<br>GGCACCTGACCCCAAAAAACTTGATTAGGGTGATGGTTCACGTAGTGGGCCATCGC<br>CCTGATAGACGGTTTTTCGCCCTTTGACGTTGGAGTCCACGTTCTTTAATAGTGGACTC<br>TTGTTCCAAACTGGAACAACACTCAACCCTATCTCGGTCTATTCTTTTGATTTATAAGG<br>GATTTTGCCGATTTCGGCCTATTGGTTAAAAAATGAGCTGATTTAACAAAAATTTAACG | |

| SEQ ID NO | Sequence | Description |
|---|---|---|
| | CGAATTTTAACAAAATATTAACGTTTACAATTTCCCAGGTGGCACTTTTCGGGGAAATG<br>TGCGCGGAACCCCTATTTGTTTATTTTTCTAAATACATTCAAATATGTATCCGCTCATGA<br>GACAATAACCCTGATAAATGCTTCAATAATATTGAAAAAGGAAGAGTATGAGTATTCA<br>ACATTTCCGTGTCGCCCTTATTCCCTTTTTTGCGGCATTTTGCCTTCCTGTTTTTGCTCAC<br>CCAGAAACGCTGGTGAAAGTAAAAGATGCTGAAGATCAGTTGGGTGCACGAGTGGG<br>TTACATCGAACTGGATCTCAACAGCGGTAAGATCCTTGAGAGTTTTCGCCCCGAAGAA<br>CGTTTTCCAATGATGAGCACTTTTAAAGTTCTGCTATGTGGCGCGGTATTATCCCGTAT<br>TGACGCCGGGCAAGAGCAACTCGGTCGCCGCATACACTATTCTCAGAATGACTTGGTT<br>GAGTACTCACCAGTCACAGAAAAGCATCTTACGGATGGCATGACAGTAAGAGAATTA<br>TGCAGTGCTGCCATAACCATGAGTGATAACACTGCGGCCAACTTACTTCTGACAACGA<br>TCGGAGGACCGAAGGAGCTAACCGCTTTTTTGCACAACATGGGGGATCATGTAACTC<br>GCCTTGATCGTTGGGAACCGGAGCTGAATGAAGCCATACCAAACGACGAGCGTGACA<br>CCACGATGCCTGTAGCAATGGCAACAACGTTGCGCAAACTATTAACTGGCGAACTACT<br>TACTCTAGCTTCCCGGCAACAATTAATAGACTGGATGAGGCGGATAAAGTTGCAGG<br>ACCACTTCTGCGCTCGGCCCTTCCGGCTGGCTGGTTTATTGCTGATAAATCTGGAGCC<br>GGTGAGCGTGGGTCTCGCGGTATCATTGCAGCACTGGGGCCAGATGGTAAGCCCTCC<br>CGTATCGTAGTTATCTACACGACGGGGAGTCAGGCAACTATGGATGAACGAAATAGA<br>CAGATCGCTGAGATAGGTGCCTCACTGATTAAGCATTGGTAACTGTCAGACCAAGTTT<br>ACTCATATATACTTTAGATTGATTTAAAACTTCATTTTTAATTTAAAAGGATCTAGGTGA<br>AGATCCTTTTTGATAATCTCATGACCAAAATCCCTTAACGTGAGTTTTCGTTCCACTGA<br>GCGTCAGACCCCGTAGAAAAGATCAAAGGATCTTCTTGAGATCCTTTTTTTCTGCGCGT<br>AATCTGCTGCTTGCAAACAAAAAAACCACCGCTACCAGCGGTGGTTTGTTTGCCGGAT<br>CAAGAGCTACCAACTCTTTTTCCGAAGGTAACTGGCTTCAGCAGAGCGCAGATACCAA<br>ATACTGTCCTTCTAGTGTAGCCGTAGTTAGGCCACCACTTCAAGAACTCTGTAGCACCG<br>CCTACATACCTCGCTCTGCTAATCCTGTTACCAGTGGCTGCTGCCAGTGGCGATAAGTC<br>GTGTCTTACCGGGTTGGACTCAAGACGATAGTTACCGGATAAGGCGCAGCGGTCGGG<br>CTGAACGGGGGGTTCGTGCACACAGCCCAGCTTGGAGCGAACGACCTACACCGAACT<br>GAGATACCTACAGCGTGAGCTATGAGAAAGCGCCACGCTTCCCGAAGGGAGAAAGG<br>CGGACAGGTATCCGGTAAGCGGCAGGGTCGGAACAGGAGAGCGCACGAGGGAGCT<br>TCCAGGGGGAAACGCCTGGTATCTTTATAGTCCTGTCGGGTTTCGCCACCTCTGACTT<br>GAGCGTCGATTTTTGTGATGCTCGTCAGGGGGCGGAGCCTATGGAAAAACGCCAGC<br>AACGCGGCCTTTTTACGGTTCCTGGCCTTTTGCTGGCCTTTTGCTCACATGTTCTTTCCT<br>GCGTTATCCCCTGATTCTGTGGATAACCGTATTACCGCCTTTGAGTGAGCTGATACCGC<br>TCGCCGCAGCCGAACGACCGAGCGCAGCGAGTCAGTGAGCGAGGAAGCGGAAGAGC<br>GCCCAATACGCAAACCGCCTCTCCCCGCGCGTTGGCCGATTCATTAATGCAGCTGGCA<br>CGACAGGTTTCCCGACTGGAAAGCGGGCAGTGAGCGCAACGCAATTAATGTGAGTTA<br>GCTCACTCATTAGGCACCCCAGGCTTTACACTTTATGCTTCCGGCTCGTATGTTGTGTG<br>GAATTGTGAGCGGATAACAATTTCACACAGGAAACAGCTATGACCATGATTACGCCAA<br>GCGCGCAATTAACCCTCACTAAAGGGAACAAAAGCTGGAGCTGCA | |
| 31 | PAAL | Linker/spacer polypeptide |
| 32 | GAGATGTGGCATGAGGGTCTGGAAGAAGCGTCTCGACTGTACTTTGGTGAGCGCAAT<br>GTGAAGGGCATGTTTGAAGTCCTCGAACCCCTTCATGCCATGATGGAACGCGGACCCC<br>AGACCTTGAAGGAGACAAGTTTTAACCAAGCTTACGGAAGAGACCTGATGGAAGCCC<br>AGGAATGGTGCAGGAAATACATGAAAAGCGGGAATGTGAAGGACTTGACCCAAGCG<br>TGGGACCTGTACTATCATGTCTTTAGGCGCATTAGTAAG | Naked FRB domain nucleic acid sequence |
| 33 | GAACAGAGAAACAGGAGAATATGGGCCAAACAGGATATCTGTGGTAAGCAGTTCCTG<br>CCCCGGCTCAGGGCCAAGAACAGTTGGAACAGCAGAATATGGGCCAAACAGGATATC<br>TGTGGTAAGCAGTTCCTGCCCCGGCTCAGGGCCAAGAACAGATGGTCCCCAGATGG<br>GTCCCGCCCTCAGCAGTTTCTAGAGAACCATCAGATGTTTCCAGGGTGCCCCAAGGAC<br>CTGAAATGACCCTGTGCCTTATTTGAACTAACCAATCAGTTCGCTTCTCGCTTCTGTTCG<br>CGCGCTTCTGCTCCCCGAGCTCTATATAAGCAGAGCTCGTTTAGTGAACCGTCAGATC<br>GCTAGC | MND promoter |
| 34 | CGGCGACGTGGAAGAGAATC | DISC HDR FP |
| 35 | GGCTGTGGTTCAGCCTGACT | DISC HDR RP |
| 36 | AGGCTCTCCCCGACCTCCC | |
| 37 | ATGCCACTGGGACTGCTGTGGCTTGGACTGGCCCTTCTTGGAGCACTGCATGCTCAGG<br>CTGGCGTGCAGGTCGAGACAATTAGTCCTGGCGACGGCCGGACCTTTCCTAAGCGA<br>GACAGACATGCGTGGTGCACTACACCGGCATGCTGGAAGATGGCAAGAAGTTCGACA<br>GCAGCCGGGACAGAAACAAGCCTTTCAAGTTCATGCTGGGCAAGCAAGAAGTGATCA<br>GAGGCTGGGAAGAGGGCGTCGCCCAGATGTCTGTTGGACAGAGAGCCAAGCTGACA<br>ATCAGCCCCGATTACGCCTATGGCGCCACAGGACACCCTGGGATCATTCCTCCACATG<br>CCACACTGGTGTTCGATGTGGAACTGCTGAAGCTCGGCGAAGGCAGCAATACCAGCA<br>AAGAGAACCCCTTCCTGTTCGCCCTGGAAGCCGTGGTTATCAGCGTGGGATCTATGGG<br>CCTGATCATCTCCCTGCTGTGCGTGTACTTCTGGCTGGAACGGACCATGCCTCGGATCC<br>CCACACTGAAGAATCTGGAAGATCTGGTCACCGAGTACCACGGCAATTTCAGCGCTTG<br>GAGTGGCGTGTCCAAAGGCCTGGCTGAAAGCCTGCAGCCTGACTACTCTGAGAGACT<br>GTGCCTGGTGTCTGAGATCCCTCCTAAAGGCGGCGCTCTCGGAGAAGGACCAGGCGC<br>TTCTCCATGCAATCAGCACAGCCCTTATTGGGCCCCTCCTTGCTACACCCTGAAGCCTG | Coding sequences for 3186 (Signal-FKBP-IL2Rg-P2A-signal-FRB-1L2Rb-P2A-FRB-P2A-GFP-FOXP3 (knock-in) |

| SEQ ID NO | Sequence | Description |
|---|---|---|
| | AAACTGGAAGCGGAGCTACTAACTTTAGCCTGCTGAAGCAGGCTGGAGACGTGGAG<br>GAGAACCCTGGACCTATGGCTCTGCCAGTGACAGCTCTGCTGCTTCCTCTGGCTCTGTT<br>GCTGCATGCCGCCAGACCTATTCTGTGGCACGAGATGTGGCATGAAGGCCTGGAAGA<br>GGCCTCCAGACTGTACTTCGGCGAGAGAAACGTGAAGGGCATGTTCGAGGTGCTGGA<br>ACCCCTGCATGCCATGATGGAAAGAGGCCCTCAGACACTGAAAGAGACAAGCTTCAA<br>CCAGGCCTACGGCCGGGATCTGATGGAAGCCCAAGAGTGGTGCCGGAAGTACATGA<br>AGTCCGGCAATGTGAAGGACCTCCTGCAGGCATGGGACCTGTACTACCACGTGTTCC<br>GGCGGATCTCTAAGGGCAAAGACACAATCCCTTGGCTGGGCCATCTGCTCGTTGGACT<br>GTCTGGCGCCTTCGGCTTCATCATCCTGGTGTACCTGCTGATCAACTGTCGGAACACA<br>GGCCCATGGCTGAAGAAAGTGCTGAAGTGCAACACCCCTGATCCGAGCAAGTTCTTT<br>AGCCAGCTGTCCAGCGAGCACGGCGGAGATGTTCAGAAGTGGCTGAGCAGCCCATTT<br>CCTAGCAGCAGCTTTAGCCCTGGCGGACTGGCTCCTGAGATCAGCCCACTGGAAGTG<br>CTGGAAAGGGACAAAGTGACCCAGCTGCTCCTGCAACAGGACAAGGTGCCAGAACCT<br>GCCAGCCTGTCTCTGAACACCGATGCCTATCTGTCCCTGCAAGAGCTGCAAGGATCCG<br>GCGCCACCAACTTTAGTCTGCTCAAGCAAGCCGGGACGTCGAGGAAAATCCTGGGC<br>CAGAAATGTGGCACGAAGGACTCGAGGAAGCCAGTCGGCTGTATTTTGGCGAGCGG<br>AATGTGAAAGGGATGTTTGAAGTGCTCGAGCCTCTCCACGCTATGATGGAACGGGGA<br>CCCCAGACTCTCAAAGAAACCAGCTTTAATCAGGCTTACGGACGCGACCTCATGGAAG<br>CTCAAGAATGGTGTAGAAAGTATATGAAGAGTGGCAACGTGAAAGATCTGCTGCAAG<br>CCTGGGATCTCTATTATCACGTGTTCAGACGCATCAGCAAAGGCAGCGGCGCCACAA<br>TTTCTCCCTGCTGAAACAGGCCGGCGACGTGGAAGAGAATCCCGGACCTATGCCTAAT<br>CCTCGGCCTTCCAAAGGCGAGGAACTGTTTACAGGCGTGGTGCCCATCCTGGTGGAA<br>CTGGACGGGGATGTGAACGGCCACAAGTTTAGCGTTAGCGGCGAAGGCGAAGGGGA<br>TGCCACATACGGAAAGCTGACCCTGAAGTTCATCTGCACCACCGGCAAGCTGCCTGTG<br>CCTTGGCCTACACTGGTCACCACACTGACATACGGCGTGCAGTGCTTCAGCAGATACC<br>CCGACCATATGAAGCAGCACGACTTCTTCAAGAGCGCCATGCCTGAGGGCTACGTGC<br>AAGAGCGGACCATCTTCTTTAAGGACGACGGCAACTACAAGACCAGGGCCGAAGTGA<br>AGTTCGAGGGCGACACCCTGGTCAACCGGATCGAGCTGAAGGGCATCGACTTCAAAG<br>AGGACGGCAACATCCTGGGCCACAAGCTCGAGTACAACTACAACAGCCACAACGTGT<br>ACATCATGGCCGACAAGCAGAAAAACGGCATCAAAGTGAACTTCAAGATCCGGCACA<br>ACATCGAGGACGGCTCTGTGCAGCTGGCCGATCACTACCAGCAGAACACACCCATCG<br>GAGATGGCCCTGTGCTGCTGCCCGATAACCACTACCTGAGCACACAGAGCGCCCTGA<br>GCAAGGACCCCAACGAGAAGAGGGATCACATGGTGCTGCTGGAATTCGTGACCGCC<br>GCTGGGCATCACACTCGGCATGGATGAGCTGTACAAGATGCCCAATCCTAGACCTGGC<br>AAGCCCAGCGCTCCTTCTCTTGCTCTTGGACCTTCTCCTGGTGCCTCGCCCAGCTGGAG<br>GGCTGCACCCAAAGCCTCAGACCTGCTGGGGGCCCGGGGCCCAGGGGGAACCTTCCA<br>GGGCCGAGATCTTCGAGGCGGGGCCCATGCCTCCTCTTCTTCCTTGAACCCCATGCCA<br>CCATCGCAGCTGCAG | |
| 38 | ATGCCACTGGGACTGCTGTGGCTTGGACTGGCCCTTCTTGGAGCACTGCATGCTCAGG<br>CTGGCGTGCAGGTCGAGACAATTAGTCCTGGCGACGGCCGGACCTTTCCTAAGCGAG<br>ACAGACATGCGTGGTGCACTACACCGGCATGCTGGAAGATGGCAAGAAGTTCGACA<br>GCAGCCGGGACAGAAACAAGCCTTTCAAGTTCATGCTGGGCAAGCAAGAAGTGATCA<br>GAGGCTGGGAAGAGGGCGTCGCCCAGATGTCTGTTGGACAGAGAGCCAAGCTGACA<br>ATCAGCCCCGATTACGCCTATGGCGCCACAGGACACCCTGGGATCATTCCTCCACATG<br>CCACACTGGTGTTCGATGTGGAACTGCTGAAGCTCGGCGAAGGCAGCAATACCAGCA<br>AAGAGAACCCCTTCCTGTTCGCCCTGGAAGCCGTGGTTATCAGCGTGGGATCTATGGG<br>CCTGATCATCTCCCTGCTGTGCGTGTACTTCTGGCTGGAACGGACCATGCCTCGGATCC<br>CCACACTGAAGAATCTGGAAGATCTGGTCACCGAGTACCACGGCAATTTCAGCGCTTG<br>GAGTGGCGTGTCCAAAGGCCTGGCTGAAAGCCTGCAGCCTGACTACTCTGAGAGACT<br>GTGCCTGGTGTCTGAGATCCCTCCTAAAGGCGGCGCTCTCGGAGAAGGACCAGGCGC<br>TTCTCCATGCAATCAGCACAGCCCTTATTGGGCCCTCCTTGCTACACCCTGAAGCCTG<br>AAACTGGAAGCGGAGCTACTAACTTTAGCCTGCTGAAGCAGGCTGGAGACGTGGAG<br>GAGAACCCTGGACCTATGGCTCTGCCAGTGACAGCTCTGCTGCTTCCTCTGGCTCTGTT<br>GCTGCATGCCGCCAGACCTATTCTGTGGCACGAGATGTGGCATGAAGGCCTGGAAGA<br>GGCCTCCAGACTGTACTTCGGCGAGAGAAACGTGAAGGGCATGTTCGAGGTGCTGGA<br>ACCCCTGCATGCCATGATGGAAAGAGGCCCTCAGACACTGAAAGAGACAAGCTTCAA<br>CCAGGCCTACGGCCGGGATCTGATGGAAGCCCAAGAGTGGTGCCGGAAGTACATGA<br>AGTCCGGCAATGTGAAGGACCTCCTGCAGGCATGGGACCTGTACTACCACGTGTTCC<br>GGCGGATCTCTAAGGGCAAAGACACAATCCCTTGGCTGGGCCATCTGCTCGTTGGACT<br>GTCTGGCGCCTTCGGCTTCATCATCCTGGTGTACCTGCTGATCAACTGTCGGAACACA<br>GGCCCATGGCTGAAGAAAGTGCTGAAGTGCAACACCCCTGATCCGAGCAAGTTCTTT<br>AGCCAGCTGTCCAGCGAGCACGGCGGAGATGTTCAGAAGTGGCTGAGCAGCCCATTT<br>CCTAGCAGCAGCTTTAGCCCTGGCGGACTGGCTCCTGAGATCAGCCCACTGGAAGTG<br>CTGGAAAGGGACAAAGTGACCCAGCTGCTCCTGCAACAGGACAAGGTGCCAGAACCT<br>GCCAGCCTGTCTAGCAATCACAGCCTGACCAGCTGCTTTACCAACCAGGGCTACTTCT<br>TCTTCCATCTGCCTGACGCTCTGGAAATCGAGGCCTGCCAGGTGTACTTCACCTACGAT<br>CCTACAGCGAAGAGGACCCCGATGAAGGTGTTGCCGGTGCTCCTACCGGAAGCTCTC<br>CTCAACCTCTGCAACCACTGAGCGGCGAGGATGACGCCTACTGCACATTCCCCAGCAG<br>AGATGACCTGCTGCTGTTCAGCCCTTCTCTGCTCGGCGGACCTTCTCCACCATCTACAG<br>CTCCAGGTGAAGCGGAGCCGGCGAGGAAAGAATGCCTCCAAGCCTGCAAGAGCGG<br>GTGCCAGAGATTGGGATCCTCAACCACTGGGCCTCCAACACCTGGCGTGCCAGATC<br>TCGTGGATTTCCAGCCTCCTCCAGAGCTGGTGCTGAGAGAAGCTGGCGAAGAAGTGC<br>CAGACGCTGGCCCTAGAGAGGGCGTTAGCTTTCCTTGGAGCAGACCTCCTGGACAGG<br>GCGAGTTCAGAGCCCTGAATGCTAGACTGCCCCTGAACACCGATGCCTATCTGTCCCT<br>GCAAGAGCTGCAAGGACAAGACCCCACACACCTGGTTGGATCCGGCGCCACCAACTT | Coding sequences<br>for 3187 (Signal-<br>FKBP-IL2Rg-P2A-<br>signal-FRB-IL2Rb-<br>P2A-FRB-P2A-HA-<br>FOXP3 (knock-in) |

| SEQ ID NO | Sequence | Description |
|---|---|---|
| | TAGTCTGCTCAAGCAAGCCGGGGACGTCGAGGAAAATCCTGGGCCAGAAATGTGGC<br>ACGAAGGACTCGAGGAAGCCAGTCGGCTGTATTTTGGCGAGCGGAATGTGAAAGGG<br>ATGTTTGAAGTGCTCGAGCCTCTCCACGCTATGATGGAACGGGGACCCCAGACTCTCA<br>AAGAAACCAGCTTTAATCAGGCTTACGACGCGACCTCATGGAAGCTCAAGAATGGT<br>GTAGAAAGTATATGAAGAGTGGCAACGTGAAAGATCTGCTGCAAGCCTGGGATCTCT<br>ATTATCACGTGTTCAGACGCATCAGCAAAGGCAGCGGCGCCACAAATTTCTCCCTGCT<br>GAAACAGGCCGGCGACGTGAAGAGAATCCCGGACCTATGTATCCATACGATGTCCC<br>AGATTATGCGCCCAATCCTAGACCTGGCAAGCCCAGCGCTCCTTCTCTTGCTCTTGGAC<br>CTTCTCCTGGTGCCTCGCCCAGCTGGAGGGCTGCACCCAAAGCCTCAGACCTGCTGGG<br>GGCCCGGGGCCCAGGGGGAACCTTCCAGGGCCGAGATCTTCGAGGCGGGGCCCATG<br>CCTCCTCTTCTTCCTTGAACCCCATGCCACCATCGCAGCTGCAG | |
| 39 | ATGCCACTGGGACTGCTGTGGCTTGGACTGGCCCTTCTTGGAGCACTGCATGCTCAGG<br>CTGGCGTGCAGGTCGAGACAATTAGTCCTGGCGACGGCCGGACCCTTCCTAAGCGAG<br>GACAGACATGCGTGGTGCACTACACCGGCATGCTGGAAGATGGCAAGAAGTTCGACA<br>GCAGCCGGGACAGAAACAAGCCTTTCAAGTTCATGCTGGGCAAGCAAGAAGTGATCA<br>GAGGCTGGGAAGAGGGCGTCGCCCAGATGTCTGTTGGACAGAGAGCCAAGCTGACA<br>ATCAGCCCCGATTACGCCTATGGCGCCACAGGACACCCTGGGATCATTCCTCCACATG<br>CCACACTGGTGTTCGATGTGGAACTGCTGAAGCTCGGCGAAGGCAGCAATACCAGCA<br>AAGAGAACCCCTTCCTGTTCGCCCTGGAAGCCGTGGTTATCAGCGTGGGATCTATGGG<br>CCTGATCATCTCCCTGCTGTGCGTGTACTTCTGGCTGGAACGGACCATGCCTCGGATCC<br>CCACACTGAAGAATCTGGAAGATCTGGTCACCGAGTACCACGGCAATTTCAGCGCTTG<br>GAGTGGCGTGTCCAAAGCCTGGCTGAAAGCCTGCAGCCTGACTACTCTGAGAGACT<br>GTGCCTGGTGTCTGAGATCCCTCCTAAAGGCGGCGCTCTCGGAGAAGGACCAGGCGC<br>TTCCTCCATGCAATCAGCACAGCCCTTATTGGGCCCCTCCTTGCTACACCCTGAAGCCTG<br>AAACTGGAAGCGGAGCTACTAACTTTAGCCTGCTGAAGCAGGCTGGAGACGTGGAG<br>GAGAACCCTATGGCTCTGCCAGTGACAGCTCTGCTGCTTCCTCTGGCTCTGTT<br>GCTGCATGCCGCCAGACCTATTCTGTGGCACGAGATGTGGCATGAAGGCCTGGAAGA<br>GGCCTCCAGACTGTACTTCGGCGAGAGAAACGTGAAGGGCATGTTCGAGGTGCTGGA<br>ACCCCTGCATGCCATGATGGAAAGAGGCCCTCAGACACTGAAAGAGACAAGCTTCAA<br>CCAGGCCTACGCCGGGATCTGATGGAAGCCCAAGAGTGGTGCCGGAAGTACATGA<br>AGTCCGGCAATGTGAAGGACCTCCTGCAGGCATGGGACCTGTACTACCACGTGTTCC<br>GGCGGATCTCTAAGGGCAAAGACACAATCCCTTGGCTGGGCCATCTGCTCGTTGGACT<br>GTCTGGCGCCTTCGGCTTCATCATCCTGGTGTACCTGCTGATCAACTGTCGGAACACA<br>GGCCCATGGCTGAAGAAAGTGCTGAAGTGCAACACCCCTGATCCGAGCAAGTTCTTT<br>AGCCAGCTGTCCAGCGAGCACGGCGGAGATGTTCAGAAGTGGCTGAGCAGCCCATTT<br>CCTAGCAGCAGCTTTAGCCCTGGCGGACTGGCTCCTGAGATCAGCCCACTGGAAGTG<br>CTGGAAAGGGACAAAGTGACCCAGCTGCCTCTGCAACAGGACAAGGTGCCAGAACCT<br>GCCAGCCTGTCTAGCAATCACAGCCTGACCAGCTGCTTTACCAACCAGGGCTACTTCTT<br>CTTCCATCTGCCTGACGCTCTGGAAATCGAGGCCTGCCAGGTGTACTTCACCTACGATC<br>CCTACAGCGAAGAGGACCCCGATGAAGGTGTTGCCGGTGCTCCTACCGGAAGCTCTC<br>CTCAACCTCTGCAACCACTGAGCGGCGAGGATGACGCCTACTGCACATTCCCCAGCAG<br>AGATGACCTGCTGCTGTTCAGCCCTTCTCTGCTCGGCGGACCTTCTCCACCATCTACAG<br>CTCCAGGTGGAAGCGGAGCCGGCGAGGAAAGAATGCCTCCAAGCCTGCAAGAGCCG<br>GTGCCCAGAGATTGGGATCCTCAACCACTGGGCCCTCCAACACCTGGCGTGCCAGATC<br>TCGTGGATTTCCAGCCTCCTCCAGAGCTGGTGCTGAGAGAAGCTGGCGAAGAAGTGC<br>CAGACGCTGGCCCTAGAGAGGGCGTTAGCTTTCCTTGGAGCAGACCTCCTGGACAGG<br>GCGAGTTCAGAGCCCTGAATGCTAGACTGCCCCTGAACACCGATGCCTATCTGTCCCT<br>GCAAGAGCTGCAAGGACAAGACCCCACACACCTGGTTGGATCCGGCGCCACCAACTT<br>TAGTCTGCTCAAGCAAGCCGGGGACGTCGAGGAAAATCCTGGGCCAGAAATGTGGC<br>ACGAAGGACTCGAGGAAGCCAGTCGGCTGTATTTTGGCGAGCGGAATGTGAAAGGG<br>ATGTTTGAAGTGCTCGAGCCTCTCCACGCTATGATGGAACGGGGACCCCAGACTCTCA<br>AAGAAACCAGCTTTAATCAGGCTTACGACGCGACCTCATGGAAGCTCAAGAATGGT<br>GTAGAAAGTATATGAAGAGTGGCAACGTGAAAGATCTGCTGCAAGCCTGGGATCTCT<br>ATTATCACGTGTTCAGACGCATCAGCAAAGGCAGCGGCGCCACAAATTTCTCCCTGCT<br>GAAACAGGCCGGCGACGTGAAGAGAATCCCGGACCTATGCCCAATCCTAGACCTGG<br>CAAGCCCAGCGCTCCTTCTCTTGCTCTTGGACCTTCTCCTGGTGCCTCGCCCAGCTGGA<br>GGGCTGCACCCAAAGCCTCAGACCTGCTGGGGGCCCGGGGCCCAGGGGGAACCTTC<br>CAGGGCCGAGATCTTCGAGGCGGGGCCCATGCCTCCTCTTCTTCCTTGAACCCCATGC<br>CACCATCGCAGCTGCAG | Coding sequences for 3195 (Signal-FKBP-IL2Rg-P2A-signal-FRB-IL2Rb-P2A-FRB-P2A-FOXP3 (knock-in) |
| 40 | TTCCAGGGCCGAGATCTTCG | T1 spacer targeting human FOXP3 |
| 41 | CGCCTCGAAGATCTCGGCCC | T3 spacer targeting human FOXP3 |
| 42 | TCGAAGATCTCGGCCCTGGA | T4 spacer targeting human FOXP3 |
| 43 | GGCCCTGGAAGGTTCCCCCT | T7 spacer targeting human FOXP3 |
| 44 | TCCAGCTGGGCGAGGCTCCT | T9 spacer targeting human FOXP3 |

| SEQ ID NO | Sequence | Description |
|---|---|---|
| 45 | TCAGACCTGCTGGGGGCCCG | T18 spacer targeting human FOXP3 |
| 46 | GAGCCCCGCCTCGAAGATCT | R1 spacer targeting human FOXP3 |
| 47 | ATTCCCAGGGCCGGTTAATG | P1 spacer targeting human AAVS1 |
| 48 | GTCCCCTCCACCCCACAGTG | P3 spacer targeting human AAVS1 |
| 49 | ACCCCACAGTGGGGCCACTA | P4 spacer targeting human AAVS1 |
| 50 | CCTCTAAGGTTTGCTTACGA | Ni spacer targeting human AAVS1 |
| 51 | TATAAGGTGGTCCCAGCTCG | N2 spacer targeting human AAVS1 |
| 52 | CCATCGTAAGCAAACCTTAG | N3 spacer targeting human AAVS1 |
| 53 | GACTCCTGGGGATGGGCCAA | mT20 spacer target murine FOXP3 |
| 54 | TTGGCCCTTGGCCCATCCCC | mT22 spacer target murine FOXP3 |
| 55 | CCAGCTTGGCAAGACTCCTG | mT23 spacer target murine FOXP3 |
| 56 | ACAAAACTGTGCTAGACATG | human TRAC spacer sequence G2 |
| 57 | TCAAGAGCAACAGTGCTG | human TRAC spacer sequence G4 |
| 58 | CCGATGCCCAACCCCAGGCC | spacer |

What is claimed is:

1. A system comprising:
a first polynucleotide comprising a nucleotide sequence encoding a soluble FK506-binding protein (FKBP)-rapamycin-binding (FRB) domain polypeptide, wherein the soluble FRB domain polypeptide comprises an amino acid sequence having at least 90% identity to SEQ ID NO: 1;
(ii) a second polynucleotide encoding a first chemically induced signaling complex (CISC) component, wherein the first CISC component comprises a first extracellular binding domain comprising an FKBP domain, a first transmembrane domain, and a first cytoplasmic signaling domain; and
(iii) a third polynucleotide encoding a second CISC component, wherein the second CISC component comprises a second extracellular binding domain comprising an FRB domain, a second transmembrane domain, and a second cytoplasmic signaling domain; and
wherein the first CISC component and the second CISC component dimerize in the presence of a ligand selected from rapamycin or a rapalog to create a signaling-competent CISC.

2. The system of claim 1, wherein the first CISC component comprises a first hinge domain, and the second CISC component comprises a second hinge domain.

3. The system of claim 1, wherein:
the first cytoplasmic signaling domain comprises an IL-2 receptor subunit gamma (IL-2Rγ) cytoplasmic domain and the second cytoplasmic signaling domain comprises an IL-2 receptor subunit beta (IL-2Rβ) cytoplasmic domain; or
(ii) the second cytoplasmic signaling domain comprises the IL-2Rγ cytoplasmic domain and the first cytoplasmic signaling domain comprises the IL-2Rβ cytoplasmic domain.

4. The system of claim 1, wherein the FKBP domain of the first extracellular binding domain comprises an amino acid sequence having at least 95% identity to an amino acid sequence of SEQ ID NO: 6.

5. The system of claim 1, wherein the FRB domain of the second extracellular binding domain comprises an amino acid sequence having at least 95% identity to an amino acid sequence of SEQ ID NO: 1.

6. The system of claim 3, wherein the IL-2Rβ cytoplasmic domain comprises an amino acid sequence having at least 95% identity to an amino acid sequence of SEQ ID NO: 5.

7. The system of claim 3, wherein the second cytoplasmic signaling domain comprises the IL-2Rβ cytoplasmic domain, wherein the second CISC component comprises an amino acid sequence having at least 95% identity to an amino acid sequence of SEQ ID NO: 7.

8. The system of claim 1, wherein the first cytoplasmic signaling domain comprises an IL-2 receptor subunit gamma (IL-2Rγ) cytoplasmic domain and the second cytoplasmic signaling domain comprises an IL-2 receptor subunit beta (IL-2Rβ) cytoplasmic domain.

9. The system of claim 1, wherein
(i) the first CISC component comprises, in N-to-C-terminal order:
(a) the FKBP domain,
(b) an IL-2 receptor subunit gamma (IL-2Rγ) transmembrane domain, and
(c) an IL-2Rγ cytoplasmic domain; and (ii) the second CISC component comprises, in N-to-C-terminal order:
(a) the FRB domain,
(b) an IL-2 receptor subunit beta (IL-2Rβ) transmembrane domain, and
(c) an IL-2Rβ cytoplasmic domain.

10. The system of claim 2, wherein the first CISC component comprises an amino acid sequence with at least 95% sequence identity to SEQ ID NO: 12.

11. The system of claim 2, wherein the second CISC component comprises an amino acid sequence with at least 95% sequence identity to SEQ ID NO: 13.

12. The system of claim 2, wherein the first CISC component comprises an amino acid sequence with at least 95% sequence identity to SEQ ID NO: 12, and the second CISC component comprises an amino acid sequence with at least 95% sequence identity to SEQ ID NO: 13.

13. The system of claim 1, wherein the soluble FRB domain polypeptide comprises an amino acid sequence of SEQ ID NO: 1.

14. The system of claim 1, wherein the soluble FRB domain polypeptide consists of an amino acid sequence of SEQ ID NO: 1.

15. The system of claim 1, wherein the soluble FRB domain comprises a T2098L substitution.

16. The system of claim 1, wherein the soluble FRB domain polypeptide comprises an amino acid sequence of SEQ ID NO: 2.

17. The system of claim 1, wherein the soluble FRB domain polypeptide consists of an amino acid sequence of SEQ ID NO: 2.

18. The system of claim 1, wherein a vector comprises the first polynucleotide, the second polynucleotide, the third polynucleotide, or a combination thereof.

19. The system of claim 18, wherein the vector comprises the first polynucleotide and the second polynucleotide.

20. The system of claim 18, wherein the vector comprises the first polynucleotide and the third polynucleotide.

21. The system of claim 18, wherein the vector is a non-viral vector.

22. The system of claim 18, wherein the vector is a viral vector.

23. The system of claim 22, wherein the viral vector is a lentiviral vector.

24. The system of claim 22, wherein the viral vector is an adeno-associated viral (AAV) vector.

25. The system of claim 1, wherein the ligand is rapamycin.

26. The system of claim 1, wherein the ligand is a rapalog selected from the group consisting of everolimus, CCI-779, C20-methallylrapamycin, C16-(S)-3-methylindolerapamycin, C16-iRap, AP21967, sodium mycophenolic acid, benidipine hydrochloride, AP1903, AP23573, a metabolite of rapamycin, and an IMID-class drug.

27. The system of claim 26, wherein the IMID-class drug is thalidomide, pomalidomide, or lenalidomide.

28. The system of claim 1, further comprising a DNA endonuclease or a fourth polynucleotide encoding the DNA endonuclease.

29. The system of claim 28, further comprising a guide RNA (gRNA) or a fifth polynucleotide encoding the gRNA, wherein the gRNA comprises a spacer sequence complementary to a target sequence in a target genomic locus.

* * * * *

UNITED STATES PATENT AND TRADEMARK OFFICE
CERTIFICATE OF CORRECTION

Page 1 of 2

PATENT NO. : 11,987,804 B2
APPLICATION NO. : 17/049782
DATED : May 21, 2024
INVENTOR(S) : Andrew M. Scharenberg et al.

It is certified that error appears in the above-identified patent and that said Letters Patent is hereby corrected as shown below:

On the Title Page

Column 2, Line 7, item (56) under Other Publications, delete "siNRA" and insert --siRNA--.

On Page 4, Column 1, Line 4, item (56) under Other Publications, delete "reapamycin-" and insert --rapamycin- --.

In the Specification

In Column 6, Line 14, delete "with" and insert --with 1 nM--.

In Column 13, Line 46, delete "IL2Rγ'" and insert --"IL2Rγ"--.

In Column 15, Line 20, delete "T-cells'" and insert --"T-cells"--.

In Column 19, Line 46, delete "1L7Ra" and insert --IL7Rα--.

In Column 19, Line 52, delete "domain" and insert --IL2Rβ domain--.

In Column 41, Line 64, delete "MET" and insert --NHEJ--.

In Column 41, Line 66, delete "NEED" and insert --NHEJ--.

In Column 46, Line 15, delete "TCM" and insert --$T_{CM}$--.

In Column 47, Line 46, delete "[(15," and insert --([1S,--.

In Column 48, Line 26, delete "21 S,23 S," and insert --21S,23S,--.

In Column 56, Line 22, delete "(2'-0-CH₃)," and insert --(2'-O-CH₃),--.

Signed and Sealed this
Twenty-seventh Day of August, 2024

Katherine Kelly Vidal
*Director of the United States Patent and Trademark Office*

CERTIFICATE OF CORRECTION (continued)
U.S. Pat. No. 11,987,804 B2

In Column 57, Line 18, delete "methylquanine" and insert --methylguanine--.

In Column 62, Line 44, delete "asialyloglycoprotein" and insert --asialoglycoprotein--.

In Column 76, Line 27, delete "'no-treatment'" and insert --''no-treatment''--.

In Column 77, Line 15 (Approx.), delete "spinnoculation" and insert --spinoculation--.

In Column 90, Line 6, delete "MDR" and insert --HDR--.

In Column 90, Line 8 (Approx.), delete "MDR" and insert --HDR--.

In the Claims

In Column 207, Claim 1, Line 3 (Approx.), before "a first polynucleotide" insert --(i)--.

SEQUENCE LISTING

<160> NUMBER OF SEQ ID NOS: 58

<210> SEQ ID NO 1
<211> LENGTH: 90
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: naked FRB wild-type polypeptide

<400> SEQUENCE: 1

Met Glu Met Trp His Glu Gly Leu Glu Glu Ala Ser Arg Leu Tyr Phe
1               5                   10                  15

Gly Glu Arg Asn Val Lys Gly Met Phe Glu Val Leu Glu Pro Leu His
            20                  25                  30

Ala Met Met Glu Arg Gly Pro Gln Thr Leu Lys Glu Thr Ser Phe Asn
        35                  40                  45

Gln Ala Tyr Gly Arg Asp Leu Met Glu Ala Gln Glu Trp Cys Arg Lys
    50                  55                  60

Tyr Met Lys Ser Gly Asn Val Lys Asp Leu Thr Gln Ala Trp Asp Leu
65                  70                  75                  80

Tyr Tyr His Val Phe Arg Arg Ile Ser Lys
            85                  90

<210> SEQ ID NO 2
<211> LENGTH: 90
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: naked FRB mutant polypeptide

<400> SEQUENCE: 2

Met Glu Met Trp His Glu Gly Leu Glu Glu Ala Ser Arg Leu Tyr Phe
1               5                   10                  15

Gly Glu Arg Asn Val Lys Gly Met Phe Glu Val Leu Glu Pro Leu His
                20                  25                  30

Ala Met Met Glu Arg Gly Pro Gln Thr Leu Lys Glu Thr Ser Phe Asn
            35                  40                  45

Gln Ala Tyr Gly Arg Asp Leu Met Glu Ala Gln Glu Trp Cys Arg Lys
        50                  55                  60

Tyr Met Lys Ser Gly Asn Val Lys Asp Leu Leu Gln Ala Trp Asp Leu
65                  70                  75                  80

Tyr Tyr His Val Phe Arg Arg Ile Ser Lys
            85                  90

<210> SEQ ID NO 3
<211> LENGTH: 4187
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: DISC vector DNA

<400> SEQUENCE: 3
gaacagagaa acaggagaat atgggccaaa caggatatct gtggtaagca gttcctgccc      60
cggctcaggg ccaagaacag ttggaacagc agaatatggg ccaaacagga tatctgtggt     120
aagcagttcc tgccccggct cagggccaag aacagatggt ccccagatgc ggtcccgccc     180
tcagcagttt ctagagaacc atcagatgtt tccaggtgc cccaaggacc tgaaatgacc      240
ctgtgcctta tttgaactaa ccaatcagtt cgcttctcgc ttctgttcgc gcgcttctgc     300
tccccgagct ctatataagc agagctcgtt tagtgaaccg tcagatcgct agcaccggtg     360
ccgccaccat gcctctgggc ctgctgtggc tgggcctggc cctgctgggc gccctgcacg     420
cccaggccgg cgtgcaggtg gagacaatct ccccaggcga cggacgcaca ttccctaagc     480
ggggccagac ctgcgttgtg cactatacag gcatgctgga ggatggcaag aagtttgaca     540
gctcccggga tagaaacaag ccattcaagt ttatgctggg caagcaggaa gtgatcagag     600
gctgggagga gggcgtggcc cagatgtctg tgggccagag ggccaagctg accatcagcc     660
cagactacgc ctatggagca acaggccacc caggaatcat cccacctcac gccaccctgg     720
tgttcgatgt ggagctgctg aagctgggcg agggatccaa cacatcaaaa gagaccccct     780 tctgttcgc attggaggcc gtagtcatat ctgttggatc catgggactt attatctccc      840
tgttgtgtgt gtacttctgg ctggaacgga tatgcccag atccccacg ctcaagaatc       900 tggaagatct cgtcacagaa taccatggta atttcagcgc ctggagcgga gtctctaagg     960

```
gtctggccga atccctccaa cccgattatt ctgaacggtt gtgcctcgta tccgaaatac    1020
caccaaaagg cggggctctg ggtgagggcc caggggcgag tccgtgcaat caacacagcc    1080
cgtattgggc ccctccttgt tatacgttga agcccgaaac tggaagcgga gctactaact    1140
tcagcctgct gaagcaggct ggagacgtgg aggagaaccc tggacctatg gcactgcccg    1200
tgaccgccct gctgctgcct ctggccctgc tgctgcacgc agcccggcct atcctgtggc    1260
acgagatgtg gcacgagggc ctggaggagg ccagcaggct gtattttggc gagcgcaacg    1320
tgaagggcat gttcgaggtg ctggagcctc tgcacgccat gatggagaga ggcccacaga    1380
ccctgaagga gacatccttt aaccaggcct atggacggga cctgatggag gcacaggagt    1440
ggtgcagaaa gtacatgaag tctggcaatg tgaaggacct gctgcaggcc tgggatctgt    1500
actatcacgt gtttcggaga atctccaagg gcaaagacac gattccgtgg cttgggcatc    1560
tgctcgttgg gctgagtggt gcgtttggtt tcatcatctt ggtctatctc ttgatcaatt    1620
gcagaaatac aggcccttgg ctgaaaaaag tgctcaagtg taatacccccc gacccaagca    1680
agttcttctc ccagctttct tcagagcatg gaggcgatgt gcagaaatgg ctctcttcac    1740
cttttccctc ctcaagcttc tccccgggag ggctggcgcc cgagatttca cctcttgagg    1800
tacttgaacg agacaaggtt acccaacttc tccttcaaca ggataaggta cccgaacctg    1860
cgagccttag ctccaaccac tctcttacga gctgcttcac caatcaggga tacttctttt    1920
tccaccttcc cgatgcgctg gaaatcgaag cttgtcaagt ttactttacc tatgatccat    1980
atagcgagga agatcccgac gaaggagtcg ccggtgcgcc cacgggttcc tcaccccaac    2040
ctctccagcc tctctcagga gaagatgatg cttattgcac ttttcccagt agagacgatc    2100
tcctcctctt ttctccatct cttttggggg gaccttcccc ccttctacg gcacctggcg    2160
ggtctggtgc tggcgaggag cggatgccgc cgtccctcca ggagcgagta ccacgagatt    2220
gggatcccca gccacttgga ccccccaccc ccggcgtacc tgaccttgtc gattttcaac    2280
ctcccctga attggtgctg cgagaggctg ggaggaagt tccggacgct gggccgaggg    2340
agggcgtgtc ctttccatgg agtaggcctc caggtcaagg cgagtttagg gctctcaacg    2400
cgcggctgcc gttgaataca gacgcttatc tctcactgca ggaactgcaa ggtcaggacc    2460
caacacatct tgtaggatct ggtgctacta atttttctct tttgaagcaa gctggagatg    2520
ttgaagagaa ccccggtccg gagatgtggc atgagggtct ggaagaagcg tctcgactgt    2580
actttggtga gcgcaatgtg aagggcatgt ttgaagtcct cgaaccccttt catgccatga    2640
tggaacgcgg accccagacc ttgaaggaga caagttttaa ccaagcttac ggaagagacc    2700
tgatggaagc ccaggaatgg tgcaggaaat acatgaaaag cgggaatgtg aaggacttgc    2760
tccaagcgtg ggacctgtac tatcatgtct ttaggcgcat tagtaagggc agcggcgcca    2820
ccaacttcag cctgctgaag caggccggcg acgtggagga gaaccccggc cccgtgagca    2880
agggcgagga ggataacatg gccatcatca aggagttcat gcgcttcaag gtgcacatgg    2940
agggctccgt gaacggccac gagttcgaga tcgagggcga gggcgagggc cgcccctacg    3000
agggcaccca gaccgccaag ctgaaggtga ccaagggtgg ccccctgccc ttcgcctggg    3060
acatcctgtc ccctcagttc atgtacggct ccaaggccta cgtgaagcac cccgccgaca    3120
tccccgacta cttgaagctg tccttccccg agggcttcaa gtgggagcgc gtgatgaact    3180
tcgaggacgg cggcgtggtg accgtgaccc aggactcctc tctgcaggac ggcgagttca    3240
tctacaaggt gaagctgcgc ggcaccaact tcccctccga cggccccgta atgcagaaga    3300
agaccatggg ctgggaggcc tcctccgagc ggatgtaccc cgaggacggc gccctgaagg    3360
```

```
gcgagatcaa gcagaggctg aagctgaagg acggcggcca ctacgacgct gaggtcaaga    3420
ccacctacaa ggccaagaag cccgtgcagc tgcccggcgc ctacaacgtc aacatcaagt    3480
tggacatcac ctcccacaac gaggactaca ccatcgtgga acagtacgaa cgcgccgagg    3540
gccgccactc caccggcggc atggacgagc tgtacaagtg aactagtgtc gacaatcaac    3600
ctctggatta caaaatttgt gaaagattga ctggtattct taactatgtt gctccttta    3660 cgctatgtgg atacgctgct ttaatgcctt tgtatcatgc tattgcttcc cgtatggctt    3720 tcatttctc ctccttgtat aaatcctggt tgctgtctct ttatgaggag ttgtggcccg    3780
ttgtcaggca acgtggcgtg gtgtgcactg tgtttgctga cgcaaccccc actggttggg    3840
gcattgccac cacctgtcag ctcctttccg ggactttcgc tttccccctc cctattgcca    3900
cggcggaact catcgccgcc tgccttgccc gctgctggac aggggctcgg ctgttgggca    3960
ctgacaattc cgtggtgttg tcggggaagc tgacgtcctt tccatggctg ctcgcctgtg    4020
ttgccacctg gattctgcgc gggacgtcct tctgctacgt cccttcggcc ctcaatccag    4080
cggaccttcc ttcccgcggc ctgctgccgg ctctgcggcc tcttccgcgt cttcgccttc    4140
gccctcagac gagtcggatc tccctttggg ccgcctcccc gcctgga             4187

<210> SEQ ID NO 4
<211> LENGTH: 393
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: micro-DISC DNA (cytoplasmic tail only; codon
      diverged)

<400> SEQUENCE: 4
ccagcagctc tcggcaaaga cacgattccg tggcttgggc atctgctcgt tgggctgagc      60
ggtgcgtttg gtttcatcat cttggtctat ctcttgatca attgcagaaa tacaggccct     120
tggctgaaaa aagtgctcaa gtgtaatacc cccgacccaa gcaagttctt ctcccagctt     180
tcttcagagc atggaggcga tgtgcagaaa tggctctctt cacctttcc ctcctcaagc      240 ttctccccgg gagggctggc gcccgagatt tcacctcttg aggtacttga acgagacaag     300
gttacccaac ttctccttca acaggataag gtacccgaac ctgcgagcct tagcttgaat     360
acagacgctt atctctcact gcaggaactg caa                                  393

<210> SEQ ID NO 5
<211> LENGTH: 131
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: micro-DISC polypeptide (cytoplasmic tail only)

<400> SEQUENCE: 5

Pro Ala Ala Leu Gly Lys Asp Thr Ile Pro Trp Leu Gly His Leu Leu
1               5                  10                  15

Val Gly Leu Ser Gly Ala Phe Gly Phe Ile Ile Leu Val Tyr Leu Leu
            20                  25                  30

Ile Asn Cys Arg Asn Thr Gly Pro Trp Leu Lys Lys Val Leu Lys Cys
        35                  40                  45
```

```
Asn Thr Pro Asp Pro Ser Lys Phe Phe Ser Gln Leu Ser Ser Glu His
    50                  55                  60

Gly Gly Asp Val Gln Lys Trp Leu Ser Ser Pro Phe Pro Ser Ser Ser
65                  70                  75                  80

Phe Ser Pro Gly Gly Leu Ala Pro Glu Ile Ser Pro Leu Glu Val Leu
                85                  90                  95

Glu Arg Asp Lys Val Thr Gln Leu Leu Leu Gln Gln Asp Lys Val Pro
                100                 105                 110

Glu Pro Ala Ser Leu Ser Leu Asn Thr Asp Ala Tyr Leu Ser Leu Gln
            115                 120                 125

Glu Leu Gln
    130
```

```
<210> SEQ ID NO 6
<211> LENGTH: 108
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: FKBP CISC domain

<400> SEQUENCE: 6
```

```
Gly Val Gln Val Glu Thr Ile Ser Pro Gly Asp Gly Arg Thr Phe Pro
1               5                   10                  15

Lys Arg Gly Gln Thr Cys Val Val His Tyr Thr Gly Met Leu Glu Asp
                20                  25                  30

Gly Lys Lys Phe Asp Ser Ser Arg Asp Arg Asn Lys Pro Phe Lys Phe
            35                  40                  45

Met Leu Gly Lys Gln Glu Val Ile Arg Gly Trp Glu Glu Gly Val Ala
50                  55                  60

Gln Met Ser Val Gly Gln Arg Ala Lys Leu Thr Ile Ser Pro Asp Tyr
65                  70                  75                  80

Ala Tyr Gly Ala Thr Gly His Pro Gly Ile Ile Pro Pro His Ala Thr
                85                  90                  95

Leu Val Phe Asp Val Glu Leu Leu Lys Leu Gly Glu
                100                 105
```

```
<210> SEQ ID NO 7
<211> LENGTH: 245
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Entire micro-DISC polypeptide (FRB-truncated
      IL2Rbeta)

<400> SEQUENCE: 7
```

```
Met Ala Leu Pro Val Thr Ala Leu Leu Leu Pro Leu Ala Leu Leu Leu
1               5                   10                  15

His Ala Ala Arg Pro Ile Leu Trp His Glu Met Trp His Glu Gly Leu
                20                  25                  30

Glu Glu Ala Ser Arg Leu Tyr Phe Gly Glu Arg Asn Val Lys Gly Met
            35                  40                  45

Phe Glu Val Leu Glu Pro Leu His Ala Met Met Glu Arg Gly Pro Gln
50                  55                  60

Thr Leu Lys Glu Thr Ser Phe Asn Gln Ala Tyr Gly Arg Asp Leu Met
```

```
                65                  70                  75                  80
        Glu Ala Gln Glu Trp Cys Arg Lys Tyr Met Lys Ser Gly Asn Val Lys
                        85                  90                  95

Asp Leu Leu Gln Ala Trp Asp Leu Tyr Tyr His Val Phe Arg Arg Ile
                        100                 105                 110

Ser Lys Pro Ala Ala Leu Gly Lys Asp Thr Ile Pro Trp Leu Gly His
                        115                 120                 125

Leu Leu Val Gly Leu Ser Gly Ala Phe Gly Phe Ile Ile Leu Val Tyr
                130                 135                 140

Leu Leu Ile Asn Cys Arg Asn Thr Gly Pro Trp Leu Lys Lys Val Leu
        145                 150                 155                 160

Lys Cys Asn Thr Pro Asp Pro Ser Lys Phe Phe Ser Gln Leu Ser Ser
                        165                 170                 175

Glu His Gly Gly Asp Val Gln Lys Trp Leu Ser Ser Pro Phe Pro Ser
                        180                 185                 190

Ser Ser Phe Ser Pro Gly Gly Leu Ala Pro Glu Ile Ser Pro Leu Glu
                        195                 200                 205

Val Leu Glu Arg Asp Lys Val Thr Gln Leu Leu Leu Gln Gln Asp Lys
                        210                 215                 220

Val Pro Glu Pro Ala Ser Leu Ser Leu Asn Thr Asp Ala Tyr Leu Ser
        225                 230                 235                 240

Leu Gln Glu Leu Gln
                        245

<210> SEQ ID NO 8
<211> LENGTH: 3623
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: micro-DISC vector DNA

<400> SEQUENCE: 8
gaacagagaa acaggagaat atgggccaaa caggatatct gtggtaagca gttcctgccc      60
cggctcaggg ccaagaacag ttggaacagc agaatatggg ccaaacagga tatctgtggt     120
aagcagttcc tgccccggct cagggccaag aacagatggt ccccagatgc ggtcccgccc     180
tcagcagttt ctagagaacc atcagatgtt tccagggtgc cccaaggacc tgaaatgacc     240
ctgtgcctta tttgaactaa ccaatcagtt cgcttctcgc ttctgttcgc gcgcttctgc     300
tccccgagct ctatataagc agagctcgtt tagtgaaccg tcagatcgct agcaccggtg     360
ccgccaccat gcctctgggc ctgctgtggc tgggcctggc cctgctgggc gccctgcacg     420
cccaggccgg cgtgcaggtg gagacaatct ccccaggcga cggacgcaca ttccctaagc     480
ggggccagac ctgcgttgtg cactatacag gcatgctgga ggatggcaag aagtttgaca     540
gctcccggga tagaaacaag ccattcaagt ttatgctggg caagcaggaa gtgatcagag     600
gctgggagga gggcgtggcc cagatgtctg tgggccagag ggccaagctg accatcagcc     660
cagactacgc ctatggagca caggccacc aggaatcat cccacctcac gccaccctgg     720
tgttcgatgt ggagctgctg aagctgggcg agggatccaa cacatcaaaa gagaacccct     780
ttctgttcgc attggaggcc gtagtcatat ctgttggatc catgggactt attatctccc     840
tgttgtgtgt gtacttctgg ctggaacgga catatgccca gatccccacg ctcaagaatc     900
tggaagatct cgtcacagaa taccatggta atttcagcgc ctggagcgga gtctctaagg     960
```

```
gtctggccga atccctccaa cccgattatt ctgaacggtt gtgcctcgta tccgaaatac   1020
caccaaaagg cggggctctg ggtgagggcc caggggcgag tccgtgcaat caacacagcc   1080
cgtattgggc ccctccttgt tatacgttga agcccgaaac tggaagcgga gctactaact   1140
tcagcctgct gaagcaggct ggagacgtgg aggagaaccc tggacctatg gcactgcccg   1200
tgaccgccct gctgctgcct ctggccctgc tgctgcacgc agcccggcct atcctgtggc   1260
acgagatgtg gcacgagggc ctggaggagg ccagcaggct gtattttggc gagcgcaacg   1320
tgaagggcat gttcgaggtg ctggagcctc tgcacgccat gatggagaga ggcccacaga   1380
ccctgaagga gacatccttt aaccaggcct atggacggga cctgatggag gcacaggagt   1440
ggtgcagaaa gtacatgaag tctggcaatg tgaaggacct gctgcaggcc tgggatctgt   1500
actatcacgt gtttcggaga atctccaagg gcaaagacac gattccgtgg cttgggcatc   1560
tgctcgttgg gctgagtggt gcgtttggtt tcatcatctt ggtctatctc ttgatcaatt   1620
gcagaaatac aggcccttgg ctgaaaaaag tgctcaagtg taataccccc gacccaagca   1680
agttcttctc ccagctttct tcagagcatg gaggcgatgt gcagaaatgg ctctcttcac   1740
cttttccctc ctcaagcttc tccccggag ggctggcgcc cgagatttca cctcttgagg   1800
tacttgaacg agacaaggtt acccaacttc tccttcaaca ggataaggta cccgaacctg   1860
cgagccttag cttgaataca gacgcttatc tctcactgca ggaactgcaa ggatctggtg   1920
ctactaattt ttctcttttg aagcaagctg gagatgttga agagaacccc ggtccggaga   1980
tgtggcatga gggtctggaa gaagcgtctc gactgtactt tggtgagcgc aatgtgaagg   2040
gcatgtttga agtcctcgaa ccccttcatg ccatgatgga acgcggaccc cagaccttga   2100
aggagacaag ttttaaccaa gcttacggaa gagacctgat ggaagcccag gaatggtgca   2160
ggaaatacat gaaaagcggg aatgtgaagg acttgctcca agcgtgggac ctgtactatc   2220
atgtctttag gcgcattagt aagggcagcg gcgccaccaa cttcagcctg ctgaagcagg   2280
ccggcgacgt ggaggagaac cccggccccg tgagcaaggg cgaggaggat aacatggcca   2340
tcatcaagga gttcatgcgc ttcaaggtgc acatggaggg ctccgtgaac ggccacgagt   2400
tcgagatcga gggcgagggc gagggccgcc cctacgaggg cacccagacc gccaagctga   2460
aggtgaccaa gggtggcccc ctgcccttcg cctgggacat cctgtcccct cagttcatgt   2520
acggctccaa ggcctacgtg aagcaccccg ccgacatccc cgactacttg aagctgtcct   2580
tccccgaggg cttcaagtgg gagcgcgtga tgaacttcga ggacggcggc gtggtgaccg   2640
tgacccagga ctcctctctg caggacgcg agttcatcta caaggtgaag ctgcgcggca   2700
ccaacttccc ctccgacggc cccgtaatgc agaagaagac catgggctgg gaggcctcct   2760
ccgagcggat gtaccccgag gacggcgccc tgaagggcga gatcaagcag aggctgaagc   2820
tgaaggacgg cggccactac gacgctgagg tcaagaccac ctacaaggcc aagaagcccg   2880
tgcagctgcc cggcgcctac aacgtcaaca tcaagttgga catcacctcc cacaacgagg   2940
actacaccat cgtggaacag tacgaacgcg ccgagggccg ccactccacc ggcggcatgg   3000
acgagctgta caagtgaact agtgtcgaca atcaacctct ggattacaaa atttgtgaaa   3060
gattgactgg tattcttaac tatgttgctc cttttacgct atgtggatac gctgctttaa   3120
tgcctttgta tcatgctatt gcttcccgta tggctttcat tttctcctcc ttgtataaat   3180
cctggttgct gtctctttat gaggagttgt ggcccgttgt caggcaacgt ggcgtggtgt   3240
gcactgtgtt tgctgacgca accccactg gttggggcat tgccaccacc tgtcagctcc   3300
```

-continued

```
ttccgggac tttcgctttc cccctcccta ttgccacggc ggaactcatc gccgcctgcc   3360
ttgcccgctg ctggacaggg gctcggctgt tgggcactga caattccgtg gtgttgtcgg   3420
ggaagctgac gtcctttcca tggctgctcg cctgtgttgc cacctggatt ctgcgcggga   3480
cgtccttctg ctacgtccct tcggccctca atccagcgga ccttccttcc cgcggcctgc   3540
tgccggctct gcggcctctt ccgcgtcttc gccttcgccc tcagacgagt cggatctccc   3600
tttgggccgc ctccccgcct gga                                          3623
```

<210> SEQ ID NO 9
<211> LENGTH: 251
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: IL2Rgamma-CISC polypeptide

<400> SEQUENCE: 9

```
Met Pro Leu Gly Leu Leu Trp Leu Gly Leu Ala Leu Leu Gly Ala Leu
1               5                   10                  15

His Ala Gln Ala Gly Val Gln Val Glu Thr Ile Ser Pro Gly Asp Gly
            20                  25                  30

Arg Thr Phe Pro Lys Arg Gly Gln Thr Cys Val Val His Tyr Thr Gly
        35                  40                  45

Met Leu Glu Asp Gly Lys Lys Phe Asp Ser Ser Arg Asp Arg Asn Lys
    50                  55                  60

Pro Phe Lys Phe Met Leu Gly Lys Gln Glu Val Ile Arg Gly Trp Glu
65                  70                  75                  80

Glu Gly Val Ala Gln Met Ser Val Gly Gln Arg Ala Lys Leu Thr Ile
                85                  90                  95

Ser Pro Asp Tyr Ala Tyr Gly Ala Thr Gly His Pro Gly Ile Ile Pro
            100                 105                 110

Pro His Ala Thr Leu Val Phe Asp Val Glu Leu Leu Lys Leu Gly Glu
        115                 120                 125

Gly Ser Asn Thr Ser Lys Glu Asn Pro Phe Leu Phe Ala Leu Glu Ala
    130                 135                 140

Val Val Ile Ser Val Gly Ser Met Gly Leu Ile Ile Ser Leu Leu Cys
145                 150                 155                 160

Val Tyr Phe Trp Leu Glu Arg Thr Met Pro Arg Ile Pro Thr Leu Lys
                165                 170                 175

Asn Leu Glu Asp Leu Val Thr Glu Tyr His Gly Asn Phe Ser Ala Trp
            180                 185                 190

Ser Gly Val Ser Lys Gly Leu Ala Glu Ser Leu Gln Pro Asp Tyr Ser
        195                 200                 205

Glu Arg Leu Cys Leu Val Ser Glu Ile Pro Pro Lys Gly Gly Ala Leu
    210                 215                 220

Gly Glu Gly Pro Gly Ala Ser Pro Cys Asn Gln His Ser Pro Tyr Trp
225                 230                 235                 240

Ala Pro Pro Cys Tyr Thr Leu Lys Pro Glu Thr
                245                 250
```

<210> SEQ ID NO 10
<211> LENGTH: 352
<212> TYPE: PRT
<213> ORGANISM: Artificial sequence
<220> FEATURE:

<223> OTHER INFORMATION: Synthetic polypeptide
<220> FEATURE:
<221> NAME/KEY: misc_feature
<223> OTHER INFORMATION: IL2Rgamma-CISC polypeptide

<400> SEQUENCE: 10

```
Met Pro Leu Gly Leu Leu Trp Leu Gly Leu Ala Leu Leu Gly Ala Leu
1               5                   10                  15

His Ala Gln Ala Gly Val Gln Val Glu Thr Ile Ser Pro Gly Asp Gly
            20                  25                  30

Arg Thr Phe Pro Lys Arg Gly Gln Thr Cys Val Val His Tyr Thr Gly
        35                  40                  45

Met Leu Glu Asp Gly Lys Lys Phe Asp Ser Ser Arg Asp Arg Asn Lys
    50                  55                  60

Pro Phe Lys Phe Met Leu Gly Lys Gln Glu Val Ile Arg Gly Trp Glu
65                  70                  75                  80

Glu Gly Val Ala Gln Met Ser Val Gly Gln Arg Ala Lys Leu Thr Ile
                85                  90                  95

Ser Pro Asp Tyr Ala Tyr Gly Ala Thr Gly His Pro Gly Ile Ile Pro
            100                 105                 110

Pro His Ala Thr Leu Val Phe Asp Val Glu Leu Leu Lys Leu Glu Gly
        115                 120                 125

Gly Gly Ser Gln Asn Leu Val Ile Pro Trp Ala Pro Glu Asn Leu Thr
    130                 135                 140

Leu His Lys Leu Ser Glu Ser Gln Leu Glu Leu Asn Trp Asn Asn Arg
145                 150                 155                 160

Phe Leu Asn His Cys Leu Glu His Leu Val Gln Tyr Arg Thr Asp Trp
                165                 170                 175

Asp His Ser Trp Thr Glu Gln Ser Val Asp Tyr Arg His Lys Phe Ser
            180                 185                 190

Leu Pro Ser Val Asp Gly Gln Lys Arg Tyr Thr Phe Arg Val Arg Ser
        195                 200                 205

Arg Phe Asn Pro Leu Cys Gly Ser Ala Gln His Trp Ser Glu Trp Ser
    210                 215                 220

His Pro Ile His Trp Gly Ser Asn Thr Ser Lys Glu Asn Pro Phe Leu
225                 230                 235                 240

Phe Ala Leu Glu Ala Val Val Ile Ser Val Gly Ser Met Gly Leu Ile
                245                 250                 255

Ile Ser Leu Leu Cys Val Tyr Phe Trp Leu Glu Arg Thr Met Pro Arg
            260                 265                 270

Ile Pro Thr Leu Lys Asn Leu Glu Asp Leu Val Thr Glu Tyr His Gly
        275                 280                 285

Asn Phe Ser Ala Trp Ser Gly Val Ser Lys Gly Leu Ala Glu Ser Leu
    290                 295                 300

Gln Pro Asp Tyr Ser Glu Arg Leu Cys Leu Val Ser Glu Ile Pro Pro
305                 310                 315                 320

Lys Gly Gly Ala Leu Gly Glu Gly Pro Gly Ala Ser Pro Cys Asn Gln
                325                 330                 335

His Ser Pro Tyr Trp Ala Pro Pro Cys Tyr Thr Leu Lys Pro Glu Thr
            340                 345                 350
```

<210> SEQ ID NO 11
<211> LENGTH: 349
<212> TYPE: PRT
<213> ORGANISM: Artificial sequence
<220> FEATURE:

<223> OTHER INFORMATION: Synthetic polypeptide
<220> FEATURE:
<221> NAME/KEY: misc_feature
<223> OTHER INFORMATION: IL2Rgamma-CISC polypeptide

<400> SEQUENCE: 11

```
Met Pro Leu Gly Leu Leu Trp Leu Gly Leu Ala Leu Leu Gly Ala Leu
1               5                   10                  15

His Ala Gln Ala Gly Val Gln Val Glu Thr Ile Ser Pro Gly Asp Gly
            20                  25                  30

Arg Thr Phe Pro Lys Arg Gly Gln Thr Cys Val Val His Tyr Thr Gly
        35                  40                  45

Met Leu Glu Asp Gly Lys Lys Phe Asp Ser Ser Arg Asp Arg Asn Lys
    50                  55                  60

Pro Phe Lys Phe Met Leu Gly Lys Gln Glu Val Ile Arg Gly Trp Glu
65                  70                  75                  80

Glu Gly Val Ala Gln Met Ser Val Gly Gln Arg Ala Lys Leu Thr Ile
                85                  90                  95

Ser Pro Asp Tyr Ala Tyr Gly Ala Thr Gly His Pro Gly Ile Ile Pro
            100                 105                 110

Pro His Ala Thr Leu Val Phe Asp Val Glu Leu Leu Lys Leu Glu Gly
        115                 120                 125

Gln Asn Leu Val Ile Pro Trp Ala Pro Glu Asn Leu Thr Leu His Lys
    130                 135                 140

Leu Ser Glu Ser Gln Leu Glu Leu Asn Trp Asn Asn Arg Phe Leu Asn
145                 150                 155                 160

His Cys Leu Glu His Leu Val Gln Tyr Arg Thr Asp Trp Asp His Ser
                165                 170                 175

Trp Thr Glu Gln Ser Val Asp Tyr Arg His Lys Phe Ser Leu Pro Ser
            180                 185                 190

Val Asp Gly Gln Lys Arg Tyr Thr Phe Arg Val Arg Ser Arg Phe Asn
        195                 200                 205

Pro Leu Cys Gly Ser Ala Gln His Trp Ser Glu Trp Ser His Pro Ile
210                 215                 220

His Trp Gly Ser Asn Thr Ser Lys Glu Asn Pro Phe Leu Phe Ala Leu
225                 230                 235                 240

Glu Ala Val Val Ile Ser Val Gly Ser Met Gly Leu Ile Ile Ser Leu
                245                 250                 255

Leu Cys Val Tyr Phe Trp Leu Glu Arg Thr Met Pro Arg Ile Pro Thr
            260                 265                 270

Leu Lys Asn Leu Glu Asp Leu Val Thr Glu Tyr His Gly Asn Phe Ser
        275                 280                 285

Ala Trp Ser Gly Val Ser Lys Gly Leu Ala Glu Ser Leu Gln Pro Asp
    290                 295                 300

Tyr Ser Glu Arg Leu Cys Leu Val Ser Glu Ile Pro Pro Lys Gly Gly
305                 310                 315                 320

Ala Leu Gly Glu Gly Pro Gly Ala Ser Pro Cys Asn Gln His Ser Pro
                325                 330                 335

Tyr Trp Ala Pro Pro Cys Tyr Thr Leu Lys Pro Glu Thr
            340                 345
```

<210> SEQ ID NO 12
<211> LENGTH: 251
<212> TYPE: PRT
<213> ORGANISM: Artificial sequence
<220> FEATURE:

<223> OTHER INFORMATION: Synthetic polypeptide
<220> FEATURE:
<221> NAME/KEY: misc_feature
<223> OTHER INFORMATION: IL2Rgamma-CISC polypeptide

<400> SEQUENCE: 12

Met Pro Leu Gly Leu Leu Trp Leu Gly Leu Ala Leu Leu Gly Ala Leu
1               5                   10                  15

His Ala Gln Ala Gly Val Gln Val Glu Thr Ile Ser Pro Gly Asp Gly
            20                  25                  30

Arg Thr Phe Pro Lys Arg Gly Gln Thr Cys Val Val His Tyr Thr Gly
        35                  40                  45

Met Leu Glu Asp Gly Lys Lys Phe Asp Ser Ser Arg Asp Arg Asn Lys
    50                  55                  60

Pro Phe Lys Phe Met Leu Gly Lys Gln Glu Val Ile Arg Gly Trp Glu
65                  70                  75                  80

Glu Gly Val Ala Gln Met Ser Val Gly Gln Arg Ala Lys Leu Thr Ile
                85                  90                  95

Ser Pro Asp Tyr Ala Tyr Gly Ala Thr Gly His Pro Gly Ile Ile Pro
            100                 105                 110

Pro His Ala Thr Leu Val Phe Asp Val Glu Leu Leu Lys Leu Glu Gly
        115                 120                 125

Gly Ser Asn Thr Ser Lys Glu Asn Pro Phe Leu Phe Ala Leu Glu Ala
    130                 135                 140

Val Val Ile Ser Val Gly Ser Met Gly Leu Ile Ile Ser Leu Leu Cys
145                 150                 155                 160

Val Tyr Phe Trp Leu Glu Arg Thr Met Pro Arg Ile Pro Thr Leu Lys
                165                 170                 175

Asn Leu Glu Asp Leu Val Thr Glu Tyr His Gly Asn Phe Ser Ala Trp
            180                 185                 190

Ser Gly Val Ser Lys Gly Leu Ala Glu Ser Leu Gln Pro Asp Tyr Ser
        195                 200                 205

Glu Arg Leu Cys Leu Val Ser Glu Ile Pro Pro Lys Gly Gly Ala Leu
    210                 215                 220

Gly Glu Gly Pro Gly Ala Ser Pro Cys Asn Gln His Ser Pro Tyr Trp
225                 230                 235                 240

Ala Pro Pro Cys Tyr Thr Leu Lys Pro Glu Thr
                245                 250

<210> SEQ ID NO 13
<211> LENGTH: 429
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: IL2Rbeta-CISC polypeptide

<400> SEQUENCE: 13

Met Ala Leu Pro Val Thr Ala Leu Leu Leu Pro Leu Ala Leu Leu Leu
1               5                   10                  15

His Ala Ala Arg Pro Ile Leu Trp His Glu Met Trp His Glu Gly Leu
            20                  25                  30

Glu Glu Ala Ser Arg Leu Tyr Phe Gly Glu Arg Asn Val Lys Gly Met
        35                  40                  45

Phe Glu Val Leu Glu Pro Leu His Ala Met Met Glu Arg Gly Pro Gln
    50                  55                  60

Thr Leu Lys Glu Thr Ser Phe Asn Gln Ala Tyr Gly Arg Asp Leu Met
 65                  70                  75                  80

Glu Ala Gln Glu Trp Cys Arg Lys Tyr Met Lys Ser Gly Asn Val Lys
                 85                  90                  95

Asp Leu Leu Gln Ala Trp Asp Leu Tyr Tyr His Val Phe Arg Arg Ile
            100                 105                 110

Ser Lys Gly Lys Asp Thr Ile Pro Trp Leu Gly His Leu Leu Val Gly
        115                 120                 125

Leu Ser Gly Ala Phe Gly Phe Ile Ile Leu Val Tyr Leu Leu Ile Asn
130                 135                 140

Cys Arg Asn Thr Gly Pro Trp Leu Lys Lys Val Leu Lys Cys Asn Thr
145                 150                 155                 160

Pro Asp Pro Ser Lys Phe Phe Ser Gln Leu Ser Ser Glu His Gly Gly
                165                 170                 175

Asp Val Gln Lys Trp Leu Ser Ser Pro Phe Pro Ser Ser Ser Phe Ser
            180                 185                 190

Pro Gly Gly Leu Ala Pro Glu Ile Ser Pro Leu Glu Val Leu Glu Arg
        195                 200                 205

Asp Lys Val Thr Gln Leu Leu Leu Gln Gln Asp Lys Val Pro Glu Pro
210                 215                 220

Ala Ser Leu Ser Ser Asn His Ser Leu Thr Ser Cys Phe Thr Asn Gln
225                 230                 235                 240

Gly Tyr Phe Phe Phe His Leu Pro Asp Ala Leu Glu Ile Glu Ala Cys
                245                 250                 255

Gln Val Tyr Phe Thr Tyr Asp Pro Tyr Ser Glu Glu Asp Pro Asp Glu
            260                 265                 270

Gly Val Ala Gly Ala Pro Thr Gly Ser Ser Pro Gln Pro Leu Gln Pro
        275                 280                 285

Leu Ser Gly Glu Asp Asp Ala Tyr Cys Thr Phe Pro Ser Arg Asp Asp
290                 295                 300

Leu Leu Leu Phe Ser Pro Ser Leu Leu Gly Gly Pro Ser Pro Pro Ser
305                 310                 315                 320

Thr Ala Pro Gly Gly Ser Gly Ala Gly Glu Arg Met Pro Pro Ser
                325                 330                 335

Leu Gln Glu Arg Val Pro Arg Asp Trp Asp Pro Gln Pro Leu Gly Pro
            340                 345                 350

Pro Thr Pro Gly Val Pro Asp Leu Val Asp Phe Gln Pro Pro Pro Glu
        355                 360                 365

Leu Val Leu Arg Glu Ala Gly Glu Glu Val Pro Asp Ala Gly Pro Arg
370                 375                 380

Glu Gly Val Ser Phe Pro Trp Ser Arg Pro Pro Gly Gln Gly Glu Phe
385                 390                 395                 400

Arg Ala Leu Asn Ala Arg Leu Pro Leu Asn Thr Asp Ala Tyr Leu Ser
                405                 410                 415

Leu Gln Glu Leu Gln Gly Gln Asp Pro Thr His Leu Val
            420                 425

<210> SEQ ID NO 14
<211> LENGTH: 543
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: IL2Rbeta-CISC polypeptide

<400> SEQUENCE: 14

```
Met Ala Leu Pro Val Thr Ala Leu Leu Leu Pro Leu Ala Leu Leu Leu
1               5                   10                  15

His Ala Ala Arg Pro Ile Leu Trp His Glu Met Trp His Glu Gly Leu
            20                  25                  30

Glu Glu Ala Ser Arg Leu Tyr Phe Gly Glu Arg Asn Val Lys Gly Met
        35                  40                  45

Phe Glu Val Leu Glu Pro Leu His Ala Met Met Glu Arg Gly Pro Gln
    50                  55                  60

Thr Leu Lys Glu Thr Ser Phe Asn Gln Ala Tyr Gly Arg Asp Leu Met
65                  70                  75                  80

Glu Ala Gln Glu Trp Cys Arg Lys Tyr Met Lys Ser Gly Asn Val Lys
                85                  90                  95

Asp Leu Leu Gln Ala Trp Asp Leu Tyr Tyr His Val Phe Arg Arg Ile
            100                 105                 110

Ser Lys Gly Gly Ser Lys Pro Phe Glu Asn Leu Arg Leu Met Ala Pro
        115                 120                 125

Ile Ser Leu Gln Val Val His Val Glu Thr His Arg Cys Asn Ile Ser
    130                 135                 140

Trp Glu Ile Ser Gln Ala Ser His Tyr Phe Glu Arg His Leu Glu Phe
145                 150                 155                 160

Glu Ala Arg Thr Leu Ser Pro Gly His Thr Trp Glu Ala Pro Leu
                165                 170                 175

Leu Thr Leu Lys Gln Lys Gln Glu Trp Ile Cys Leu Glu Thr Leu Thr
            180                 185                 190

Pro Asp Thr Gln Tyr Glu Phe Gln Val Arg Val Lys Pro Leu Gln Gly
        195                 200                 205

Glu Phe Thr Thr Trp Ser Pro Trp Ser Gln Pro Leu Ala Phe Arg Thr
    210                 215                 220

Lys Pro Ala Ala Leu Gly Lys Asp Thr Ile Pro Trp Leu Gly His Leu
225                 230                 235                 240

Leu Val Gly Leu Ser Gly Ala Phe Gly Phe Ile Ile Leu Val Tyr Leu
                245                 250                 255

Leu Ile Asn Cys Arg Asn Thr Gly Pro Trp Leu Lys Lys Val Leu Lys
            260                 265                 270

Cys Asn Thr Pro Asp Pro Ser Lys Phe Phe Gln Leu Ser Ser Glu His
        275                 280                 285

Gly Gly Asp Val Gln Lys Trp Leu Ser Ser Pro Phe Pro Ser Ser Ser
    290                 295                 300

Phe Ser Pro Gly Gly Leu Ala Pro Glu Ile Ser Pro Leu Glu Val Leu
305                 310                 315                 320

Glu Arg Asp Lys Val Thr Gln Leu Leu Leu Gln Gln Asp Lys Val Pro
                325                 330                 335

Glu Pro Ala Ser Leu Ser Ser Asn His Ser Leu Thr Ser Cys Phe Thr
            340                 345                 350

Asn Gln Gly Tyr Phe Phe Phe His Leu Pro Asp Ala Leu Glu Ile Glu
        355                 360                 365

Ala Cys Gln Val Tyr Phe Thr Tyr Asp Pro Tyr Ser Glu Glu Asp Pro
    370                 375                 380

Asp Glu Gly Val Ala Gly Ala Pro Thr Gly Ser Ser Pro Gln Pro Leu
385                 390                 395                 400
```

```
Gln Pro Leu Ser Gly Glu Asp Ala Tyr Cys Thr Phe Pro Ser Arg
            405                 410                 415

Asp Asp Leu Leu Leu Phe Ser Pro Ser Leu Leu Gly Pro Ser Pro
            420                 425                 430

Pro Ser Thr Ala Pro Gly Gly Ser Gly Ala Gly Glu Glu Arg Met Pro
            435                 440                 445

Pro Ser Leu Gln Glu Arg Val Pro Arg Asp Trp Asp Pro Gln Pro Leu
450                 455                 460

Gly Pro Pro Thr Pro Gly Val Pro Asp Leu Val Asp Phe Gln Pro Pro
465                 470                 475                 480

Pro Glu Leu Val Leu Arg Glu Ala Gly Glu Glu Val Pro Asp Ala Gly
            485                 490                 495

Pro Arg Glu Gly Val Ser Phe Pro Trp Ser Arg Pro Pro Gly Gln Gly
            500                 505                 510

Glu Phe Arg Ala Leu Asn Ala Arg Leu Pro Leu Asn Thr Asp Ala Tyr
            515                 520                 525

Leu Ser Leu Gln Glu Leu Gln Gly Gln Asp Pro Thr His Leu Val
            530                 535                 540

<210> SEQ ID NO 15
<211> LENGTH: 541
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: IL2Rbeta-CISC polypeptide

<400> SEQUENCE: 15

Met Ala Leu Pro Val Thr Ala Leu Leu Leu Pro Leu Ala Leu Leu Leu
1               5                   10                  15

His Ala Ala Arg Pro Ile Leu Trp His Glu Met Trp His Glu Gly Leu
            20                  25                  30

Glu Glu Ala Ser Arg Leu Tyr Phe Gly Glu Arg Asn Val Lys Gly Met
        35                  40                  45

Phe Glu Val Leu Glu Pro Leu His Ala Met Met Glu Arg Gly Pro Gln
    50                  55                  60

Thr Leu Lys Glu Thr Ser Phe Asn Gln Ala Tyr Gly Arg Asp Leu Met
65                  70                  75                  80

Glu Ala Gln Glu Trp Cys Arg Lys Tyr Met Lys Ser Gly Asn Val Lys
                85                  90                  95

Asp Leu Leu Gln Ala Trp Asp Leu Tyr Tyr His Val Phe Arg Arg Ile
            100                 105                 110

Ser Lys Lys Pro Phe Glu Asn Leu Arg Leu Met Ala Pro Ile Ser Leu
        115                 120                 125

Gln Val Val His Val Glu Thr His Arg Cys Asn Ile Ser Trp Glu Ile
    130                 135                 140

Ser Gln Ala Ser His Tyr Phe Glu Arg His Leu Glu Phe Glu Ala Arg
145                 150                 155                 160

Thr Leu Ser Pro Gly His Thr Trp Glu Glu Ala Pro Leu Leu Thr Leu
                165                 170                 175

Lys Gln Lys Gln Glu Trp Ile Cys Leu Glu Thr Leu Thr Pro Asp Thr
            180                 185                 190

Gln Tyr Glu Phe Gln Val Arg Val Lys Pro Leu Gln Gly Glu Phe Thr
        195                 200                 205
```

```
Thr Trp Ser Pro Trp Ser Gln Pro Leu Ala Phe Arg Thr Lys Pro Ala
    210                 215                 220

Ala Leu Gly Lys Asp Thr Ile Pro Trp Leu Gly His Leu Leu Val Gly
225                 230                 235                 240

Leu Ser Gly Ala Phe Gly Phe Ile Ile Leu Val Tyr Leu Leu Ile Asn
                245                 250                 255

Cys Arg Asn Thr Gly Pro Trp Leu Lys Lys Val Leu Lys Cys Asn Thr
                260                 265                 270

Pro Asp Pro Ser Lys Phe Phe Ser Gln Leu Ser Ser Glu His Gly Gly
            275                 280                 285

Asp Val Gln Lys Trp Leu Ser Ser Pro Phe Pro Ser Ser Ser Phe Ser
290                 295                 300

Pro Gly Gly Leu Ala Pro Glu Ile Ser Pro Leu Glu Val Leu Glu Arg
305                 310                 315                 320

Asp Lys Val Thr Gln Leu Leu Leu Gln Gln Asp Lys Val Pro Glu Pro
                325                 330                 335

Ala Ser Leu Ser Ser Asn His Ser Leu Thr Ser Cys Phe Thr Asn Gln
                340                 345                 350

Gly Tyr Phe Phe Phe His Leu Pro Asp Ala Leu Glu Ile Glu Ala Cys
            355                 360                 365

Gln Val Tyr Phe Thr Tyr Asp Pro Tyr Ser Glu Glu Asp Pro Asp Glu
370                 375                 380

Gly Val Ala Gly Ala Pro Thr Gly Ser Ser Pro Gln Pro Leu Gln Pro
385                 390                 395                 400

Leu Ser Gly Glu Asp Asp Ala Tyr Cys Thr Phe Pro Ser Arg Asp Asp
                405                 410                 415

Leu Leu Leu Phe Ser Pro Ser Leu Leu Gly Gly Pro Ser Pro Pro Ser
                420                 425                 430

Thr Ala Pro Gly Gly Ser Gly Ala Gly Glu Glu Arg Met Pro Pro Ser
            435                 440                 445

Leu Gln Glu Arg Val Pro Arg Asp Trp Asp Pro Gln Pro Leu Gly Pro
450                 455                 460

Pro Thr Pro Gly Val Pro Asp Leu Val Asp Phe Gln Pro Pro Pro Glu
465                 470                 475                 480

Leu Val Leu Arg Glu Ala Gly Glu Glu Val Pro Asp Ala Gly Pro Arg
                485                 490                 495

Glu Gly Val Ser Phe Pro Trp Ser Arg Pro Pro Gly Gln Gly Glu Phe
            500                 505                 510

Arg Ala Leu Asn Ala Arg Leu Pro Leu Asn Thr Asp Ala Tyr Leu Ser
            515                 520                 525

Leu Gln Glu Leu Gln Gly Gln Asp Pro Thr His Leu Val
530                 535                 540

<210> SEQ ID NO 16
<211> LENGTH: 379
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: IL7Ralpha-CISC polypeptide

<400> SEQUENCE: 16

Met Ala Leu Pro Val Thr Ala Leu Leu Leu Pro Leu Ala Leu Leu Leu
1               5                   10                  15
```

```
His Ala Ala Arg Pro Ile Leu Trp His Glu Met Trp His Glu Gly Leu
            20                  25                  30

Glu Glu Ala Ser Arg Leu Tyr Phe Gly Glu Arg Asn Val Lys Gly Met
        35                  40                  45

Phe Glu Val Leu Glu Pro Leu His Ala Met Met Glu Arg Gly Pro Gln
 50                  55                  60

Thr Leu Lys Glu Thr Ser Trp Leu Gly His Leu Leu Val Gly Leu Ser
 65                  70                  75                  80

Gly Ala Phe Gly Phe Ile Ile Leu Val Tyr Leu Leu Ile Asn Cys Arg
                85                  90                  95

Asn Thr Gly Pro Trp Leu Lys Lys Val Leu Lys Cys Asn Thr Pro Asp
            100                 105                 110

Pro Ser Lys Phe Phe Ser Gln Leu Ser Ser Glu His Gly Gly Asp Val
            115                 120                 125

Gln Lys Trp Leu Ser Ser Pro Phe Pro Ser Ser Ser Phe Ser Pro Gly
    130                 135                 140

Gly Leu Ala Pro Glu Ile Ser Pro Leu Glu Val Leu Glu Arg Asp Lys
145                 150                 155                 160

Val Thr Gln Leu Leu Leu Gln Gln Asp Lys Val Pro Glu Pro Ala Ser
                165                 170                 175

Leu Ser Ser Asn His Ser Leu Thr Ser Cys Phe Thr Asn Gln Gly Tyr
            180                 185                 190

Phe Phe Phe His Leu Pro Asp Ala Leu Glu Ile Glu Ala Cys Gln Val
            195                 200                 205

Tyr Phe Thr Tyr Asp Pro Tyr Ser Glu Glu Asp Pro Asp Glu Gly Val
    210                 215                 220

Ala Gly Ala Pro Thr Gly Ser Ser Pro Gln Pro Leu Gln Pro Leu Ser
225                 230                 235                 240

Gly Glu Asp Asp Ala Tyr Cys Thr Phe Pro Ser Arg Asp Asp Leu Leu
                245                 250                 255

Leu Phe Ser Pro Ser Leu Leu Gly Gly Pro Ser Pro Pro Ser Thr Ala
            260                 265                 270

Pro Gly Gly Ser Gly Ala Gly Glu Glu Arg Met Pro Pro Ser Leu Gln
            275                 280                 285

Glu Arg Val Pro Arg Asp Trp Asp Pro Gln Pro Leu Gly Pro Pro Thr
290                 295                 300

Pro Gly Val Pro Asp Leu Val Asp Phe Gln Pro Pro Pro Glu Leu Val
305                 310                 315                 320

Leu Arg Glu Ala Gly Glu Glu Val Pro Asp Ala Gly Pro Arg Glu Gly
                325                 330                 335

Val Ser Phe Pro Trp Ser Arg Pro Pro Gly Gln Gly Glu Phe Arg Ala
            340                 345                 350

Leu Asn Ala Arg Leu Pro Leu Asn Thr Asp Ala Tyr Leu Ser Leu Gln
            355                 360                 365

Glu Leu Gln Gly Gln Asp Pro Thr His Leu Val
    370                 375

<210> SEQ ID NO 17
<211> LENGTH: 345
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: IL7Ralpha-CISC polypeptide
```

<400> SEQUENCE: 17

```
Met Ala Leu Pro Val Thr Ala Leu Leu Leu Pro Leu Ala Leu Leu Leu
1               5                   10                  15

His Ala Ala Arg Pro Ile Leu Trp His Glu Met Trp His Glu Gly Leu
            20                  25                  30

Glu Glu Ala Ser Arg Leu Tyr Phe Gly Glu Arg Asn Val Lys Gly Met
        35                  40                  45

Phe Glu Val Leu Glu Pro Leu His Ala Met Met Glu Arg Gly Pro Gln
50                  55                  60

Thr Leu Lys Glu Thr Ser Phe Asn Gln Ala Tyr Gly Arg Asp Leu Met
65                  70                  75                  80

Glu Ala Gln Glu Trp Cys Arg Lys Tyr Met Lys Ser Gly Asn Val Lys
                85                  90                  95

Asp Leu Leu Gln Ala Trp Asp Leu Tyr Tyr His Val Phe Arg Arg Ile
            100                 105                 110

Ser Lys Gly Glu Ile Asn Asn Ser Ser Gly Glu Met Asp Pro Ile Leu
        115                 120                 125

Leu Thr Ile Ser Ile Leu Ser Phe Phe Ser Val Ala Leu Leu Val Ile
130                 135                 140

Leu Ala Cys Val Leu Trp Lys Lys Arg Ile Lys Pro Ile Val Trp Pro
145                 150                 155                 160

Ser Leu Pro Asp His Lys Lys Thr Leu Glu His Leu Cys Lys Lys Pro
            165                 170                 175

Arg Lys Asn Leu Asn Val Ser Phe Asn Pro Glu Ser Phe Leu Asp Cys
        180                 185                 190

Gln Ile His Arg Val Asp Asp Ile Gln Ala Arg Asp Glu Val Glu Gly
    195                 200                 205

Phe Leu Gln Asp Thr Phe Pro Gln Gln Leu Glu Glu Ser Glu Lys Gln
210                 215                 220

Arg Leu Gly Gly Asp Val Gln Ser Pro Asn Cys Pro Ser Glu Asp Val
225                 230                 235                 240

Val Ile Thr Pro Glu Ser Phe Gly Arg Asp Ser Ser Leu Thr Cys Leu
            245                 250                 255

Ala Gly Asn Val Ser Ala Cys Asp Ala Pro Ile Leu Ser Ser Ser Arg
        260                 265                 270

Ser Leu Asp Cys Arg Glu Ser Gly Lys Asn Gly Pro His Val Tyr Gln
    275                 280                 285

Asp Leu Leu Leu Ser Leu Gly Thr Thr Asn Ser Thr Leu Pro Pro Pro
290                 295                 300

Phe Ser Leu Gln Ser Gly Ile Leu Thr Leu Asn Pro Val Ala Gln Gly
305                 310                 315                 320

Gln Pro Ile Leu Thr Ser Leu Gly Ser Asn Gln Glu Glu Ala Tyr Val
            325                 330                 335

Thr Met Ser Ser Phe Tyr Gln Asn Gln
        340                 345
```

<210> SEQ ID NO 18
<211> LENGTH: 4
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Linker polypeptide -continued

```
<400> SEQUENCE: 18

Gly Gly Gly Ser
1

<210> SEQ ID NO 19
<211> LENGTH: 7
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Linker polypeptide

<400> SEQUENCE: 19

Gly Gly Gly Ser Gly Gly Gly
1               5

<210> SEQ ID NO 20
<211> LENGTH: 3
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Linker polypeptide

<400> SEQUENCE: 20

Gly Gly Gly
1

<210> SEQ ID NO 21
<211> LENGTH: 3
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Linker polypeptide

<400> SEQUENCE: 21

Gly Gly Ser
1

<210> SEQ ID NO 22
<211> LENGTH: 4
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Linker polypeptide

<400> SEQUENCE: 22

Gly Gly Ser Pro
1

<210> SEQ ID NO 23
<211> LENGTH: 251
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
```

<223> OTHER INFORMATION: IL2Rgamma-CISC polypeptide

<400> SEQUENCE: 23

Met Pro Leu Gly Leu Leu Trp Leu Gly Leu Ala Leu Leu Gly Ala Leu
1               5                   10                  15

His Ala Gln Ala Gly Val Gln Val Glu Thr Ile Ser Pro Gly Asp Gly
            20                  25                  30

Arg Thr Phe Pro Lys Arg Gly Gln Thr Cys Val Val His Tyr Thr Gly
        35                  40                  45

Met Leu Glu Asp Gly Lys Lys Val Asp Ser Ser Arg Asp Arg Asn Lys
    50                  55                  60

Pro Phe Lys Phe Met Leu Gly Lys Gln Glu Val Ile Arg Gly Trp Glu
65                  70                  75                  80

Glu Gly Val Ala Gln Met Ser Val Gly Gln Arg Ala Lys Leu Thr Ile
                85                  90                  95

Ser Pro Asp Tyr Ala Tyr Gly Ala Thr Gly His Pro Gly Ile Ile Pro
            100                 105                 110

Pro His Ala Thr Leu Val Phe Asp Val Glu Leu Leu Lys Leu Glu Gly
        115                 120                 125

Gly Ser Asn Thr Ser Lys Glu Asn Pro Phe Leu Phe Ala Leu Glu Ala
    130                 135                 140

Val Val Ile Ser Val Gly Ser Met Gly Leu Ile Ile Ser Leu Leu Cys
145                 150                 155                 160

Val Tyr Phe Trp Leu Glu Arg Thr Met Pro Arg Ile Pro Thr Leu Lys
                165                 170                 175

Asn Leu Glu Asp Leu Val Thr Glu Tyr His Gly Asn Phe Ser Ala Trp
            180                 185                 190

Ser Gly Val Ser Lys Gly Leu Ala Glu Ser Leu Gln Pro Asp Tyr Ser
        195                 200                 205

Glu Arg Leu Cys Leu Val Ser Glu Ile Pro Pro Lys Gly Gly Ala Leu
    210                 215                 220

Gly Glu Gly Pro Gly Ala Ser Pro Cys Asn Gln His Ser Pro Tyr Trp
225                 230                 235                 240

Ala Pro Pro Cys Tyr Thr Leu Lys Pro Glu Thr
                245                 250

<210> SEQ ID NO 24
<211> LENGTH: 443
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: IL2Rbeta-CISC polypeptide

<400> SEQUENCE: 24

Met Pro Leu Gly Leu Leu Trp Leu Gly Leu Ala Leu Leu Gly Ala Leu
1               5                   10                  15

His Ala Gln Ala Gly Val Gln Val Glu Thr Ile Ser Pro Gly Asp Gly
            20                  25                  30

Arg Thr Phe Pro Lys Arg Gly Gln Thr Cys Val Val His Tyr Thr Gly
        35                  40                  45

Met Leu Glu Asp Gly Lys Lys Val Asp Ser Ser Arg Asp Arg Asn Lys
    50                  55                  60

Pro Phe Lys Phe Met Leu Gly Lys Gln Glu Val Ile Arg Gly Trp Glu
65                  70                  75                  80

```
Glu Gly Val Ala Gln Met Ser Val Gly Gln Arg Ala Lys Leu Thr Ile
                85                  90                  95

Ser Pro Asp Tyr Ala Tyr Gly Ala Thr Gly His Pro Gly Ile Ile Pro
            100                 105                 110

Pro His Ala Thr Leu Val Phe Asp Val Glu Leu Leu Lys Leu Glu Gly
        115                 120                 125

Gly Lys Asp Thr Ile Pro Trp Leu Gly His Leu Leu Val Gly Leu Ser
    130                 135                 140

Gly Ala Phe Gly Phe Ile Ile Leu Val Tyr Leu Leu Ile Asn Cys Arg
145                 150                 155                 160

Asn Thr Gly Pro Trp Leu Lys Lys Val Leu Lys Cys Asn Thr Pro Asp
                165                 170                 175

Pro Ser Lys Phe Phe Ser Gln Leu Ser Ser Glu His Gly Gly Asp Val
            180                 185                 190

Gln Lys Trp Leu Ser Ser Pro Phe Pro Ser Ser Ser Phe Ser Pro Gly
        195                 200                 205

Gly Leu Ala Pro Glu Ile Ser Pro Leu Glu Val Leu Glu Arg Asp Lys
    210                 215                 220

Val Thr Gln Leu Leu Leu Gln Gln Asp Lys Val Pro Glu Pro Ala Ser
225                 230                 235                 240

Leu Ser Ser Asn His Ser Leu Thr Ser Cys Phe Thr Asn Gln Gly Tyr
                245                 250                 255

Phe Phe Phe His Leu Pro Asp Ala Leu Glu Ile Glu Ala Cys Gln Val
            260                 265                 270

Tyr Phe Thr Tyr Asp Pro Tyr Ser Glu Glu Asp Pro Asp Glu Gly Val
        275                 280                 285

Ala Gly Ala Pro Thr Gly Ser Ser Pro Gln Pro Leu Gln Pro Leu Ser
    290                 295                 300

Gly Glu Asp Asp Ala Tyr Cys Thr Phe Pro Ser Arg Asp Asp Leu Leu
305                 310                 315                 320

Leu Phe Ser Pro Ser Leu Leu Gly Gly Pro Ser Pro Ser Thr Ala
                325                 330                 335

Pro Gly Gly Ser Gly Ala Gly Glu Glu Arg Met Pro Pro Ser Leu Gln
            340                 345                 350

Glu Arg Val Pro Arg Asp Trp Asp Pro Gln Pro Leu Gly Pro Pro Thr
        355                 360                 365

Pro Gly Val Pro Asp Leu Val Asp Phe Gln Pro Pro Pro Glu Leu Val
    370                 375                 380

Leu Arg Glu Ala Gly Glu Val Pro Asp Ala Gly Pro Arg Glu Gly
385                 390                 395                 400

Val Ser Phe Pro Trp Ser Arg Pro Pro Gly Gln Gly Glu Phe Arg Ala
                405                 410                 415

Leu Asn Ala Arg Leu Pro Leu Asn Thr Asp Ala Tyr Leu Ser Leu Gln
            420                 425                 430

Glu Leu Gln Gly Gln Asp Pro Thr His Leu Val
        435                 440

<210> SEQ ID NO 25
<211> LENGTH: 358
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
```

<223> OTHER INFORMATION: IL2Ralpha-CISC polypeptide

<400> SEQUENCE: 25

Met Pro Leu Gly Leu Leu Trp Leu Gly Leu Ala Leu Leu Gly Ala Leu
1               5                   10                  15

His Ala Gln Ala Gly Val Gln Val Glu Thr Ile Ser Pro Gly Asp Gly
            20                  25                  30

Arg Thr Phe Pro Lys Arg Gly Gln Thr Cys Val Val His Tyr Thr Gly
        35                  40                  45

Met Leu Glu Asp Gly Lys Lys Val Asp Ser Ser Arg Asp Arg Asn Lys
    50                  55                  60

Pro Phe Lys Phe Met Leu Gly Lys Gln Glu Val Ile Arg Gly Trp Glu
65                  70                  75                  80

Glu Gly Val Ala Gln Met Ser Val Gly Gln Arg Ala Lys Leu Thr Ile
                85                  90                  95

Ser Pro Asp Tyr Ala Tyr Gly Ala Thr Gly His Pro Gly Ile Ile Pro
            100                 105                 110

Pro His Ala Thr Leu Val Phe Asp Val Glu Leu Leu Lys Leu Glu Gly
        115                 120                 125

Glu Ile Asn Asn Ser Ser Gly Glu Met Asp Pro Ile Leu Leu Thr Ile
    130                 135                 140

Ser Ile Leu Ser Phe Phe Ser Val Ala Leu Leu Val Ile Leu Ala Cys
145                 150                 155                 160

Val Leu Trp Lys Lys Arg Ile Lys Pro Ile Val Trp Pro Ser Leu Pro
                165                 170                 175

Asp His Lys Lys Thr Leu Glu His Leu Cys Lys Lys Pro Arg Lys Asn
            180                 185                 190

Leu Asn Val Ser Phe Asn Pro Glu Ser Phe Leu Asp Cys Gln Ile His
        195                 200                 205

Arg Val Asp Asp Ile Gln Ala Arg Asp Glu Val Glu Gly Phe Leu Gln
    210                 215                 220

Asp Thr Phe Pro Gln Gln Leu Glu Glu Ser Glu Lys Gln Arg Leu Gly
225                 230                 235                 240

Gly Asp Val Gln Ser Pro Asn Cys Pro Ser Glu Asp Val Val Ile Thr
                245                 250                 255

Pro Glu Ser Phe Gly Arg Asp Ser Ser Leu Thr Cys Leu Ala Gly Asn
            260                 265                 270

Val Ser Ala Cys Asp Ala Pro Ile Leu Ser Ser Ser Arg Ser Leu Asp
        275                 280                 285

Cys Arg Glu Ser Gly Lys Asn Gly Pro His Val Tyr Gln Asp Leu Leu
    290                 295                 300

Leu Ser Leu Gly Thr Thr Asn Ser Thr Leu Pro Pro Pro Phe Ser Leu
305                 310                 315                 320

Gln Ser Gly Ile Leu Thr Leu Asn Pro Val Ala Gln Gly Gln Pro Ile
                325                 330                 335

Leu Thr Ser Leu Gly Ser Asn Gln Glu Glu Ala Tyr Val Thr Met Ser
            340                 345                 350

Ser Phe Tyr Gln Asn Gln
        355

<210> SEQ ID NO 26
<211> LENGTH: 358
<212> TYPE: PRT
<213> ORGANISM: Artificial sequence
<220> FEATURE:

```
<223> OTHER INFORMATION: Synthetic polypeptide
<220> FEATURE:
<221> NAME/KEY: misc_feature
<223> OTHER INFORMATION: IL7Ralpha-CISC polypeptide

<400> SEQUENCE: 26

Met Pro Leu Gly Leu Leu Trp Leu Gly Leu Ala Leu Leu Gly Ala Leu
1               5                   10                  15

His Ala Gln Ala Gly Val Gln Val Glu Thr Ile Ser Pro Gly Asp Gly
            20                  25                  30

Arg Thr Phe Pro Lys Arg Gly Gln Thr Cys Val Val His Tyr Thr Gly
        35                  40                  45

Met Leu Glu Asp Gly Lys Lys Val Asp Ser Ser Arg Asp Arg Asn Lys
    50                  55                  60

Pro Phe Lys Phe Met Leu Gly Lys Gln Glu Val Ile Arg Gly Trp Glu
65                  70                  75                  80

Glu Gly Val Ala Gln Met Ser Val Gly Gln Arg Ala Lys Leu Thr Ile
                85                  90                  95

Ser Pro Asp Tyr Ala Tyr Gly Ala Thr Gly His Pro Gly Ile Ile Pro
            100                 105                 110

Pro His Ala Thr Leu Val Phe Asp Val Glu Leu Leu Lys Leu Glu Gly
        115                 120                 125

Glu Ile Asn Asn Ser Ser Gly Glu Met Asp Pro Ile Leu Leu Thr Ile
    130                 135                 140

Ser Ile Leu Ser Phe Phe Ser Val Ala Leu Leu Val Ile Leu Ala Cys
145                 150                 155                 160

Val Leu Trp Lys Lys Arg Ile Lys Pro Ile Val Trp Pro Ser Leu Pro
                165                 170                 175

Asp His Lys Lys Thr Leu Glu His Leu Cys Lys Lys Pro Arg Lys Asn
            180                 185                 190

Leu Asn Val Ser Phe Asn Pro Glu Ser Phe Leu Asp Cys Gln Ile His
        195                 200                 205

Arg Val Asp Asp Ile Gln Ala Arg Asp Glu Val Glu Gly Phe Leu Gln
    210                 215                 220

Asp Thr Phe Pro Gln Gln Leu Glu Glu Ser Glu Lys Gln Arg Leu Gly
225                 230                 235                 240

Gly Asp Val Gln Ser Pro Asn Cys Pro Ser Glu Asp Val Val Ile Thr
                245                 250                 255

Pro Glu Ser Phe Gly Arg Asp Ser Ser Leu Thr Cys Leu Ala Gly Asn
            260                 265                 270

Val Ser Ala Cys Asp Ala Pro Ile Leu Ser Ser Ser Arg Ser Leu Asp
        275                 280                 285

Cys Arg Glu Ser Gly Lys Asn Gly Pro His Val Tyr Gln Asp Leu Leu
    290                 295                 300

Leu Ser Leu Gly Thr Thr Asn Ser Thr Leu Pro Pro Pro Phe Ser Leu
305                 310                 315                 320

Gln Ser Gly Ile Leu Thr Leu Asn Pro Val Ala Gln Gly Gln Pro Ile
                325                 330                 335

Leu Thr Ser Leu Gly Ser Asn Gln Glu Glu Ala Tyr Val Thr Met Ser
            340                 345                 350

Ser Phe Tyr Gln Asn Gln
        355

<210> SEQ ID NO 27
<211> LENGTH: 276
```

<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: MPL-CISC polypeptide

<400> SEQUENCE: 27

```
Met Pro Leu Gly Leu Leu Trp Leu Gly Leu Ala Leu Leu Gly Ala Leu
1               5                   10                  15
His Ala Gln Ala Gly Val Gln Val Glu Thr Ile Ser Pro Gly Asp Gly
            20                  25                  30
Arg Thr Phe Pro Lys Arg Gly Gln Thr Cys Val Val His Tyr Thr Gly
        35                  40                  45
Met Leu Glu Asp Gly Lys Lys Val Asp Ser Ser Arg Asp Arg Asn Lys
    50                  55                  60
Pro Phe Lys Phe Met Leu Gly Lys Gln Glu Val Ile Arg Gly Trp Glu
65                  70                  75                  80
Glu Gly Val Ala Gln Met Ser Val Gly Gln Arg Ala Lys Leu Thr Ile
                85                  90                  95
Ser Pro Asp Tyr Ala Tyr Gly Ala Thr Gly His Pro Gly Ile Ile Pro
            100                 105                 110
Pro His Ala Thr Leu Val Phe Asp Val Glu Leu Leu Lys Leu Gly Glu
        115                 120                 125
Glu Thr Ala Trp Ile Ser Leu Val Thr Ala Leu His Leu Val Leu Gly
    130                 135                 140
Leu Ser Ala Val Leu Gly Leu Leu Leu Leu Arg Trp Gln Phe Pro Ala
145                 150                 155                 160
His Tyr Arg Arg Leu Arg His Ala Leu Trp Pro Ser Leu Pro Asp Leu
                165                 170                 175
His Arg Val Leu Gly Gln Tyr Leu Arg Asp Thr Ala Ala Leu Ser Pro
            180                 185                 190
Pro Lys Ala Thr Val Ser Asp Thr Cys Glu Glu Val Glu Pro Ser Leu
        195                 200                 205
Leu Glu Ile Leu Pro Lys Ser Ser Glu Arg Thr Pro Leu Pro Leu Cys
    210                 215                 220
Ser Ser Gln Ala Gln Met Asp Tyr Arg Arg Leu Gln Pro Ser Cys Leu
225                 230                 235                 240
Gly Thr Met Pro Leu Ser Val Cys Pro Pro Met Ala Glu Ser Gly Ser
                245                 250                 255
Cys Cys Thr Thr His Ile Ala Asn His Ser Tyr Leu Pro Leu Ser Tyr
            260                 265                 270
Trp Gln Gln Pro
        275
```

<210> SEQ ID NO 28
<211> LENGTH: 9405
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: CISC vector DNA

<400> SEQUENCE: 28
agcttaatgt agtcttatgc aatactcttg tagtcttgca acatggtaac gatgagttag    60

-continued

```
caacatgcct tacaaggaga gaaaaagcac cgtgcatgcc gattggtgga agtaaggtgg    120
tacgatcgtg ccttattagg aaggcaacag acgggtctga catggattgg acgaaccact    180
gaattgccgc attgcagaga tattgtattt aagtgcctag ctcgatacaa taaacgggtc    240
tctctggtta gaccagatct gagcctggga gctctctggc taactaggga acccactgct    300
taagcctcaa taaagcttgc cttgagtgct tcaagtagtg tgtgcccgtc tgttgtgtga    360
ctctggtaac tagagatccc tcagacccct ttagtcagtg tggaaaatct ctagcagtgg    420
cgcccgaaca gggacttgaa agcgaaaggg aaaccagagg agctctctcg acgcaggact    480
cggcttgctg aagcgcgcac ggcaagaggc gaggggcggc gactggtgag tacgccaaaa    540
attttgacta gcggaggcta aaggagaga gatgggtgcg agagcgtcag tattaagcgg    600
gggagaatta gatcgcgatg ggaaaaaatt cggttaaggc cagggggaaa gaaaaaatat    660
aaattaaaac atatagtatg ggcaagcagg gagctagaac gattcgcagt taatcctggc    720
ctgttagaaa catcagaagg ctgtagacaa atactgggac agctacaacc atcccttcag    780
acaggatcag aagaacttag atcattatat aatacagtag caaccctcta ttgtgtgcat    840
caaaggatag agataaaaga caccaaggaa gctttagaca agatagagga agagcaaaac    900
aaaagtaaga ccaccgcaca gcaagcggcc gctgatcttc agacctggag gaggagatat    960
gagggacaat tggagaagtg aattatataa atataaagta gtaaaattg aaccattagg    1020
agtagcaccc accaaggcaa agagaagagt ggtgcagaga gaaaaagag cagtgggaat    1080
aggagctttg ttccttgggt tcttgggagc agcaggaagc actatgggcg cagcctcaat    1140
gacgctgacg gtacaggcca gacaattatt gtctggtata gtgcagcagc agaacaattt    1200
gctgagggct attgaggcgc aacagcatct gttgcaactc acagtctggg gcatcaagca    1260
gctccaggca agaatcctgg ctgtggaaag atacctaaag gatcaacagc tcctggggat    1320
ttggggttgc tctggaaaac tcatttgcac cactgctgtg ccttggaatg ctagttggag    1380
taataaatct ctggaacaga tttggaatca cacgacctgg atggagtggg acagagaaat    1440
taacaattac acaagcttaa tacactcctt aattgaagaa tcgcaaaacc agcaagaaaa    1500
gaatgaacaa gaattattgg aattagataa atgggcaagt ttgtggaatt ggtttaacat    1560
aacaaattgg ctgtggtata taaaattatt cataatgata gtaggaggct tggtaggttt    1620
aagaatagtt tttgctgtac tttctatagt gaatagagtt aggcagggat attcaccatt    1680
atcgtttcag acccacctcc caaccccgag gggacccgac aggcccgaag gaatagaaga    1740
agaaggtgga gagagagaca gagacagatc cattcgatta gtgaacggat ctcgacggta    1800
tcggttaact tttaaaagaa aagggggat tgggggtac agtgcagggg aaagaatagt    1860
agacataata gcaacagaca tacaaactaa agaattacaa aaacaaatta caaaaattca    1920
aaattttatc gatcacgaga ctagcctcga gaagcttgat atcgaattcc cacggggttg    1980
gacgcgtagg aacagagaaa caggagaata tgggccaaac aggatatctg tggtaagcag    2040
ttcctgcccc ggctcagggc caagaacagt tggaacagca gaatatgggc caaacaggat    2100
atctgtggta agcagttcct gccccggctc agggccaaga acagatggtc cccagatgcg    2160
gtcccgccct cagcagtttc tagagaacca tcagatgttt ccaggtgccc caaggacct    2220
gaaatgaccc tgtgccttat ttgaactaac caatcagttc gcttctcgct tctgttcgcg    2280
cgcttctgct ccccgagctc tatataagca gagctcgttt agtgaaccgt cagatcgcta    2340
gcaccggtgc cgccaccatg cctctgggcc tgctgtggct gggcctggcc ctgctgggcg    2400
ccctgcacgc ccaggccggc gtgcaggtgg agacaatctc cccaggcgac ggacgcacat    2460
```

-continued

```
tccctaagcg gggccagacc tgcgtggtgc actatacagg catgctggag gatggcaaga    2520
agtttgacag ctcccgggat agaaacaagc cattcaagtt tatgctgggc aagcaggaag    2580
tgatcagagg ctgggaggag ggcgtggccc agatgtctgt gggccagagg gccaagctga    2640
ccatcagccc agactacgcc tatggagcaa caggccaccc aggaatcatc ccacctcacg    2700
ccaccctggt gttcgatgtg gagctgctga agctgggcga gggatccaac acatcaaaag    2760
agaaccccct tctgttcgca ttggaggccg tagtcatatc tgttggatcc atgggactta    2820
ttatctccct gttgtgtgtg tacttctggc tggaacggac tatgcccagg atccccacgc    2880
tcaagaatct ggaagatctc gtcacagaat accatggtaa tttcagcgcc tggagcggag    2940
tctctaaggg tctggccgaa tccctccaac ccgattattc tgaacggttg tgcctcgtat    3000
ccgaaatacc accaaaaggc ggggctctgg gtgagggccc aggggcgagt ccgtgcaatc    3060
aacacagccc gtattgggcc cctccttgtt atacgttgaa gcccgaaact ggaagcggag    3120
ctactaactt cagcctgctg aagcaggctg gagacgtgga ggagaaccct ggacctatgg    3180
cactgcccgt gaccgccctg ctgctgcctc tggccctgct gctgcacgca gcccggccta    3240
tcctgtggca cgagatgtgg cacgagggcc tggaggaggc cagcaggctg tattttggcg    3300
agcgcaacgt gaagggcatg ttcgaggtgc tggagcctct gcacgccatg atggagagag    3360
gcccacagac cctgaaggag acatcccttta accaggccta tggacgggac ctgatggagg    3420
cacaggagtg gtgcagaaag tacatgaagt ctggcaatgt gaaggacctg ctgcaggcct    3480
gggatctgta ctatcacgtg tttcggagaa tctccaaggg caaagacacg attccgtggc    3540
ttgggcatct gctcgttggg ctgagtggtg cgtttggttt catcatcttg gtctatctct    3600
tgatcaattg cagaaataca ggcccttggc tgaaaaaagt gctcaagtgt aatacccccg    3660
acccaagcaa gttcttctcc cagctttctt cagagcatgg aggcgatgtg cagaaatggc    3720
tctcttcacc ttttcccctcc tcaagcttct ccccggagg gctggcgccc agatttcac     3780 ctcttgaggt acttgaacga gacaaggtta cccaacttct ccttcaacag gataaggtac    3840
ccgaacctgc gagccttagc tccaaccact ctcttacgag ctgcttcacc aatcagggat    3900
acttcttttt ccaccttccc gatgcgctgg aaatcgaagc ttgtcaagtt tactttacct    3960
atgatccata tagcgaggaa gatcccgacg aaggagtcgc cggtgcgccc acgggttcct    4020
caccccaacc tctccagcct ctctcaggag aagatgatgc ttattgcact tttcccagta    4080
gagacgatct cctcctcttt tctccatctc ttttgggggg accttccccc ccttctacgg    4140
cacctggcgg gtctggtgct ggcgaggagc ggatgccgcc gtccctccag gagcgagtac    4200
cacgagattg ggatccccag ccacttggac cccccacccc cggcgtacct gaccttgtcg    4260
attttcaacc tcccccctgaa ttggtgctgc gagaggctgg ggaggaagtt ccggacgctg    4320
ggccgaggga gggcgtgtcc tttccatgga gtaggcctcc aggtcaaggc gagtttaggg    4380
ctctcaacgc gcggctgccg ttgaatacag acgcttatct ctcactgcag gaactgcaag    4440
gtcaggaccc aacacatctt gtaggatctg gtgctactaa ttttttctctt ttgaagcaag    4500 ctggagatgt tgaagagaac cctggtccag tgagcaaggg cgaggagctg ttcaccgggg    4560
tggtgcccat cctggtcgag ctggacggcg acgtaaacgg ccacaagttc agcgtgtccg    4620
gcgagggcga gggcgatgcc acctacggca agctgaccct gaagttcatc tgcaccaccg    4680
gcaagctgcc cgtgccctgg cccacccctcg tgaccaccct gacctacggc gtgcagtgct    4740
tcagccgcta ccccgaccac atgaagcagc acgacttctt caagtccgcc atgcccgaag    4800
```

-continued

```
gctacgtcca ggagcgcacc atcttcttca aggacgacgg caactacaag acccgcgccg    4860
aggtgaagtt cgagggcgac accctggtga accgcatcga gctgaagggc atcgacttca    4920
aggaggacgg caacatcctg gggcacaagc tggagtacaa ctacaacagc cacaacgtct    4980
atatcatggc cgacaagcag aagaacggca tcaaggtgaa cttcaagatc cgccacaaca    5040
tcgaggacgg cagcgtgcag ctcgccgacc actaccagca gaacacccc atcggcgacg    5100 gccccgtgct gctgcccgac aaccactacc tgagcaccca gtccgccctg agcaaagacc    5160
ccaacgagaa gcgcgatcac atggtcctgc tggagttcgt gaccgccgcc gggatcactc    5220
tcggcatgga cgagctgtac aagtaaacta gtgtcgacaa tcaacctctg gattacaaaa    5280
tttgtgaaag attgactggt attcttaact atgttgctcc ttttacgcta tgtggatacg    5340
ctgctttaat gcctttgtat catgctattg cttcccgtat ggctttcatt ttctcctcct    5400
tgtataaatc ctggttgctg tctctttatg aggagttgtg gcccgttgtc aggcaacgtg    5460
gcgtggtgtg cactgtgttt gctgacgcaa cccccactgg ttgggcatt gccaccacct    5520 gtcagctcct ttccgggact ttcgctttcc cctcccctat tgccacggcg gaactcatcg    5580
ccgcctgcct tgcccgctgc tggacagggg ctcggctgtt gggcactgac aattccgtgg    5640
tgttgtcggg gaagctgacg tccttttccat ggctgctcgc ctgtgttgcc acctggattc    5700
tgcgcgggac gtccttctgc tacgtccctt cggccctcaa tccagcggac cttccttccc    5760
gcggcctgct gccggtctctg cggcctcttc cgcgtcttcg ccttcgccct cagacgagtc    5820
ggatctccct ttgggccgcc tccccgcctg gaattcgagc tcggtacctt aagaccaat    5880 gacttacaag gcagctgtag atcttagcca ctttttaaaa gaaaaggggg gactggaagg    5940
gctaattcac tcccaacgaa gacaagatct gcttttgct tgtactgggt ctctctggtt    6000
agaccagatc tgagcctggg agctctctgg ctaactaggg aacccactgc ttaagcctca    6060
ataaagcttg ccttgagtgc ttcaagtagt gtgtgcccgt ctgttgtgtg actctggtaa    6120
ctagagatcc ctcagaccct tttagtcagt gtggaaaatc tctagcagta gtagttcatg    6180
tcatcttatt attcagtatt tataacttgc aaagaaatga atatcagaga gtgagaggaa    6240
cttgtttatt gcagcttata atggttacaa ataaagcaat agcatcacaa atttcacaaa    6300
taaagcattt ttttcactgc attctagttg tggtttgtcc aaactcatca atgtatctta    6360
tcatgtctgg ctctagctat cccgccccta actccgccca gttccgccca ttctccgccc    6420
catggctgac taatttttt tatttatgca gaggccgagg ccgcctcggc ctctgagcta    6480
ttccagaagt agtgaggagg ctttttgga ggcctaggct tttgcgtcga cgtacccca    6540 attcgcccta tagtgagtcg tattacgcgc gctcactggc cgtcgtttta caacgtcgtg    6600
actgggaaaa ccctggcgtt acccaactta atcgccttgc agcacatccc ctttcgcca    6660 gctggcgtaa tagcgaagag gcccgcaccg atcgcccttc ccaacagttg cgcagcctga    6720
atggcgaatg gcgcgacgcg ccctgtagcg gcgcattaag cgcggcgggt gtggtggtta    6780
cgcgcagcgt gaccgctaca cttgccagcg ccctagcgcc cgctcctttc gctttcttcc    6840
cttcctttct cgccacgttc gccggctttc cccgtcaagc tctaaatcgg ggctcccttt    6900
agggttccga tttagtgct ttacggcacc tcgaccccaa aaaacttgat tagggtgatg    6960
gttcacgtag tgggccatcg ccctgataga cggtttttcg ccctttgacg ttggagtcca    7020
cgttctttaa tagtggactc ttgttccaaa ctggaacaac actcaaccct atctcggtct    7080
attcttttga tttataaggg attttgccga tttcggccta ttggttaaaa atgagctga    7140 tttaacaaaa atttaacgcg aattttaaca aaatattaac gtttacaatt tcccaggtgg    7200
```

-continued

```
cacttttcgg ggaaatgtgc gcggaacccc tatttgttta ttttctaaa tacattcaaa    7260 tatgtatccg ctcatgagac aataaccctg ataaatgctt caataatatt gaaaaggaa     7320 gagtatgagt attcaacatt tccgtgtcgc ccttattccc tttttgcgg cattttgcct    7380 tcctgttttt gctcacccag aaacgctggt gaaagtaaaa gatgctgaag atcagttggg    7440
tgcacgagtg ggttacatcg aactggatct caacagcggt aagatccttg agagttttcg    7500
ccccgaagaa cgttttccaa tgatgagcac ttttaaagtt ctgctatgtg gcgcggtatt    7560
atcccgtatt gacgccggc aagagcaact cggtcgccgc atacactatt ctcagaatga    7620
cttggttgag tactcaccag tcacagaaaa gcatcttacg gatggcatga cagtaagaga    7680
attatgcagt gctgccataa ccatgagtga taacactgcg gccaacttac ttctgacaac    7740
gatcggagga ccgaaggagc taaccgcttt tttgcacaac atgggggatc atgtaactcg    7800
ccttgatcgt tgggaaccgg agctgaatga agccatacca aacgacgagc gtgacaccac    7860
gatgcctgta gcaatggcaa caacgttgcg caaactatta actggcgaac tacttactct    7920
agcttcccgg caacaattaa tagactggat ggaggcggat aaagttgcag gaccacttct    7980
gcgctcggcc cttccggctg gctggtttat tgctgataaa tctggagccg gtgagcgtgg    8040
gtctcgcggt atcattgcag cactggggcc agatggtaag ccctcccgta tcgtagttat    8100
ctacacgacg gggagtcagg caactatgga tgaacgaaat agacagatcg ctgagatagg    8160
tgcctcactg attaagcatt ggtaactgtc agaccaagtt tactcatata ctttagat     8220 tgatttaaaa cttcattttt aatttaaaag gatctaggtg aagatccttt ttgataatct    8280
catgaccaaa atcccttaac gtgagttttc gttccactga gcgtcagacc ccgtagaaaa    8340
gatcaaagga tcttcttgag atcctttttt tctgcgcgta atctgctgct tgcaaacaaa    8400
aaaaccaccg ctaccagcgg tggtttgttt gccggatcaa gagctaccaa ctcttttcc     8460 gaaggtaact ggcttcagca gagcgcagat accaaatact gtccttctag tgtagccgta    8520
gttaggccac cacttcaaga actctgtagc accgcctaca tacctcgctc tgctaatcct    8580
gttaccagtg gctgctgcca gtggcgataa gtcgtgtctt accgggttgg actcaagacg    8640
atagttaccg gataaggcgc agcggtcggg ctgaacgggg ggttcgtgca cacagcccag    8700
cttggagcga acgacctaca ccgaactgag atacctacag cgtgagctat gagaaagcgc    8760
cacgcttccc gaagggagaa aggcggacag gtatccggta agcggcaggg tcggaacagg    8820
agagcgcacg agggagcttc caggggggaaa cgcctggtat ctttatagtc ctgtcgggtt    8880 tcgccaccte tgacttgagc gtcgattttt gtgatgctcg tcaggggggc ggagcctatg    8940
gaaaaacgcc agcaacgcgg cctttttacg gttcctggcc ttttgctggc cttttgctca    9000
catgttcttt cctgcgttat cccctgattc tgtggataac cgtattaccg cctttgagtg    9060
agctgatacc gctcgccgca gccgaacgac cgagcgcagc gagtcagtga gcgaggaagc    9120
ggaagagcgc ccaatacgca aaccgcctct ccccgcgcgt tggccgattc attaatgcag    9180
ctggcacgac aggtttcccg actggaaagc gggcagtgag cgcaacgcaa ttaatgtgag    9240
ttagctcact cattaggcac cccaggcttt acactttatg cttccggctc gtatgttgtg    9300
tggaattgtg agcggataac aatttcacac aggaaacagc tatgaccatg attacgccaa    9360
gcgcgcaatt aaccctcact aaagggaaca aaagctggag ctgca                    9405
```

<210> SEQ ID NO 29
<211> LENGTH: 10053
<212> TYPE: DNA

<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: CISC vector DNA

<400> SEQUENCE: 29

```
agcttaatgt agtcttatgc aatactcttg tagtcttgca acatggtaac gatgagttag     60
caacatgcct tacaaggaga gaaaaagcac cgtgcatgcc gattggtgga agtaaggtgg    120
tacgatcgtg ccttattagg aaggcaacag acgggtctga catggattgg acgaaccact    180
gaattgccgc attgcagaga tattgtattt aagtgcctag ctcgatacaa taaacgggtc    240
tctctggtta gaccagatct gagcctggga gctctctggc taactaggga acccactgct    300
taagcctcaa taaagcttgc cttgagtgct tcaagtagtg tgtgcccgtc tgttgtgtga    360
ctctggtaac tagagatccc tcagaccctt ttagtcagtg tggaaaatct ctagcagtgg    420
cgcccgaaca gggacttgaa agcgaaaggg aaaccagagg agctctctcg acgcaggact    480
cggcttgctg aagcgcgcac ggcaagaggc gaggggcggc gactggtgag tacgccaaaa    540
attttgacta gcggaggcta aaggagaga gatgggtgcg agagcgtcag tattaagcgg    600
gggagaatta gatcgcgatg ggaaaaaatt cggttaaggc cagggggaaa gaaaaaatat    660
aaattaaaac atatagtatg ggcaagcagg gagctagaac gattcgcagt taatcctggc    720
ctgttagaaa catcagaagg ctgtagacaa atactgggac agctacaacc atcccttcag    780
acaggatcag aagaacttag atcattatat aatacagtag caaccctcta ttgtgtgcat    840
caaaggatag agataaaaga caccaaggaa gctttagaca atagagga agagcaaaac    900
aaaagtaaga ccaccgcaca gcaagcggcc gctgatcttc agacctggag gaggagatat    960
gagggacaat tggagaagtg aattatataa atataaagta gtaaaattg aaccattagg   1020
agtagcaccc accaaggcaa agagaagagt ggtgcagaga gaaaaaagag cagtgggaat   1080
aggagctttg ttccttgggt tcttgggagc agcaggaagc actatgggcg cagcctcaat   1140
gacgctgacg gtacaggcca gacaattatt gtctggtata gtgcagcagc agaacaattt   1200
gctgagggct attgaggcgc aacagcatct gttgcaactc acagtctggg gcatcaagca   1260
gctccaggca agaatcctgg ctgtggaaag atacctaaag gatcaacagc tcctggggat   1320
ttggggttgc tctggaaaac tcatttgcac cactgctgtg ccttggaatg ctagttggag   1380
taataaatct ctggaacaga tttggaatca cacgacctgg atggagtggg acagagaaat   1440
taacaattac acaagcttaa tacactcctt aattgaagaa tcgcaaaacc agcaagaaaa   1500
gaatgaacaa gaattattgg aattagataa atgggcaagt ttgtggaatt ggtttaacat   1560
aacaaattgg ctgtggtata taaaattatt cataatgata gtaggaggct tggtaggttt   1620
aagaatagtt tttgctgtac tttctatagt gaatagagtt aggcagggat attcaccatt   1680
atcgtttcag acccacctcc caacccccgag gggacccgac aggcccgaag gaatagaaga   1740
agaaggtgga gagagagaca gagacagatc cattcgatta gtgaacggat ctcgacggta   1800
tcggttaact tttaaaagaa agggggggat tggggggtac agtgcagggg aaagaatagt   1860
agacataata gcaacagaca tacaaactaa agaattacaa aaacaaatta caaaaattca   1920
aaattttatc gatcacgaga ctagcctcga gaagcttgat atcgaattcc cacggggttg   1980
gacgcgtagg aacagagaaa caggagaata tgggccaaac aggatatctg tggtaagcag   2040
ttcctgcccc ggctcagggc caagaacagt tggaacagca gaatatgggc caaacaggat   2100
```

|  |  |  |  |  |
|---|---|---|---|---|
| atctgtggta | agcagttcct | gccccggctc | agggccaaga | acagatggtc cccagatgcg | 2160 |
| gtcccgccct | cagcagtttc | tagagaacca | tcagatgttt | ccagggtgcc ccaaggacct | 2220 |
| gaaatgaccc | tgtgccttat | ttgaactaac | caatcagttc | gcttctcgct tctgttcgcg | 2280 |
| cgcttctgct | ccccgagctc | tatataagca | gagctcgttt | agtgaaccgt cagatcgcta | 2340 |
| gcaccggtgc | cgccaccatg | cctctgggcc | tgctgtggct | gggcctggcc ctgctgggcg | 2400 |
| ccctgcacgc | ccaggccggc | gtgcaggtgg | agacaatctc | cccaggcgac ggacgcacat | 2460 |
| tccctaagcg | gggccagacc | tgcgtggtgc | actatacagg | catgctggag gatggcaaga | 2520 |
| agtttgacag | ctcccgggat | agaaacaagc | cattcaagtt | tatgctgggc aagcaggaag | 2580 |
| tgatcagagg | ctgggaggag | ggcgtggccc | agatgtctgt | gggccagagg gccaagctga | 2640 |
| ccatcagccc | agactacgcc | tatggagcaa | caggccaccc | aggaatcatc ccacctcacg | 2700 |
| ccaccctggt | gttcgatgtg | gagctgctga | agctgggcga | gggcggtagt cagaaccttg | 2760 |
| tgataccatg | ggccccagaa | aatctcacac | ttcataaact | ttccgaatca caactcgaac | 2820 |
| tcaactggaa | taaccggttc | ctgaatcact | gtcttgaaca | cctggtacaa tatcggaccg | 2880 |
| actgggatca | ctcatggaca | gaacaatctg | tggactatag | cacaaattc tcactcccaa | 2940 |
| gcgtagacgg | ccaaaaaaga | tacacttttc | gcgtacgatc | ccgctttaat cctctctgcg | 3000 |
| gctctgctca | gcactggagt | gaatggtccc | atcccattca | ttgggatcc aacacatcaa | 3060 |
| aagagaaccc | ctttctgttc | gcattggagg | ccgtagtcat | atctgttgga tccatgggac | 3120 |
| ttattatctc | cctgttgtgt | gtgtacttct | ggctggaacg | gactatgccc aggatcccca | 3180 |
| cgctcaagaa | tctggaagat | ctcgtcacag | aataccatgg | taatttcagc gcctggagcg | 3240 |
| gagtctctaa | gggtctggcc | gaatccctcc | aacccgatta | ttctgaacgg ttgtgcctcg | 3300 |
| tatccgaaat | accaccaaaa | ggcgggctc | tgggtgaggg | cccaggggcg agtccgtgca | 3360 |
| atcaacacag | cccgtattgg | gcccctcctt | gttatacgtt | gaagcccgaa actggaagcg | 3420 |
| gagctactaa | cttcagcctg | ctgaagcagg | ctggagacgt | ggaggagaac cctgacccta | 3480 |
| tggcactgcc | cgtgaccgcc | ctgctgctgc | ctctggccct | gctgctgcac gcagcccggc | 3540 |
| ctatcctgtg | gcacgagatg | tggcacgagg | gcctggagga | ggccagcagg ctgtattttg | 3600 |
| gcgagcgcaa | cgtgaagggc | atgttcgagg | tgctggagcc | tctgcacgcc atgatggaga | 3660 |
| gaggcccaca | gaccctgaag | gagacatcct | ttaaccaggc | ctatggacgg gacctgatgg | 3720 |
| aggcacagga | gtggtgcaga | agtacatga | agtctggcaa | tgtgaaggac ctgctgcagg | 3780 |
| cctgggatct | gtactatcac | gtgtttcgga | gaatctccaa | gggaggttca aaaccttttg | 3840 |
| agaaccttag | actgatggcg | cccatctctc | tgcaggtagt | tcacgttgag acccatagat | 3900 |
| gcaatataag | ctgggaaatc | tcacaagcca | gccattactt | tgaacggcat ttggaattcg | 3960 |
| aggcccgaac | actttccccc | ggtcatacgt | gggaagaagc | tcctctcttg acgctgaagc | 4020 |
| agaagcagga | gtggatttgt | ctggagactt | tgactcctga | tactcagtat gagttccaag | 4080 |
| ttcgggtgaa | accactccaa | ggcgagttca | cgacgtggtc | tccgtggagt caaccgttgg | 4140 |
| cgttccgcac | gaagcccgct | gcccttggca | agacacgat | tccgtggctt gggcatctgc | 4200 |
| tcgttgggct | gagtggtgcg | tttggtttca | tcatcttggt | ctatctcttg atcaattgca | 4260 |
| gaaatacagg | cccttggctg | aaaaaagtgc | tcaagtgtaa | tacccccgac ccaagcaagt | 4320 |
| tcttctccca | gctttcttca | gagcatggag | gcgatgtgca | gaaatggctc tcttcacctt | 4380 |
| ttccctcctc | aagcttctcc | ccggggaggc | tggcgcccga | gatttcacct cttgaggtac | 4440 |
| ttgaacgaga | caaggttacc | caacttctcc | ttcaacagga | taaggtaccc gaacctgcga | 4500 |

```
gccttagctc caaccactct cttacgagct gcttcaccaa tcagggatac ttctttttcc    4560
accttcccga tgcgctggaa atcgaagctt gtcaagttta ctttacctat gatccatata    4620
gcgaggaaga tcccgacgaa ggagtcgccg gtgcgcccac gggttcctca ccccaacctc    4680
tccagcctct ctcaggagaa gatgatgctt attgcacttt tcccagtaga gacgatctcc    4740
tcctcttttc tccatctctt ttgggggggac cttccccccc ttctacggca cctggcgggt    4800
ctggtgctgg cgaggagcgg atgccgccgt ccctccagga gcgagtacca cgagattggg    4860
atccccagcc acttggaccc cccaccccccg gcgtacctga ccttgtcgat tttcaacctc    4920
cccctgaatt ggtgctgcga gaggctgggg aggaagttcc ggacgctggg ccgagggagg    4980
gcgtgtcctt tccatggagt aggcctccag gtcaaggcga gtttagggct ctcaacgcgc    5040
ggctgccgtt gaatacagac gcttatctct cactgcagga actgcaaggt caggacccaa    5100
cacatcttgt aggatctggt gctactaatt tttctctttt gaagcaagct ggagatgttg    5160
aagagaaccc tggtccagtg agcaagggcg aggagctgtt caccggggtg gtgcccatcc    5220
tggtcgagct ggacggcgac gtaaacggcc acaagttcag cgtgtccggc gagggcgagg    5280
gcgatgccac ctacggcaag ctgaccctga agttcatctg caccaccggc aagctgcccg    5340
tgccctggcc caccctcgtg accaccctga cctacggcgt gcagtgcttc agccgctacc    5400
ccgaccacat gaagcagcac gacttcttca gtccgccat gcccgaaggc tacgtccagg    5460
agcgcaccat cttcttcaag gacgacggca actacaagac ccgcgccgag gtgaagttcg    5520
agggcgacac cctggtgaac cgcatcgagc tgaagggcat cgacttcaag gaggacggca    5580
acatcctggg gcacaagctg gagtacaact acaacagcca caacgtctat atcatggccg    5640
acaagcagaa gaacggcatc aaggtgaact tcaagatccg ccacaacatc gaggacggca    5700
gcgtgcagct cgccgaccac taccagcaga acacccccat cggcgacggc cccgtgctgc    5760
tgcccgacaa ccactacctg agcacccagt ccgccctgag caaagacccc aacgagaagc    5820
gcgatcacat ggtcctgctg gagttcgtga ccgccgccgg gatcactctc ggcatggacg    5880
agctgtacaa gtaaactagt gtcgacaatc aacctctgga ttacaaaatt tgtgaaagat    5940
tgactggtat tcttaactat gttgctcctt ttacgctatg tggatacgct gctttaatgc    6000
ctttgtatca tgctattgct tcccgtatgg ctttcatttt ctcctccttg tataaatcct    6060
ggttgctgtc tctttatgag gagttgtggc ccgttgtcag gcaacgtggc gtggtgtgca    6120
ctgtgtttgc tgacgcaacc cccactggtt ggggcattgc caccacctgt cagctccttt    6180
ccgggacttt cgctttcccc ctccctattg ccacggcgga actcatcgcc gcctgccttg    6240
cccgctgctg gacagggget cggctgttgg gcactgacaa ttccgtggtg ttgtcgggga    6300
agctgacgtc ctttccatgg ctgctcgcct gtgttgccac ctggattctg cgcgggacgt    6360
ccttctgcta cgtcccttcg gccctcaatc cagcggacct tccttcccgc ggcctgctgc    6420
cggctctgcg gcctcttccg cgtcttcgcc ttcgccctca gacgagtcgg atctcccttt    6480
gggccgcctc cccgcctgga attcgagctc ggtacctta agaccaatga cttacaaggc    6540
agctgtagat cttagccact tttttaaaaga aaaggggggga ctggaagggc taattcactc    6600
ccaacgaaga caagatctgc ttttttgcttg tactgggtct ctctggttag accagatctg    6660
agcctgggag ctctctggct aactagggaa cccactgctt aagcctcaat aaagcttgcc    6720
ttgagtgctt caagtagtgt gtgcccgtct gttgtgtgac tctggtaact agagatccct    6780
cagacccttt tagtcagtgt ggaaaatctc tagcagtagt agttcatgtc atcttattat    6840
```

```
tcagtatttta taacttgcaa agaaatgaat atcagagagt gagaggaact tgtttattgc  6900
agcttataat ggttacaaat aaagcaatag catcacaaat ttcacaaata aagcattttt  6960
ttcactgcat tctagttgtg gtttgtccaa actcatcaat gtatcttatc atgtctggct  7020
ctagctatcc cgcccctaac tccgcccagt tccgcccatt ctccgcccca tggctgacta  7080 attttttta tttatgcaga ggccgaggcc gcctcggcct ctgagctatt ccagaagtag  7140
tgaggaggct tttttggagg cctaggcttt tgcgtcgaga cgtacccaat tcgccctata  7200
gtgagtcgta ttacgcgcgc tcactggccg tcgttttaca acgtcgtgac tgggaaaacc  7260
ctggcgttac ccaacttaat cgccttgcag cacatccccc tttcgccagc tggcgtaata  7320
gcgaagaggc ccgcaccgat cgcccttccc aacagttgcg cagcctgaat ggcgaatggc  7380
gcgacgcgcc ctgtagcggc gcattaagcg cggcgggtgt ggtggttacg cgcagcgtga  7440
ccgctacact tgccagcgcc ctagcgcccg ctcctttcgc tttcttccct tcctttctcg  7500
ccacgttcgc cggctttccc cgtcaagctc taaatcgggg gctcccttta gggttccgat  7560
ttagtgcttt acggcacctc gaccccaaaa aacttgatta gggtgatggt tcacgtagtg  7620
ggccatcgcc ctgatagacg gttttcgcc ctttgacgtt ggagtccacg ttctttaata  7680
gtggactctt gttccaaact ggaacaacac tcaaccctat ctcggtctat tcttttgatt  7740
tataagggat tttgccgatt tcggcctatt ggttaaaaaa tgagctgatt taacaaaaat  7800
ttaacgcgaa ttttaacaaa atattaacgt ttacaatttc ccaggtggca cttttcgggg  7860
aaatgtgcgc ggaaccccta tttgtttatt tttctaaata cattcaaata tgtatccgct  7920
catgagacaa taaccctgat aaatgcttca ataatattga aaaggaaga gtatgagtat  7980 tcaacatttc cgtgtcgccc ttattccctt ttttgcggca ttttgccttc ctgttttgc   8040 tcacccagaa acgctggtga agtaaaaga tgctgaagat cagttgggtg cacgagtggg  8100
ttacatcgaa ctggatctca acagcggtaa gatccttgag agttttcgcc ccgaagaacg  8160
ttttccaatg atgagcactt ttaaagttct gctatgtggc gcggtattat cccgtattga  8220
cgccgggcaa gagcaactcg gtcgccgcat acactattct cagaatgact tggttgagta  8280
ctcaccagtc acagaaaagc atcttacgga tggcatgaca gtaagagaat tatgcagtgc  8340
tgccataacc atgagtgata acactgcggc caacttactt ctgacaacga tcggaggacc  8400
gaaggagcta accgcttttt tgcacaacat ggggatcat gtaactcgcc ttgatcgttg  8460
ggaaccggag ctgaatgaag ccataccaaa cgacgagcgt gacaccacga tgcctgtagc  8520
aatggcaaca acgttgcgca aactattaac tggcgaacta cttactctag cttcccggca  8580
acaattaata gactggatgg aggcggataa agttgcagga ccacttctgc gctcggccct  8640
tccggctggc tggtttattg ctgataaatc tggagccggt gagcgtgggt ctcgcggtat  8700
cattgcagca ctggggccag atggtaagcc ctcccgtatc gtagttatct acacgacggg  8760
gagtcaggca actatggatg aacgaaatag acagatcgct gagataggtg cctcactgat  8820
taagcattgg taactgtcag accaagttta ctcatatata ctttagattg atttaaaact  8880
tcatttttaa tttaaaagga tctaggtgaa gatcctttt gataatctca tgaccaaaat  8940
cccttaacgt gagttttcgt tccactgagc gtcagacccc gtagaaaaga tcaaaggatc  9000
ttcttgagat cctttttttc tgcgcgtaat ctgctgcttg caaacaaaaa aaccaccgct  9060
accagcggtg gtttgtttgc cggatcaaga gctaccaact ctttttccga aggtaactgg  9120
cttcagcaga gcgcagatac caaatactgt ccttctagtg tagccgtagt taggccacca  9180
cttcaagaac tctgtagcac cgcctacata cctcgctctg ctaatcctgt taccagtggc  9240
```

```
tgctgccagt ggcgataagt cgtgtcttac cgggttggac tcaagacgat agttaccgga      9300
taaggcgcag cggtcgggct gaacgggggg ttcgtgcaca cagcccagct tggagcgaac      9360
gacctacacc gaactgagat acctacagcg tgagctatga gaaagcgcca cgcttcccga      9420
agggagaaag gcggacaggt atccggtaag cggcagggtc ggaacaggag agcgcacgag      9480
ggagcttcca gggggaaacg cctggtatct ttatagtcct gtcgggtttc gccacctctg      9540
acttgagcgt cgatttttgt gatgctcgtc aggggggcgg agcctatgga aaaacgccag      9600
caacgcggcc ttttacggt tcctggcctt ttgctggcct tttgctcaca tgttctttcc       9660
tgcgttatcc cctgattctg tggataaccg tattaccgcc tttgagtgag ctgataccgc      9720
tcgccgcagc cgaacgaccg agcgcagcga gtcagtgagc gaggaagcgg aagagcgccc      9780
aatacgcaaa ccgcctctcc ccgcgcgttg gccgattcat taatgcagct ggcacgacag      9840
gtttcccgac tggaaagcgg gcagtgagcg caacgcaatt aatgtgagtt agctcactca      9900
ttaggcaccc caggctttac actttatgct tccggctcgt atgttgtgtg gaattgtgag      9960
cggataacaa tttcacacag gaaacagcta tgaccatgat tacgccaagc gcgcaattaa     10020
ccctcactaa agggaacaaa agctggagct gca                                  10053

<210> SEQ ID NO 30
<211> LENGTH: 10035
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: CISC vector DNA

<400> SEQUENCE: 30
agcttaatgt agtcttatgc aatactcttg tagtcttgca acatggtaac gatgagttag        60
caacatgcct tacaaggaga aaaaagcac cgtgcatgcc gattggtgga agtaaggtgg       120
tacgatcgtg ccttattagg aaggcaacag acgggtctga catggattgg acgaaccact       180
gaattgccgc attgcagaga tattgtattt aagtgcctag ctcgatacaa taaacgggtc       240
tctctggtta gaccagatct gagcctggga gctctctggc taactaggga acccactgct       300
taagcctcaa taaagcttgc cttgagtgct tcaagtagtg tgtgcccgtc tgttgtgtga       360
ctctggtaac tagagatccc tcagaccctt ttagtcagtg tggaaaatct ctagcagtgg       420
cgcccgaaca gggacttgaa agcgaaaggg aaaccagagg agctctctcg acgcaggact       480
cggcttgctg aagcgcgcac ggcaagaggc gaggggcggc gactggtgag tacgccaaaa       540
attttgacta gcggaggcta aaggagaga atgggtgcg agagcgtcag tattaagcgg       600
gggagaatta gatcgcgatg ggaaaaaatt cggttaaggc caggggaaa gaaaaaatat        660 aaattaaaac atatagtatg ggcaagcagg gagctagaac gattcgcagt taatcctggc       720
ctgttagaaa catcagaagg ctgtagacaa atactgggac agctacaacc atcccttcag       780
acaggatcag aagaacttag atcattatat aatacagtag caaccctcta ttgtgtgcat       840
caaaggatag agataaaaga caccaaggaa gctttagaca agatagagga agagcaaaac       900
aaaagtaaga ccaccgcaca gcaagcggcc gctgatcttc agacctggag gaggagatat       960
gagggacaat tggagaagtg aattatataa atataaagta gtaaaattg aaccattagg      1020 agtagcaccc accaaggcaa agagaagagt ggtgcagaga gaaaaaagag cagtgggaat      1080
aggagctttg ttccttgggt tcttgggagc agcaggaagc actatgggcg cagcctcaat      1140
```

```
gacgctgacg gtacaggcca gacaattatt gtctggtata gtgcagcagc agaacaattt   1200
gctgagggct attgaggcgc aacagcatct gttgcaactc acagtctggg gcatcaagca   1260
gctccaggca agaatcctgg ctgtggaaag atacctaaag gatcaacagc tcctggggat   1320
ttggggttgc tctggaaaac tcatttgcac cactgctgtg ccttggaatg ctagttggag   1380
taataaatct ctggaacaga tttggaatca cacgacctgg atggagtggg acagagaaat   1440
taacaattac acaagcttaa tacactcctt aattgaagaa tcgcaaaacc agcaagaaaa   1500
gaatgaacaa gaattattgg aattagataa atgggcaagt tgtggaatt ggtttaacat    1560 aacaaattgg ctgtggtata taaaattatt cataatgata gtaggaggct tggtaggttt   1620
aagaatagtt tttgctgtac tttctatagt gaatagagtt aggcagggat attcaccatt   1680
atcgtttcag acccacctcc caaccccgag gggacccgac aggcccgaag gaatagaaga   1740
agaaggtgga gagagagaca gagacagatc cattcgatta gtgaacggat ctcgacggta   1800
tcggttaact tttaaaagaa aaggggggat tgggggtac agtgcagggg aaagaatagt    1860
agacataata gcaacagaca tacaaactaa agaattacaa aaacaaatta caaaaattca   1920
aaattttatc gatcacgaga ctagcctcga gaagcttgat atcgaattcc cacggggttg   1980
gacgcgtagg aacagagaaa caggagaata tgggccaaac aggatatctg tggtaagcag   2040
ttcctgcccc ggctcagggc caagaacagt tggaacagca gaatatgggc caaacaggat   2100
atctgtggta agcagttcct gccccggctc agggccaaga acagatggtc cccagatgcg   2160
gtcccgccct cagcagtttc tagagaacca tcagatgttt ccagggtgcc caaggacct    2220 gaaatgaccc tgtgccttat ttgaactaac caatcagttc gcttctcgct tctgttcgcg   2280
cgcttctgct ccccgagctc tatataagca gagctcgttt agtgaaccgt cagatcgcta   2340
gcaccggtgc cgccaccatg cctctgggcc tgctgtggct gggcctggcc ctgctgggcg   2400
ccctgcacgc ccaggccggc gtgcaggtgg acaatctc cccaggcgac ggacgcacat      2460
tccctaagcg gggccagacc tgcgtggtgc actatacagg catgctggag gatggcaaga   2520
agtttgacag ctcccgggat agaaacaagc cattcaagtt tatgctgggc aagcaggaag   2580
tgatcagagg ctgggaggag ggcgtggccc agatgtctgt gggccagagg gccaagctga   2640
ccatcagccc agactacgcc tatggagcaa caggccaccc aggaatcatc ccacctcacg   2700
ccaccctggt gttcgatgtg gagctgctga agctgggcga gcaaaacttg gtgattcctt   2760 gggcccccaga aaatctcacg cttcacaagt tgtccgaatc ccagctcgag ctcaactgga   2820
ataatagatt tcttaatcat tgtttggaac acctggttca atatagaacg gattgggacc   2880
actcatggac cgagcagtca gttgactacc gccacaaatt ttcacttccc agcgtagatg   2940
ggcagaagag gtacacattt agggtcgat ccaggtttaa tcctctgtgt ggttctgctc     3000
aacactggtc tgagtggagc catccgatcc actgggctc aaatacctct aaagaaaatc     3060
cgttcctctt tgcgctcgaa gccgttgtta tcagcgtcgg aagcatggga cttatcattt   3120
cccttctctg cgtgtacttc tggctggagc ggacgatgcc gcggattccg acgctcaaaa   3180
acctggagga ccttgtaaca gaatatcacg gtaatttctc cgcttggagt ggcgtatcaa   3240
aggggcttgc tgagtcccctt caaccggatt actctgagcg cctctgcttg gtgtccgaga   3300
tacctcccaa aggaggtgca cttggggagg ggccaggcgc gtccccttgc aatcagcata   3360
gtccgtattg ggcgccccc tgttataccc tcaaaccgga aacgggaagc ggagctacta    3420
acttcagcct gctgaagcag gctggagacg tggaggagaa ccctggacct atggcactgc   3480
```

```
ccgtgaccgc cctgctgctg cctctggccc tgctgctgca cgcagcccgg cctatcctgt   3540
ggcacgagat gtggcacgag ggcctggagg aggccagcag gctgtatttt ggcgagcgca   3600
acgtgaaggg catgttcgag gtgctggagc ctctgcacgc catgatggag agaggcccac   3660
agaccctgaa ggagacatcc tttaaccagg cctatggacg ggacctgatg gaggcacagg   3720
agtggtgcag aaagtacatg aagtctggca atgtgaagga cctgctgcag gcctgggatc   3780
tgtactatca cgtgtttcgg agaatctcca agaaaccttt tgagaacctt agactgatgg   3840
cgcccatctc tctgcaggta gttcacgttg agacccatag atgcaatata agctgggaaa   3900
tctcacaagc cagccattac tttgaacggc atttggaatt cgaggcccga acactttccc   3960
ccggtcatac gtgggaagaa gctcctctct tgacgctgaa gcagaagcag gagtggattt   4020
gtctggagac tttgactcct gatactcagt atgagttcca agttcgggtg aaaccactcc   4080
aaggcgagtt cacgacgtgg tctccgtgga gtcaaccgtt ggcgttccgc acgaagcccg   4140
ctgcccttgg caaagacacg attccgtggc ttgggcatct gctcgttggg ctgagtggtg   4200
cgtttggttt catcatcttg gtctatctct tgatcaattg cagaaataca ggcccttggc   4260 tgaaaaagt gctcaagtgt aatacccccg acccaagcaa gttcttctcc cagctttctt   4320
cagagcatgg aggcgatgtg cagaaatggc tctcttcacc ttttccctcc tcaagcttct   4380
ccccgggagg gctggcgccc gagatttcac ctcttgaggt acttgaacga gacaaggtta   4440
cccaacttct ccttcaacag gataaggtac ccgaacctgc gagccttagc tccaaccact   4500
ctcttacgag ctgcttcacc aatcagggat acttcttttt ccaccttccc gatgcgctgg   4560
aaatcgaagc ttgtcaagtt tactttacct atgatccata tagcgaggaa gatcccgacg   4620
aaggagtcgc cggtgcgccc acgggttcct cacccccaacc tctccagcct ctctcaggag   4680
aagatgatgc ttattgcact tttcccagta gagacgatct cctcctcttt tctccatctc   4740 ttttggggg accttccccc ccttctacgg cacctggcgg gtctggtgct ggcgaggagc   4800
ggatgccgcc gtccctccag gagcgagtac cacgagattg ggatccccag ccacttggac   4860 ccccacccc cggcgtacct gaccttgtcg attttcaacc tcccctgaa ttggtgctgc   4920 gagaggctgg ggaggaagtt ccggacgctg ggccgaggga gggcgtgtcc tttccatgga   4980
gtaggcctcc aggtcaaggc gagtttaggg ctctcaacgc gcggctgccg ttgaatacag   5040
acgcttatct ctcactgcag gaactgcaag gtcaggaccc aacacatctt gtaggatctg   5100
gtgctactaa ttttttctctt ttgaagcaag ctggagatgt tgaagagaac cctggtccag   5160
tgagcaaggg cgaggagctg ttcaccgggg tggtgcccat cctggtcgag ctggacggcg   5220
acgtaaacgg ccacaagttc agcgtgtccg gcgagggcga gggcgatgcc acctacggca   5280
agctgaccct gaagttcatc tgcaccaccg gcaagctgcc cgtgccctgg cccaccctcg   5340
tgaccaccct gacctacggc gtgcagtgct tcagccgcta ccccgaccac atgaagcagc   5400
acgacttctt caagtccgcc atgcccgaag gctacgtcca ggagcgcacc atcttcttca   5460
aggacgacgg caactacaag acccgcgccg aggtgaagtt cgagggcgac accctggtga   5520
accgcatcga gctgaagggc atcgacttca aggaggacgg caacatcctg gggcacaagc   5580
tggagtacaa ctacaacagc cacaacgtct atatcatggc cgacaagcag aagaacggca   5640
tcaaggtgaa cttcaagatc cgccacaaca tcgaggacgg cagcgtgcag ctcgccgacc   5700
actaccagca gaacaccccc atcggcgacg gccccgtgct gctgcccgac aaccactacc   5760
tgagcaccca gtccgccctg agcaaagacc ccaacgagaa gcgcgatcac atggtcctgc   5820
tggagttcgt gaccgccgcc gggatcactc tcggcatgga cgagctgtac aagtaaacta   5880
```

```
gtgtcgacaa tcaacctctg gattacaaaa tttgtgaaag attgactggt attcttaact   5940
atgttgctcc ttttacgcta tgtggatacg ctgctttaat gcctttgtat catgctattg   6000
cttcccgtat ggcttcatt ttctcctcct tgtataaatc ctggttgctg tctctttatg    6060
aggagttgtg gcccgttgtc aggcaacgtg gcgtggtgtg cactgtgttt gctgacgcaa   6120
cccccactgg ttggggcatt gccaccacct gtcagctcct ttccgggact ttcgctttcc   6180
ccctccctat tgccacggcg gaactcatcg ccgcctgcct tgcccgctgc tggacagggg   6240
ctcggctgtt gggcactgac aattccgtgg tgttgtcggg aagctgacg tccttccat    6300
ggctgctcgc ctgtgttgcc acctggattc tgcgcgggac gtccttctgc tacgtccctt   6360
cggccctcaa tccagcggac cttccttccc gcggcctgct gccggctctg cggcctcttc   6420
cgcgtcttcg ccttcgccct cagacgagtc ggatctccct ttgggccgcc tccccgcctg   6480
gaattcgagc tcggtacctt aagaccaat gacttacaag gcagctgtag atcttagcca    6540
ctttttaaaa gaaaaggggg gactggaagg gctaattcac tcccaacgaa gacaagatct   6600
gcttttgct tgtactgggt ctctctggtt agaccagatc tgagcctggg agctctctgg    6660
ctaactaggg aacccactgc ttaagcctca ataaagcttg ccttgagtgc ttcaagtagt   6720
gtgtgcccgt ctgttgtgtg actctggtaa ctagagatcc ctcagaccct tttagtcagt   6780
gtggaaaatc tctagcagta gtagttcatg tcatcttatt attcagtatt tataacttgc   6840
aaagaaatga atatcagaga gtgagaggaa cttgtttatt gcagcttata atggttacaa   6900
ataaagcaat agcatcacaa atttcacaaa taaagcattt ttttcactgc attctagttg   6960
tggtttgtcc aaactcatca atgtatctta tcatgtctgg ctctagctat cccgccccta   7020
actccgccca gttccgccca ttctccgccc catggctgac taattttttt tatttatgca   7080
gaggccgagg ccgcctcggc ctctgagcta ttccagaagt agtgaggagg ctttttttgga  7140
ggcctaggct tttgcgtcga dacgtaccca attcgcccta tagtgagtcg tattacgcgc   7200
gctcactggc cgtcgtttta caacgtcgtg actgggaaaa ccctggcgtt acccaactta   7260
atcgccttgc agcacatccc cctttcgcca gctggcgtaa tagcgaagag gcccgcaccg   7320
atcgccctc ccaacagttg cgcagcctga atggcgaatg gcgcgacgcg cctgtagcg     7380
gcgcattaag cgcggcgggt gtggtggtta cgcgcagcgt gaccgctaca cttgccagcg   7440
ccctagcgcc cgctccttc gctttcttcc cttcctttct cgccacgttc gccggctttc    7500
cccgtcaagc tctaaatcgg gggctccctt tagggttccg atttagtgct ttacggcacc   7560
tcgacccaa aaaacttgat tagggtgatg gttcacgtag tgggccatcg ccctgataga   7620
cggttttcg cccctttgacg ttggagtcca cgttctttaa tagtggactc ttgttccaaa   7680
ctggaacaac actcaaccct atctcggtct attctttga tttataaggg attttgccga    7740
tttcggccta ttggttaaaa aatgagctga tttaacaaaa atttaacgcg aattttaaca   7800
aaatattaac gttacaatt tcccaggtgg cacttttcgg ggaaatgtgc gcggaacccc    7860
tatttgttta tttttctaaa tacattcaaa tatgtatccg ctcatgagac aataaccctg   7920
ataaatgctt caataatatt gaaaaaggaa gagtatgagt attcaacatt tccgtgtcgc   7980
ccttattccc ttttttgcgg catttgcct tcctgttttt gctcacccag aaacgctggt    8040
gaaagtaaaa gatgctgaag atcagttggg tgcacgagtg ggttacatcg aactggatct   8100
caacagcgg aagatccttg agagttttcg ccccgaagaa cgttttccaa tgatgagcac    8160
ttttaaagtt ctgctatgtg gcgcggtatt atcccgtatt gacgccgggc aagagcaact   8220
```

```
cggtcgccgc atacactatt ctcagaatga cttggttgag tactcaccag tcacagaaaa    8280
gcatcttacg gatggcatga cagtaagaga attatgcagt gctgccataa ccatgagtga    8340
taacactgcg gccaacttac ttctgacaac gatcggagga ccgaaggagc taaccgcttt    8400
tttgcacaac atgggggatc atgtaactcg ccttgatcgt tgggaaccgg agctgaatga    8460
agccatacca aacgacgagc gtgacaccac gatgcctgta gcaatggcaa caacgttgcg    8520
caaactatta actggcgaac tacttactct agcttcccgg caacaattaa tagactggat    8580
ggaggcggat aaagttgcag gaccacttct gcgctcggcc cttccggctg gctggtttat    8640
tgctgataaa tctggagccg gtgagcgtgg gtctcgcggt atcattgcag cactggggcc    8700
agatggtaag ccctcccgta tcgtagttat ctacacgacg gggagtcagg caactatgga    8760
tgaacgaaat agacagatcg ctgagatagg tgcctcactg attaagcatt ggtaactgtc    8820
agaccaagtt tactcatata ctttagat tgatttaaaa cttcattttt aatttaaaag    8880
gatctaggtg aagatccttt ttgataatct catgaccaaa atcccttaac gtgagttttc    8940
gttccactga gcgtcagacc ccgtagaaaa gatcaaagga tcttcttgag atcctttttt    9000
tctgcgcgta atctgctgct tgcaaacaaa aaaaccaccg ctaccagcgg tggtttgttt    9060
gccggatcaa gagctaccaa ctcttttcc gaaggtaact ggcttcagca gagcgcagat    9120
accaaatact gtccttctag tgtagccgta gttaggccac cacttcaaga actctgtagc    9180
accgcctaca tacctcgctc tgctaatcct gttaccagtg gctgctgcca gtggcgataa    9240
gtcgtgtctt accgggttgg actcaagacg atagttaccg gataaggcgc agcggtcggg    9300
ctgaacgggg ggttcgtgca cacagcccag cttggagcga acgacctaca ccgaactgag    9360
atacctacag cgtgagctat gagaaagcgc cacgcttccc gaagggagaa aggcggacag    9420
gtatccggta agcggcaggg tcggaacagg agagcgcacg agggagcttc caggggggaaa    9480 cgcctggtat ctttatagtc ctgtcgggtt tcgccacctc tgacttgagc gtcgattttt    9540
gtgatgctcg tcaggggggc ggagcctatg gaaaaacgcc agcaacgcgg cctttttacg    9600
gttcctggcc ttttgctggc cttttgctca catgttcttt cctgcgttat cccctgattc    9660
tgtggataac cgtattaccg cctttgagtg agctgatacc gctcgccgca gccgaacgac    9720
cgagcgcagc gagtcagtga gcgaggaagc ggaagagcgc ccaatacgca aaccgcctct    9780
ccccgcgcgt tggccgattc attaatgcag ctggcacgac aggtttcccg actggaaagc    9840
gggcagtgag cgcaacgcaa ttaatgtgag ttagctcact cattaggcac cccaggcttt    9900
acactttatg cttccggctc gtatgttgtg tggaattgtg agcggataac aatttcacac    9960
aggaaacagc tatgaccatg attacgccaa gcgcgcaatt aaccctcact aaagggaaca   10020
aaagctggag ctgca                                                    10035
```

<210> SEQ ID NO 31
<211> LENGTH: 4
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<223> OTHER INFORMATION: Linker/spacer polypeptide

<400> SEQUENCE: 31

Pro Ala Ala Leu
1

```
<210> SEQ ID NO 32
<211> LENGTH: 267
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Naked FRB domain nucleic acid sequence

<400> SEQUENCE: 32
gagatgtggc atgagggtct ggaagaagcg tctcgactgt actttggtga gcgcaatgtg      60
aagggcatgt ttgaagtcct cgaacccctt catgccatga tggaacgcgg accccagacc     120
ttgaaggaga caagttttaa ccaagcttac ggaagagacc tgatggaagc ccaggaatgg     180
tgcaggaaat acatgaaaag cgggaatgtg aaggacttga cccaagcgtg ggacctgtac     240
tatcatgtct ttaggcgcat tagtaag                                         267

<210> SEQ ID NO 33
<211> LENGTH: 353
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: MND promoter

<400> SEQUENCE: 33
gaacagagaa acaggagaat atgggccaaa caggatatct gtggtaagca gttcctgccc      60
cggctcaggg ccaagaacag ttggaacagc agaatatggg ccaaacagga tatctgtggt    120
aagcagttcc tgccccggct cagggccaag aacagatggt ccccagatgc ggtcccgccc    180
tcagcagttt ctagagaacc atcagatgtt tccagggtgc cccaaggacc tgaaatgacc    240
ctgtgcctta tttgaactaa ccaatcagtt cgcttctcgc ttctgttcgc gcgcttctgc    300
tccccgagct ctatataagc agagctcgtt tagtgaaccg tcagatcgct agc           353

<210> SEQ ID NO 34
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: DICS HDR FP

<400> SEQUENCE: 34
cggcgacgtg gaagagaatc                                                  20

<210> SEQ ID NO 35
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: DISC HDR RP

<400> SEQUENCE: 35
ggctgtggtt cagcctgact                                                  20

<210> SEQ ID NO 36
```

```
<211> LENGTH: 19
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: DISC HDR probe (FAM)

<400> SEQUENCE: 36
aggctctccc cgacctccc                                              19

<210> SEQ ID NO 37
<211> LENGTH: 2880
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Coding sequences for 3186
      (Signal-FKBP-IL2Rg-P2A-signal-FRB-IL2Rb-P2A-FRB-P2A-GFP-FOXP3
      (knock-in)

<400> SEQUENCE: 37
atgccactgg gactgctgtg gcttggactg gcccttcttg gagcactgca tgctcaggct    60
ggcgtgcagg tcgagacaat tagtcctggc gacggccgga cctttcctaa gcgaggacag   120
acatgcgtgg tgcactacac cggcatgctg aagatggaga gaagttcga cagcagccgg    180 gacagaaaca agcctttcaa gttcatgctg ggcaagcaag aagtgatcag aggctgggaa   240
gagggcgtcg cccagatgtc tgttggacag agagccaagc tgacaatcag ccccgattac   300
gcctatggcg ccacaggaca ccctgggatc attcctccac atgccacact ggtgttcgat   360
gtggaactgc tgaagctcgg cgaaggcagc aataccagca agagaaaccc cttcctgttc   420
gccctggaag ccgtggttat cagcgtggga tctatgggcc tgatcatctc cctgctgtgc   480
gtgtacttct ggctgaacg gaccatgcct cggatcccca cactgaagaa tctggaagat   540
ctggtcaccg agtaccacgg caatttcagc gcttggagtg gcgtgtccaa aggcctggct   600
gaaagcctgc agcctgacta ctctgagaga ctgtgcctgg tgtctgagat ccctcctaaa   660
ggcggcgctc tcggagaagg accaggcgct tctccatgca atcagcacag cccttattgg   720 gccctcctt gctacaccct gaagcctgaa actggaagcg agctactaa ctttagcctg    780 ctgaagcagg ctggagacgt ggaggagaac cctggaccta tggctctgcc agtgacagct   840
ctgctgcttc tctggctgct gttgctgcat gccgccagac ctattctgtg cacgagatg    900 tggcatgaag gcctggaaga ggcctccaga ctgtacttcg gcagagaaaa cgtgaagggc   960
atgttcgagg tgctggaacc cctgcatgcc atgatggaaa gaggccctca gacactgaaa  1020
gagacaagct tcaaccaggc ctacggccgg gatctgatgg aagcccaaga gtggtgccgg  1080
aagtacatga gtccggcaa tgtgaaggac ctcctgcagg catgggacct gtactaccac   1140
gtgttccggc ggatctctaa gggcaaagac acaatcccttt ggctgggcca tctgctcgtt  1200
ggactgtctg gcgccttcgg cttcatcatc ctggtgtacc tgctgatcaa ctgtcggaac  1260
acaggcccat ggctgaagaa agtgctgaag tgcaacaccc ctgatccgag caagttcttt   1320
agccagctgt ccagcgagca cggcggagat gttcagaagt ggctgagcag cccatttcct  1380
agcagcagct ttagccctgg cggactggct cctgagatca gcccactgga agtgctggaa  1440
agggacaaag tgacccagct gctcctgcaa caggacaagg tgccagaacc tgccagcctg  1500
tctctgaaca ccgatgccta tctgtccctg caagagctgc aaggatccgg cgccaccaac  1560
```

-continued

```
tttagtctgc tcaagcaagc cggggacgtc gaggaaaatc ctgggccaga aatgtggcac      1620
gaaggactcg aggaagccag tcggctgtat tttggcgagc ggaatgtgaa agggatgttt      1680
gaagtgctcg agcctctcca cgctatgatg gaacggggac cccagactct caaagaaacc      1740
agctttaatc aggcttacgg acgcgacctc atggaagctc aagaatggtg tagaaagtat      1800
atgaagagtg gcaacgtgaa agatctgctg caagcctggg atctctatta tcacgtgttc      1860
agacgcatca gcaaaggcag cggcgccaca aatttctccc tgctgaaaca ggccggcgac      1920
gtggaagaga atcccggacc tatgcctaat cctcggcctt ccaaaggcga ggaactgttt      1980
acaggcgtgg tgcccatcct ggtggaactg acggggatg tgaacggcca aagtttagc       2040 gttagcggcg aaggcgaagg ggatgccaca tacggaaagc tgaccctgaa gttcatctgc      2100
accaccggca gctgcctgt gccttggcct acactggtca ccacactgac atacggcgtg      2160
cagtgcttca gcagataccc cgaccatatg aagcagcacg acttcttcaa gagcgccatg      2220
cctgagggct acgtgcaaga gcggaccatc ttctttaagg acgacggcaa ctacaagacc      2280
agggccgaag tgaagttcga gggcgacacc ctggtcaacc ggatcgagct gaagggcatc      2340
gacttcaaag aggacggcaa catcctgggc cacaagctcg agtacaacta acagccac       2400 aacgtgtaca tcatggccga caagcagaaa acggcatca aagtgaactt caagatccgg      2460
cacaacatcg aggacggctc tgtgcagctg gccgatcact accagcagaa cacccatc       2520 ggagatggcc ctgtgctgct gcccgataac cactacctga gcacacagag cgccctgagc      2580
aaggacccca cgagaagag ggatcacatg gtgctgctgg aattcgtgac cgccgctggc      2640
atcacactcg gcatggatga gctgtacaag atgcccaatc ctagacctgg caagcccagc      2700
gctccttctc ttgctcttgg accttctcct ggtgcctcgc ccagctggag ggctgcaccc      2760
aaagcctcag acctgctggg ggcccggggc ccaggggaa ccttccaggg ccgagatctt      2820
cgaggcgggg cccatgcctc ctcttcttcc ttgaacccca tgccaccatc gcagctgcag      2880
```

<210> SEQ ID NO 38
<211> LENGTH: 2742
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: Coding sequences for 3187
(Signal-FKBP-IL2Rg-P2A-signal-FRB-IL2Rb-P2A-FRB-P2A-HA-FOXP3
(knock-in)

<400> SEQUENCE: 38

```
atgccactgg gactgctgtg gcttggactg gcccttcttg gagcactgca tgctcaggct        60
ggcgtgcagg tcgagacaat tagtcctggc gacggccgga cctttcctaa gcgaggacag       120
acatgcgtgg tgcactacac cggcatgctg aagatggca agaagttcga cagcagccgg       180
gacagaaaca agcctttcaa gttcatgctg ggcaagcaag aagtgatcag aggctgggaa       240
gagggcgtcg cccagatgtc tgttggacag agagccaagc tgacaatcag ccccgattac       300
gcctatggcg ccacaggaca ccctgggatc attcctccac atgccacact ggtgttcgat       360
gtggaactgc tgaagctcgg cgaaggcagc aataccagca agagaaaccc cttcctgttc       420
gccctggaag ccgtggttat cagcgtggga tctatggcc tgatcatctc cctgctgtgc       480
gtgtacttct ggctggaacg gaccatgcct cggatcccca cactgaagaa tctggaagat       540
ctggtcaccg agtaccacgg caatttcagc gcttggagtg gcgtgtccaa aggcctggct       600
```

```
gaaagcctgc agcctgacta ctctgagaga ctgtgcctgg tgtctgagat ccctcctaaa    660
ggcggcgctc tcggagaagg accaggcgct tctccatgca atcagcacag cccttattgg    720 gccccteett gctacaccct gaagcctgaa actggaagcg gagctactaa ctttagcctg    780
ctgaagcagg ctggagacgt ggaggagaac cctggaccta tggctctgcc agtgacagct    840
ctgctgcttc ctctggctct gttgctgcat gccgccagac ctattctgtg gcacgagatg    900
tggcatgaag gcctggaaga ggcctccaga ctgtacttcg gcgagagaaa cgtgaagggc    960
atgttcgagg tgctggaacc cctgcatgcc atgatggaaa gaggccctca gacactgaaa   1020
gagacaagct tcaaccaggc ctacggccgg gatctgatgg aagcccaaga gtggtgccgg   1080
aagtacatga agtccggcaa tgtgaaggac ctcctgcagg catgggacct gtactaccac   1140
gtgttccggc ggatctctaa gggcaaagac acaatcccct tggctgggcc atctgctcgt t   1200 ggactgtctg gcgccttcgg cttcatcatc ctggtgtacc tgctgatcaa ctgtcggaac   1260
acaggcccat ggctgaagaa agtgctgaag tgcaacaccc ctgatccgag caagttcttt   1320
agccagctgt ccagcgagca cggcggagat gttcagaagt ggctgagcag cccatttcct   1380
agcagcagct ttagccctgg cggactggct cctgagatca gcccactgga agtgctggaa   1440
agggacaaag tgacccagct gctcctgcaa caggacaagg tgccagaacc tgccagcctg   1500
tctagcaatc acagcctgac cagctgcttt accaaccagg gctacttctt cttccatctg   1560
cctgacgctc tggaaatcga ggcctgccag gtgtacttca cctacgatcc ctacagcgaa   1620
gaggaccccg atgaaggtgt tgccggtgct cctaccggaa gctctcctca acctctgcaa   1680
ccactgagcg gcgaggatga cgcctactgc acattcccca gcagagatga cctgctgctg   1740
ttcagccctt ctctgctcgg cggaccttct ccaccatcta cagctccagg tggaagcgga   1800
gccggcgagg aaagaatgcc tccaagcctg caagagcggg tgcccagaga ttgggatcct   1860
caaccactgg gccctccaac acctggcgtg ccagatctcg tggatttcca gcctcctcca   1920
gagctggtgc tgagagaagc tggcgaagaa gtgccagacg ctggccctag agagggcgtt   1980
agctttcctt ggagcagacc tcctggacag ggcgagttca gagccctgaa tgctagactg   2040
cccctgaaca ccgatgccta tctgtccctg caagagctgc aaggacaaga ccccacacac   2100
ctggttggat ccggcgccac caactttagt ctgctcaagc aagccgggga cgtcgaggaa   2160
aatcctgggc cagaaatgtg gcacgaagga ctcgaggaag ccagtcggct gtattttggc   2220
gagcggaatg tgaaagggat gtttgaagtg ctcgagcctc tccacgctat gatggaacgg   2280
ggaccccaga ctctcaaaga aaccagcttt aatcaggctt acggacgcga cctcatggaa   2340
gctcaagaat ggtgtagaaa gtatatgaag agtggcaacg tgaaagatct gctgcaagcc   2400
tgggatctct attatcacgt gttcagacgc atcagcaaag gcagcggcgc cacaaatttc   2460
tccctgctga acaggccgg cgacgtggaa gagaatcccg gacctatgta tccatacgat   2520
gtcccagatt atgcgcccaa tcctagacct ggcaagccca cgctccttc tcttgctctt   2580 ggaccttctc ctggtgcctc gcccagctgg agggctgcac ccaaagcctc agacctgctg   2640
ggggcccggg gccaggggg aaccttccag ggccgagatc ttcgaggcgg ggcccatgcc   2700
tcctcttctt ccttgaaccc catgccacca tcgcagctgc ag                      2742
```

<210> SEQ ID NO 39
<211> LENGTH: 2715
<212> TYPE: DNA
<213> ORGANISM: Artificial sequence
<220> FEATURE:

<223> OTHER INFORMATION: Synthetic polynucleotide
<220> FEATURE:
<221> NAME/KEY: misc_feature
<223> OTHER INFORMATION: Coding sequences for 3195
(Signal-FKBP-IL2Rg-P2A-signal-FRB-IL2Rb-P2A-FRB-P2A-FOXP3
(knock-in)

<400> SEQUENCE: 39

```
atgccactgg gactgctgtg gcttggactg gcccttcttg gagcactgca tgctcaggct    60
ggcgtgcagg tcgagacaat tagtcctggc gacggccgga cctttcctaa gcgaggacag   120
acatgcgtgg tgcactacac cggcatgctg aagatggca agaagttcga cagcagccgg   180
gacagaaaca agccttttcaa gttcatgctg ggcaagcaag aagtgatcag aggctgggaa   240
gagggcgtcg cccagatgtc tgttggacag agagccaagc tgacaatcag ccccgattac   300
gcctatggcg ccacaggaca ccctgggatc attcctccac atgccacact ggtgttcgat   360
gtggaactgc tgaagctcgg cgaaggcagc aataccagca agagaaaccc cttcctgttc   420
gccctggaag ccgtggttat cagcgtggga tctatgggcc tgatcatctc cctgctgtgc   480
gtgtacttct ggctggaacg gaccatgcct cggatcccca cactgaagaa tctggaagat   540
ctggtcaccg agtaccacgg caatttcagc gcttggagtg gcgtgtccaa aggcctggct   600
gaaagcctgc agcctgacta ctctgagaga ctgtgcctgg tgtctgagat ccctcctaaa   660
ggcggcgctc tcggagaagg accaggcgct ctccatgca atcagcacag cccttattgg   720
gcccctcctt gctacaccct gaagcctgaa actggaagcg gagctactaa ctttagcctg   780
ctgaagcagg ctggagacgt ggaggagaac cctggaccta tggctctgcc agtgacagct   840
ctgctgcttc ctctggctct gttgctgcat gccgccagac ctattctgtg gcacgagatg   900
tggcatgaag gcctggaaga ggcctccaga ctgtacttcg gcgagagaaa cgtgaagggc   960
atgttcgagg tgctggaacc cctgcatgcc atgatggaaa gaggccctca gacactgaaa  1020
gagacaagct tcaaccaggc ctacggccgg atctgatgg aagcccaaga gtggtgccgg  1080
aagtacatga agtccggcaa tgtgaaggac ctcctgcagg catgggacct gtactaccac  1140
gtgttccggc ggatctctaa gggcaaagac acaatcccctt ggctgggcca tctgctcgtt  1200
ggactgtctg gcgccttcgg cttcatcatc ctggtgtacc tgctgatcaa ctgtcggaac  1260
acaggcccat ggctgaagaa agtgctgaag tgcaacaccc ctgatccgag caagttcttt  1320
agccagctgt ccagcgagca cggcggagat gttcagaagt ggctgagcag cccatttcct  1380
agcagcagct ttagccctgg cggactggct cctgagatca gcccactgga agtgctggaa  1440
agggacaaag tgacccagct gctcctgcaa caggacaagg tgccagaacc tgccagcctg  1500
tctagcaatc acagcctgac cagctgcttt accaaccagg gctacttctt cttccatctg  1560
cctgacgctc tggaaatcga ggcctgccag gtgtacttca cctacgatcc ctacagcgaa  1620
gaggacccccg atgaaggtgt tgccggtgct cctaccggaa gctctcctca acctctgcaa  1680
ccactgagcg gcgaggatga cgcctactgc acattcccca gcagagatga cctgctgctg  1740
ttcagcccctt ctctgctcgg cggaccttct ccaccatcta cagctccagg tggaagcgga  1800
gccggcgagg aaagaatgcc tccaagcctg caagagcggg tgcccagaga ttgggatcct  1860
caaccactgg gccctccaac acctggcgtg ccagatctcg tggatttcca gcctcctcca  1920
gagctggtgc tgagagaagc tggcgaagaa gtgccagacg ctggccctag agagggcgtt  1980
agcttttcctt ggagcagacc tcctggacag ggcgagttca gagccctgaa tgctagactg  2040
cccctgaaca ccgatgccta tctgtccctg caagagctgc aaggacaaga ccccacacac  2100
```

```
ctggttggat ccggcgccac caactttagt ctgctcaagc aagccgggga cgtcgaggaa    2160
aatcctgggc cagaaatgtg gcacgaagga ctcgaggaag ccagtcggct gtattttggc    2220
gagcggaatg tgaaagggat gtttgaagtg ctcgagcctc tccacgctat gatggaacgg    2280 ggacccccaga ctctcaaaga aaccagcttt aatcaggctt acggacgcga cctcatggaa   2340
gctcaagaat ggtgtagaaa gtatatgaag agtggcaacg tgaaagatct gctgcaagcc    2400
tgggatctct attatcacgt gttcagacgc atcagcaaag gcagcggcgc cacaaatttc    2460
tccctgctga acaggccgg cgacgtggaa gagaatcccg gacctatgcc caatcctaga     2520
cctggcaagc ccagcgctcc ttctcttgct cttggacctt ctcctggtgc ctcgcccagc    2580
tggagggctg cacccaaagc ctcagacctg ctggggcc ggggcccagg gggaaccttc      2640
cagggccgag atcttcgagg cggggcccat gcctcctctt cttccttgaa ccccatgcca    2700
ccatcgcagc tgcag                                                     2715

<210> SEQ ID NO 40
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: T1 spacer targeting human FOXP3

<400> SEQUENCE: 40
ttccagggcc gagatcttcg                                                  20

<210> SEQ ID NO 41
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: T3 spacer targeting human FOXP3

<400> SEQUENCE: 41
cgcctcgaag atctcggccc                                                  20

<210> SEQ ID NO 42
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: T4 spacer targeting human FOXP3

<400> SEQUENCE: 42
tcgaagatct cggccctgga                                                  20

<210> SEQ ID NO 43
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: T7 spacer targeting human FOXP3

<400> SEQUENCE: 43
```
ggccctggaa ggttccccct                                              20

<210> SEQ ID NO 44
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: T9 spacer targeting human FOXP3

<400> SEQUENCE: 44
tccagctggg cgaggctcct                                              20

<210> SEQ ID NO 45
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: T18 spacer targeting human FOXP3

<400> SEQUENCE: 45
tcagacctgc tgggggcccg                                              20

<210> SEQ ID NO 46
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: R1 spacer targeting human FOXP3

<400> SEQUENCE: 46
gagccccgcc tcgaagatct                                              20

<210> SEQ ID NO 47
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: P1 spacer targeting human AAVS1

<400> SEQUENCE: 47
attcccaggg ccggttaatg                                              20

<210> SEQ ID NO 48
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: P3 spacer targeting human AAVS1

<400> SEQUENCE: 48
gtcccctcca ccccacagtg                                              20

```
<210> SEQ ID NO 49
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: P4 spacer targeting human AAVS1

<400> SEQUENCE: 49
accccacagt ggggccacta                                               20

<210> SEQ ID NO 50
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: N1 spacer targeting human AAVS1

<400> SEQUENCE: 50
cctctaaggt ttgcttacga                                               20

<210> SEQ ID NO 51
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: N2 spacer targeting human AAVS1

<400> SEQUENCE: 51
tataaggtgg tcccagctcg                                               20

<210> SEQ ID NO 52
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: N3 spacer targeting human AAVS1

<400> SEQUENCE: 52
ccatcgtaag caaaccttag                                               20

<210> SEQ ID NO 53
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: mT20 spacer target murine FOXP3

<400> SEQUENCE: 53
gactcctggg gatgggccaa                                               20

<210> SEQ ID NO 54
<211> LENGTH: 20
<212> TYPE: DNA
<213> ORGANISM: Artificial sequence
```

```
<220> FEATURE:
<223> OTHER INFORMATION: Synthetic polynucleotide
<220> FEATURE:
<221> NAME/KEY: misc_feature
<223> OTHER INFORMATION: mT22 spacer target murine FOXP3

<400> SEQUENCE: 54
ttggcccttg gcccatcccc                                                 20

<210> SEQ ID NO 55
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: mT23 spacer target murine FOXP3

<400> SEQUENCE: 55
ccagcttggc aagactcctg                                                 20

<210> SEQ ID NO 56
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: human TRAC spacer sequence G2

<400> SEQUENCE: 56
acaaaactgt gctagacatg                                                 20

<210> SEQ ID NO 57
<211> LENGTH: 18
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: human TRAC spacer sequence G4

<400> SEQUENCE: 57
tcaagagcaa cagtgctg                                                   18

<210> SEQ ID NO 58
<211> LENGTH: 20
<212> TYPE: DNA
<213> ORGANISM: Artificial sequence
<220> FEATURE:
<223> OTHER INFORMATION: Synthetic polynucleotide
<220> FEATURE:
<221> NAME/KEY: misc_feature
<223> OTHER INFORMATION: spacer sequence

<400> SEQUENCE: 58
ccgatgccca accccaggcc                                                 20
```